(12) United States Patent
Jamieson, Jr. et al.

(10) Patent No.: US 10,472,677 B2
(45) Date of Patent: *Nov. 12, 2019

(54) TRANSLATIONAL DYSFUNCTION BASED THERAPEUTICS

(71) Applicant: Translational Therapeutics, Inc., Arlington, MA (US)

(72) Inventors: Gordon A. Jamieson, Jr., Arlington, MA (US); Katherine L. B. Borden, St. Laurent (CA); Biljana Culjkovic, Montreal (CA); Alex Kentsis, New York, NY (US)

(73) Assignee: Translational Therapeutics, Inc., Arlington, MA (US)

( * ) Notice: Subject to any disclaimer, the term of this patent is extended or adjusted under 35 U.S.C. 154(b) by 401 days.

This patent is subject to a terminal disclaimer.

(21) Appl. No.: 13/938,510

(22) Filed: Jul. 10, 2013

(65) Prior Publication Data

US 2014/0199692 A1 Jul. 17, 2014

Related U.S. Application Data

(63) Continuation of application No. 12/163,449, filed on Jun. 27, 2008, now Pat. No. 8,497,292, which is a continuation-in-part of application No. PCT/US2006/049450, filed on Dec. 28, 2006, said application No. 12/163,449 is a continuation-in-part of application No. PCT/US2007/021167, filed on Oct. 1, 2007.

(60) Provisional application No. 60/754,461, filed on Dec. 28, 2005, provisional application No. 60/794,048, filed on Apr. 22, 2006, provisional application No. 60/848,583, filed on Sep. 29, 2006, provisional application No. 60/854,404, filed on Oct. 25, 2006, provisional application No. 60/848,583, filed on Sep. 29, 2006, provisional application No. 60/854,404, filed on Oct. 25, 2006, provisional application No. 60/942,884, filed on Jun. 8, 2007.

(51) Int. Cl.
C12Q 1/6881 (2018.01)
C12Q 1/6809 (2018.01)
A61K 31/4196 (2006.01)
G01N 33/569 (2006.01)

(52) U.S. Cl.
CPC ........ C12Q 1/6881 (2013.01); A61K 31/4196 (2013.01); G01N 33/56966 (2013.01)

(58) Field of Classification Search
None
See application file for complete search history.

(56) References Cited

U.S. PATENT DOCUMENTS

| | | | |
|---|---|---|---|
| 5,405,837 A | 4/1995 | Weber | |
| 6,153,594 A | 11/2000 | Børretzen et al. | |
| 6,316,425 B1 | 11/2001 | Myhren et al. | |
| 6,335,322 B1 | 1/2002 | Myhren et al. | |
| 6,384,019 B1 | 5/2002 | Myhren et al. | |
| 6,548,486 B1 | 4/2003 | Dalen et al. | |
| 6,576,636 B2 | 6/2003 | Webb et al. | |
| 6,762,175 B2 | 7/2004 | Myhren et al. | |
| 2002/0042391 A1 | 4/2002 | Myhren et al. | |
| 2005/0019785 A1* | 1/2005 | Baker | C12Q 1/6886 435/6.12 |
| 2005/0159372 A1 | 7/2005 | Tam et al. | |
| 2006/0019256 A1 | 1/2006 | Clarke et al. | |
| 2007/0135436 A1 | 6/2007 | Myhren et al. | |
| 2007/0225248 A1 | 9/2007 | Myhren et al. | |
| 2008/0280851 A1 | 11/2008 | Myhren et al. | |
| 2009/0209477 A1 | 8/2009 | Silverman et al. | |
| 2009/0209482 A1 | 8/2009 | Silverman et al. | |
| 2009/0286752 A1 | 11/2009 | Etter et al. | |
| 2010/0062996 A1 | 3/2010 | Myhren et al. | |

FOREIGN PATENT DOCUMENTS

| | | |
|---|---|---|
| GB | 1 010 380 | 11/1965 |
| JP | 2004-509061 A | 3/2004 |
| JP | 3503049 B2 | 3/2004 |
| JP | 2005-524662 A | 8/2005 |
| WO | WO-89/06132 | 7/1989 |
| WO | WO-01/60379 | 8/2001 |
| WO | WO-03/073989 A2 | 9/2003 |
| WO | WO-2004/012769 | 2/2004 |
| WO | WO-2004027432 A2 | 4/2004 |
| WO | WO-2004/100995 A1 | 11/2004 |
| WO | WO-2006016110 A1 | 2/2006 |
| WO | WO-2006022895 A2 | 3/2006 |
| WO | WO-2006098628 A1 | 9/2006 |
| WO | WO-2007047754 A2 | 4/2007 |
| WO | WO-2007067071 A1 | 6/2007 |
| WO | WO-2008115069 A2 | 9/2008 |

(Continued)

OTHER PUBLICATIONS

Berkel et al. Expression of the Translation Initiation Factor eIF4e in the Polyp-Cancer Sequence in the Colon. Jun. 2001. Cancer Epidemiology Biomarkers Prev. vol. 10, pp. 663-666.*

(Continued)

*Primary Examiner* — Channing S Mahatan
(74) *Attorney, Agent, or Firm* — Foley Hoag LLP

(57) ABSTRACT

Provided are methods and compositions for inhibiting eukaryotic translation initiation factor eIF4E. Such methods and compositions may be used alone or in conjunction with other therapies, such as gene therapies, for inhibiting cell proliferation and/or treating cancer.

23 Claims, 38 Drawing Sheets

Specification includes a Sequence Listing.

(56) References Cited

FOREIGN PATENT DOCUMENTS

| WO | WO-2009042766 A1 | 4/2009 |
|---|---|---|
| WO | WO-2009042767 A1 | 4/2009 |
| WO | WO-2009/139888 A1 | 11/2009 |
| WO | WO-2010/039039 A1 | 4/2010 |

OTHER PUBLICATIONS

Denkert et al. Expression of the ELAV-like protein HuR in human colon cancer: association with tumor stage and cyclooxygenase-2. Aug. 2006. Modern Pathology. vol. 19, p. 1261-1269.*
Ribavirin—Drugbank. www.drugbank.ca/drugs/DB00811. Drug created on Jun. 13, 2005. Access online on Feb. 20, 2018. 12 pages.*
Bachmann, M., et al. "The serine/threonine kinase Pim-1," Int J Biochem & Cell Biol. 37: 726-30 (2005).
Bergamini, G., et al. "Picornavirus IRESes and the poly(A) tail jointly promote cap-independent translation in a mammalian cell-free system," RNA 6: 1781-1790 (2000).
Boisvert, F.M., et al. "Promyelocytic Leukemia (PML) Nuclear Bodies Are Protein Structures that Do Not Accumulate RNA," J. Cell Biol. 148(2): 283-292 (Jan. 24, 2000).
Borden, K.L.B., et al. "The solution structure of the RING finger domain from the acute promyelocytic leukaemia proto-oncoprotein PML," EMBO J. 14(7): 1532-1541 (1995).
Borden, K.L. "Pondering the Promyelocytic Leukemia Protein (PML) Puzzle: Possible Functions for PML Nuclear Bodies," Mol Cell Biol. 22(15): 5259-69; (Aug. 2002).
Calero, G., et al. "Structural basis of m7GpppG binding to the nuclear cap-binding protein complex," Nat. Struct. Biol. 9(12): 912-917 (Dec. 2002).
Campbell Dwyer, E. J., et al. "The Lymphocytic Choriomeningitis Virus RING Protein Z Associates with Eukaryotic Initiation Factor 4E and Selectively Represses Translation in a RING-Dependent Manner," J. Virol. 74(7): 3293-3300 (Apr. 2000).
Cao, Q., et al. "Dissolution of the maskin-eIF4E complex by cytoplasmic polyadenylation and poly(A)-binding protein controls cyclin B1 mRNA translation and oocyte maturation," EMBO J. 21(14): 3852-62 (2002).
Camp, et al. "Automated subcellular localization and quantification of protein expression in tissue microarrays," Nature Medicine, 8(11): 1323-1327 (Nov. 1, 2002).
Capili, A. D., et al. "Structure of the C-terminal RING Finger from a RING-IBR-RING/TRIAD Motif Reveals a Novel Zinc-binding Domain Distinct from a RING," J. Mol. Biol. 340:1117-1129 (2004).
Carberry, S.E., et al. "A Spectroscopic Study of the Binding of m7GTP and m7GpppG to Human Protein Synthesis Initiation Factor 4E," Biochemistry 28: 8078-8083 (1989).
Chen, Y.C., et al. "Overexpression of NBS1 Contributes to Transformation through the Activation of Phosphatidylinositol 3-Kinase/Akt," J Biol Chem. 280(37): 32505-11 (Sep. 16, 2005).
Clemens, M.J., et al. "Translational control: the cancer connection," Int J Biochem Cell Biol. 31:1-23 (1999).
Clever, J., et al. "RNA Secondary Structure and Binding Sites for gag Gene Products in the 5' Packaging Signal of Human Immunodeficiency Virus Type 1," J Virol. 69(4):2101-9 (Apr. 1995).
Cohen, N., et al. "PML RING suppresses oncogenic transformation by reducing the affinity of eIF4E for mRNA," EMBO J., 20(16): 4547-4559 (2001).
Colby, T. D., et al. "Crystal structure of human type II inosine monophoshate dehydrogenase: Implications for ligand binding and drug design," Proc. Natl. Acad. Sci. USA 96: 3531-3536 (Mar. 1999).
Colomer, R., et al. "erbB-2 antisense oligonucleotides inhibit the proliferation of breast carcinoma cells with erbB-2 oncogene amplication," Br. J. Cancer 70: 819-825 (1994).
Crotty, S., et al. "Ribavirin's antiviral mechanism of action: lethal mutagenesis?" J. Mol. Med. 80: 86-95 (2002).

Crotty, S., et al. "RNA virus error catastrophe: Direct molecular test by using ribavirin," Proc. Natl. Acad. Sci. USA 98(12): 6895-6900 (Jun. 5, 2001).
Crotty, S., et al. "The broad-spectrum antiviral ribonucleoside ribavirin is an RNA virus mutagen," Nat. Med. 6(12): 1375-1379 (Dec. 2000).
Crotty, S., et al. ERRATA "The broad-spectrum antiviral ribonucleoside ribavirin is an RNA virus mutagen," Nature Med. 7(2): 255 (Feb. 2001).
Culjkovic et al., "Controlling Gene Expression through RNA Regulons," Cell Cycle 6(1):65-69 (2007).
Culjkovic et al., "eIF4E is a central node of an RNA regulon that governs cellular proliferation," J. Cell Biology, 175(3):415-426 (2006).
Culjkovic et al., "eIF4E promotes nuclear export of cyclin D1 and mRNAs via an element in the 3'UTR," J. Cell Biology, 169(2):245-256 (2005).
Culjkovic et al., "The eIF4E RNA regulon promotes the Akt signaling pathway," J. Cell Biology, 181(1):51-63 (2008).
Cullen, B.R. "Nuclear mRNA export: insights from virology," Trends Biochem Sci. 28(8): 419-24 (Aug. 2003a).
Cullen, B.R. "Nuclear RNA export," J Cell Sci. 116: 587-97 (2003b).
Cullen, B.R. "Nuclear RNA Export Pathways," Mol Cell Biol. 20(12): 4181-4187 (Jun. 2000).
De Benedetti et al., "eIF-4E expression and its role in malignancies and metastases," Oncogene, 23:3189-3199 (2004).
De Benedetti, A., et al. "eIF4E expression in tumors: its possible role in progression of malignancies," Int. J. Biochem. Cell Biol. 31: 59-72 (1999).
De Gregorio, E., et al. "Tethered-function analysis reveals that eIF4E can recruit ribosomes independent of its binding to the cap structure," RNA 7: 106-113 (2001).
DeFatta, R. J., et al. "Antisense RNA to eIF4E Suppresses Oncogenic Properties of a Head and Neck Squamous Cell Carcinoma Cell Line," Laryngoscope 110, 928-933 (Jun. 2000).
Dostie, J., et al. "A novel shuttling protein, 4E-T, mediates the nuclear import of the mRNA 5' cap-binding protein, eIF4E," EMBO J. 19(12): 3142-3156 (2000).
Dostie, J., et al. "Nuclear Eukaryotic Initiation Factor 4E (eIF4E) Colocalizes with Splicing Factors in Speckles," J. Cell Biol. 148(2): 239-245 (Jan. 24, 2000).
Faivre et al., "Current development of mTOR inhibitors as anticancer agents," Nature Reviews—Drug Discovery, 5(8):671-688 (2006).
Fletcher, C.M. et al. "The interaction of eIF4E with 4E-BP1 is an induced fit to a completely disordered protein," Protein Sci. 7: 1639-1642 (1998).
Gao, Y., et al. "Regulation of the selenoprotein SelS by glucose deprivation and endoplasmic reticulum stress—SelS is a novel glucose-regulated protein," FEBS Lett. 563:185-90 (2004).
Gingras, A. C., et al. "eIF4 Initiation Factors: Effectors of mRNA Recruitment to Ribosomes and Regulators of Translation," Annu. Rev. Biochem. 68: 913-963 (1999).
Graff, J. R., et al. "Translational control and metastatic progression: Enhanced activity of the mRNA cap-binding protein eIF-4E selectively enhances translation of metastasis-related mRNAs," Clin. Exp. Metastasis 20: 265-273 (2003).
Graff, J. R., et al. "Translation of ODC mRNA and Polyamine Transport Are Suppressed in ras-Transformed CREF Cells by Depleting Translation Initiation Factor 4E," Biochem. Biophys. Res. Commun. 240: 15-20 (1997).
Grillo, G., et al. "PatSearch: a program for the detection of patterns and structural motifs in nucleotide sequences," Nucleic Acids Res. 31(13): 3608-12 (2003).
Herold, A., et al. "NXF1/p15 heterodimers are essential for mRNA nuclear export in *Drosophila*," RNA, 7: 1768-80 (2001).
Hidalgo et al., "Microarray comparative genomic hybridization detection of chromosomal imbalances in uterine cervix carcinoma," BMC Cancer, 5(77):107 (2005).
Hieronymus, H., et al. "A systems view of mRNP biology," Genes Dev. 18: 2845-60 (2004).

(56) References Cited

OTHER PUBLICATIONS

Hieronymus, H., et al. "Genome-wide analysis of RNA-protein interactions illustrates specificity of the mRNA export machinery," Nature Genet. 33: 155-61 (Feb. 2003).
Hieronymus, H., et al. "Genome-wide mRNA surveillance is coupled to mRNA export," Genes & Dev. 18: 2652-62 (2004).
Hoover, D.S., et al. "Pim-1 Protein Expression Is Regulated by Its 5'-Untranslated Region and Translation Initiation Factor eIF-4E1," Cell Growth Differ. 8: 1371-80 (Dec. 1997).
Ibarra, Kristie D., et al.; "Reduced Ribavirin Antiviral Efficacy via Nucleoside Transporter-Mediated Drug Resistance," Journal of Virology, 83(9):4538-4547 (May 2009).
Iborra, F. J., et al. "Coupled Transcription and Translation Within Nuclei of Mammalian Cells," Science 293: 1139-1142 (Aug. 10, 2001).
Ishigaki, Y., et al. "Evidence for a Pioneer Round of mRNA Translation: mRNAs Subject to Nonsense-Mediated Decay in Mammalian Cells Are Bound by CBP80 and CBP20," Cell. 106: 607-617 (2001).
Izaurralde, E., et al. "A cap-binding protein complex mediating U snRNA export," Nature, 376: 709-712 (Aug. 24, 1995).
Jain, M., et al. "Sustained Loss of a Neoplastic Phenotype by Brief Inactivation of MYC," Science 297: 102-104 (Jul. 5, 2002).
Keene, J.D., et al. "Eukaryotic mRNPs May Represent Post-transcriptional Operons," Mol Cell. 9: 1161-7 (Jun. 2002).
Keene, J.D.,et al. "Post-transcriptional operons and regulons co-ordinating gene expression," Chromosome Res. 13: 327-37 (2005).
Kentsis, A., et al. "Control of biochemical reactions through supramolecular RING domain self-assembly," Proc. Natl. Acad. Sci. USA 99(24): 15404-15409 (Nov. 26, 2002).
Kentsis, A., et al. "The RING Domains of the Promyelocytic Leukemia Protein Pml and the Arenaviral Protein Z Repress Translation by Directly Inhibiting Translation Initiation Factor eIF4E," J. Mol. Biol. 312: 609-623 (2001).
Kentsis et al., "Further evidence that ribavirin interacts with eIF4E," RNA, 11(12):1762-1766 (2005).
Kentsis et al., "Ribavirin suppresses EIF4E-mediated oncogenic transformation by physical mimicry of the 7-methyl guanosine mRNA cap," Proc. National Acad. Sci. USA, 101(52):18105-18110 (2004).
Lai, H.K., et al. "The promyelocytic leukemia (PML) protein suppresses cyclin D1 protein production by altering the nuclear cytoplasmic distribution of cyclin D1 mRNA," Oncogene. 19: 1623-1634 (2000).
Lang, V., et al. "Initiation Factor eIF-4E of *Saccharomyces cerevisiae*," J. Biol. Chem. 269(8): 6117-6123 (Feb. 25, 1994).
Lazaris-Karatzas, A., et al. "Malignant transformation by a eukaryotic initiation factor subunit that binds to mRNA 5' cap," Nature 345: 544-547 (Jun. 7, 1990).
Lazaris-Karatzas, A., et al. "The mRNA 5' Cap-Binding Protein, eIF-4E, Cooperates with v-myc or E1A in the Transformation of Primary Rodent Fibroblasts," Mol. Cell. Biol. 12(3): 1234-1238 (Mar. 1992).
Lejbkowicz, F., et al. "A fraction of the mRNA 5' cap-binding protein, eukaryotic initiation factor 4E, localizes to the nucleus," Proc. Natl. Acad. Sci. USA. 89: 9612-9616 (Oct. 1992).
Lejeune, F., Y. et al. "The exon junction complex is detected on CBP80-bound but not eIF4E-bound mRNA in mammalian cells: dynamics of mRNP remodeling," EMBO J., 21(13): 3536-3545 (2002).
Liang, J., et al. "Multiple Roles of the P13K/PKB (Akt) Pathway in Cell Cycle Progression," Cell Cycle, 2(4): 339-45 (Jul./Aug. 2003).
Maag, D., et al. "Hepatitis C Virus RNA-dependent RNA Polymerase (NS5B) as a Mediator of the Antiviral Activity of Ribavirin," J. Biol. Chem. 276(49): 46094-46098 (Dec. 7, 2001).
Marcotrigiano, J., et al. "Cocrystal Structure of the Messenger RNA 5' Cap-Binding Protein (eIF4E) Bound to 7-methyl-GDP," Cell 89: 951-961 (Jun. 13, 1997).

Matsuo, H., et al. "Structure of translation factor eIF4E bound to m7GDP and interaction with 4E-binding protein," Nat. Struct. Biol. 4(9): 717-724 (Sep. 1997).
McGuire, A. M., et al. "Internal and overall motions of the translation factor eIF4E: Cap binding and insertion in a CHAPS detergent micelle," J. Biomol. NMR 12: 73-88 (1998).
McKendrick, L., et al. "Interaction of Eukaryotic Translation Initiation Factor 4G with the Nuclear Cap-Binding Complex Provides a Link between Nuclear and Cytoplasmic Functions of the m7 Guanosine Cap," Mol. Cell. Biol. 21(11): 3632-3641 (Jun. 2001).
Michel, Y.M., et al. "Cap-Poly(A) Synergy in Mammalian Cell-free Extracts," J. Biol. Chem. 275(41): 32268-32276 (Oct. 13, 2000).
Morley, S.J., et al. "Hormone-induced meiotic maturation in *Xenopus oocytes* occurs independently of p70s6k activation and is associated with enhanced initiation factor (eIF)-4F phosphorylation and complex formation," J. Cell Sci. 108: 1751-1760 (1995).
Moy, T.I., et al. "Requirements for the nuclear export of the small ribosomal subunit," J Cell Sci. 115: 2985-95 (May 7, 2002).
Nathan, C. A., et al. "Elevated expression of eIF4E and FGF-2 isoforms during vascularization of breast carcinomas," Oncogene 15: 1087-1094 (1997).
Naumann, F., et al. "Gene structure and expression of the 5'-(CGG)n-3'-binding protein (CGGBP1)," Genomics, 83:106-118 (2004).
Niedzwiecka, A., et al. "Biophysical Studies of eIF4E Cap-binding Protein: Recognition of mRNA 5' Cap Structure and Synthetic Fragments of eIF4G and 4E-BP1 Proteins," J. Mol. Biol. 319: 615-635 (2002).
Page, T., et al. "The Metabolism of Ribavirin in Erythrocytes and Nucleated Cells," Int. J. Biochem. 22(4): 379-383 (1990).
Pegg, A.E. "Regulation of Ornithine," J Biol Chem. 281(21):14529-32 (May 26, 2006).
Perez-Roger, I., et al. "Cyclins D1 and D2 mediate Myc-induced proliferation via sequestration of p27kip1 and p21Cip1," EMBO J. 18(19):5310-5320 (1999).
Pomeroy, S. L., et al., "Prediction of central nervous system embryonal tumour outcome based on gene expression," Nature 415: 436-442 (Jan. 24, 2002).
Rau, M., et al. "A Reevaluation of the Cap-binding Protein, eIF4E, as a Rate-limiting Factor for Initiation of Translation in Reticulocyte Lysate*," J. Biol. Chem. 271(15): 8983-8990 (1996).
Rosenwald, I. B., et al. "Upregulation of protein synthesis initiation factor eIF-4E is an early event during colon carcinogenesis," Oncogene 18: 2507-2517 (1999).
Rousseau, D., et al. "Translation initation of ornithine decarboxylase and nucleocytoplasmic transport of cyclin D1 mRNA are increased in cells overexpressing eukaryotic initiation factor 4E," Proc. Natl. Acad. Sci. USA 93: 1065-1070 (Feb. 1996).
Roy, H., et al. "Biology of vascular endothelial growth factors," FEBS Lett. 580: 2879-87 (2006).
Sarkar, S. et al. "tRNA Nuclear Export in *Saccharomyces cerevisiae*: In Situ Hybridization Analysis," Mol Biol Cell. 9: 3041-55 (Nov. 1998).
Schmidt, E.V. "The role of c-myc in regulation of translation initiation," Oncogene, 23: 3217-21 (2004).
Schweppe, Rebecca E., et al.; "Deoxyribonucleic Acid Profiling Analysis of 40 Human Thyroid Cancer Cell Lines Reveals Cross-Contamination Resulting in Cell Line Redundancy and Misidentification," J. Clin. Endocrinol Metab., 93(11):4331-4341 (Nov. 2008).
Schütz, S., et al. "Stimulated Expression of mRNAs in Activated T Cells Depends on a Functional CRM1 Nuclear Export Pathway," J Mol Biol., 358: 997-1009 (2006).
Sidwell, R. W., et al. "Broad-Spectrum Antiviral Activity of Virazole: 1-β-D-Ribofuranosyl-1, 2, 4-triazole-3-carboxamide," Science 177(4050): 705-706 (Aug. 25, 1972).
Sonenberg, N., et al. "Poliovirus Translation: A Paradigm for a Novel Initiation Mechanism," BioEssays 11(5): 128-132 (Nov. 1989).
Sonenberg, N., et al. "The mRNA 5' cap-binding protein eIF4E and control of cell growth," Curr. Opin. Cell Biol. 10: 268-275 (1998).
Sorrells, D. L., et al. "Competitive PCR to Detect eIF4E Gene Amplification in Head and Neck Cancer," Head and Neck Cancer, 21: 60-65 (Jan. 1999).

(56) References Cited

OTHER PUBLICATIONS

Stier, S., et al. "Identification of p54nrb and the 14-3-3 Protein HS1 as TNF-α-Inducible Genes Related to Cell Cycle Control and Apoptosis in Human Arterial Endothelial Cells," J Biochem Mol Biol. 38(4): 447-56 (Jul. 2005).
Strudwick, S., et al. "The emerging roles of translation factor eIF4E in the nucleus," Differentiation 70: 10-22 (2002).
Stuurman, N., et al. "A monoclonal antibody recognizing nuclear matrix-associated nuclear bodies," J. Cell Sci., 101: 773-784 (1992).
Svitkin, Y.V., et al. "An Efficient System for Cap- and Poly(A)-Dependent Translation In Vitro," Methods Mol. Biol. 257: 155-170 (2004).
Svitkin, Y.V., et al. "Poly(A)-binding protein interaction with eIF4G stimulates picornavirus IRES-dependent translation," RNA 7: 1743-1752 (2001).
Sweeney et al., "Experimental Antitumor Activity of Pyrazomycin," Cancer Research, 33(11):2619-2623 (1973).
Tam, R. C., et al. "Mechanisms of action of ribavirin in antiviral therapies," Antiviral Chem. Chemother. 12: 261-272 (2001).
Thompson, J.D., et al. "CLUSTAL W: improving the sensitivity of progressive multiple sequence alignment through sequence weighting, position-spcific gap penalties and weight matrix choice," Nucleic Acids Res. 22(22): 4673-4680 (1994).
Topisirovic, I., et al. "Aberrant Eukaryotic Translation Initiation Factor 4E-Dependent mRNA Transport Impedes Hematopoietic Differentiation and Contributes to Leukemogenesis," Mol. Cell Biol. 23(24): 8992-9002 (2003b).
Topisirovic, I., et al. "Eukaryotic Translation Initiation Factor 4E Activity Is Modulated by HOXA9 at Multiple Levels," Mol Cell Biol. 25(3): 1100-12 (2005).
Topisirovic, I., et al. "Gamma Interferon and Cadmium Treatments Modulate Eukaryotic Initiation Factor 4E-Dependent mRNA Transport of Cyclin D1 in a PML-Dependent Manner," Mol. Cell. Biol. 22(17): 6183-6198 (2002).
Topisirovic, I., et al. "Homeodomain proteins and eukaryotic translation initiation factor 4E (eIF4E): an unexpected relationship," Histol Histopathol. 20: 1275-84 (2005).
Topisirovic, I., M. et al. "Phosphorylation of the Eukaryotic Translation Initiation Factor eIF4E Contributes to Its Transformation and mRNA Transport Activities," Cancer Res. 64: 8639-8642 (2004).
Topisirovic, I., et al. "The proline-rich homeodomain protein, PRH, is a tissue-specific inhibitor of eIF4E-dependent cyclin D1 mRNA transport and growth," EMBO J. 22(3): 689-703 (2003).
Trifillis, P., et al. "Finding the right RNA: Identification of cellular mRNA substrates for RNA-binding proteins," RNA. 5: 1071-1082 (1999).
Visa, N., et al. "A Nuclear Cap-binding Complex Binds Balbiani Ring Pre-mRNA Cotranscriptionally and Accompanies the Ribonucleoprotein Particle during Nuclear Export," J. Cell Biol. 133(1): 5-14 (Apr. 1996).
von der Haar, T., et al. "The mRNA cap-binding protein eIF4E in post-transcriptional gene expression," Nat. Struct. Mol. Biol. 11(6): 503-511 (Jun. 2004).
Von Grotthuss, et al. "mRNA Cap-1 Methyltransferase in the SARS Genome," Cell 113: 701-702 (Jun. 13, 2003).
Wang, S., et al., "Expression of the Eukaryotic Translation Initiation Factors 4E and 2α in Non-Hodgkin's Lymphomas," Am. J. Pathol. 155(1): 247-255 (Jul. 1999).
Wang, H., et al. "C/EBPα Arrests Cell Proliferation through Direct Inhibition of Cdk2 and Cdk4," Mol Cell. 8:817-28 (Oct. 2001).
Wang, Songtao, et al.; "Expression of Eukaryotic Translation Initiation Factors 4E and 2α Correlates with the Progression of Thyroid Carcinoma," Thyroid, 11(12):1101-1107 (2001).
Weinstein, I. B. "Disorders in cell circuitry during multistage carcinogenesis: the role of homeostasis," Carcinogenesis 21(5): 857-864 (2000).
Wendel et al., "Survival signalling by Akt and eIF4E in oncogenesis and cancer therapy," Nature, 428:332-337 (2004).
Westman, B., et al. "The antiviral drug ribavirin does not mimic the 7-methylguanosine moiety of the mRNA cap structure in vitro," RNA (in press) (2005).
Yan, Y., et al. "Ribavirin is not a functional mimic of the 7-methyl guanosine mRNA cap," RNA 11: 1238-1244 (2005).
Zhou, P., et al. "A solubility-enhancement tag (SET) for NMR studies of poorly behaving proteins," J. Biomol. NMR 20: 11-14 (2001).
Zhu, N., et al. "Transcriptional repression of the eukaryotic initiation factor 4E gene by wild type p53," Biochem Biophys Res Commun. 335: 1272-79 (2005).
Zoulim, F., et al. "Ribavirin monotherapy in patients with chronic hepatitis C: a retrospective study of 95 patients," J. Viral Hepat. 5, 193-198 (1998).
Australian Examination Report for 2006342447 dated Oct. 26, 2011.
Examination Report in Australian Patent Application No. 2007320026 dated Aug. 2, 2012.
Examination Report for EP 07867193.0 dated Nov. 18, 2011.
Examination Report and Notice of Acceptance of Complete Specification, NZ Application No. 569883 dated Nov. 29, 2011.
International Search Report for PCT/US06/49450 dated Dec. 19, 2007.
International Search Report dated Jul. 7, 2008 from PCT/US07/21167.
Office Action for JP Application No. 2009-530471 dated Feb. 7, 2012.
New Zealand Examination Report for 569883 dated Oct. 26, 2011.
Examination Report for New Zealand Patent Application No. 596694 dated Nov. 29, 2011.
Supplementary European Search Report dated Oct. 8, 2009 from EP 06 85 0026.
Supplementary European Search Report dated Jun. 18, 2010 from EP 07 86 7193.
Schlossser, Stephan F., et al. "Ribavirin and Alpha Interferon Enhance Death Receptor-Mediated Apoptosis and Caspase Activation in Human Hepatoma Cells," Antimicrobial Agents and Chemotherapy 47(6): 1912-1921 (Jun. 2003).
JP Application No. 2008-548731 Office Action dated Aug. 14, 2012.
Office Action for CA Application No. 2,633,715 dated Nov. 6, 2012.
Topisirovic et al., "Stability of eukaryotic translation initiation factor 4E mRNA is regulated by HuR, and this activity is dysregulated in cancer," Mol Cell Biol, 29(5): 1152-1162 (2009).

\* cited by examiner

FIGURE 27

Western blot of Akt activation.
C control
Rib ribavirin
Rap rapamycin
RR Rib+Rap

SEQUENCE LISTING

<160> NUMBER OF SEQ ID NOS: 34

<210> SEQ ID NO 1
<211> LENGTH: 92
<212> TYPE: DNA
<213> ORGANISM: Homo sapiens

<400> SEQUENCE: 1
tttttaaaca ctaaaatata taatttatag ttaaggctaa aaagtatatt tattgcagag    60
gatgttcata aggccagtat gatttataaa tg    92

<210> SEQ ID NO 2

-continued

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctacactga caactctatc cg                                            22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tagcaggaga ggaagttgtt gg                                            22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accacagtcc atgccatcac                                               20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tccaccaccc tgttgctgta                                               20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctgacacca atctcctcaa cg                                            22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcttcgcact tctgctcctc ac                                            22

<210> SEQ ID NO 8
<211> LENGTH: 20
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tgccaagtgg tcccaggctg                                                    20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cggcttgaag atgtactcta t                                                  21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gcatcagctt tcacgcttg                                                     19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tcacccacat gcatttcagg                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
cagcgagcag cagagtccgc                                                    20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
acaggagctg gtgttccatg gc                                                 22

<210> SEQ ID NO 14
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 14
accacagtcc atgccatcac                                              20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tccaccaccc gttgctgta                                               19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacttcctct ccaaaatgcc a                                            21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctggcgcag gcttgactc                                               19

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atctggcacc acaccttcta caatgagctg cg                                32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgtcatactc ctgcttgctg atccacatct gc                                32

<210> SEQ ID NO 20
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
cggtcgctac cattaccagt t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacgttgtaa aacgacggga t                                              21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catggaacac cagctcctgt                                                20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcagccacc acgctccc                                                  18

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
accacagtcc atgccatcac                                                20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tccaccaccc tgttgctggg g                                              21

<210> SEQ ID NO 26
<211> LENGTH: 93
<212> TYPE: DNA
<213> ORGANISM: Mus musculus
```

<400> SEQUENCE: 26
cttttaaaca ctaaaatgtc taatttatac ttaaggctac agaagagtat ttatgggaaa    60
ggctgcccat gaccagtgtg actcaaagca atg    93

<210> SEQ ID NO 27
<211> LENGTH: 93
<212> TYPE: DNA
<213> ORGANISM: Rattus norvegicus

<400> SEQUENCE: 27
cttttaaaca ctaaaatctc taatttatac gtaaggctac agaagagtat ttattgggaa    60
ggttgcccat gacccgtgtg actcaaagca atg    93

<210> SEQ ID NO 28
<211> LENGTH: 96
<212> TYPE: DNA
<213> ORGANISM: Gallus gallus

<400> SEQUENCE: 28
tttttaaaca ctaaaatata taatttatag ttaaggctaa aagaatatt tattgcagag    60 gatgttcgta aggccagtat gatttgtaaa ataatg    96

<210> SEQ ID NO 29
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
acacuaaaau auauaauuua uaguuaaggc uaaaaaguau    40

<210> SEQ ID NO 30
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gggacucagg cgggacagug cugcagcucc cuggcuucug ugggcccc    48

<210> SEQ ID NO 31
<211> LENGTH: 93
<212> TYPE: DNA
<213> ORGANISM: Mus musculus

<400> SEQUENCE: 31
cttttaaaca ctaaaatgtc taatttatac ttaaggctac agaagagtat ttatgggaaa    60
ggctgcccat gaccagtgtg actcaaagca atg    93

<210> SEQ ID NO 32
<211> LENGTH: 93
<212> TYPE: DNA
<213> ORGANISM: Rattus norvegicus

<400> SEQUENCE: 32
cttttaaaca ctaaaatctc taatttatac gtaaggctac agaagagtat ttattgggaa    60
ggttgcccat gacccgtgtg actcaaagca atg    93

```
<210> SEQ ID NO 33
<211> LENGTH: 90
<212> TYPE: DNA
<213> ORGANISM: Homo sapiens

<400> SEQUENCE: 33
tttttaaaca ctaaaatata taatttatag ttaaggctaa aagtatattt attgcagagg    60
atgttcataa ggccagtatg atttataatg                                    90

<210> SEQ ID NO 34
<211> LENGTH: 96
<212> TYPE: DNA
<213> ORGANISM: Gallus gallus

<400> SEQUENCE: 34
tttttaaaca ctaaaatata taatttatag ttaaggctaa aaagaatatt tattgcagag    60
gatgttcgta aggccagtat gatttgtaaa ataatg                             96
```

TRANSLATIONAL DYSFUNCTION BASED THERAPEUTICS

CROSS-REFERENCE TO RELATED APPLICATIONS

This application is a continuation of U.S. patent application Ser. No. 12/163,449 filed Jun. 27, 2008, now U.S. Pat. No. 8,497,292, which is a continuation-in part of PCT/US06/049450, which claims priority to U.S. Provisional Patent Applications 60/754,461 filed Dec. 28, 2005, 60/794,048 filed Apr. 22, 2006, 60/848,583 filed Sep. 29, 2006 and 60/854,404 filed Oct. 25, 2006. This application is also a continuation-in part of PCT/US07/021167, which claims priority to U.S. Provisional Patent Applications 60/848,583 filed Sep. 29, 2006 and 60/854,404 filed Oct. 25, 2006, and 60/942,884 filed Jun. 8, 2007. The contents of each of these applications are hereby incorporated herein by reference in their entireties.

GOVERNMENT SUPPORT

The subject invention was made in part with support from the U.S. Government under Grant Numbers CA 88991, PO1 AI44236-01, CA 80728, CA 98571, S10 RRO 9145, CA 98571, and 807282241 awarded by the NIH and Grant Number DBI-9724504 awarded by the NSF. Accordingly, the U.S. Government has certain rights in this invention.

BACKGROUND

The eukaryotic translation initiation factor eIF4E ("4E") is involved in the modulation of cellular growth. Moderate overexpression of 4E leads to dysregulated growth and malignant transformation. Both the nuclear and cytoplasmic function of 4E contribute to its ability to transform cells. Overexpression of 4E in vivo results in frank tumor formation, and the onset of tumor formation is greatly enhanced when 4E overexpression is placed within the context of a myc mouse background, suggesting again that 4E acts in concert with other oncogenes to promote neoplastic transformation. 4E is believed to represent one of the seven genes whose expression, when up-regulated in cancers, is predictive of metastatic disease. A variety of studies have been done demonstrating that existence of elevated 4E activity within surgical margins is a poor prognosis factor.

In the cytoplasm, 4E is required for cap-dependent translation, a process highly conserved from yeast to humans. 4E is believed to bind the methyl-7-guanosine cap moiety present on the 5' end of mRNAs and subsequently recruits the given mRNA to the ribosome.

In the nucleus, 4E is a critical node in an RNA regulon that impacts nearly every stage of cell cycle progression. Specifically, 4E coordinately promotes the mRNA export, and in some cases also translation, of several genes involved in cell cycle progression. For example, 4E functions to promote export from the nucleus to the cytoplasm of at least two mRNAs, cyclin D1 and ornithine decarboxylase (ODC), while having no impact on the nuclear to cytoplasmic transport of GAPDH or actin mRNAs. Moreover, there is evidence that the mRNA export function of 4E is linked to its oncogenic transformation activity.

Dysregulated expression of tumor suppressors and oncogenes that maintain and enhance the malignant phenotype have been described. Among these molecules are tumor suppressors like p53, Rb, and APC and oncogenes such as myc, cyclin D1 and 4E. Their interaction constitute a network of self-reinforcing feedback loops wherein inactivation of principal elements can lead to the reversal and at times even the sustained loss of the neoplastic phenotype.

4E is overexpressed in a wide variety of malignant cell lines and primary human tumors including tumors of the breast, colon, head and neck, thyroid, lung, non-Hodgkin's lymphoma, prostate, cervix, bladder and chronic and acute myelogenous leukemias. Consistently, even moderate overexpression of 4E in rodent cells leads to deregulated proliferation and malignant transformation.

Despite being essential for growth and survival of eukaryotes by acting at a critical step of cap-dependent translation and recruiting transcripts to the ribosome as a result of its specific interaction with the 5' 7-methylguanosine mRNA cap structure, up-regulation of 4E does not increase translation of all cap-dependent transcripts, but only of a specific subset of 4E-sensitive transcripts.

As much as 70% of 4E is present in the nuclei of mammalian cells, where it associates with nuclear bodies in a wide variety of organism, including yeast, *Xenopus* and humans. Here, 4E promotes transport of mRNAs of a specific subset of transcripts such as cyclin D1, but not of housekeeping genes such as B-actin and GAPDH. Post-transcriptional regulation of gene expression at the level of 4E mediated mRNA transport and translation exhibits different gene specificities, with some gene being regulated at the level of transport (e.g. cyclin D1) and some at the level of translation (VEGF), others at both levels (ODC), and still yet others at neither level (GAPDH). Binding to the m7G cap is required both for mRNA transport and translation by 4E, both of which contribute to this ability to transform cells.

Past observation indicates that 4E's capacity to discriminate between cyclin D1 and GAPDH is surprising seeing that the traditional view is that 4E binds the m7G cap found on all mRNAs regardless of other sequence specific features. Thus, this functional discrimination presents a conundrum in terms of our understanding of 4E mRNA recognition in the nucleus.

Elevated 4E activity has been observed to mediate selectively the translation (but not transcription) of a subset of the total collection of mRNAs expressed within cells, tissues, organs. Specifically, within cells, tumors and/or cancers where 4E activity is present at elevated levels, the translation of mRNA transcripts possessing complex 5'UTR regions is selectively upregulated. The repertoire of genes whose translation is thereby upregulated in circumstances where elevated 4E activity exists is a who's who of genes known to be involved in the regulation of the cell cycle, angiogenesis, proliferation and the like.

Existing cancer therapies are not effectively targeted/selective, thereby forcing patients to experience significant toxicity and side effects and/or they are not capable of addressing a wide range of cancers; neither are they capable of transforming cancer from a terminal disease process to one that can be managed long-term as are many others diseases (cardiovascular, diabetes to name a few). Existing gene therapeutics are conditional replicating lytic viruses, vectors/viruses containing RNAs encoding prodrug (aka suicide genes), anti-angiogenic agents, immune regulatory cytokines, tumor suppressors toxins and lytic peptides. Current gene therapeutic vectors/viruses are dependent upon the presence of elevated levels of 4E protein for the delivery of suicide genes, toxins, lytic peptides and/or proteins and/or processes.

SUMMARY

Current therapeutic methods and clinical treatment paradigms do not provide for enhanced control for viral oncolysis, enhanced control for virus or vector replication, or enhanced control for gene therapeutic expression. Also, there are no methods for providing enhanced efficacy and/or safety of gene therapeutic activities. Alternatives or supplements to gene therapy, such as small molecule inhibitors of 4E activity, do not exist. Furthermore, current diagnostic, segmentation and stratification methodologies do not provide for the enhanced detection, analysis and therapeutic monitoring of 4E regulon activity. Neither do current methods provide for the identification of therapeutic methods and clinical treatment paradigms that regulate 4E regulon activity.

Provided are small molecule inhibitors of mRNA nuclear to cytoplasmic transport and/or protein translational processes. Such inhibitors selectively target the biological impact of elevated 4E activity, and in particular, 4E regulon activity, within cells, tissues, tumors and/or cancers.

Further provided herein are compositions comprising gene therapeutic vectors and viruses that, among other things, enhance regulation of mRNA nuclear to cytoplasmic transport and/or mRNA translation. The vectors and viruses may comprise mRNAs encoding proteins contained within gene therapeutic vector/virus required for vector and/or viral replication and/or lysis, mRNAs encoding therapeutic proteins required for gene therapeutic activity including but not limited to toxins, lytic peptides and/or proteins and/or processes and therapeutic proteins including but not limited to prodrug converting enzymes (aka suicide genes), anti-angiogenic proteins, apoptosis cascade enzymes, tumor suppressors, cytokines and immunologically active proteins, RNAi anti-sense, and the like.

The small molecule compositions and compositions comprising gene therapeutic vectors and viruses may be used alone or in combination to inhibit elevated 4E activity, in particular, 4E regulon activity, within cells and tissues, particularly cancer and tumor cells and tissues, and in mammals. Further, the small molecule compositions and compositions comprising gene therapeutic vectors and viruses may be used alone or in combination to inhibit cellular proliferation within cells and tissues, particularly cancer and tumor cells and tissues, and in mammals. Such cells, tissues and mammals preferably may also possess elevated 4E activity and/or elevated 4E regulon activity and/or 4E regulon components.

Such enhanced methods and composition for the treatment of cell proliferative disorders in which there exists elevated 4E activity and/or elevated 4E regulon activity and/or 4E regulon components where administration of small molecules and/or gene therapeutic alone or in combination fail to eradicate the cell proliferative disorder or cancer or tumor, yet inhibit its continued proliferation and expansion thus providing either an opportunity for the host immune system to eradicate the cell proliferative disorder or tumor or cancer; or serving to make the cell proliferative disorder or tumor or cancer manageable through the routine administration of small molecules with or without the periodic co-administration of additional systemic agents/biologics, and/or the periodic co-administration of any one/more of the gene therapeutics methodologies disclosed herein.

Further provided are enhanced imaging and visualization compositions and methods for cells, tissues and tumors, for example, those possessing elevated 4E activity. Such enhanced imaging and visualization compositions and methods may be used, for example, for the detection of elevated 4E conditions. Detection of elevated 4E conditions may be used as method of diagnosing, detecting during surgery, following clinical course of therapeutic efficacy and disease progression/regression.

Regulatory mechanisms described herein coordinately provide for the integrated regulation of 4E activity within normal and cancerous cell types. Our work provides insight into these processes and provides for assays and/or screens which can be used to identify second generation therapeutic regulators of 4E activity that can be used to therapeutic advantage for the treatment of human cancers. Further, the comparison of the relative nuclear/cytoplasmic localization of 4E (absolute differences or ratios) and factors revealed herein to provide diagnostic criteria upon which the use of eIF4E inhibitors (direct/indirect) will be determined to provide a therapeutic benefit. Moreover, coordinated/multiplexed analysis of human tissue samples/biopsies/tissue arrays directly or post laser capture microscope excision of tumor material from slide mounted biopsy materials provide the means of identifying human conditions wherein 4E is dysfunctionally regulated via both the relative and absolute levels of 4E protein and/or activity as well as the levels of 4E regulon elements and the absolute levels and phosphorylation status of 4E, 4E-BP1 and the like. Via either plasma-based or tissue based approaches, the above procedures are envisioned to enable both the diagnosis of relevant 4E regulon mediated disease as well providing a useful mechanism of following the therapeutic response of individuals to therapies that modulate eIF4E and eIF4E regulon activities.

Accordingly, provided are methods and compositions for the identification, diagnosis and monitoring of 4E regulon activity and for the discovery of agents that modulate 4E regulon activity. The methods, compositions and agents may be used alone, in combination with or in conjunction with other therapies for the detection and treatment of diseases wherein 4E regulon activity is dysfunctional, including cellular hypertrophy, cancer, and ischemia reperfusion.

Further provided herein are diagnostic, indication segmentation and stratification, therapeutic and disease monitoring compositions and methods that provide among other things, for the identification of conditions and clinical indications in which 4E regulon activity is dysfunctionally regulated. Further methods and compositions for detection, identification and characterization of agents which modulate 4E and 4E regulon activity are provided.

Diagnostic compositions and methods may be used alone or in combination to identify, detect and monitor 4E regulon activity and their modulation of therapeutic agents. Further, compositions and methods may be used alone or in composition to identify and characterize compounds and agents that modulate 4E regulon activity including but not restricted to the modulation of 4E regulon component activities.

Further provided are methods and compositions for the identification, detection and monitoring of 4E regulon activity in conditions where the therapeutic modulation of 4E activity and 4E regulon activity in a fashion or manner that serves to increase 4E and in particular 4E regulon activity. Such conditions to include but are not limited to ischemia reperfusion injury and like conditions.

Further provided are enhanced imaging and visualization compositions and methods for cells, tissues and tumors, for example, those possessing elevated 4E regulon activity. Such enhanced imaging and visualization compositions and methods may be used, for example, for the detection of elevated 4E conditions. Detection of elevated 4E conditions may be used as method of diagnosing, monitoring prior, during and after administration of small molecule therapeutics alone or in combination with additional treatments and/or agents as described herein, monitoring before, during and after during surgery, and following clinical course of therapeutic efficacy and disease progression/regression.

Kits for the practice of the methods are also described herein.

These embodiments of the present invention, other embodiments, and their features and characteristics will be apparent from the description, drawings, and claims that follow.

Figure 7:
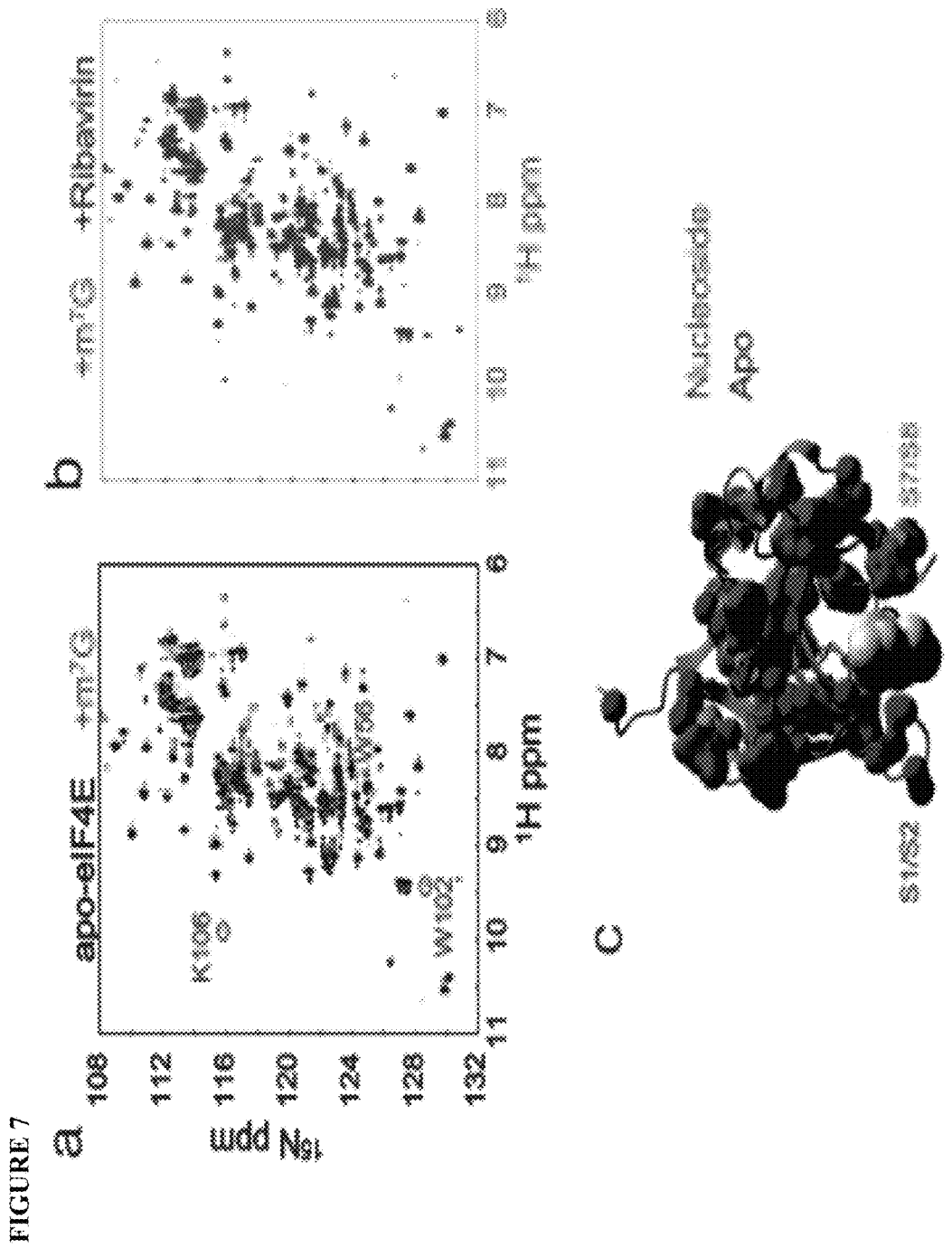

FIG. 7. Ribavirin and m7G mRNA cap are recognized similarly by eIF4E. (a) 1H, 15N HSQC NMR spectra of eIF4E in the absence (black) and presence (red) of saturating concentrations of m7G nucleoside. Note that of the 273 residues of the construct, 207 resonances are observed. (b) 1H, 15N HSQC NMR spectra of eIF4E in the presence of saturating concentrations of m7G (red) and Ribavirin nucleosides (blue). (c) eIF4E backbone residues that exhibit (red) and do not exhibit (blue) 1H, 15N HSQC NMR chemical shift perturbation upon binding of Ribavirin and m7G mRNA cap. The difference between conformational rearrangements upon cap binding of mouse eIF4E observed here and those reported for yeast eIF4E may be because of differences between mouse and yeast proteins as well as micelle binding to yeast eIF4E.

Figure 8:
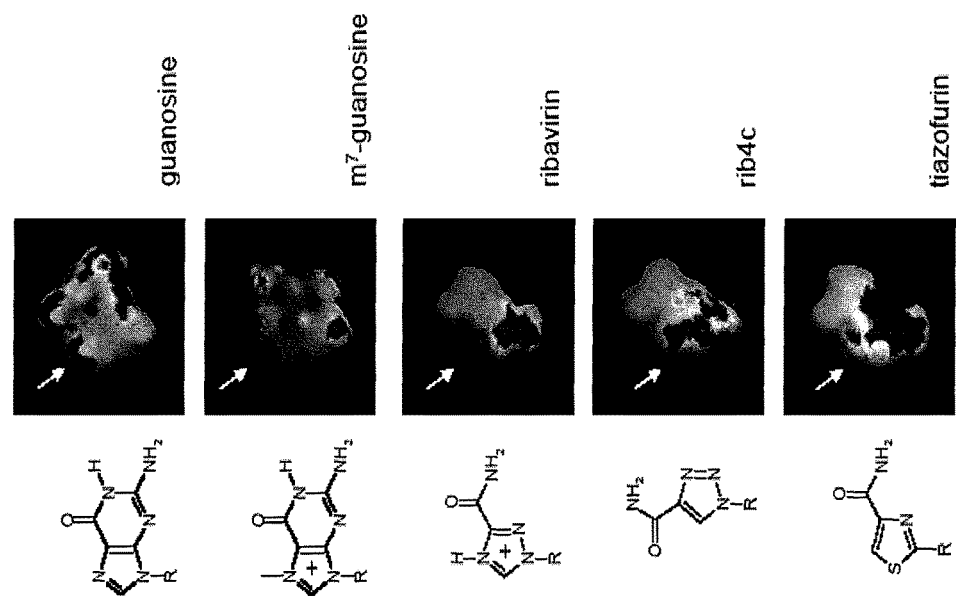

FIG. 8. Ribavirin is a physical mimic of 7-methyl guanosine ($m^7G$). Isocontour electrostatic potential molecular surfaces of guanosine, $m^7G$, Ribavirin, Rib4C, and tiazofurin bases and their chemical structures, with blue to red color gradient corresponding to gradient of decreasing electropositive and increasing electronegative potential. Arrow indicates the seventh position in the aromatic ring. R, ribose.

Figure 9:

FIG. 9. Apparent binding of Ribavirin to recombinant eIF4E in vitro is method and condition dependent. (a) As published previously, 20 uL of m7GTP-Sepharose (Amersham) was mixed with 1 ug of eIF4E in Buffer B (0.3 M NaCl, 0.1 M sodium phosphate at pH 7.5, 10 uM protease free BSA [UBS], 0.1% NP-40) with 0.1 mM GTP for 30 min at room temperature. Washed beads (three times with 75 bed volumes) were incubated with 50 uM of compounds as indicated for 30 min at room temperature. Beads were washed (three times with 75 bed volumes) to remove dissociated eIF4E, and eIF4E remaining bound to beads was resolved using SDS-PAGE, and visualized using Western blotting and chemiluminescence. Please note that here the buffer contained 0.1 mM GTP in order to emphasize the specificity of Ribavirin's competition of m7G:eIF4E binding. Also, here we used a fusion of mouse eIF4E with the B1 domain of protein G (G4E), which was a kind gift of Gerhard Wagner (Harvard Medical School, Boston, Mass.), as described in Zhou et al. (2001) and Kentsis et al. (2004). (b) As described by Yan et al. (2005), 1 ug of eIF4E was mixed with 20 uL of m7GTP-Sepharose (Amersham) in 50 bed volumes of LCB buffer (10 mM HEPES at pH 8.0, 100 mM KCl, 0.2 mM EDTA at pH 8.0), supplemented with 10 uM protease-free BSA (UBS), 0.1% NP-40, and 0.1 mM GTP, for 20 min at presumed 4° C., as the experimental temperature was not described (Yan et al. 2005). Washed beads (five times with 50 bed volumes of LCB buffer) were incubated with 5 bed volumes of 50 uM of compounds as indicated for 20 min at 4° C. Then 20 uL of the supernatant containing dissociated eIF4E was transferred to a new tube, cleared of trace beads containing bound eIF4E, and resolved using SDS-PAGE, and visualized using Western blotting and chemiluminescence.

Figure 10:
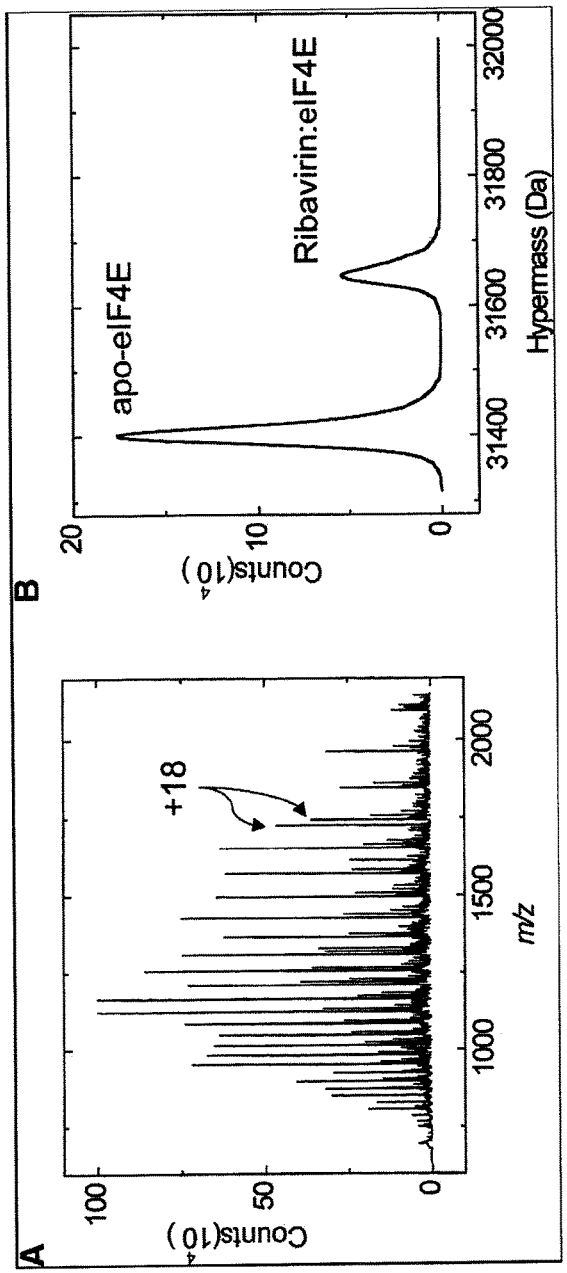

FIG. 10. Direct observation of specific binding of Ribavirin to purified eIF4E in vitro. Mass spectra were recorded using the Agilent Technologies 1100 LC/MSD integrated liquid chromatograph single quadrupole electrospray mass spectrometer (ES-MS) operating in positive ion mode. A solution of 20 uM purified G4E (Zhou et al. 2001; Kentsis et al. 2004) was incubated with a mixture of 80 uM Ribavirin (Calbiochem) and 80 uM GTP (Sigma) in 5% aqueous acetonitrile, 20 mM ammonium acetate (pH 6.5), for 1 min at room temperature. The solution was electrosprayed directly at 200 mL/min using nebulizer pressure of 20 psi, drying nitrogen gas at 200° C. and 10 L/min, and capillary voltage of 4.5 kV. (a) ES-MS spectrum plotting ion abundance in 20 uL of the above mixture as a function of the mass/charge ratio is shown. An ion of ca. 1740 amu/z is labeled, corresponding to a +18 protonation state of apo-G4E (higher peak) and the complex of Ribavirin with G4E (lower peak). (b) Hypermass reconstruction of the spectrum shown above was done according to standard methods (De Hoffmann and Stroobant 2001) and contains two species of population-weighted mean molecular masses of 31,402 and 31,649 Da, corresponding to apo-G4E and G4E bound to Ribavirin (243 Da) with a molecular stoichiometry of 1:1, respectively. Please note that only a fraction of total ionized eIF4E appears to be bound to Ribavirin because of the differences in ionization efficiencies of the apo- and ligand-bound species of eIF4E, wherein ligand binding occurs to the folded, more native-like, and therefore less ionizable, states (De Hoffmann and Stroobant 2001). Thus, obtaining affinities from mass spectrometry data is confounded by these differences in ionization. For comparison, we obtained Kd's for eIF4E-Ribavirin of 8.4 uM and for eIF4E-RTP, 0.13 uM, using fluorescence spectroscopy paralleling those differences previously observed for m7-guanosine and m7GTP (Kentsis et al. 2004).

Figure 11:
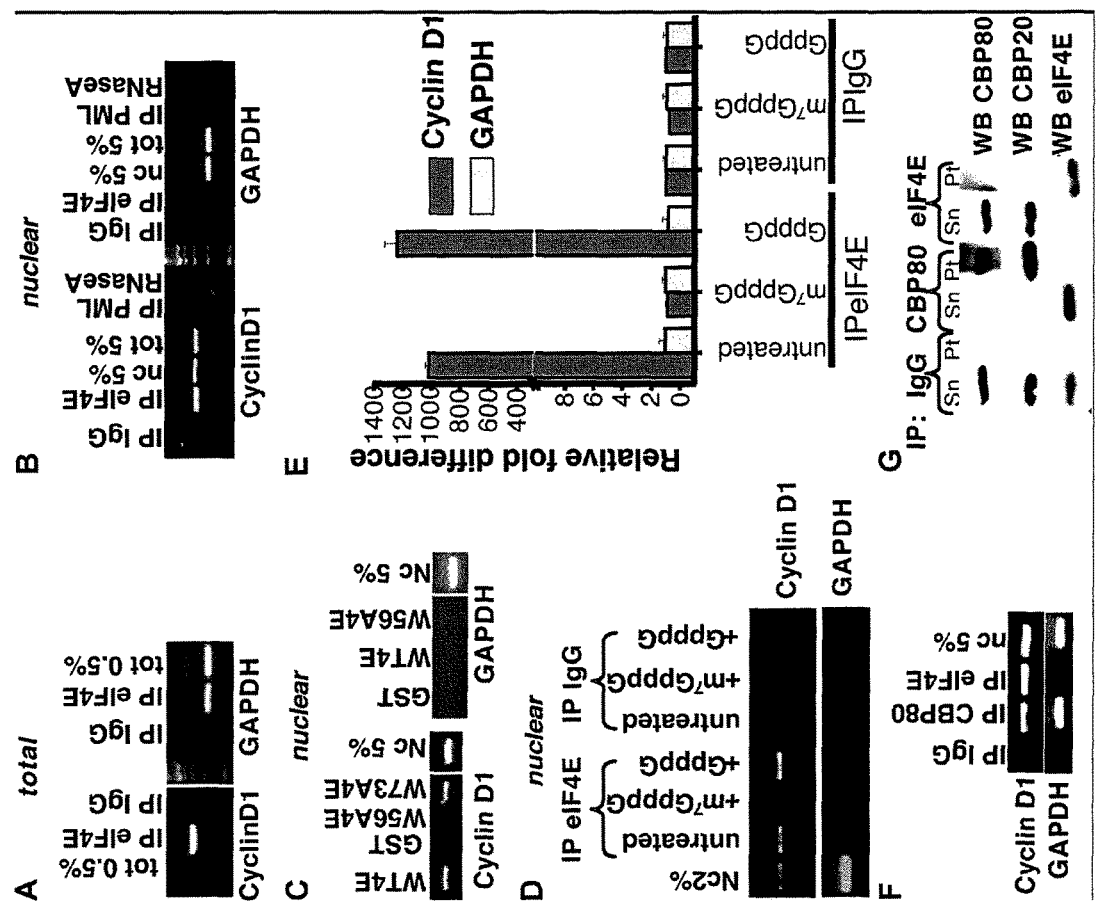

FIG. 11. eIF4E associates with cyclin D1 but not GAPDH mRNA in the nuclear fraction of U2OS or HEK293T cells. (a) U2OS total cell lysates were immunoprecipitated (IP) with either an eIF4E antibody or mouse immunoglobulin (IgG) as a control. RNAs were detected by RT-PCR as indicated. Tot represents 0.5% of input RNA. (b) U2OS nuclear lysates were immunoprecipitated using antibodies to eIF4E (mAb eIF4E), PML (mAb PG-M3), or mouse IgG. RNase A indicates treatment before IP as a negative control. Total and nuclear (nc) represent 5% of RNA input. (c) U2OS nuclear lysates were subjected to SNAAP analysis with eIF4EWT-GST and mutant (W56A and W73A) fusion proteins. GST only was used as a negative control. Bound RNAs were detected by RT-PCR. Nc represents the percentage of input as indicated. RT-PCRs for A-C were detected by ethidium bromide staining. (d) As a control for cap dependence, the ability to compete for eIF4E binding by addition of 50 uM 7 GpppG cap analogue or 50 uM GpppG negative control was tested in the nuclear fraction of HEK293T cells. The ability of cyclin D1 and GAPDH mRNA to immunoprecipitate with eIF4E after treatments as indicated was monitored by semi-quantitative PCR. (e) Parallel RT-PCR methods to the experiments in A-C confirm the above results indicating eIF4E selectively binds cyclin D1 in a cap-dependent manner. Relative fold values were as calculated as described in the Materials and Methods for both cyclin D1 and GAPDH mRNAs. (f) K562 nuclear lysates were immunoprecipitated using antibodies to eIF4E (mAb eIF4E), CBC (pAb CBP80), or mouse IgG; nc represent 5% of RNA input. (g) Proteins from immunoprecipitations by eIF4E and CBP antibodies or mouse IgG were analyzed by Western blot (WB). White line indicates that intervening lanes have been spliced out.

Figure 12:
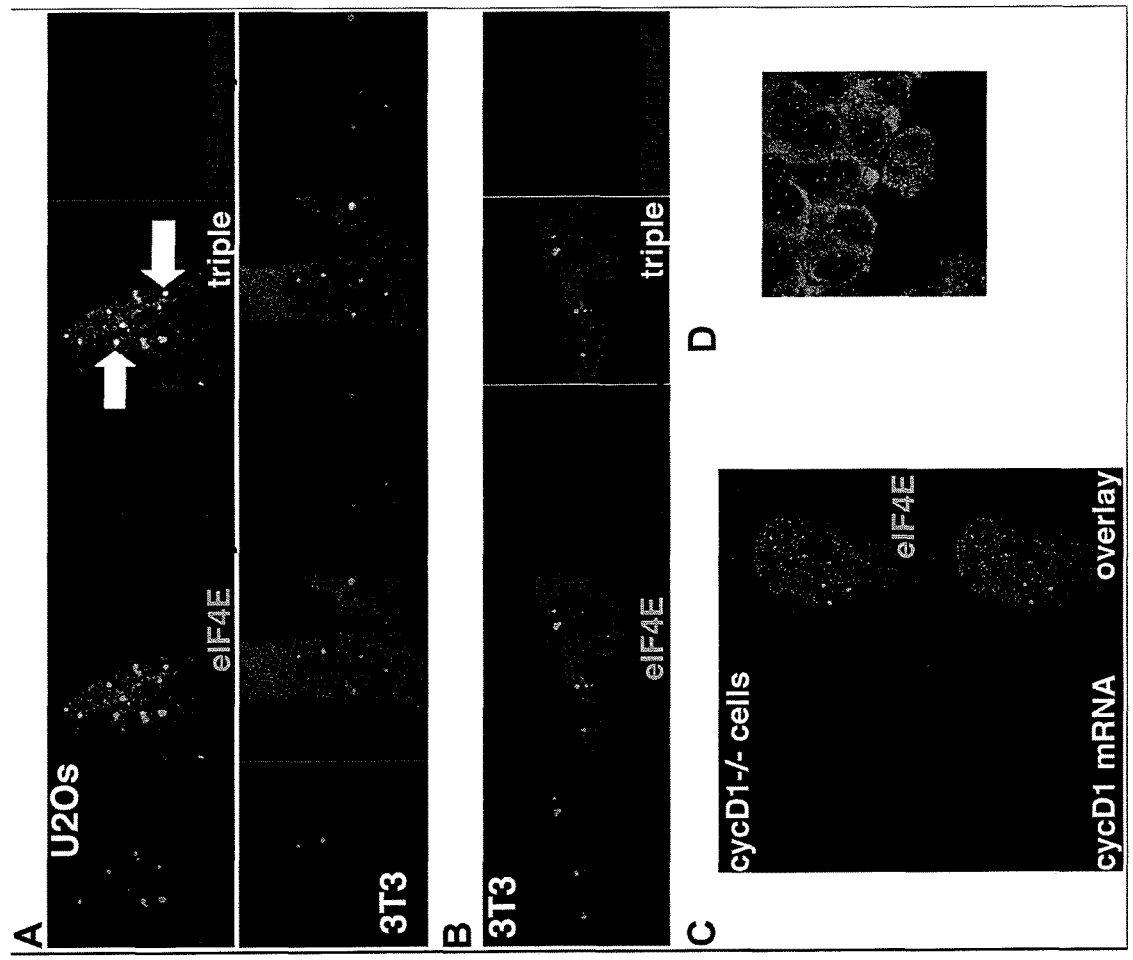

FIG. 12. Cyclin D1 but not GAPDH mRNAs colocalize with a subset of eIF4E nuclear bodies. (a) Co-localization of cyclin D1 mRNA with PML and eIF4E proteins was analyzed in U2OS or NIH3T3 cells. Cyclin D1 mRNA was detected using in situ hybridization with a digoxigenin labeled nick-translated probe to cyclin D1 (red). Cells were then immunostained using an eIF4E mAb conjugated directly to FITC (green) and PML mAb 5E10 (blue). (b) The same as in A, except digoxigenin nick-translated probes to GAPDH were used for in situ hybridization. Within these panels, different combinations of overlays of the same micrographs are shown to highlight the localization of cyclin D1 mRNAs with eIF4E nuclear bodies (see arrows). (c) In situ hybridization for cyclin D1 mRNAs and immunostaining for eIF4E protein in cyclin D1−/− cells was performed as described above. (d) HEK293T cells contain eIF4E bodies similar in size, number and morphology observed for other cell types. Cells were stained with a pAb to eIF4E (Morley and Pain, 1995) Staining with mAb eIF4E gave identical results (not depicted). For all panels, confocal micrographs represent a single optical section through the plane of the cell.

Figure 13:
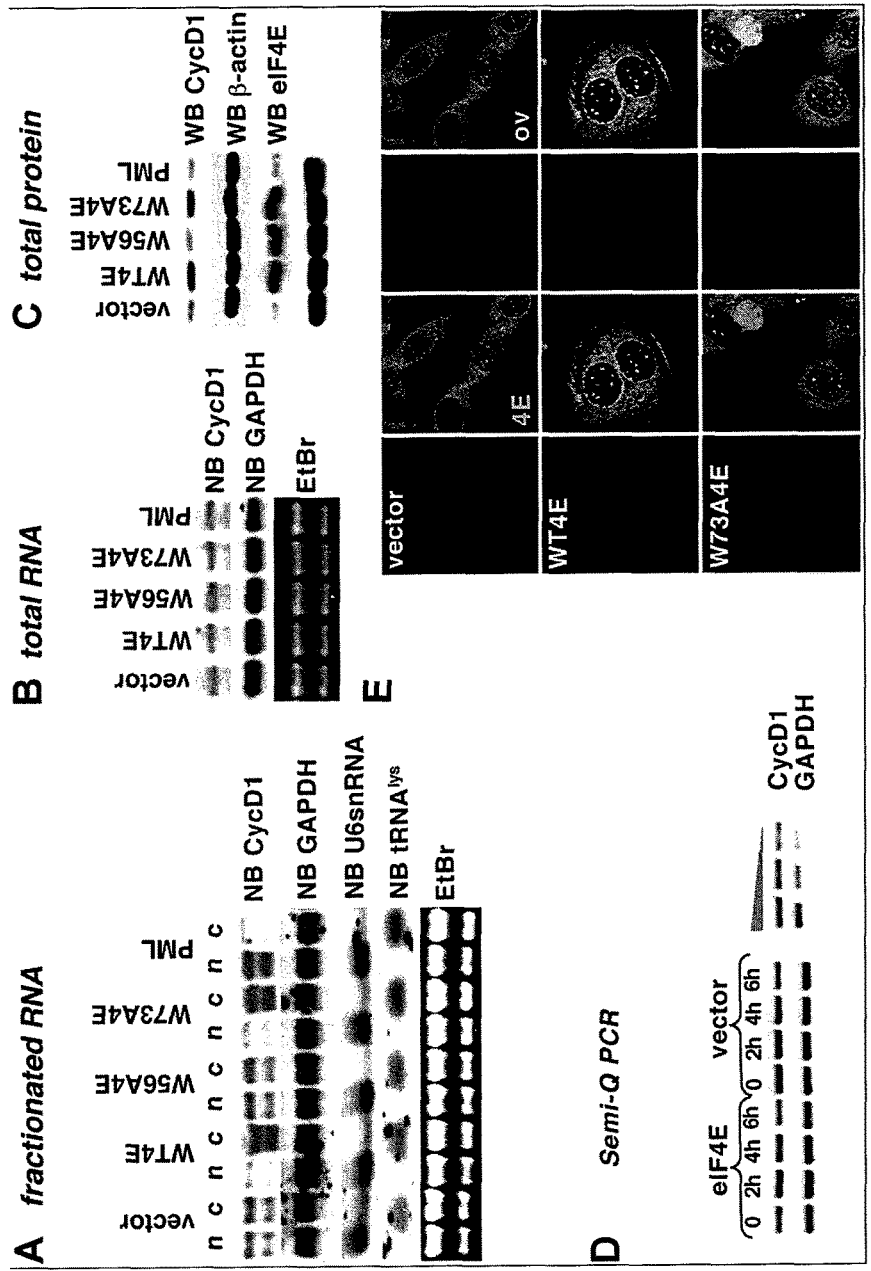

FIG. 13. eIF4E enhanced nucleocytoplasmic transport of cyclin D1 RNA. (a) Nuclear (n) and cytoplasmic (c) fractions were isolated from NIH3T3 cells stably transfected with eIF4E WT, eIF4E mutants (W56A and W73A) or PML and RNAs were detected by Northern blot (NB) as indicated. U6snRNA (nuclear) and tRNALys (cytoplasmic) were used as markers for the quality of the fractionation. (b) Northern blot analysis of total RNAs isolated from NIH3T3 cells transfected as described in A. Ethidium bromide stained gels in A and B demonstrate the quality of the isolated RNA. (c) eIF4E enhanced mRNA transport leads to up-regulated protein levels of corresponding mRNAs. Total cell lysates from NIH3T3 cells transfected as indicated were analyzed for protein content by Western blot (WB). (d) Semi-quantitative PCR indicates that eIF4E overexpression does not alter cyclin D1 mRNA stability. Act D indicates hours of actinomycin treatment. Right panel represents decreasing amounts of RNA used in RT-PCR showing that conditions are semi-quantitative. (e) Mutant and wild-type eIF4E proteins still form nuclear bodies. NIH3T3 cells overexpressing Xpress-tagged eIF4E wild-type or W73A mutant were immunostained with anti-Xpress antibody to detect exogenous eIF4E (red) and or mAb eIF4E directly conjugated to FITC (green) to detect both endogenous and exogenous protein. The confocal micrograph represents a single optical section through the cell.

Figure 14:
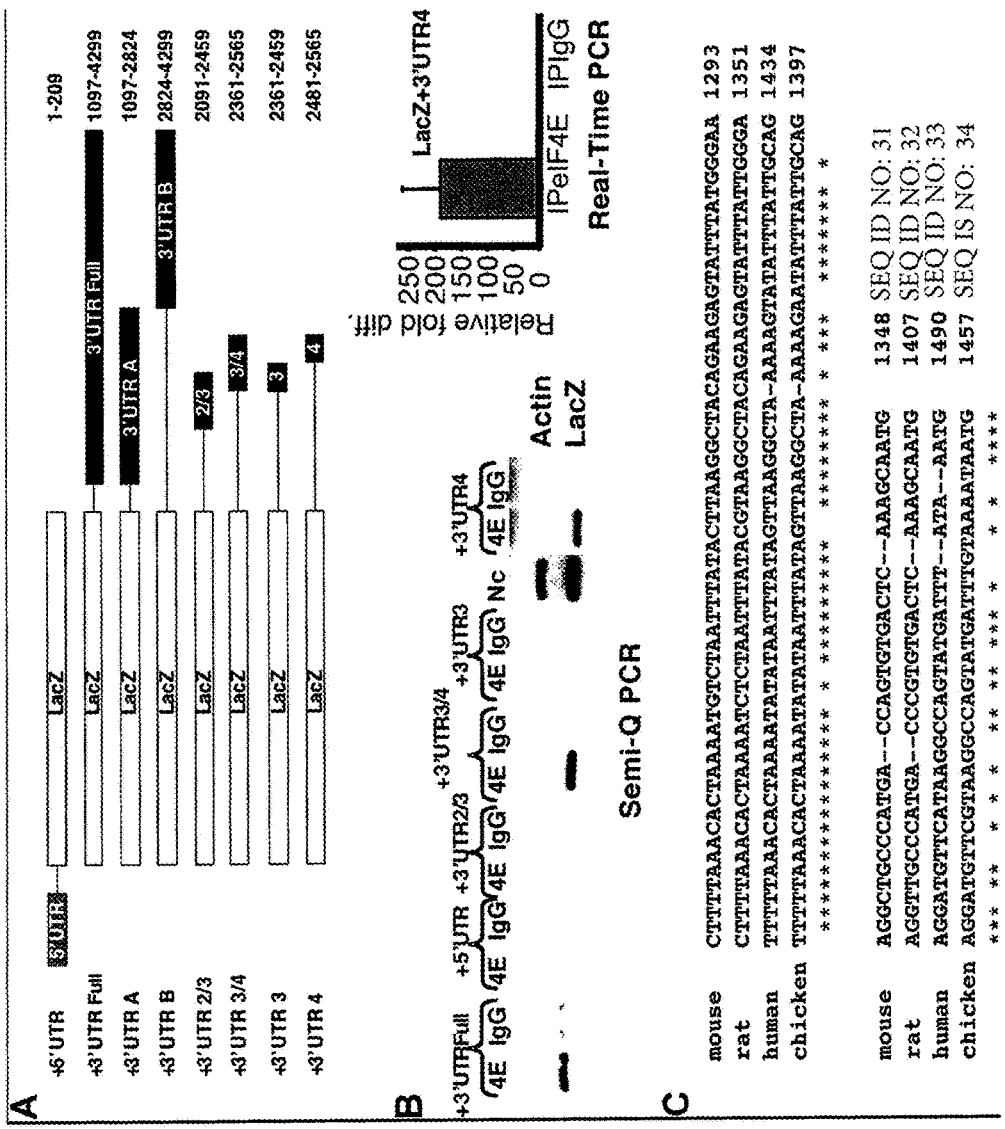

FIG. 14. eIF4E specifically associates with 4E-SE from the 3'UTR of cyclin D1. (a) Schematic representation of chimeric constructs used in this study. Full 5' and 3'UTR and different parts of 3'UTR of human cyclin D1 mRNA were cloned up- or downstream of LacZ, respectively. Numbers represent position of UTR fragments in cyclin D1 mRNA. (b) NIH3T3 cells were transiently transfected with chimeric LacZ constructs containing UTR-LacZ, LacZ-3'UTR, or LacZ constructs different parts of cyclin D1 3'UTR. The nuclear fractions of the transfected cells were immunoprecipitated with mAb eIF4E or mouse IgG for a control. LacZ and B-actin were detected by semi-quantitative RT-PCR and ethidium bromide staining (left). Nc indicates the nuclear fraction before IP and is 5% input of nuclear mRNA. For the RT-PCR method (right), relative fold enrichment is shown for the IP eIF4E fraction versus the IP IgG fraction indicating the enrichment of LacZ 3'UTR4 in the IP eIF4E. (c) Sequence alignment of cyclin D1 4E-SE from ClustalW (Thompson et al., 1994). GenBank/EMBL/DDBJ accession numbers are: human gi: 16950654 (SEQ ID NO: 33), mouse gi: 6680867 (SEQ ID NO: 31) and rat gi: 31377522 (SEQ ID NO: 32). GenBank/EMBL/DDBJ accession no. for chicken is from the Ensembl database is gallus Gallus|5.14792937-14795000 and gi: U40844 (SEQ ID NO: 34).

Figure 15:
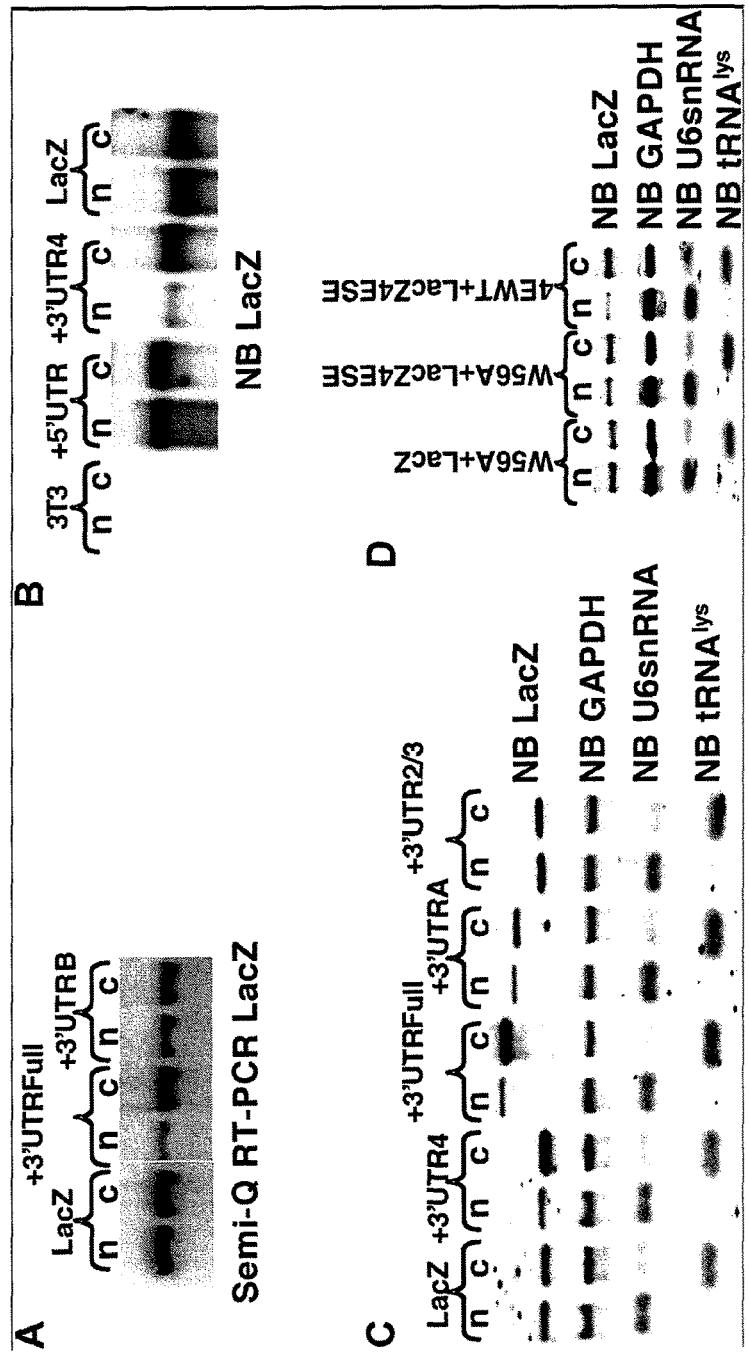

FIG. 15. 4E-SE is sufficient for eIF4E-mediated mRNA transport. PolyA RNA purified from nuclear (n) and cytoplasmic (c) fractions of NIH3T3 cells, cotransfected with eIF4E-2Flag and chimeric LacZ constructs (as indicated), were analyzed by (a) semi-quantitative RT-PCR and ethidium bromide staining (left) or (b) Northern blot (NB). (c and d) Northern blot analysis of polyA RNA purified from nuclear (n) and cytoplasmic (c) fractions of HEK293T cells cotransfected with eIF4E or W56A eIF4E and chimeric LacZ constructs (as indicated). Corresponding aliquots taken before polyA RNA purification indicate quality of the fractionations.

Figure 16:
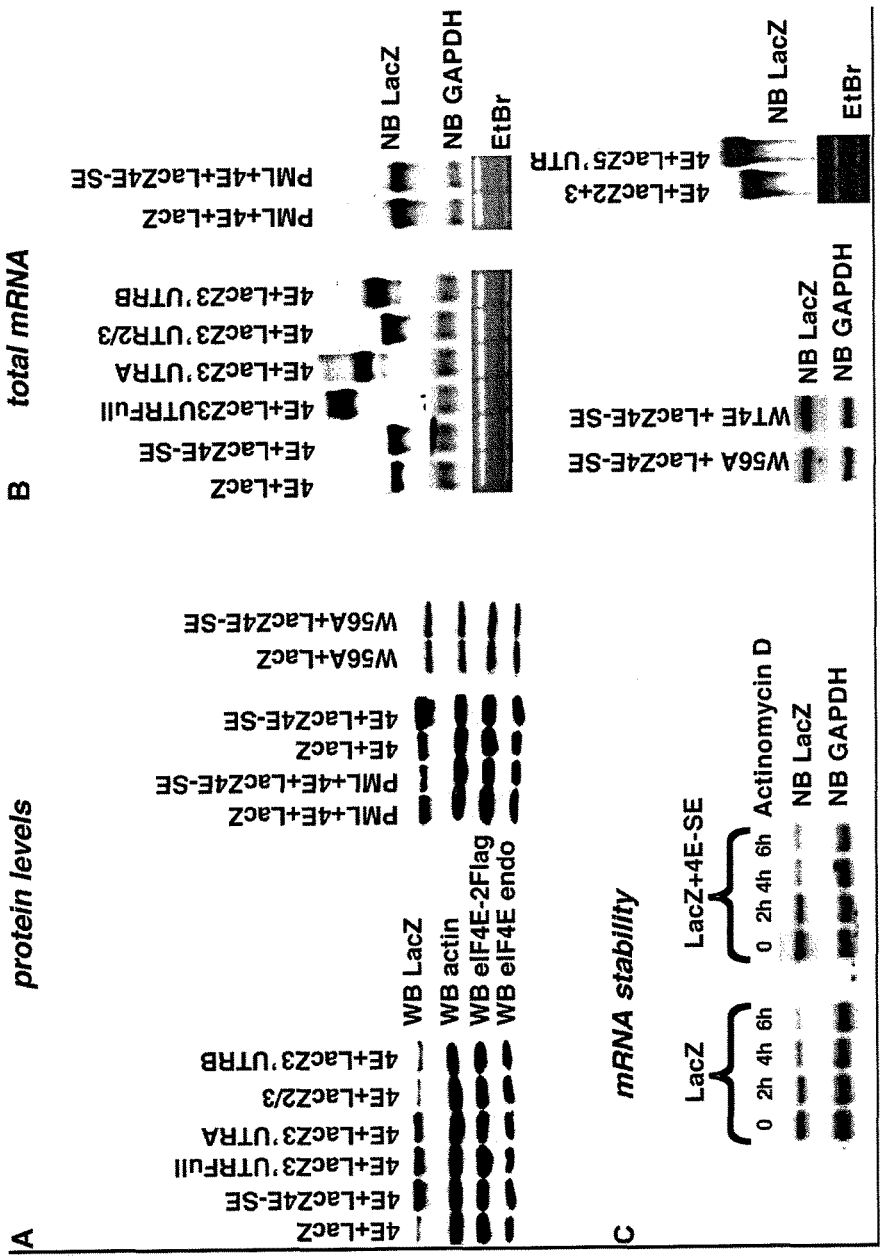

FIG. 16. The presence of the 4E-SE correlates with increased LacZ protein levels. (a) Protein levels were analyzed by Western blot (WB) of total cell lysates from HEK293T cells transiently cotransfected with eIF4E-2Flag constructs and indicated chimeric LacZ constructs or PML, eIF4E-2Flag, and chimeric LacZ constructs. Note that HEK293T cells have eIF4E nuclear bodies (FIG. 13c). (b) Northern blot (NB) analysis of total RNA from HEK293T cells cotransfected as indicated. Note that none of the total RNA levels are altered by any of the transfections. (c) Semi-Q PCR analysis indicates that the presence of the 4E-SE does not detectably alter LacZ mRNA stability. Act D indicates hours treated with actinomycin D. GAPDH is shown as a loading control.

Figure 17:
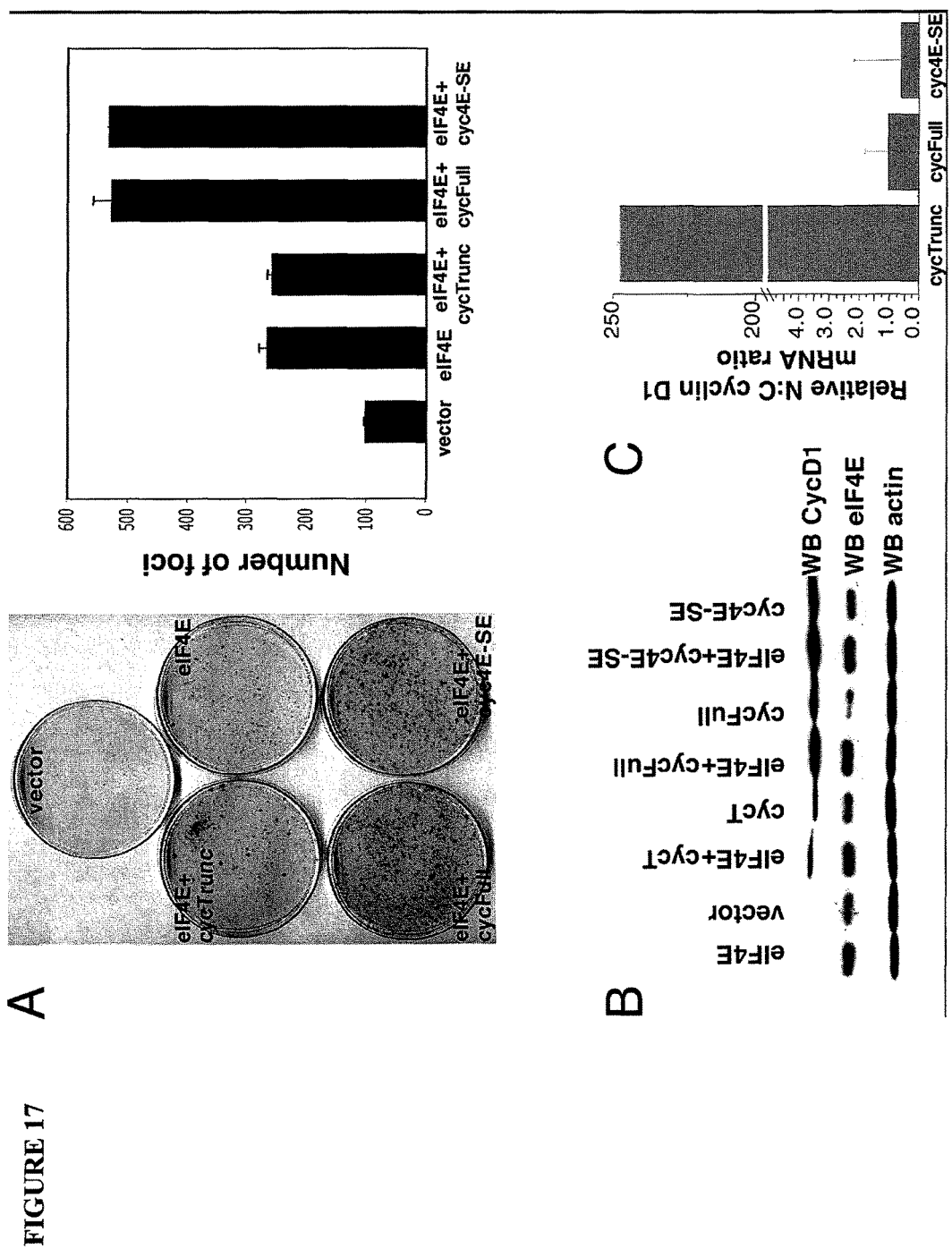

FIG. 17. The 4E-SE contributes to eIF4E mediated oncogenic transformation. (a) Cyclin D1−/− cells were stably transfected with eIF4E or cotransfected with either the coding region of cyclin D1 constructs without the 3' UTR (cycTrunc), the coding region of cyclin D1 with the full-length 3' UTR (cycFull), and the coding region of cyclin D1 with only the 100 nt 4E-SE (cyc4E-SE), and analyzed for anchorage-dependent foci formation assays. Three independent experiments were preformed in triplicate and error bars indicate +/−SD. Number of foci are relative to vector control, which was set to 100%. (b) Western blot analysis (WB) of total cell lysates from cyclin D1−/− cells stably transfected as indicated, showing increased cyclin D1 protein level in cells transfected with constructs containing full-length 3'UTR or 4E-SE compared with the truncated form lacking the 3'UTR sequence. (c) Results of quantitative RT-PCR experiments using endogenous eIF4E in cyclin D1−/− cells. The relative ratios of nuclear (N)/cytoplasmic (C) cyclin D1 mRNA was determined using RT-PCR with the relative standard curves method. Values were normalized to CycFull by setting its ratio arbitrarily to 1. Standard methods were used to propagate SDs from these experiments.

Figure 18:
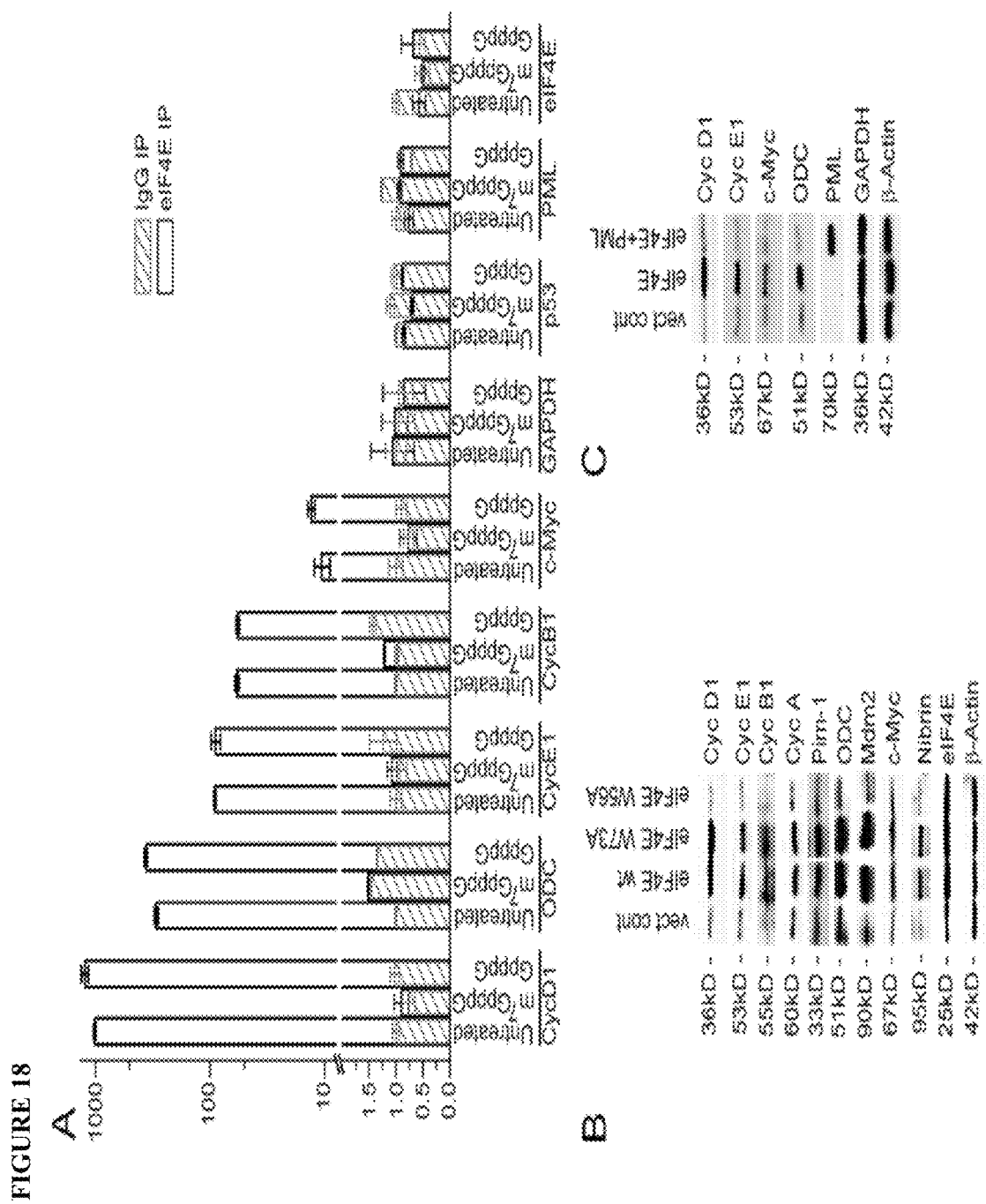

FIG. 18. Enhanced mRNA export corresponds to elevated protein levels of eIF4E sensitive targets. (a) Relative fold difference of mRNAs bound to nuclear eIF4E. mRNAs were immunoprecipitated from untreated nuclear lysates or those treated with m$^7$GpppG or GpppG (50 µM). Values represent relative fold±sd (normalized against untreated IP IgG which was set to 1). Calculations of fold were carried out using the relative standard curve method (user bulletin#2 ABI Prism 7700). Relative amounts of the target mRNA=$10^{[C(t)-b]/a}$ were determined for each PCR reaction. Average values±sd were calculated for each set of triplicates. Average values obtained for the IPs (i.e., average relative amount of IP-ed target mRNA) were divided by values obtained for 5% nuclear input (i.e., average relative amount of target mRNA present in the 5% of the amount of nuclear extract used for IP). Obtained values±sd (i.e., avIP/av5% nuclear) were normalized by setting "untreated IgG IP" value to 1. B&C) eIF4E enhanced mRNA transport leads to upregulated protein levels of corresponding mRNAs. Total cell lysates from U937 (b) or NIH3T3 (c) cells transfected as indicated were analyzed for protein content by western methods. Note that in panel c, where human PML was overexpressed, the 5E10 mAb PML antibody only recognizes the human PML, not the endogenous mouse PML.

Figure 19:
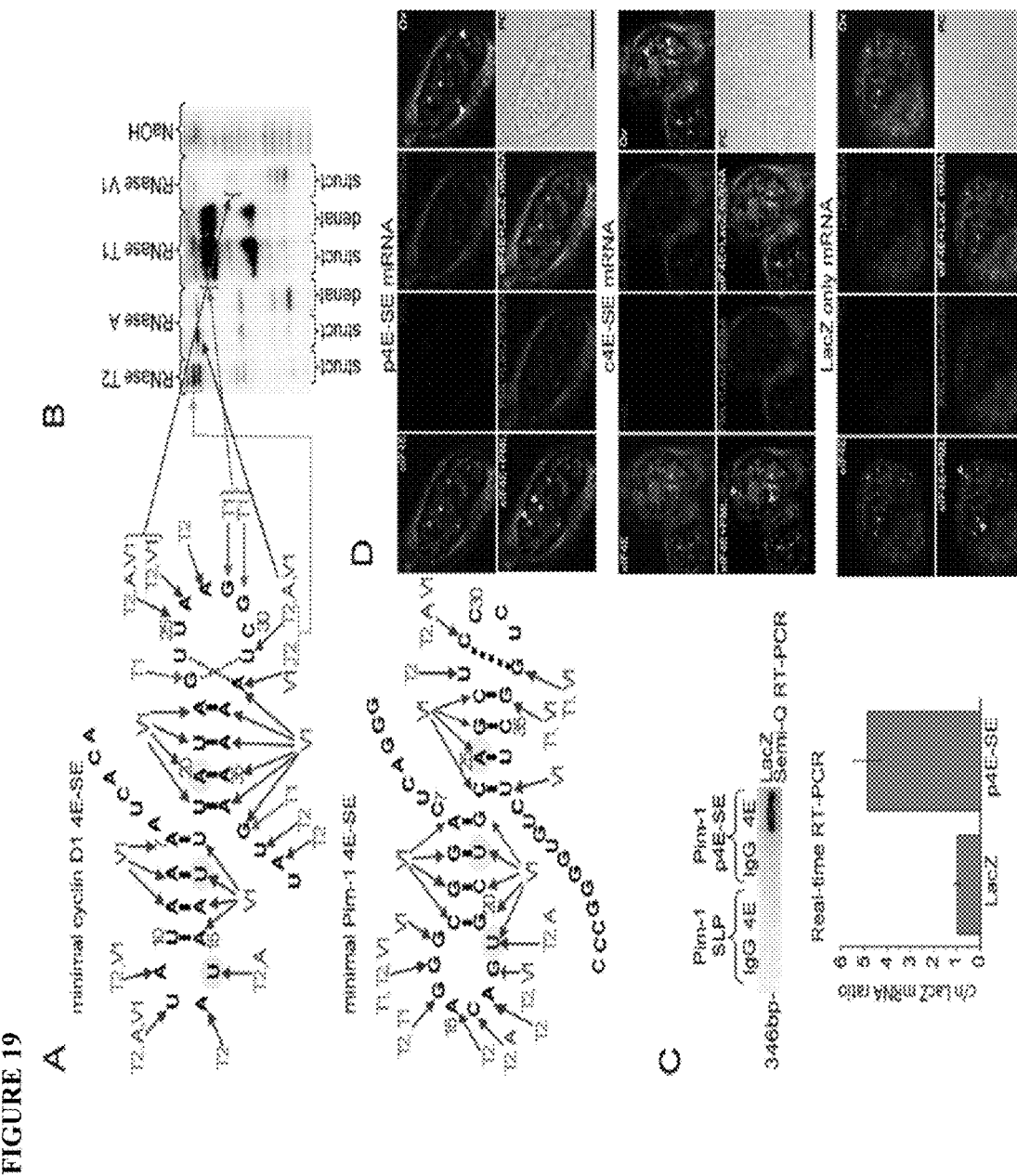

FIG. 19. A common secondary structure for the 4E-SE that acts as a zipcode for eIF4E nuclear bodies. (a) Secondary structure for cyclin D1 4E-SE (c4E-SE) and Pim-1 4E-SE (p4E-SE) as determined by RNase mapping experiments. Conserved set of A and U nucleotides ($UX_2UX_2A$) are yellow highlighted. Panel (b) shows a sample gel. (c) Mapping of p4E-SE:p4E-SE immunoprecipitates with eIF4E (upper panel); eIF4E promotes export of LacZ mRNA that contains minimal p4E-SE (lower panel). Cytoplasmic/nuclear (c/n) values represent relative fold±sd, normalized to LacZ control, which was set to 1. (d) Co-localization of LacZ-p4E-SE, LacZ-c4E-SE or LacZ transcripts with PML and eIF4E protein was examined in U2OS cells transfected with LacZ/LacZ-4E-SE. LacZ mRNA was detected using in situ hybridization with a biotin labeled nick translated probe to LacZ (red). Cells were then immunostained using an eIF4E mAb conjugated directly to FITC (green) and PML mAb 5E10 (blue). Importantly, LacZ mRNAs containing the 4E-SE from either cyclin D1 or Pim-1 co-localize to eIF4E nuclear bodies (see arrows). As we showed previously for endogenous cyclin D1 mRNA, there are two populations of eIF4E nuclear bodies, those that co-localize with LacZ mRNA and those that co-localize with PML. Magnification was 100× and 3× (for LacZ and c4ESE) or 4× (p4ESE) digital zoom. Scale bar=10 µM.

Figure 20:
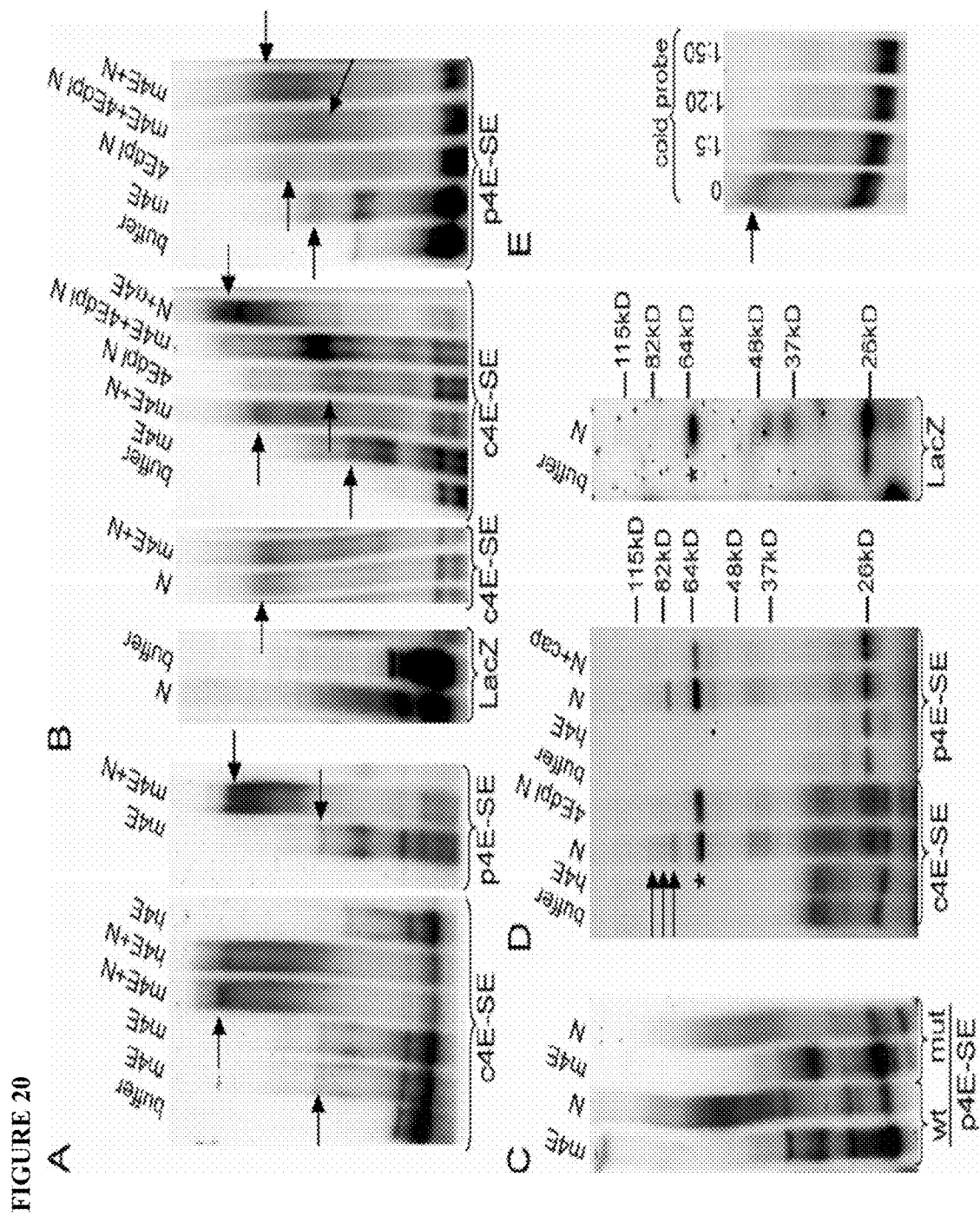

FIG. 20. The 4E-SE is required for formation of eIF4E dependent complexes. (a) and (b) EMSA analysis indicate that LacZ transcripts which contain either the cyclin D1 4E-SE (c4E-SE) or the Pim-1 4E-SE (p4E-SE) formed high molecular weight complexes in the presence of nuclear lysates (nc). LacZ transcripts (control) without the 4E-SE did not form these complexes. Addition of purified murine eIF4E with a 6 kD solubility tag (m4E) or untagged human eIF4E (h4E) causes partial shifts relative to shifts observed with nc lysate. With nuclear lysates immunodepleted of eIF4E (dpl nc), gel shifts were not observed. These complexes could be supershifted by an anti-eIF4E antibody (nc+α4E). (c) Mutation of the Pim-1 4E-SE (p4E-SE) reduces the efficacy of the gel shift. (d) UV cross-linking studies showed formation of specific complexes in the 75-90 kD mass range (indicated by arrows). These complexes are specifically depleted in the presence of excess $m^7GpppG$ cap (cap) or if lysates are immunodepleted of eIF4E (dpl nc). * indicates complex that is cap and 4E-SE independent. (e) Addition of ribo-oligonucleotide corresponding to the p4E-SE complexes in the presence of nuclear lysates indicates that this element can efficiently compete for complex formation. All transcripts were capped and 3' end labeled.

Figure 21:
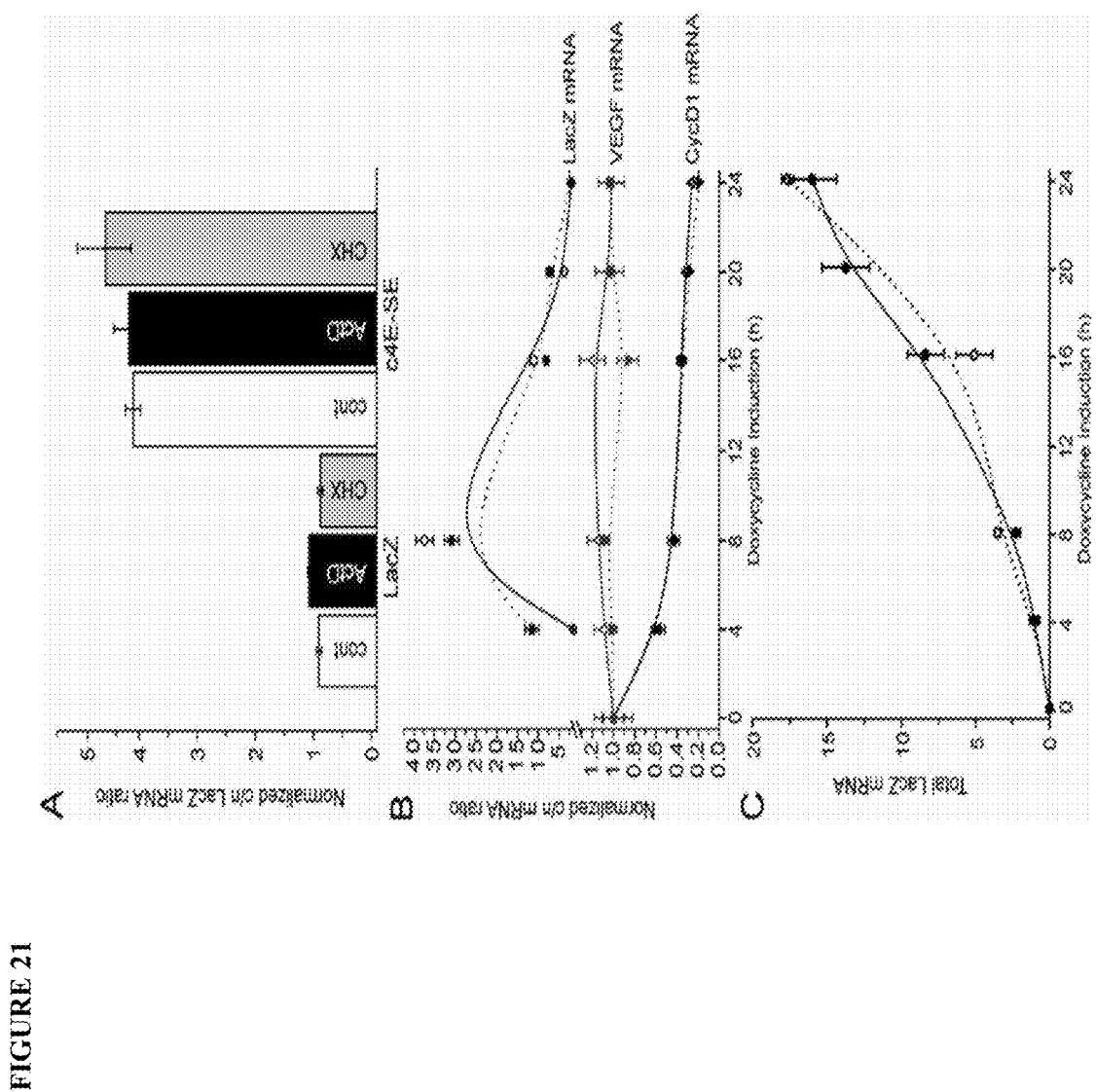

FIG. 21. Export of 4E-SE containing mRNAs is independent of ongoing RNA and protein synthesis, and the pathway is saturated by excess 4E-SE. (a) Quantitative real time PCR analysis of mRNA export of LacZ-c4E-SE and LacZ in eIF4E overexpressing cells is shown. Cytoplasmic/nuclear (c/n) values represent relative fold±sd, normalized to LacZ untreated control, which was set to 1. Treatments: actinomycin D (10 µg/ml) for 1 hour; cycloheximide (100 µg/ml) for 1 hour. (b) and (c) LacZ mRNA export was monitored as a function of both time and expression of LacZ transcripts −/+4E-SE, induced with doxicycline. Expression as a function of time is shown. In parallel, the extent of export was monitored as the ratio of c/n mRNA for each case. Full lines represent trends in cells expressing LacZ-c4E-SE; dotted lines are for cells expressing LacZ-p4E-SE. Endogenous mRNAs from the same samples were also examined. Cyclin D1 mRNA export was reduced in cells expressing either LacZ-c4E-SE or LacZ-p4E-SE. Importantly, VEGF, which does not contain a 4E-SE, did not have its export affected in either case. Clearly, as the amount of 4E-SE containing mRNAs increases in the cell (C), the ability to export these is reduced presumably because the 4E-SE dependent export was saturated (b). c/n values represent relative fold±sd, normalized to LacZ only for each time point. For total RNAs, values represent relative fold±sd, normalized to the first time point of induction for each transcript (4 h), which was set to 1. Average values of LacZ mRNA obtained for each time point were normalized by GAPDH mRNA values obtained for the same sample.

Figure 22:
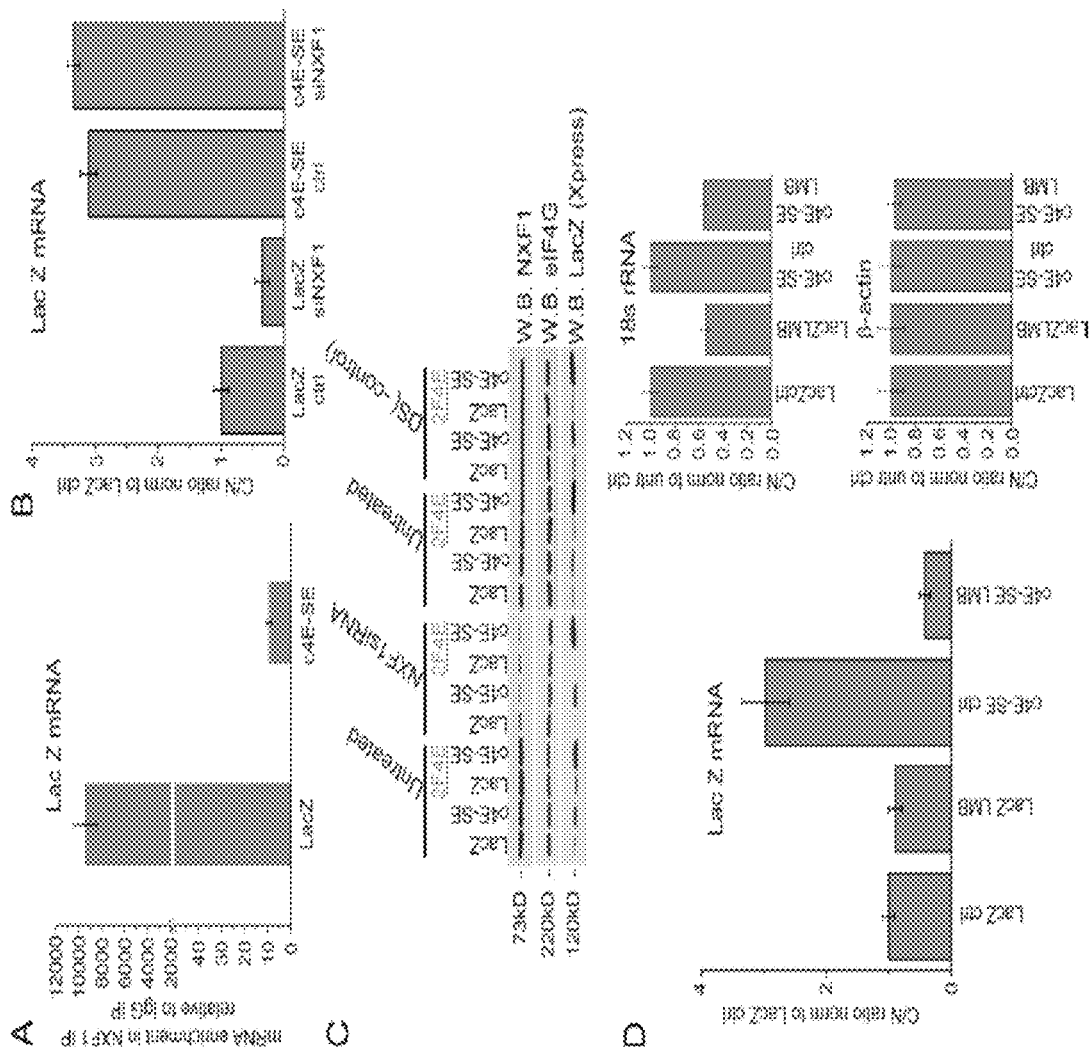

FIG. 22. eIF4E dependent export is NXF1 independent and CRM1 dependent. (a) Comparison of LacZ mRNA in the NXF1 IP fractions. Cells were cotransfected with Flag-NXF1/Flagp15 and LacZ or LacZ-c4E-SE Immunoprecipitations were done with anti-Flag-antibody. LacZ/LacZ-c4E-SE mRNA was monitored by real-time PCR and normalized to IgG controls (as described in FIG. 18a). (b) NXF1 siRNA treatment (72 h) inhibits export of LacZ but not LacZ-c4E-SE containing mRNAs. The c/n ratios of LacZ or LacZ-c4E-SE mRNAs in cells overexpressing eIF4E, as a function of siRNA treatment are shown. C/N values represent relative fold±sd, normalized to LacZ untreated control, which was set to 1. LacZ mRNAs levels were normalized to 18S rRNA, whose c/n ratio is unaffected by NXF1 siRNA. (c) Western blot (WB) analysis indicates that NXF1 protein levels are reduced by siRNA treatment but not by scrambled controls (DS (-control)). A WB for eIF4G is shown as a negative control. LacZ protein levels correspond to alterations in mRNA export shown in panel b. (d) Dependence of c4E-SE export on leptomycin B (LMB). The c/n ratio of LacZ-c4E-SE mRNA in eIF4E overexpressing U2OS cells indicated that 4E-SE export was sensitive to LMB (10 ng/ml for 4 h), while LacZ was not significantly so. 18S rRNA export was inhibited by LMB as expected, while β-actin mRNA export was not affected by LMB treatment, as expected. C/N values represent relative fold±sd, normalized to LacZ untreated control, which was set to 1. All RNAs were normalized to GAPDH mRNA.

Figure 23:
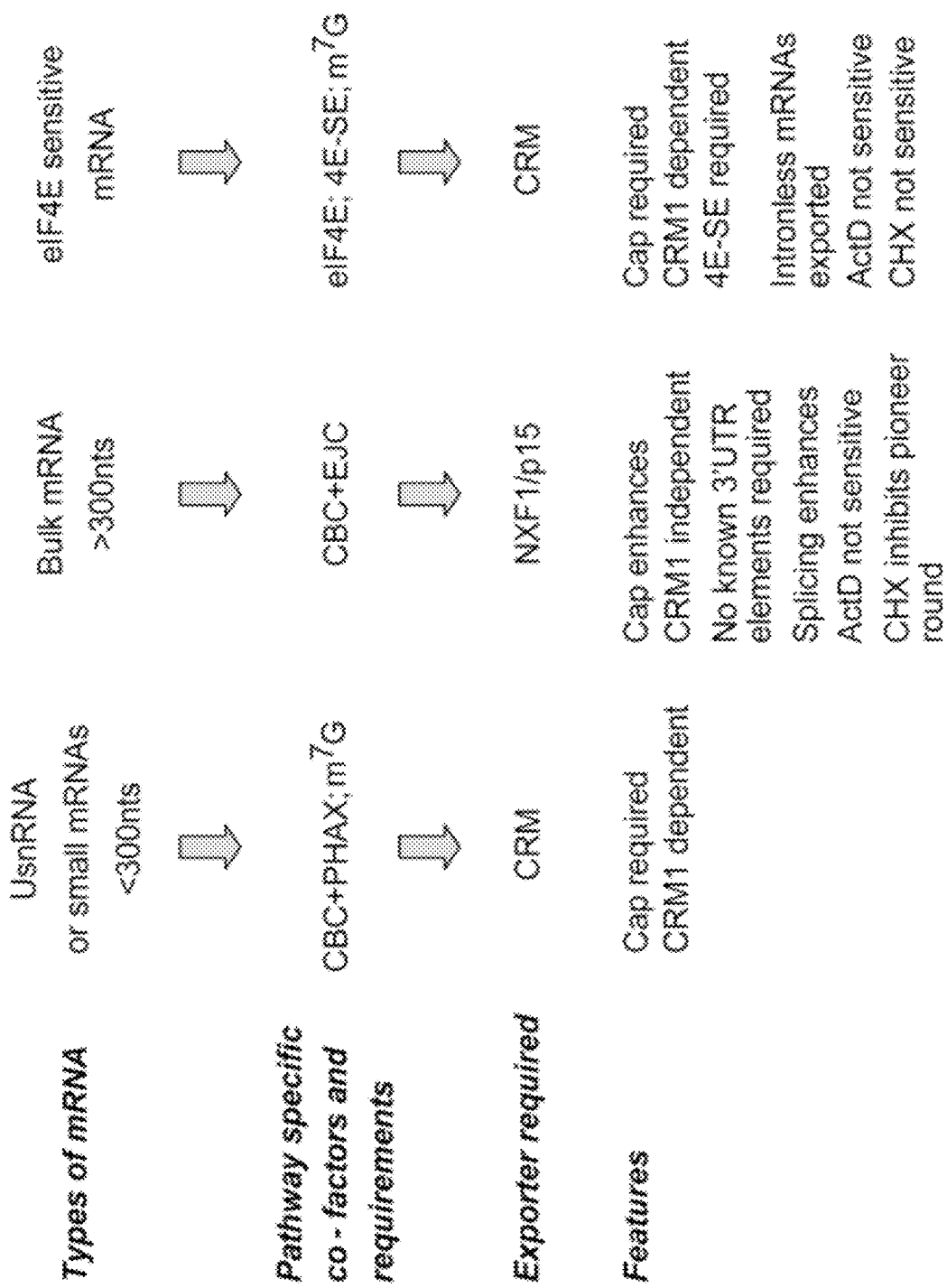

FIG. 23. Schematic representation of mechanisms for export of different classes of RNA. Overview of characteristic features delineating export of mRNAs via CRM1 or NXF1/p15 pathways are shown together with features of eIF4E mediated export of mRNAs.

Figure 24:
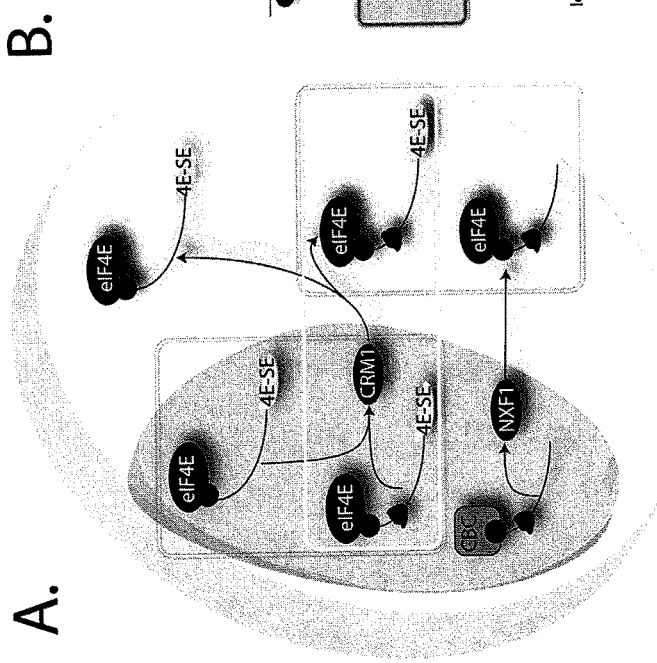

FIG. 24. A model of the eIF4E RNA regulon. (a) The nuclear compartment is shaded gray. In the nucleus both cap binding proteins, eIF4E and the cap binding complex CBC are shown. Bulk mRNA export is depicted by mRNAs bound to the CBC and exiting the nucleus in an NXF1 dependent way. mRNAs are depicted as black lines with black balls denoting the 5' $m^7G$ cap. mRNAs with the 4E-SE (in green) can be exported in a CRM1 dependent manner. Once in the cytoplasm, mRNAs with highly structured 5' UTRs (shown in red) are preferentially translated in an eIF4E dependent manner. Coloured boxes correspond to the level of control shown in part B. (b) Schematic representation of the regulon showing that eIF4E impacts on mRNA export and translation depending on the presence of the correct USER code. Example RNAs for each level of modulation are given. Below, example cellular regulators are given. Finally, compounds that modulate the given step in the regulon are shown. Although many RNAs fall into each category and many other regulators and compounds may exist at each step of control, we have only given examples for the sake of clarity. Further, the position of regulators and compounds in this diagram does not preclude any other unrelated activities these may have in the cell, but simply refers to their currently known role in the eIF4E regulon.

Figure 25:
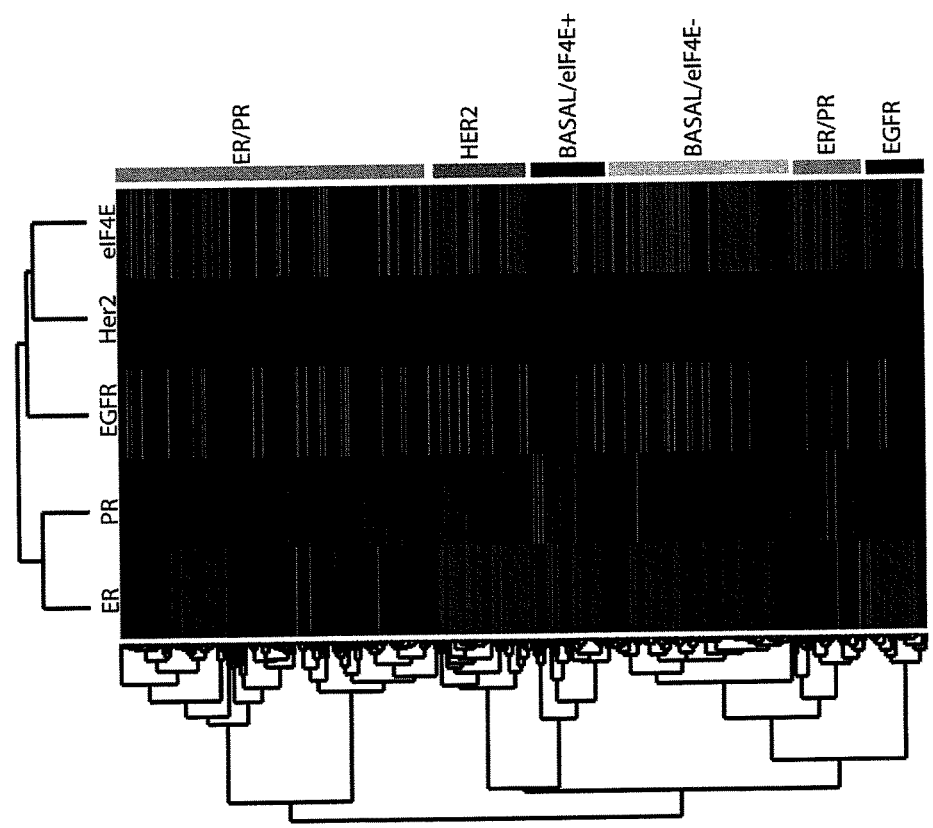

FIG. 25 depicts unsupervised hierarchical clustering analysis of protein expression level in breast cancers performed using AQUA scores for estrogen receptor (ER), progesterone receptor (PR), epidermal growth factor receptor (EGFR), Her2, and eIF4E. For additional details, see Example 5.

Figure 26:
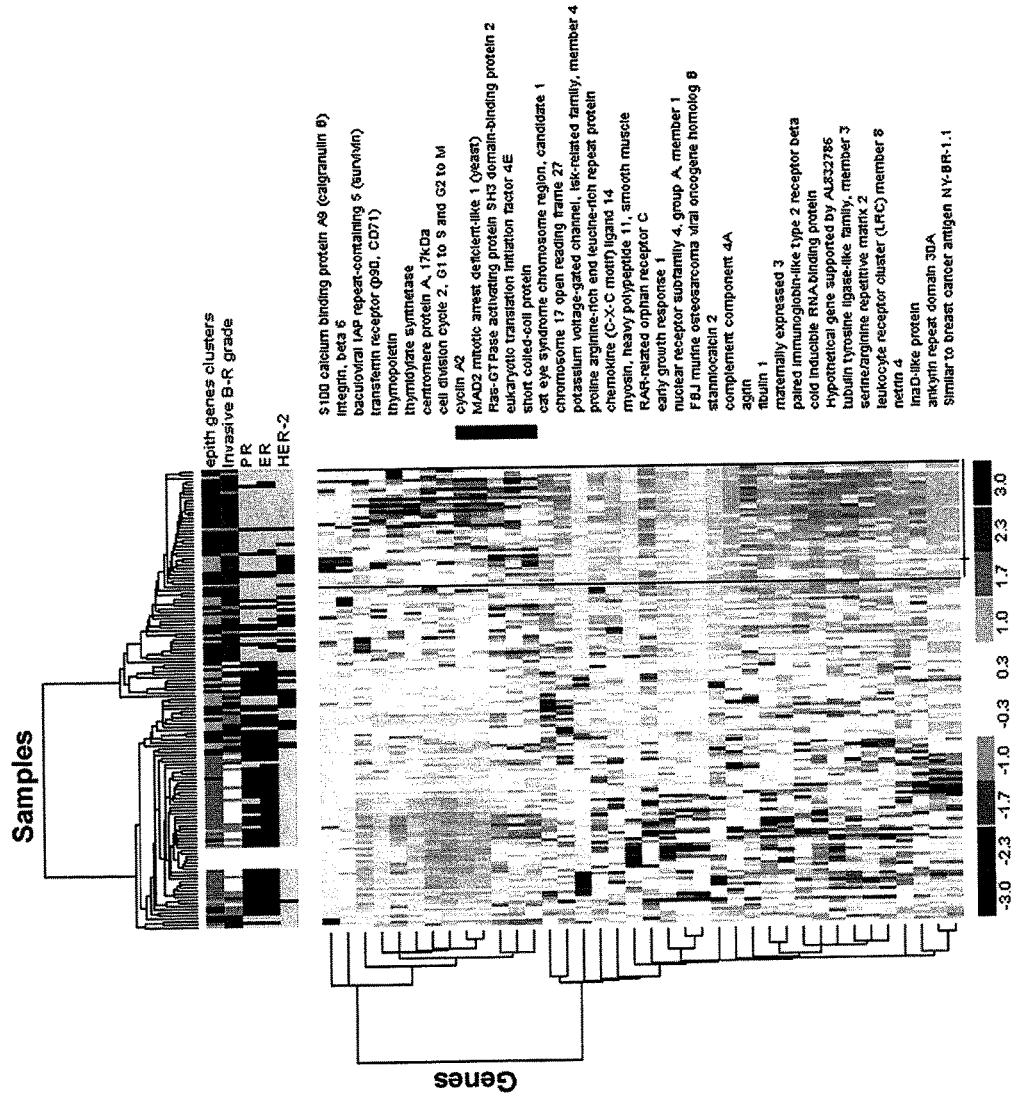

FIG. 26 depicts expression analysis performed from bulk tumor RNA extracted from 141 primary breast cancers and run on Affymetrix U133 plus 2.0 arrays (Andrea Richardson Dana-Farber Cancer Institute). The analysis was performed using hierarchical clustering function of dChip software. The genes displayed are those that are differentially expressed (at least 1.5 fold with 90% confidence) between tumors with high expression (>2 fold above mean) of 4E compared to tumors with low expression (>2 fold below mean).

Figure 27:
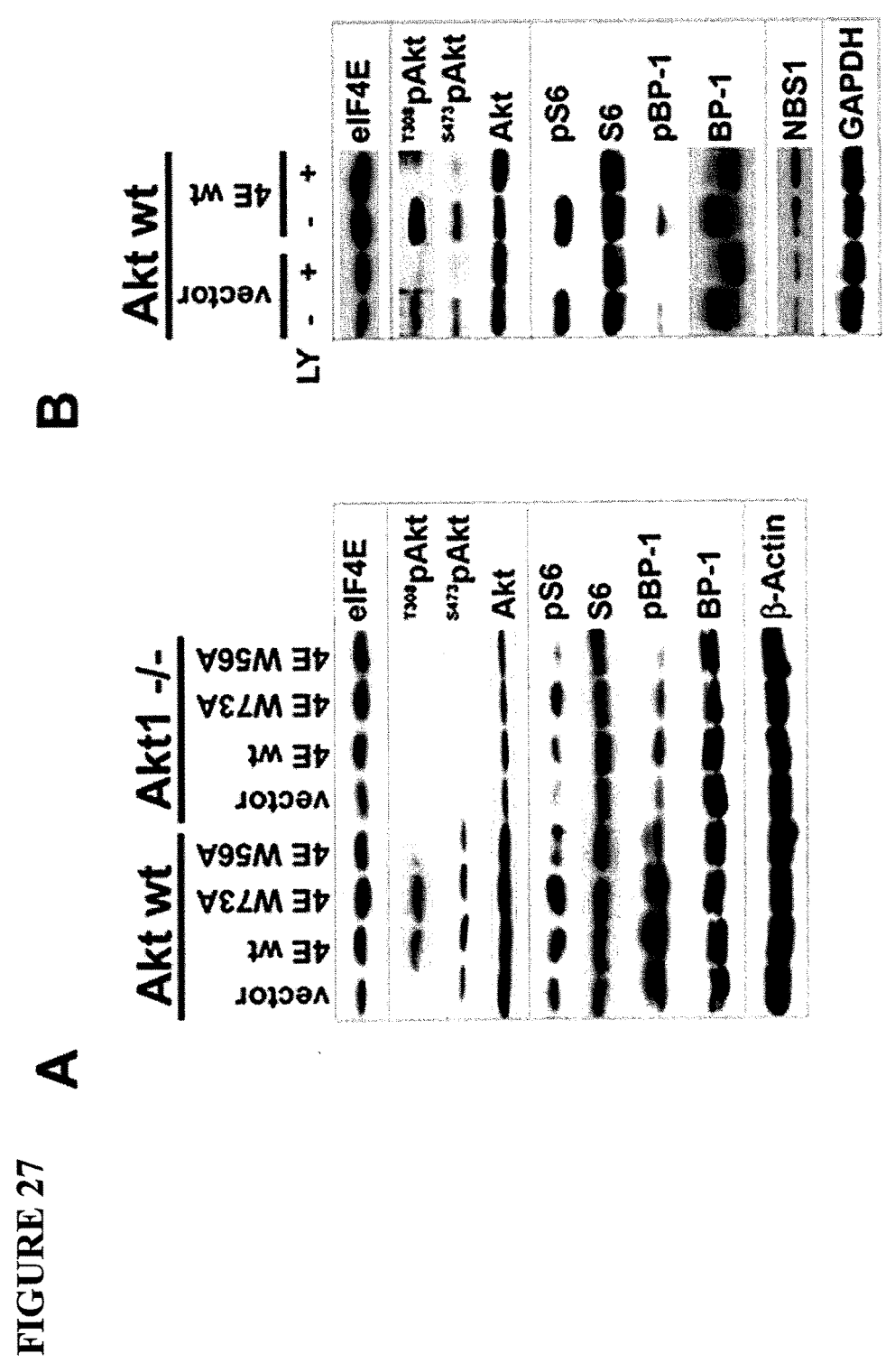

FIG. 27 shows that elevated expression of 4E alters the activity of Akt1 and downstream effectors. (A) Western blot analysis of whole-cell extracts from cells over-expressing 4E wt or mutants in MEF Akt1 wt and −/− lines. Proteins detected are as indicated. Bactin is shown as a protein loading control. (B) Western blot analysis of whole-cell extracts from MEF Akt1 wt derived cells treated with the PI3K inhibitor, LY294002 (LY; 50 μM for 1 hr). Proteins detected are as indicated. GAPDH is shown as a protein loading control.

Figure 28:
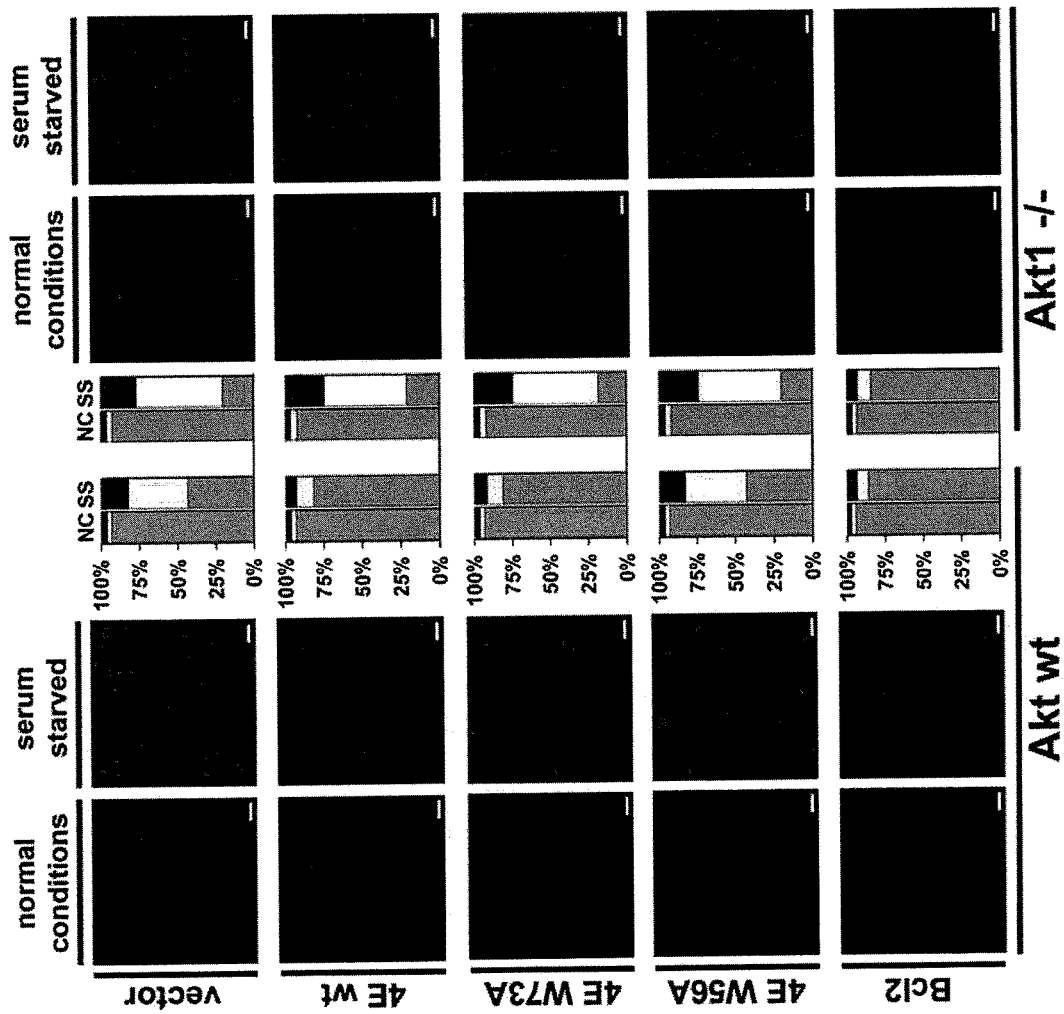

FIG. 28 shows that Akt 1 is required for 4E mediated apoptotic rescue of serum starved cells. Panels shown are representative fields from TUNEL experiments (blue—DAPI (viable), red—apoptotic; see Materials and Methods) of 4E over-expressing cells derived from MEF Akt1 wt and −/− lines. Scale bar is set at 50 μm. Graphs represent quantitative measurements by flow cytometry of apoptosis using Annexin V (Ann.V) and propidium iodide (PI) staining of indicated cells (see Materials and Methods). Bar color is as follows: Ann.V−/PI− (blue), Ann.V+/PI− (yellow), Ann.V+/PI+ (red), Ann.V−/PI+ (black). Error as within 5% (data not shown). NC—normal condition, SS—serum starvation.

Figure 29:
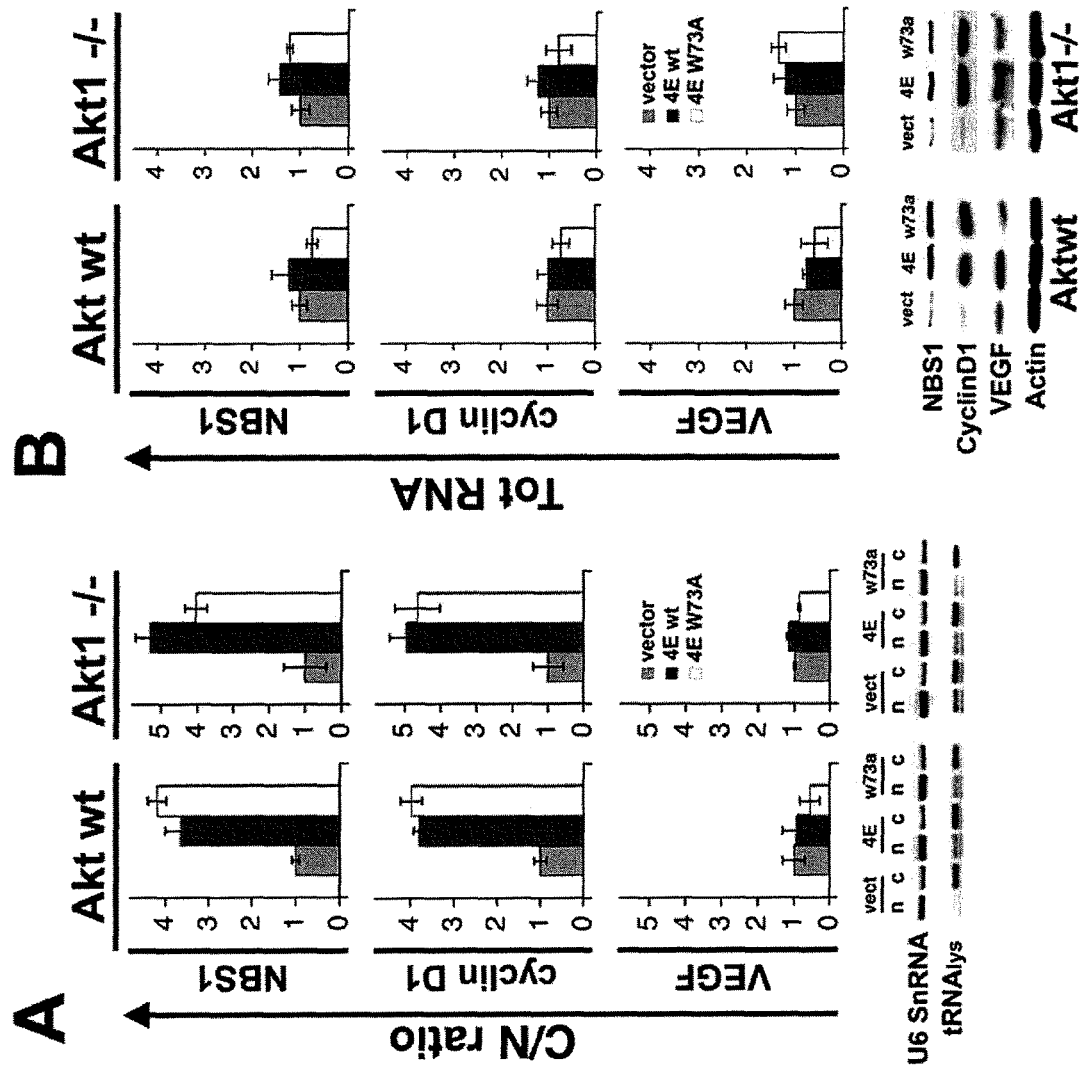

FIG. 29 shows that the absence of Akt1 does not impede 4E-dependent nuclear-cytoplasmic transport of reported sensitive RNA targets. (A) RNA quantification from parallel real time PCR experiments from MEF Akt1 wt and Akt1−/− derived cells show the relative fold increase (y-axis) of the cytoplasmic/nuclear ratio of NBS1, cyclin D1 (positive control for 4E dependent mRNA export) and VEGF (negative control) mRNAs. Shown below are controls for sample fractionation (U6 SnRNA—nuclear, tRNAlys—cytoplasmic). (B) Control experiment showing total levels of NBS1, cyclin D1 or VEGF RNA, with western analysis shown below indicating changes at the protein expression level. Bar representation is as indicated. Cytoplasmic/nuclear ratios represent relative fold difference SD normalized to vector control which was set to 1. Averaged values of all analyzed mRNAs were normalized to GAPDH mRNA values.

Figure 30:
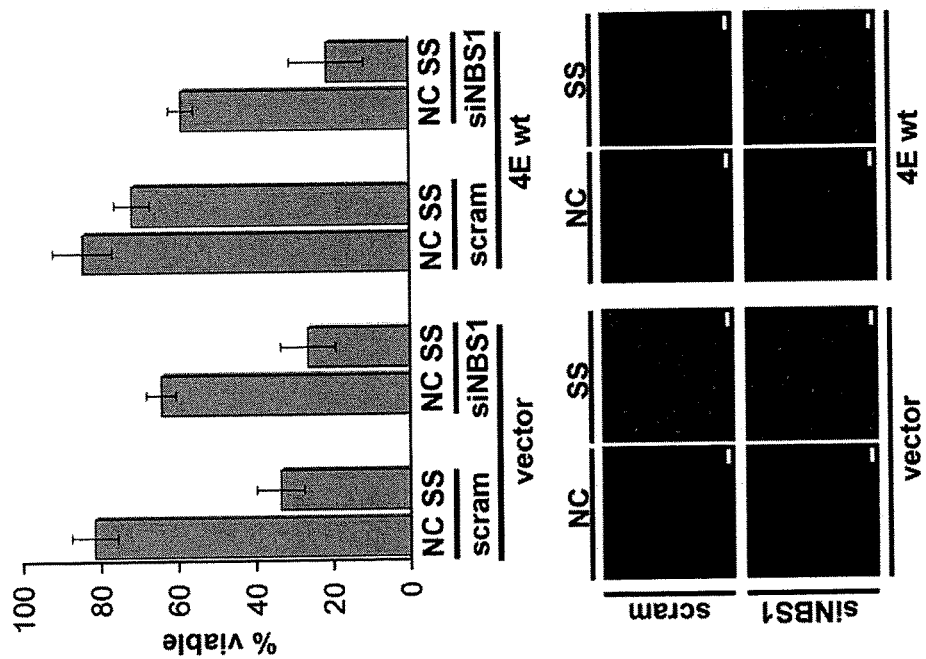
Figure 30:
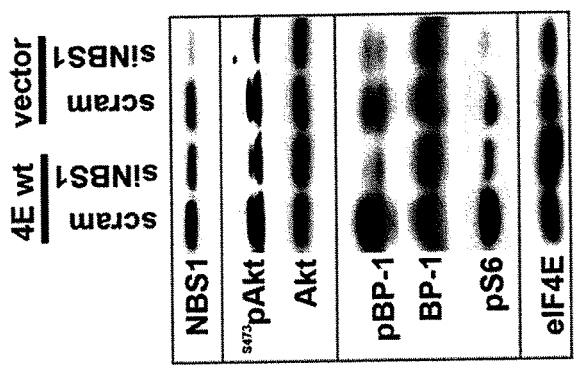

FIG. 30 shows that NBS1 expression is necessary for upregulation of the Akt1 pathway by 4E. (A) Western blot analysis of whole-cell extracts from siRNA treated MEF Akt wt derived cells; scram=scrambled control, siNBS1=extracts from cells treated with siRNA for NBS1. Proteins detected are as indicated. ß-actin is shown as a protein loading control. (B) Quantification of viable cells from apoptosis assays (Ann.V−/PI−) of siNBS1 treated Akt1 wt derived cells (vector versus 4E). Error was within 10%. NC—normal condition, SS—serum starvation. (C) Visual confirmation of apoptosis of siNBS1 treated Akt1 wt derived cells (as indicated) from TUNEL experiments (panels: blue—DAPI (viable), red—apoptotic). Scale bar is set at 50 μm.

Figure 31:
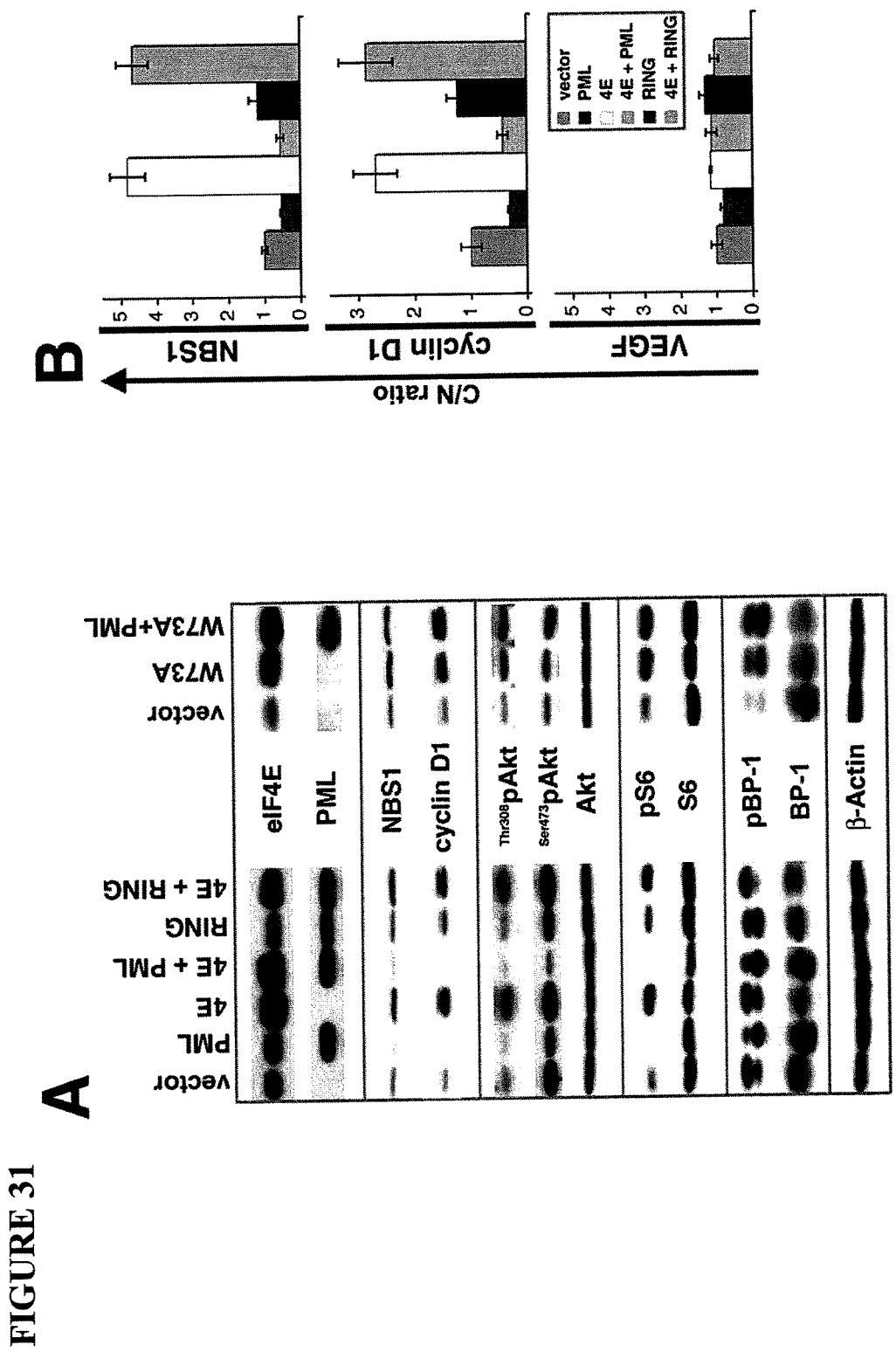

FIG. 31 shows that overexpression of the 4E inhibitor, PML, abrogates the 4E—Akt1 pathway, while the PML RING mutant does not inhibit these 4E dependent activities. (A) Western blot analysis of whole-cell extracts from stably transfected NIH3T3 cells over-expressing 4E wt/W73A and/or PML/RING. Proteins detected are as indicated. Note that the antibody used for PML detection only binds to the exogenous PML. ß-actin is shown as a protein loading control. (B) Parallel qPCR experiments showing relative fold increase (y-axis) of the cytoplasmic/nuclear ratio of 4E target mRNAs from NIH3T3 derived cells. Bar representation is as indicated.

Figure 32:
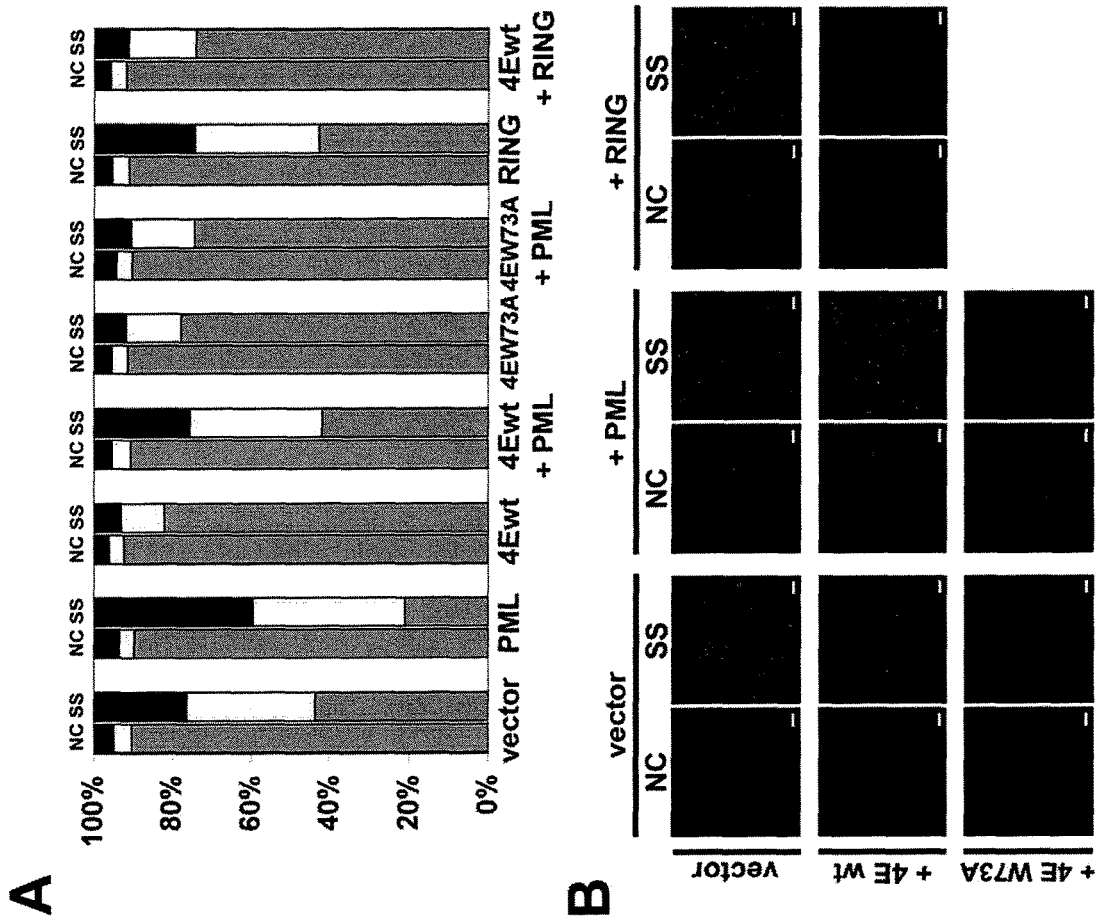

FIG. 32 shows that the 4E inhibitor, PML, relieves cells from 4E-dependent apoptotic rescue through the RING domain of PML. (A) Bar graphs represent quantitative measurements of apoptosis using Annexin V (Ann.V) and propidium iodide (PI) staining of indicated NIH3T3 derived cells. Bar color is as follows: Ann.V−/PI− (blue), Ann.V+/PI− (yellow), Ann.V+/PI+ (red), Ann.V−/PI+ (black). Error was within 5% (data not shown). NC—normal condition, SS—serum starvation. (B) Visual confirmation of apoptosis from TUNEL experiments (panels: blue—DAPI, red—apoptotic). Scale bar is set at 50 mm.

Figure 33:
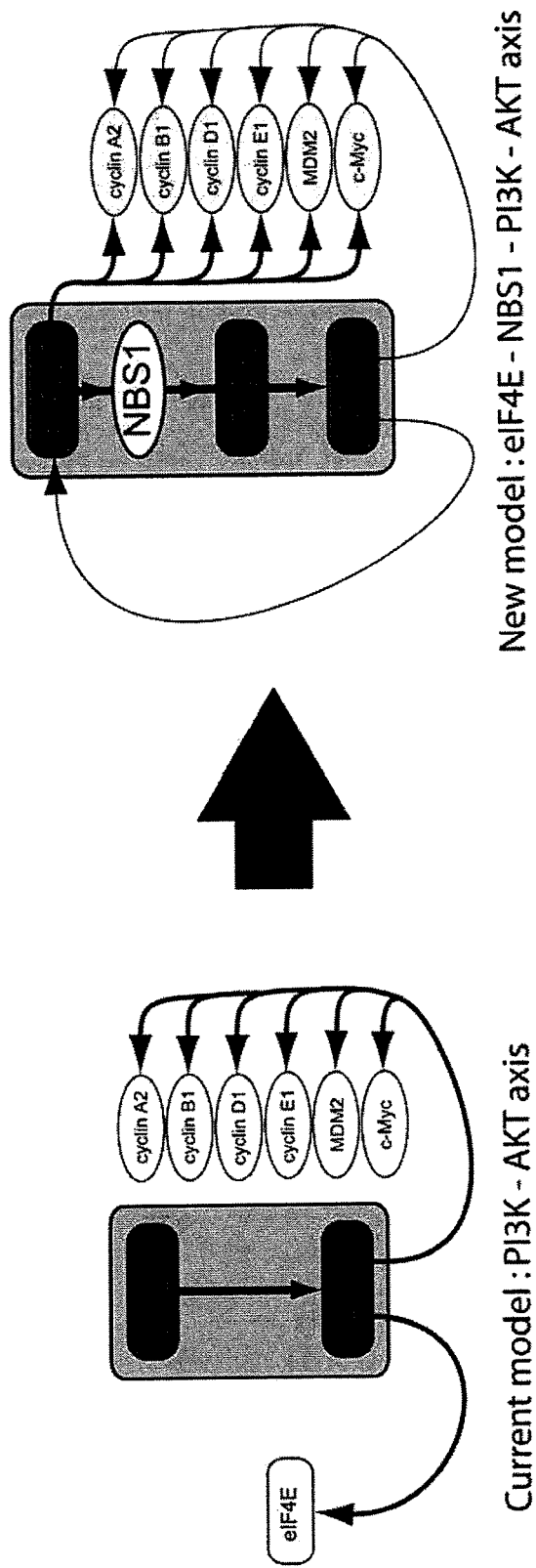

FIG. 33 depicts comparison models summarizing how 4E is not only downstream of PI3K-AKT pathway (left), but can modulate this PI3K-Akt axis through NBS1 (right). Further, several downstream targets of Akt (eg: cyclin A2, B1, D1, E; Mdm2, and c-Myc) are also targets for 4E regulation at the mRNA transport level, giving rise to a putative feedback loop. For simplicity, arrows indicate downstream effects (such as phosphorylation), thus arrows do not necessarily indicate a single step process. Boxed in yellow are some of the known subset of mRNAs sensitive to 4E transport activity that also play a role in the Akt pathway.

Figure 34:
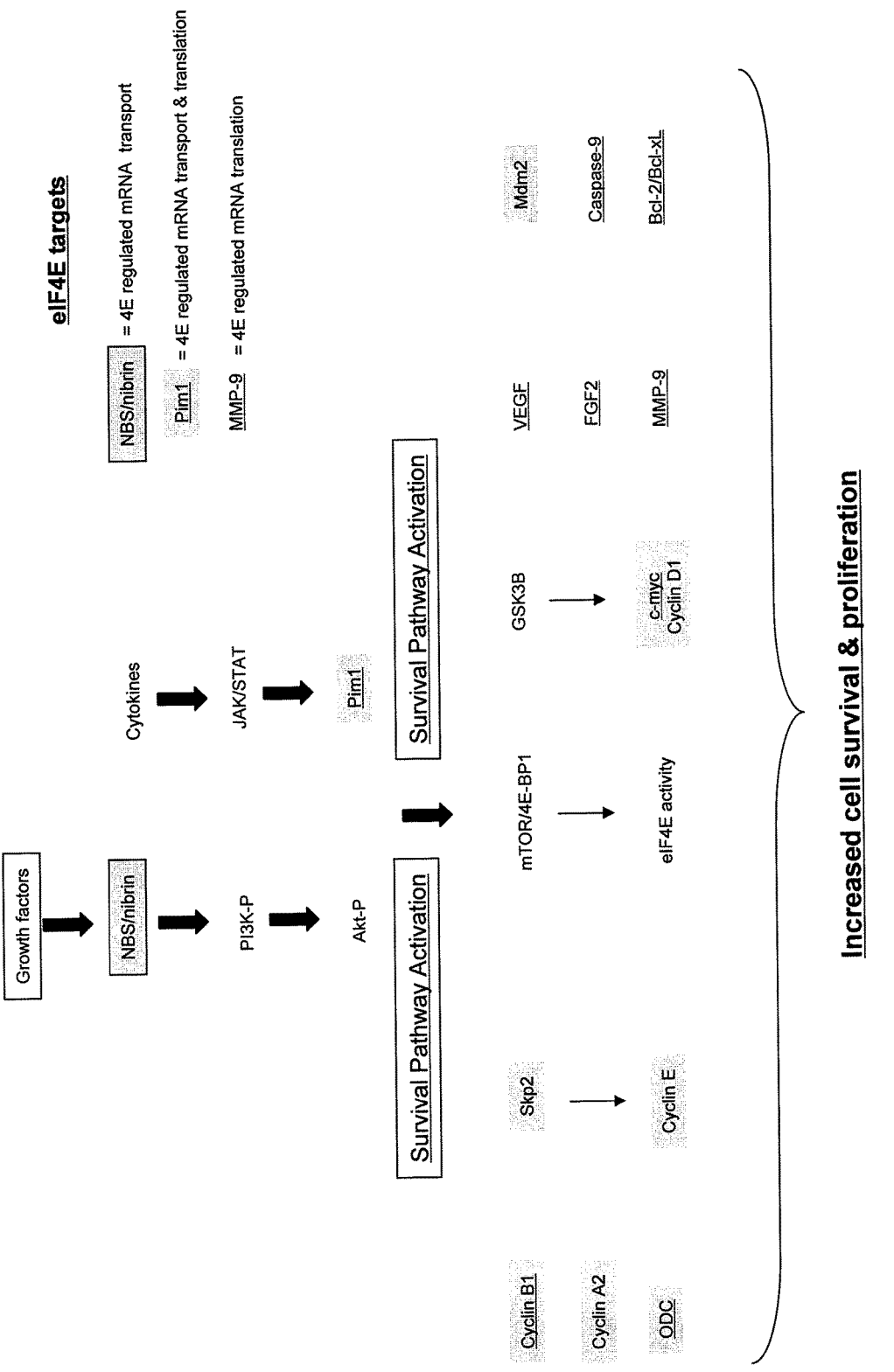

FIG. 34 depicts the components of the 4E regulon.

Figure 35:
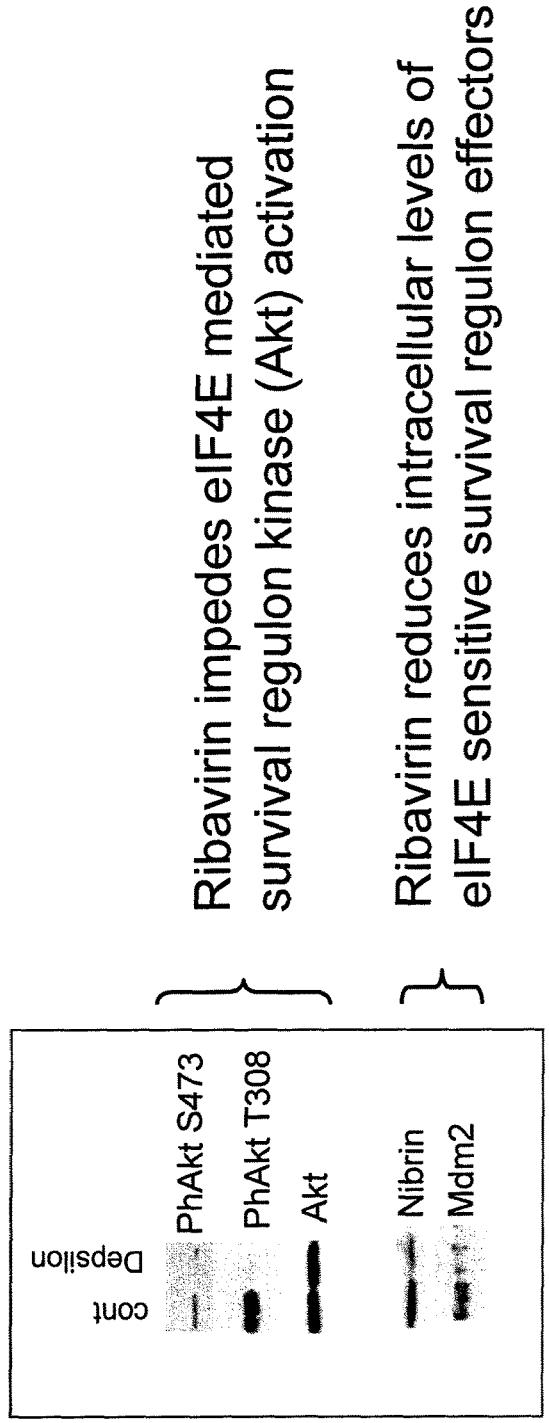
Figure 36:
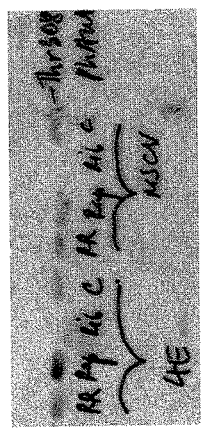

FIGS. 35 and 36 show that Akt phosphorylation is required for activation of Akt. Ribavirin inhibits Akt phosphorylation while Rapamycin increases Akt phosphorylation.

Figure 37:
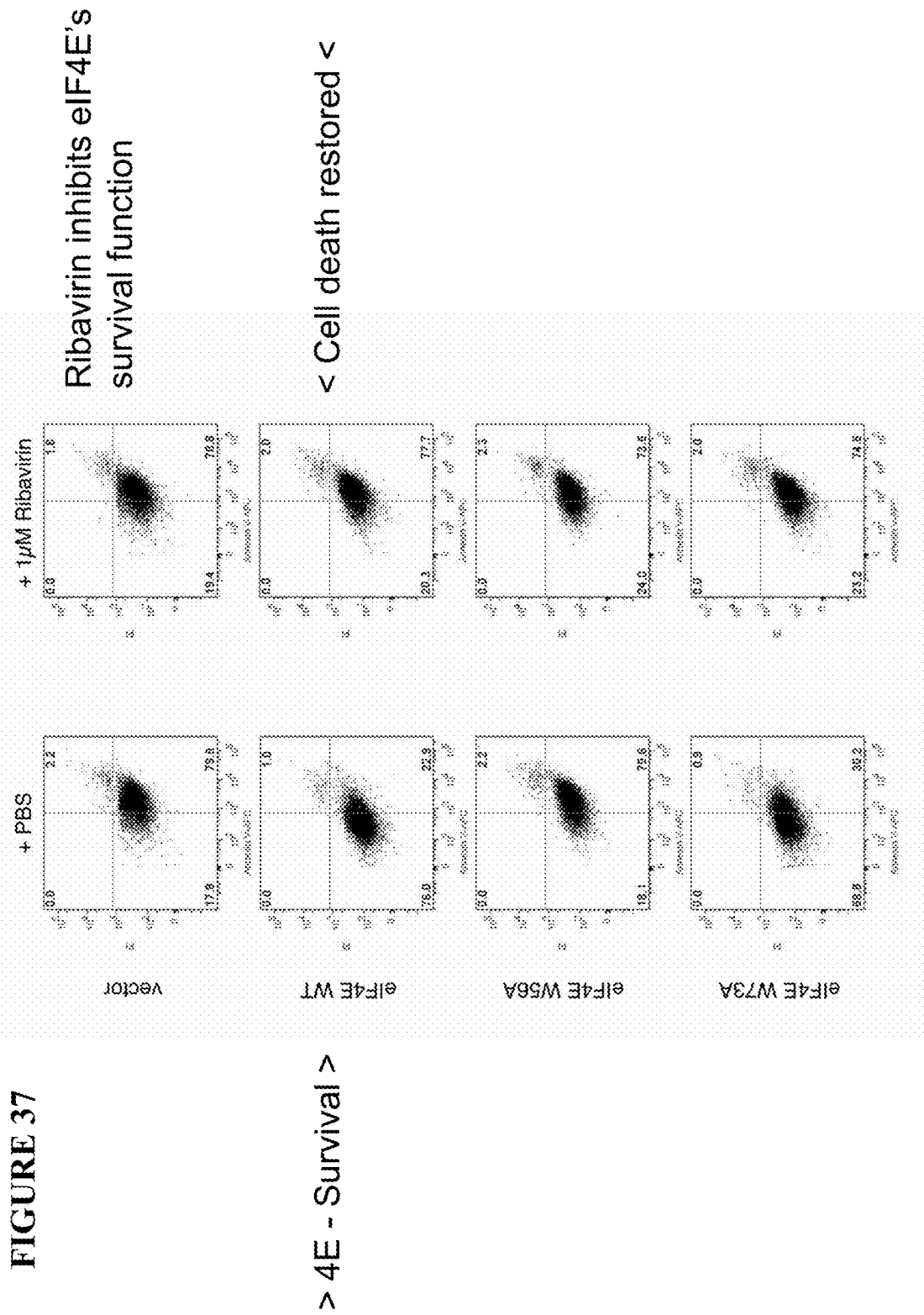

FIG. 37 shows that Ribavirin blocks 4E mediated apoptotic rescue and Rapamycin partially inhibits Ribavirin effect on 4E mediated apoptotic rescue.

Figure 38:
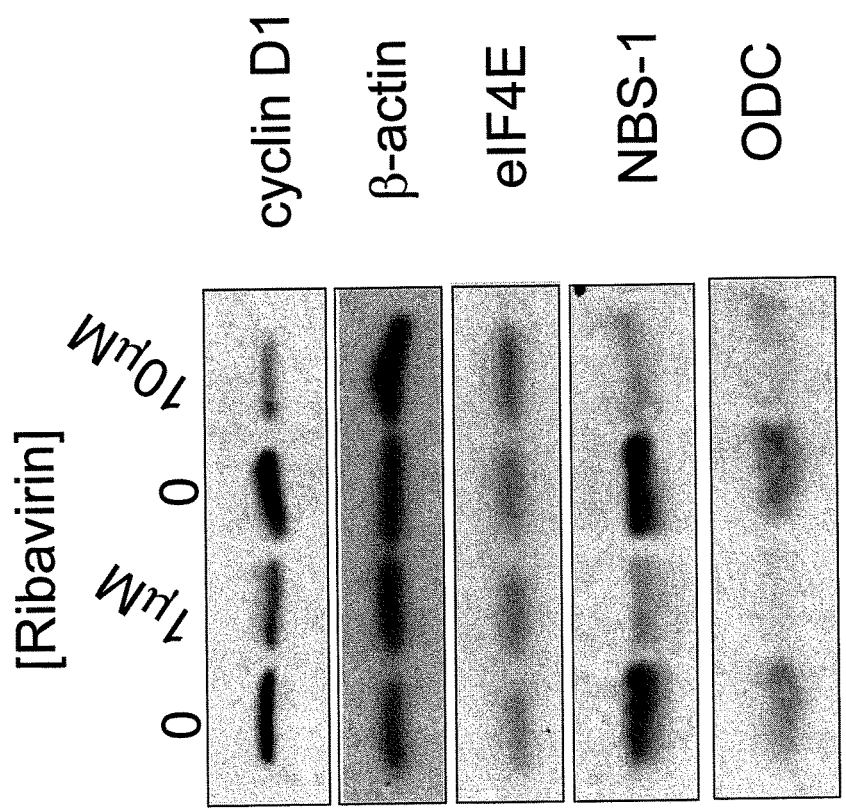

FIG. 38 depicts the effect of Ribavirin on the protein levels of 4E, actin, NBS1, Cyclin D1 and ODC on FaDu cells were grown in culture and treated with Ribavirin for 48 hours prior to preparation of protein extracts and western blot analysis.

DETAILED DESCRIPTION

A. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The terms "4E" and "eIF4e" are used herein interchangeably.

The term "4E activity" or "activity of 4E" includes any of the biological effects of the 4E gene or protein, including but not limited to elevated expression of 4E, elevated protein levels of 4E, 4E regulon activity and/or activation of 4E regulon components, expression and/or activity or level of components under control of the 4E regulon, elevated transport of selected messages (especially cyclin D1 and additional messages as detailed in Examples 2 and 4) from the nucleus to the cytoplasm, and phosphorylation state of 4E and levels of eIF4EBP1.

The term "4E regulon activity" or "4E regulon component activity" or "activity of a 4E regulon component" refers the activity of 4E as a mediator of the 4E regulon and also includes 4E regulon activation, expression, transport and/or activity of the 4E regulon components.

The term "4E regulon component" refers to 4E, any of the components of its regulon, and any modifier of the regulon such as HuR. The 4E regulon is illustrated in FIGS. 24 and 34. Exemplary 4E regulon elements include: eIF4E (gi: 54873625); Cyclin D1 (gi: 77628152); NBS/Nibrin (gi: 67189763); Pim-1 (gi: 31543400); Cyclin B1 (gi: 34304372); Cyclin A2 (gi: 16950653); ODC (gi: 4505488); VEGF (gi: 71051577); Skp2 (gi: 16306594, 16306593); Cyclin E1 (gi: 17318558); c-myc (gi: 71774082); FGF2 (gi: 153285460); MMP-9 (gi: 74272286); mdm2 (gi: 46488903); caspase-9 (gi: 14790123, 14790127); bcl2 (gi: 72198188, 72198345); Bcl/xL (gi: 20336334); Fbox1 (gi: 16306583); CGGbp1 (gi: 56550052); P54nrb/NONO.1 (gi: 34932413); Selenoprotein S (gi: 45439347); eIF4E-BP1 (gi: 117938308); Akt1 (gi: 62241012, 62241010, 62241014); PI3K (gi: 54792081, 212377724); GSK3B (gi: 21361339); HuR (gi: 38201713); and mTOR/FRAP1 (gi: 19924298). Preferred 4E regulon components (elements) to be used in certain of the below-described methods are 4E, 4E-BP1, NBS/Nibrin, Pim-1, VEGF, Cyclin D1, Cyclin A2, ODC and HuR. A "regulon" is a family of multiple mRNAs that are coordinately regulated in a sequence specific fashion by one or more RNA binding proteins that orchestrate and control their splicing, export, stability, localization and/or translation.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

The articles "a" and "an" are used herein to refer to one or to more than one (i.e., to at least one) of the grammatical object of the article. By way of example, "an element" means one element or more than one element.

The term "acylamino" is art-recognized and includes a moiety that may be represented by the general formula:

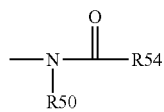

wherein R50 is as defined above, and R54 represents a hydrogen, an alkyl, an alkenyl or —(CH$_2$)$_m$—R61, where m and R61 are as defined above.

The term "administering" includes any method of delivery of a compound of the present invention, including but not limited to, a pharmaceutical composition or therapeutic agent, into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "agonist", as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The terms "alkenyl" and "alkynyl" are art-recognized, and include unsaturated aliphatic groups analogous in length and possible substitution to the alkyls described above, but that contain at least one double or triple bond respectively.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The terms "alkoxyl" or "alkoxy" are art-recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., C$_1$-C$_{30}$ for straight chain, C$_3$-C$_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN, and the like.

The definition of each expression, e.g. alkyl, m, n, etc., when it occurs more than once in any structure, is intended to be independent of its definition elsewhere in the same structure unless otherwise indicated expressly or by the context.

The term "alkylthio" is art-recognized and includes an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "amido" is art-recognized as an amino-substituted carbonyl and includes a moiety that may be represented by the general formula:

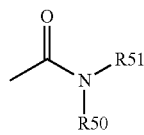

wherein R50 and R51 are as defined above. Certain embodiments of the amide in the present invention will not include imides which may be unstable.

The terms "amine" and "amino" are art-recognized and include both unsubstituted and substituted amines, e.g., a moiety that may be represented by the general formulas:

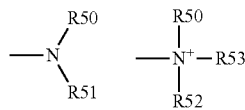

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "aralkyl" is art-recognized, and includes alkyl groups substituted with an aryl group (e.g., an aromatic or heteroaromatic group).

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that down-regulates expression of a gene or which reduces the amount of expressed protein present.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "binding" refers to an association, which may be a stable association, between two molecules, e.g., between a polypeptide of the invention and a binding partner, due to, for example, electrostatic, hydrophobic, ionic and/or hydrogen-bond interactions under physiological conditions.

"Biological activity" or "bioactivity" or "activity" or "biological function", which are used interchangeably, refer to an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulator, ability to bind damaged DNA, phosphorylation state, etc. A bioactivity may be modulated by directly affecting the subject polypeptide. Alternatively, a bioactivity may be altered by modulating the level of the polypeptide, such as by modulating expression of the corresponding gene.

The term "biological sample", or "sample" as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The term "cancer" refers in general to any malignant neoplasm or spontaneous growth or proliferation of cells. The term as used herein encompasses both fully developed malignant neoplasms, as well as premalignant lesions. A subject having "cancer", for example, may have a tumor or a white blood cell proliferation such as leukemia. In certain embodiments, a subject having cancer is a subject having a tumor, such as a solid tumor. Cancers include but are not limited to non small cell lung cancer (NSCLC), testicular cancer, lung cancer, ovarian cancer, uterine cancer, cervical cancer, pancreatic cancer, colorectal cancer (CRC), breast cancer, prostate cancer, gastric cancer, skin cancer, stomach cancer, esophageal cancer, bladder cancer, thyroid cancer, parathyroid cancer, brain cancer, biliary cancer, rhabdomyosarcoma, head and neck cancer, tuberous sclerosis and blood cancers including but not limited to non-Hodgkin's lymphoma (NHL), acute myelogenous leukemia (AML) and blast crisis of chronic myelogenous leukemia (bc-CML).

The term "carbocycle" is art-recognized and includes an aromatic or non-aromatic ring in which each atom of the ring is carbon. The following art-recognized terms have the following meanings: "nitro" means —$NO_2$; the term "halogen" designates —F, —Cl, —Br or —I; the term "sulfhydryl" means —SH; the term "hydroxyl" means —OH; and the term "sulfonyl" means —$SO_2^-$.

The term "carbonyl" is art-recognized and includes such moieties as may be represented by the general formulas:

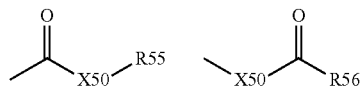

wherein X50 is a bond or represents an oxygen or a sulfur, and R55 represents a hydrogen, an alkyl, an alkenyl, —$(CH_2)_m$—R61, or a pharmaceutically acceptable salt. R56 represents a hydrogen, an alkyl, an alkenyl or —$(CH_2)_m$—R61, where m and R61 are defined above. Where X50 is an oxygen and R55 or R56 is not hydrogen, the Formula represents an "ester". Where X50 is an oxygen, and R55 is as defined above, the moiety is referred to herein as a carboxyl group, and particularly when R55 is a hydrogen, the Formula represents a "carboxylic acid". Where X50 is an oxygen, and R56 is hydrogen, the Formula represents a "formate". In general, where the oxygen atom of the above Formula is replaced by sulfur, the Formula represents a "thiocarbonyl" group. Where X50 is a sulfur and R55 or R56 is not hydrogen, the Formula represents a "thioester." Where X50 is a sulfur and R55 is hydrogen, the Formula represents a "thiocarboxylic acid." Where X50 is a sulfur and R56 is hydrogen, the Formula represents a "thioformate." On the other hand, where X50 is a bond, and R55 is not hydrogen, the above Formula represents a "ketone" group. Where X50 is a bond, and R55 is hydrogen, the above Formula represents an "aldehyde" group.

A "combinatorial library" or "library" is a plurality of compounds, which may be termed "members," synthesized or otherwise prepared from one or more starting materials by employing either the same or different reactants or reaction conditions at each reaction in the library. In general, the members of any library show at least some structural diversity, which often results in chemical diversity. A library may have anywhere from two different members to about $10^8$ members or more. In certain embodiments, libraries of the present invention have more than about 12, 50 and 90 members. In certain embodiments of the present invention, the starting materials and certain of the reactants are the same, and chemical diversity in such libraries is achieved by varying at least one of the reactants or reaction conditions during the preparation of the library. Combinatorial libraries of the present invention may be prepared in solution or on the solid phase.

The terms "comprise" and "comprising" are used in the inclusive, open sense, meaning that additional elements may be included.

The term "diagnosing" refers to determining the presence of a disease in a patient.

A "disease wherein 4E regulon activity is dysfunctional" refers to any condition in a subject where the expression level of, activity of, amounts of, or phosphorylation states of the 4E regulon components differ statistically significantly from those observed in a nondiseased subject. Exemplary diseases wherein 4E regulon activity is dysfunctional include cancer, proliferation disorders, ischemia reperfusion and hypertrophy.

The term "effective amount" refers to that amount of a compound, material, or composition comprising a compound of the present invention which is sufficient to effect a desired result, including, but not limited to, for example, reducing tumor volume either in vitro or in vivo. An effective amount of a pharmaceutical composition of the present invention is an amount of the pharmaceutical composition that is sufficient to effect a desired clinical result, including but not limited to, for example, ameliorating, stabilizing, preventing or delaying the development of cancer in a patient. In either case, an effective amount of the compounds of the present invention can be administered in one or more administrations. Detection and measurement of these above indicators are known to those of skill in the art, including, but not limited for example, reduction in tumor burden, inhibition of tumor size, reduction in proliferation of secondary tumors, expression of genes in tumor tissue, presence of biomarkers, lymph node involvement, histologic grade, and nuclear grade.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59, McGraw Hill Book Company, New York, (1977). The Hammett constant values are generally negative for electron donating groups (σ(P)=−0.66 for $NH_2$) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

"Gene" or "recombinant gene" refers to a nucleic acid molecule comprising an open reading frame and including at least one exon and (optionally) an intron sequence. "Intron" refers to a DNA sequence present in a given gene which is spliced out during mRNA maturation.

By "gene product" it is meant a molecule that is produced as a result of transcription of a gene. Gene products include RNA molecules transcribed from a gene, as well as proteins translated from such transcripts.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "hydrocarbon" is art-recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "hydroxyl-protecting group" is art-recognized and includes those groups intended to protect a hydroxyl group against undesirable reactions during synthetic procedures and includes, for example, benzyl or other suitable esters or ethers groups known in the art.

The term "hypertrophy" refers in general to any abnormal enlargement of a body part or organ.

The term "including" is used to mean "including but not limited to". "Including" and "including but not limited to" are used interchangeably.

The term "ischemia reperfusion" refers in general to refers to damage to tissue caused when blood supply returns to the tissue after a period of ischemia. "Ischemia" refers to a low oxygen state usually due to obstruction of the arterial blood supply or inadequate blood flow leading to hypoxia in the tissue.

The terms "label" or "labeled" refer to incorporation or attachment, optionally covalently or non-covalently, of a detectable marker into a molecule, such as a polypeptide and especially an antibody. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance. Particular examples of labels which may be used under the invention include fluorescein, rhodamine, dansyl, umbelliferone, Texas red, luminol, NADPH, alpha-beta-galactosidase and horseradish peroxidase.

The "level of expression of a gene in a cell" or "gene expression level" refers to the level of mRNA, as well as pre-mRNA nascent transcript(s), transcript processing intermediates, mature mRNA(s) and degradation products, encoded by the gene in the cell.

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, anti-microbial agents, inhibitors of microbial infection or proliferation, and the like) by inclusion in assays. In such assays, many modulators may be screened at one time. The activity of a modulator may be known, unknown or partially known.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

A "patient" or "subject" or "host" refers to either a human or non-human animal.

The term "pharmaceutical delivery device" refers to any device that may be used to administer a therapeutic agent or agents to a subject. Non-limiting examples of pharmaceutical delivery devices include hypodermic syringes, multi-chamber syringes, stents, catheters, transcutaneous patches, microneedles, microabraders, and implantable controlled release devices. In one embodiment, the term "pharmaceutical delivery device" refers to a dual-chambered syringe capable of mixing two compounds prior to injection.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The term "phosphonamidite" is art-recognized and includes moieties represented by the general formulas:

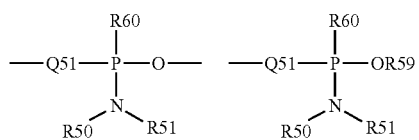

wherein Q51, R50, R51 and R59 are as defined above, and R60 represents a lower alkyl or an aryl.
The term "phosphoryl" is art-recognized and includes moieties represented by the general formula:

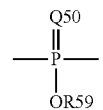

wherein Q50 represents S or O, and R59 represents hydrogen, a lower alkyl or an aryl. When used to substitute, e.g., an alkyl, the phosphoryl group of the phosphorylalkyl may be represented by the general formulas:

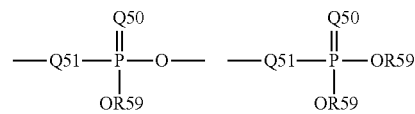

wherein Q50 and R59, each independently, are defined above, and Q51 represents O, S or N. When Q50 is S, the phosphoryl moiety is a "phosphorothioate".

The term "phosphoramidite" is art-recognized and includes moieties represented by the general formulas:

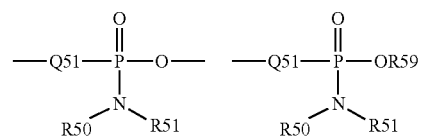

wherein Q51, R50, R51 and R59 are as defined above.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The term "prognosing" refers to determining the probable outcome of an attack of disease or the prospect as to recovery from a disease as indicated by the nature and symptoms of the case.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* 2$^{nd}$ ed., Wiley, New York, (1991).

"Protein", "polypeptide" and "peptide" are used interchangeably herein when referring to a gene product, e.g., as may be encoded by a coding sequence. By "gene product" it is meant a molecule that is produced as a result of transcription of a gene. Gene products include RNA molecules transcribed from a gene, as well as proteins translated from such transcripts.

A "regulon" is a collection of genes under regulation by the same regulatory protein. The "4E regulon" is the collection of genes ("4E regulon components") under regulation by 4E, as described in the Examples and shown in FIG. 24, and thus includes 4E as a component.

"Small molecule" is an art-recognized term. In certain embodiments, this term refers to a molecule which has a molecular weight of less than about 2000 amu, or less than about 1000 amu, and even less than about 500 amu.

The term "staging" refers to determining the degree to which a disease has progressed in a subject.

It will be understood that the terms "substitution" and "substituted with" are art-recognized and include the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "sulfonate" is art-recognized and includes a moiety that may be represented by the general formula:

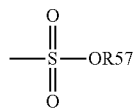

in which R57 is an electron pair, hydrogen, alkyl, cycloalkyl, or aryl.

The term "sulfate" is art-recognized and includes a moiety that may be represented by the general formula:

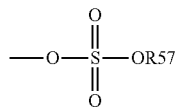

in which R57 is as defined above.

The term "sulfonamido" is art-recognized and includes a moiety that may be represented by the general formula:

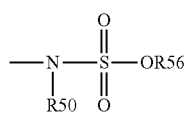

in which R50 and R56 are as defined above.

The term "sulfamoyl" is art-recognized and includes a moiety that may be represented by the general formula:

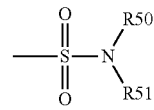

in which R50 and R51 are as defined above.

The term "sulfonyl" is art-recognized and includes a moiety that may be represented by the general formula:

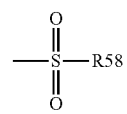

in which R58 is one of the following: hydrogen, alkyl, alkenyl, alkynyl, cycloalkyl, heterocyclyl, aryl or heteroaryl.

The term "sulfoxido" is art-recognized and includes a moiety that may be represented by the general formula:

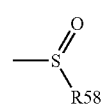

in which R58 is defined above.

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating red cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics.

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treating" as used herein is intended to encompass curing as well as ameliorating at least one symptom of any condition or disease.

For purposes of this invention, the chemical elements are identified in accordance with the Periodic Table of the Elements, CAS version, Handbook of Chemistry and Physics, 67th Ed., 1986-87, inside cover.

B. Small Molecule Compositions that Regulate 4E Activity, Cell Proliferation and Cancer In parallel studies, we examined the potential role of guanosine ribonucleoside analog and anti-viral agent Ribavirin (Sidwell, R. W., et al. (1972). *Science* 177:705-6.) in the regulation of 4E activity within the cell. Ribavirin is currently used for the treatment of infections with Lassa Fever virus, respiratory syncytial virus, hepatitis C virus and sever acute respiratory syndrome coronavirus. Mechanistically, it has been demonstrated recently that Ribavirin can misincorporated into mRNA by viral RNA-dependent RNA polymerases because of its chemical similarity to guanosine, and this outcome leads to the lethal mutagenesis of genomes of polio and HCV. Ribavirin triphosphate (RTP) binds the HCV polymerase with an observed dissociation constant of 0.58 mM which is consistent with the micromolar concentrations required to achieve a therapeutic effect against HCV clinically. By contrast to its effects at millimolar concentrations, Ribavirin inhibits the growth of human lymphocytes at micromolar levels, yet with no clear mechanism of action reported.

We determined that Ribavirin binds directly to 4E with low micromolar affinity in vitro; that this interaction occurs at concentrations 500-fold lower than those required for previously demonstrated activities of Ribavirin, that Ribavirin efficiently competes with 4E binding of the m7G mRNA cap in vitro and in cells at high nanomolar to low micromolar concentrations; that at these concentrations Ribavirin specifically mediates the disruption of 4E:m7G functions in the transport and translation of 4E-regulated genes at low micromolar concentrations in cells; that administration of high nanomolar to low micromolar concentrations of Ribavirin specifically down-regulates oncogenic protein production, induces cell cycle arrest thereby suppressing overall 4E activity in vitro and in vivo.

We have found that Ribavirin and new chemical entities/derivatives thereof possess the capacity to selectively inhibit the biological, proliferative and oncogenic properties of elevated 4E activity within cells, tissues and tumors. Unexpectedly, this targeted inhibition of elevated 4E activity does not impact other biological processes within the cells.

In particular, we have found that Ribavirin and new chemical entities/derivatives thereof possess the capacity to inhibit 4E regulon activity. Ribavirin has been observed to impede 4E regulon activity and reduce intracellular levels of 4E regulon components.

Accordingly, provided are small molecule compositions comprising small molecules of the following formula:

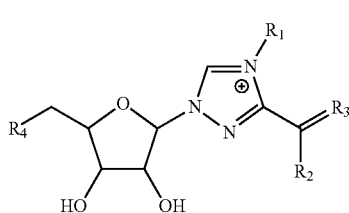

Formula I wherein:

R1 may be a linear or branched alkyl, alkenyl, hydrogen, alkynyl, and the like. Preferably, R1 is —H, —$CH_3$, or $CH_2CH_3$.

R2 may be an amine (primary, secondary, and tertiary, linear or branched), an aromatic amine, an amino group or an amido group. Preferably, R2 is —$NH_2$, —$NH_2CH_3$, —$NH_2CH_2CH_3$, —$NH_2CH_2CH_2CH_3$, —$NH_2CH(CH_3)_2$, —$NH_2CH_2CH_2CH_2OH$, —$NH_2CH_2CH_2CH(OH)CH_3$, or —$NH_2CH(CH_2OH)CH_3$.

R3 may be oxygen or sulfur; and

R4 may be a hydroxyl group, a phosphate group, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. The phosphate group, when present, may be optionally attached to at least one base, and is of the formula:

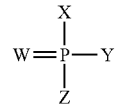

Ribovirin and its analogs are physical mimics of 7-methyl guanosine ($m^7G$). 7-methyl guanosine ($m^7G$) and analogs thereof (depicted in Formula II below) are also expected to inhibit 4E activity, in particular 4E regulon activity:

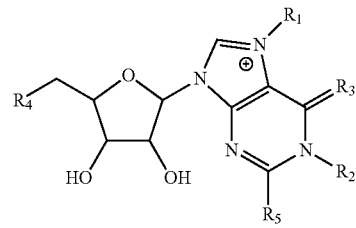

Formula II wherein:

R1 and R2 each independently may be a linear or branched alkyl, alkenyl, hydrogen, alkynyl, and the like. Preferably, R1 is —H, —$CH_3$, or $CH_2CH_3$. Preferably, R2 is —$CH_3$, —$CH_2CH_3$, —$CH_2CH_2CH_3$, —$CH(CH_3)_2$, —$CH_2CH_2CH_2OH$, —$CH_2CH_2CH(OH)CH_3$, or —$CH(CH_2OH)CH_3$;

R3 may be oxygen or sulfur;

R4 may be a hydroxyl group, a phosphate group, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. The phosphate group, when present, may be optionally attached to at least one base, and is of the formula:

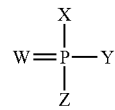

R5 may be an amine (primary, secondary, and tertiary, linear or branched), an aromatic amine, an amino group or an amido group.

Physically ribavirin is similar to the sugar D-ribose from which it is derived. It is freely soluble in water, and is re-crystallized as fine silvery needles from boiling methanol. It is only sparingly soluble in anhydrous ethanol. Classically ribaviriin is prepared from natural D-ribose by blocking the 2', 3' and 5' OH groups with benzyl groups, then derivatizing the 1' OH with an acetyl group which acts as a suitable leaving group upon nucleophilic attack. The ribose 1' carbon attack is accomplished with 1,2,4 triazole-3-carboxymethyl ester, which directly attaches the 1' nitrogen of the triazole to the 1' carbon of the ribose, in the proper 1-β-D isomeric position. The bulky benzyl groups hinder attack at the other sugar carbons. Following purification of this intermediate, treatment with ammonia in methanolic conditions then simultaneously deblocks the ribose hydroxyls, and converts the triazole carboxymethyl ester to the carboxamide. Following this step, ribavirin may be recovered in good quantity by cooling and crystallization.

Ribavirin is possibly best viewed as a ribosyl purine analogue with an incomplete purine 6-membered ring. This structural resemblance historically prompted replacement of the 2' nitrogen of the triazole with a carbon (which becomes the 5' carbon in an imidazole), in an attempt to partly "fill out" the second ring—but to no great effect. Such 5' imidazole riboside derivatives show antiviral activity with 5' hydrogen or halide, but the larger the substituent, the smaller the activity, and all proved less active than ribavirin (Harris, S. & Robins, R. K. (1980). Ribavirin: structure and antiviral activity relationships. In Ribavirin: A Broad Spectrum Antiviral Agent (Smith, R. A. & Kirkpatrick, W., Eds), pp. 1-21. Academic Press, New York, N.Y., USA). Note that two natural products were already known with this imidazole riboside structure: substitution at the 5' carbon with OH results in pyrazomycin/pyrazofurin, an antibiotic with antiviral properties but unacceptable toxicity, and replacement with an amino group results in the natural purine synthetic precursor 5-aminoimidazole-4-carboxamide-1-ß-D-ribofuranoside (AICAR), which has only modest antiviral properties.

Derivatization of the triazole 5' carbon, or replacement of it with a nitrogen (i.e., the 1,2,4,5 tetrazole 3-carboxamide) also results in substantial loss of activity, as does alkyl derivatization of the 3' carboxamide nitrogen.

The 2' deoxyribose version of ribavirin (the DNA nucleoside analogue) is not active as an antiviral, suggesting strongly that ribavirin requires RNA-dependent enzymes for its antiviral activity.

Antiviral activity is retained for acetate and phosphate derivation of the ribose hydroxyls, including the triphosphate and 3', 5' cyclic phosphates, but these compounds are no more active than the parent molecule, reflecting the high efficiency of esterase and kinase activity in the body.

Modifications of Formula I and Formula II can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein.);

(ii) alteration, e.g., replacement, of a constituent of the ribose sugar, e.g., of the 2' hydroxyl on the ribose sugar, or wholesale replacement of the ribose sugar with a structure other than ribose, e.g., an RRMS, as described herein;

(iii) wholesale replacement of the phosphate with "dephospho" linkers;

(iv) replacement or modification of the ribose-phosphate backbone (bracket II);

(v) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figures.

Certain compositions of the present invention may exist in particular geometric or stereoisomeric forms. In addition, certain compositions of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additional specific modifications are discussed in more detail below.

The Phosphate Group

The phosphate group is a negatively charged species. The charge is distributed equally over the two non-linking oxygen atoms (i.e., X and Y above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g. phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is preferred.

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

The Sugar Group

A modified RNA can include modification of all or some of the sugar groups of the ribonucleic acid. e.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.'

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; G-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

To maximize nuclease resistance, the 2' modifications can be used in combination with one or more phosphate linker modifications (e.g., phosphorothioate). The so-called "chimeric" oligonucleotides are those that contain two or more different modification.

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310).

Replacement of the Phosphate Group

The phosphate group, can be replaced by non-phosphorus containing connectors (cf. Bracket I in Formula I above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine, are fluorescent. Modified bases can reduce target specificity.

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908.

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein.

The most successful ribavirin derivative to date is the 3-carboxamidine derivative of the parent 3-carboxamide (1-[(2R,3R,4S,5S)-3,4-dihydroxy-5-(hydroxymethyl)oxolan-2-yl]-1,2,4-triazole-3-carboximidamide), first reported in 1973 by Witkowski, and now generally called viramidine (also "Ribamidine"). Considerations in designing prodrugs of ribavirin useful in the methods and compositions provided herein are discussed in Wu, et al. Journal of Antimicrobial Chemotherapy (2003) 52, 543-546.

Other ribavirin prodrugs and/or analogues/derivatives specifically contemplated for use in the methods and compositions provided herein are: methimazole, carbimazole, metronidazole, selanazofurin, showdomycin, pyrazomycin and ICN 3297, and analogs and derivatives thereof.

A number of techniques can be used to screen, identify, select and design chemical entities capable of inhibiting 4E activity, based on the structures described above. The term "chemical entity," as used herein, refers to chemical compounds, complexes of two or more chemical compounds, and fragments of such compounds or complexes. In certain instances, it is desirable to use chemical entities exhibiting a wide range of structural and functional diversity, such as compounds exhibiting different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings).

In one aspect, the method of drug design generally includes computationally evaluating the potential of a selected chemical entity to associate with 4E (or portions thereof). For example, this method may include the steps of (a) employing computational means to perform a fitting operation between the selected chemical entity and a druggable region of 4E; and (b) analyzing the results of said fitting operation to quantify the association between the chemical entity and 4E.

A chemical entity may be examined either through visual inspection or through the use of computer modeling using a docking program such as GRAM, DOCK, or AUTODOCK (Dunbrack et al., Folding & Design, 2:27-42 (1997)). This procedure can include computer fitting of chemical entities to a target to ascertain how well the shape and the chemical structure of each chemical entity will complement or interfere with the structure of the subject polypeptide (Bugg et al., Scientific American, December: 92-98 (1993); West et al., TIPS, 16:67-74 (1995)). Computer programs may also be employed to estimate the attraction, repulsion, and steric hindrance of the chemical entity to a druggable region, for example. Generally, the tighter the fit (e.g., the lower the steric hindrance, and/or the greater the attractive force) the more potent the chemical entity will be because these properties are consistent with a tighter binding constant. Furthermore, the more specificity in the design of a chemical entity the more likely that the chemical entity will not interfere with related proteins, which may minimize potential side-effects due to unwanted interactions.

A variety of computational methods for molecular design, in which the steric and electronic properties of druggable regions are used to guide the design of chemical entities, are known: Cohen et al. (1990) *J. Med. Cam.* 33: 883-894; Kuntz et al. (1982) *J. Mol. Biol* 161: 269-288; DesJarlais (1988) *J. Med. Cam.* 31: 722-729; Bartlett et al. (1989) *Spec. Publ., Roy. Soc. Chem.* 78: 182-196; Goodford et al. (1985) *J. Med. Cam.* 28: 849-857; and DesJarlais et al. *J. Med. Cam.* 29: 2149-2153. Directed methods generally fall into two categories: (1) design by analogy in which 3-D structures of known chemical entities (such as from a crystallographic database) are docked to the druggable region and scored for goodness-of-fit; and (2) de novo design, in which the chemical entity is constructed piece-wise in the druggable region. The chemical entity may be screened as part of a library or a data base of molecules. Data bases which may be used include ACD (Molecular Designs Limited), NCI (National Cancer Institute), CCDC (Cambridge Crystallographic Data Center), CAST (Chemical Abstract Service), Derwent (Derwent Information Limited), Maybridge (Maybridge Chemical Company Ltd), Aldrich (Aldrich Chemical Company), DOCK (University of California in San Francisco), and the Directory of Natural Products (Chapman & Hall). Computer programs such as CONCORD (Tripos Associates) or DB-Converter (Molecular Simulations Limited) can be used to convert a data set represented in two dimensions to one represented in three dimensions.

Chemical entities may be tested for their capacity to fit spatially with a druggable region or other portion of 4E. As used herein, the term "fits spatially" means that the three-dimensional structure of the chemical entity is accommodated geometrically by a druggable region. A favorable geometric fit occurs when the surface area of the chemical entity is in close proximity with the surface area of the druggable region without forming unfavorable interactions. A favorable complementary interaction occurs where the chemical entity interacts by hydrophobic, aromatic, ionic, dipolar, or hydrogen donating and accepting forces. Unfavorable interactions may be steric hindrance between atoms in the chemical entity and atoms in the druggable region.

If a model of the present invention is a computer model, the chemical entities may be positioned in a druggable region through computational docking. If, on the other hand, the model of the present invention is a structural model, the chemical entities may be positioned in the druggable region by, for example, manual docking. As used herein the term "docking" refers to a process of placing a chemical entity in close proximity with a druggable region, or a process of finding low energy conformations of a chemical entity/druggable region complex.

In an illustrative embodiment, the design of potential modulator begins from the general perspective of shape complimentary for the druggable region of a polypeptide of the invention, and a search algorithm is employed which is capable of scanning a database of small molecules of known three-dimensional structure for chemical entities which fit geometrically with the target druggable region. Most algorithms of this type provide a method for finding a wide assortment of chemical entities that are complementary to the shape of a druggable region of the subject polypeptide. Each of a set of chemical entities from a particular data-base, such as the Cambridge Crystallographic Data Bank (CCDB) (Allen et al. (1973) *J. Chem. Doc.* 13: 119), is individually docked to the druggable region of a polypeptide of the invention in a number of geometrically permissible orientations with use of a docking algorithm. In certain embodiments, a set of computer algorithms called DOCK, can be used to characterize the shape of invaginations and grooves that form the active sites and recognition surfaces of the druggable region (Kuntz et al. (1982) *J. Mol. Biol.* 161: 269-288). The program can also search a database of small molecules for templates whose shapes are complementary to particular binding sites of a polypeptide of the invention (DesJarlais et al. (1988) *J Med Chem* 31: 722-729).

The orientations are evaluated for goodness-of-fit and the best are kept for further examination using molecular mechanics programs, such as AMBER or CHARMM. Such algorithms have previously proven successful in finding a variety of chemical entities that are complementary in shape to a druggable region.

Goodford (1985, *J Med Chem* 28:849-857) and Boobbyer et al. (1989, *J Med Chem* 32:1083-1094) have produced a computer program (GRID) which seeks to determine regions of high affinity for different chemical groups (termed probes) of the druggable region. GRID hence provides a tool for suggesting modifications to known chemical entities that might enhance binding. It may be anticipated that some of the sites discerned by GRID as regions of high affinity correspond to "pharmacophoric patterns" determined inferentially from a series of known ligands. As used herein, a "pharmacophoric pattern" is a geometric arrangement of features of chemical entities that is believed to be important for binding. Attempts have been made to use pharmacophoric patterns as a search screen for novel ligands (Jakes et al. (1987) *J Mol Graph* 5:41-48; Brint et al. (1987) *J Mol Graph* 5:49-56; Jakes et al. (1986) *J Mol Graph* 4:12-20).

Yet a further embodiment of the present invention utilizes a computer algorithm such as CLIX which searches such databases as CCDB for chemical entities which can be oriented with the druggable region in a way that is both sterically acceptable and has a high likelihood of achieving favorable chemical interactions between the chemical entity and the surrounding amino acid residues. The method is based on characterizing the region in terms of an ensemble of favorable binding positions for different chemical groups and then searching for orientations of the chemical entities that cause maximum spatial coincidence of individual candidate chemical groups with members of the ensemble. The algorithmic details of CLIX is described in Lawrence et al. (1992) *Proteins* 12:31-41.

In this way, the efficiency with which a chemical entity may bind to or interfere with a druggable region may be tested and optimized by computational evaluation. For example, for a favorable association with a druggable region, a chemical entity must preferably demonstrate a relatively small difference in energy between its bound and fine states (i.e., a small deformation energy of binding). Thus, certain, more desirable chemical entities will be designed with a deformation energy of binding of not greater than about 10 kcal/mole, and more preferably, not greater than 7 kcal/mole. Chemical entities may interact with a druggable region in more than one conformation that is similar in overall binding energy. In those cases, the deformation energy of binding is taken to be the difference between the energy of the free entity and the average energy of the conformations observed when the chemical entity binds to the target.

In this way, the present invention provides computer-assisted methods for identifying or designing a potential modulator of the activity of 4E including: supplying a computer modeling application with a set of structure coordinates of a molecule or complex, the molecule or complex including at least a portion of a druggable region from 4E; supplying the computer modeling application with a set of structure coordinates of a chemical entity; and determining whether the chemical entity is expected to bind to the molecule or complex, wherein binding to the molecule or complex is indicative of potential modulation of the activity of 4E.

In another aspect, the present invention provides a computer-assisted method for identifying or designing a potential modulator to 4E, supplying a computer modeling application with a set of structure coordinates of a molecule or complex, the molecule or complex including at least a portion of a druggable region of 4E; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity, and determining whether the modified chemical entity is expected to bind to the molecule or complex, wherein binding to the molecule or complex is indicative of potential modulation of 4E.

An exemplary set of structural coordinates, the cap-free structure of 4E, for use in the methods is described in Volpon, et al. (2006) *EMBO J.* 25(21):5138-49. Epub 2006 Oct. 12. The activity of the eukaryotic translation initiation factor 4E is modulated through conformational response to its ligands. For example, eIF4G and 4E-BPs modulate cap affinity, and thus physiological activity of 4E, by binding a site distal to the m7G cap-binding site. Further, cap binding substantially modulates 4E's affinity for eIF4G and the 4E-BPs. Up to the date of Volpon, et al, only cap-bound 4E structures were reported. In the absence of structural information on the apo-form, the molecular underpinnings of this conformational response mechanism cannot be established. The cap-free 4E structure shows structural differences in the cap-binding site and dorsal surface relative to cap-eIF4E. Analysis of structure and dynamics of apo-eIF4E, and changes observed upon ligand binding, reveal a molecular basis for eIF4E's conformational response to these ligands. In particular, alterations in the S4-H4 loop, distal to either the cap or eIF4G binding sites, appear key to modulating these effects. Mutation in this loop mimics these effects.

Cap-bound 4E structures, such as those described in Marcotrigiano, J., et al. (1997) *Cell*, 89:951-961, Tomoo, K., et al. (2005) *Biochim Biophys Acta*, 1753:191-208, Tomoo, K., et al. (2002) *Biochem J*, 362:539-544 and Niedzwiecka, A., et al. (2002) *J Mol Biol*, 319:615-635, may also be used in the methods described herein.

In other embodiments, a potential modulator can be obtained by screening a library. A potential modulator selected in this manner could be then be systematically modified by computer modeling programs and/or by synthetic methods until one or more promising potential drugs are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). Alternatively a potential modulator may be selected from a library of chemicals such as those that can be licensed from third parties, such as chemical and pharmaceutical companies. A third alternative is to synthesize the potential modulator de novo.

Once a potential modulator is identified, it can then be tested in any standard assay for 4E activity or 4E expression and protein levels, or 4E regulon component expression and protein levels, including in high throughput assays. Further refinements to the structure of the modulator will generally be necessary and can be made by the successive iterations of any and/or all of the steps provided by the particular screening assay. These studies may be performed in conjunction with biochemical assays.

In any of the embodiments, the candidate compounds may be selected from a library of compounds. These libraries may be generated using combinatorial synthetic methods. The candidate compounds may be selected, for example, from the following classes of compounds: Ribavirin or ribaviring analogs, antisense nucleic acids, RNAi, small molecules, polypeptides, proteins, including antibodies, peptidomimetics, or nucleic acid analogs.

Specific, exemplary assays for 4E activity are described in the Exemplification below. However, any method for determining the effect of at least one candidate compound on 4E activity may be used. In certain embodiments, combinations of compounds or biologics may be screened for their effect on 4E activity to identify potential co-therapeutics or combination therapies. For example, Ribavirin or analogs or prodrugs thereof may be screened along with interferon, GMCSF, GCSF, IL-12, IL-2, compounds that inhibit or down-regulated tyrosine kinase activity, etc. In addition to measurement of cell proliferation, cell division, and/or gene expression as noted 4E polypeptide may be used to assess the activity of small molecules and other modulators in in vitro assays. In one embodiment of such an assay, agents are identified which modulate the biological activity of 4E, 4E-protein interaction of interest or 4E complex, such as an enzymatic activity, binding to other cellular components, cellular compartmentalization, signal transduction, and the like. In certain embodiments, the test agent is a small organic molecule. Analysis of the activity and/or expression levels of the components of the 4E regulon, e.g, in a cell line expressing 4E and possessing the regulon, may also be used to assess the effect of a modulator on 4E activity.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

Further provided are methods of screening compounds to identify those which modulate 4E activity. The method of screening may involve high-throughput techniques. For example, to screen for modulators, a synthetic reaction mix, a cellular compartment, such as a membrane, cell envelope or cell wall, or a preparation of any thereof, comprising 4E and a labeled substrate or ligand of such polypeptide is incubated in the absence or the presence of a candidate molecule that may be a modulator of 4E activity. The ability of the candidate molecule to modulate 4E activity is reflected in decreased binding of the labeled ligand or decreased production of product from such substrate. Detection of the rate or level of production of product from substrate may be enhanced by using a reporter system. Reporter systems that may be useful in this regard include but are not limited to colorimetric labeled substrate converted into product, a reporter gene that is responsive to changes in 4E activity, and binding assays known in the art.

Another example of an assay for a modulator of 4E activity is a competitive assay that combines 4E and a potential modulator with molecules that bind to 4E, recombinant molecules that bind to 4E, natural substrates or ligands, or substrate or ligand mimetics, under appropriate conditions for a competitive inhibition assay. The 4E can be labeled, such as by radioactivity or a colorimetric compound, such that the number of molecules of 4E bound to a binding molecule or converted to product can be determined accurately to assess the effectiveness of the potential modulator.

A number of methods for identifying a molecule which modulates 4E activity. For example, in one such method, a subject polypeptide is contacted with a test compound, and the activity of the subject polypeptide in the presence of the test compound is determined, wherein a change in the activity of the subject polypeptide is indicative that the test compound modulates the activity of the subject polypeptide. In certain instances, the test compound agonizes the activity of the subject polypeptide, and in other instances, the test compound antagonizes the activity of the subject polypeptide.

In other embodiments, a defined transformed cell type in culture may be used to assess 4E activity. Such a cell type may be produced through artificial or natural over-expression of one or more oncogenes. For example, the cell type may overexpress 4E, or a protein that is an component of the 4E regulon that affects cellular transport, transformation and proliferation, such as myc, cyclin D, etc.

Screening of modulators using cell lines possessing over-expressed oncogenes may be accomplished through the analysis of any one or combinations of the following: (1) 4E expression, protein level, cellular proliferation rate; (2) myc expression, protein level, nuclear/cytoplasmic ratio, cellular proliferation rate; (3) cyclin D1 expression, protein level, nuclear/cytoplasmic ratio, cellular proliferation rate; (4) inhibition of cyclin D1 or other regulon component mRNA transport (nucleus to cytoplasm) and/or cyclin D1 or other regulon component mRNA translation; (5) inhibition of cyclin D1 or other regulon component transcription; (6) inhibition of 4E-SE regulated mRNA transport (nucleus to cytoplasm) and/or 4E-SE mRNA translation; (7) inhibition of 4E-SE regulated mRNA gene transcription.

Once identified, a potential modulator may be used as a model structure, and analogs to the compound can be obtained. The analogs are then screened for their ability to modulate 4E activity as described above.

In a related approach, iterative drug design is used to identify modulators of 4E activity. Iterative drug design is a method for optimizing associations between a protein and a modulator by determining and evaluating the three dimensional structures of successive sets of protein/modulator complexes. In iterative drug design, crystals of a series of protein/modulator complexes are obtained and then the three-dimensional structures of each complex is solved. Such an approach provides insight into the association between the proteins and modulators of each complex. For example, this approach may be accomplished by selecting modulators with inhibitory activity, obtaining crystals of this new protein/modulator complex, solving the three dimensional structure of the complex, and comparing the associations between the new protein/modulator complex and previously solved protein/modulator complexes. By observing how changes in the modulator affected the protein/modulator associations, these associations may be optimized.

Further provided are pharmaceutical compositions comprising the above-described compounds of Formulas I and II and/or the additional compounds described herein. In one aspect, the present invention provides pharmaceutically acceptable compositions which comprise a therapeutically-effective amount of one or more of the compounds described above, formulated together with one or more pharmaceutically acceptable carriers (additives) and/or diluents. In another aspect, certain embodiments, the compounds of the invention may be administered as such or in admixtures with pharmaceutically acceptable carriers and may also be administered in conjunction with other agents. Conjunctive (combination) therapy thus includes sequential, simultaneous and separate, or co-administration of the active compound in a way that the therapeutical effects of the first administered one is not entirely disappeared when the subsequent is administered.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art. While it is possible for a compound of the present invention to be administered alone, it is preferable to administer the compound as a pharmaceutical formulation (composition). The compounds according to the invention may be formulated for administration in any convenient way for use in human or veterinary medicine, by analogy with other pharmaceuticals. In certain embodiments, a prodrug form of a compound of Formulas I or II comprises the pharmaceutical compositions of the present invention.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In one embodiment, the pharmaceutical compositions are formulated for parenteral administration. In one embodiment, the pharmaceutical composition is formulated for intraarterial injection. In another embodiment, the pharmaceutical compositions are formulated for systemic administration.

In other cases, the compounds of the present invention may contain one or more acidic functional groups and, thus, are capable of forming pharmaceutically-acceptable salts with pharmaceutically-acceptable bases.

Wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which may be combined with a carrier material to produce a single dosage form will vary depending upon the host being treated, the particular mode of administration. The amount of active ingredient which may be combined with a carrier material to produce a single dosage form will generally be that amount of the compound which produces a therapeutic effect. In certain embodiments, the carrier material is covalently linked to the compound or other agent in the composition.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate or cyclodextrin and its salts, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, cyclodextrin and its salts, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

C. Therapeutic Use of Small Molecule Compositions of Section B

The levels of compounds of Formulas I and II and/or the additional compounds described herein required to effect the inhibition of elevated 4E activity within cells, tissues, tumors and/or cancers is micromolar. Thus the therapeutic level at which Ribavirin inhibits 4E activity is 500-fold less than the quantities previously described that provide mechanistically for the use of compounds of Formulas I and II as a co-therapy with interferon for the treatment of hepatitis. Moreover, compounds of Formulas I and II that are active in inhibiting 4E activity within cells, tissues, tumors and/or cancers represent a distinctive shape and charge space from those active at millimolar levels in concert with the co-administration of IFN for the treatment of hepatitis. Indeed, in mouse models of metastases by Hairisi and colleagues, Ribavirin was observed to reduce liver metastatic disease (Jeney, A., et al. (2006) *Magy. Onkol.* 50:93-100).

Accordingly, we have discovered that compounds of Formulas I and II will inhibit the growth, proliferation and seeding of new/metastatic cancers within individuals, thereby either permitting natural/endogenous immuno-logical processes within the patient to attack and affect the complete removal of the tumor; alternatively cancer therapy based on the compounds of Formulas I and II will permit the long-term management of 4E activity cancers through chronic administration of compounds of Formulas I and II at doses 500-fold less than those required for the treatment of hepatitis and far below levels that may be toxic during the chronic administration of compounds of Formulas I and II required to affect the long-term management of disease conditions where elevated 4E activities are operative, including cancers, tumors and the like.

Prevention of the continued growth and proliferation of existing cancers (rendering them static) represents a huge advance in the management of the many cancers exhibiting elevated 4E activity—including head/neck, breast prostate, lung, cervix, among others.

In addition, as many of the angiogenic and autocrine factors produced by cancers are 4E regulated at the translational level, therapy comprising the administration of compounds of Formulas I and II therapy is anticipated to inhibit the process of angiogenesis required for the continued growth and establishment of metastatic cancers . . . .

Thus, the administration of compounds of Formulas I and II may provide therapeutic interventions that are determined to be appropriate for additional non-cancerous conditions where elevated 4E activity is determined to be a causative factor.

Accordingly, provided are methods of treating subjects in need thereof with compositions comprising compounds of Formulas I and II and/or the additional compounds described herein. The compounds of Formulas I and II inhibit elevated 4E activity, e.g. by targeting 4E. In particular, they inhibit cellular proliferation and 4E regulon activity in cells, tissues and mammals, e.g., where there exists a condition of elevated 4E activity. Thus, the compounds of Formulas I and II are expected to act as inhibitors of cancer cell proliferation, especially in cells tissues, mammals where there exists a condition of elevated 4E activity. Thus, they may be used in methods of inhibiting elevated 4E activity in a cell, tissue or mammal and in methods of inhibiting cellular proliferation in a cell, tissue or mammal.

Compositions comprising compounds of Formulas I and II and/or the additional compounds described herein also may be used in treating a subject having cancer. The compositions may be especially useful in treating conditions caused by elevated 4E activity, for example, cancer, as defined above. The compositions comprising compounds of Formulas I and II and/or the additional compounds described herein may also be used as inhibitors and/or dose-dependent regulators of any of the cancer therapeutic vectors disclosed below, as will be described in more detail below.

In certain embodiments, the compositions comprising compounds of Formulas I and II may inhibit the metastatic phenotype represented by elevated 4E activity, thus resulting in prophylactic anti-metastasis.

In certain embodiments, therapies comprising the use of compounds of Formulas I and II may also comprise the use of other cancer therapeutics, such as interferon, kinase inhibitors, gene therapy vectors as described further below in Section D and/or chemotherapeutic agents, biologics and cytotoxins described immediately below.

The term "chemotherapeutic agent" refers to any small molecule or composition used to treat disease caused by a foreign cell or malignant cell, such as a tumor cell. Non-limiting examples of chemotherapeutic agents include agents that disrupt DNA synthesis, are inhibitors of topoisomerase I, are alkylating agents, or are plant alkaloids. The term "agent that disrupts DNA synthesis" refers to any molecule or compound able to reduce or inhibit the process of DNA synthesis. Examples of agents that disrupt DNA synthesis include but are not limited to nucleoside analogs such as pyrimidine or purine analogs, including, for example but not limited to, gemcitabine or alternatively anthracycline compounds, including for example but not limited to, adriamycin, daunombicin, doxorabicin, and idambicin and epi-podophyllotoxins such as etoposide and teniposide. The term "topoisomerase I inhibitor" refers to a molecule or compound that inhibits or reduces the biological activity of a topoisomerase I enzyme. Including for example, but not limited to, camptosar. The term "alkylating agent" refers to any molecule or compound able to react with the nucleophilic groups of (for examples, amines, alcohols, phenols, organic and inorganic acids) and thus add alkyl groups (for example, ethyl or methyl groups) to another molecule such as a protein or nucleic acid. Examples of alkylating agents used as chemotherapeutic agents include bisulfan, chlorambucil, cyclophosphamide, ifosfamide, mechlorethamine, melphalan, thiotepa, various nitrosourea compounds, and platinum compounds such as cisplatin and carboplatin. The term "plant alkaloid" refers a compound belonging to a family of alkaline, nitrogen-containing molecules derived from plants that are biologically active and cytotoxic. Examples of plant alkoids include, but are not limited to, taxanes such as taxol, docetaxel and paclitaxel and vincas such as vinblastine, vincristine, and vinorelbine.

Biologics may include antibodies or antigen binding fragments thereof, that bind to a targetable component of a tumor cell, tumor vasculature or tumor stroma. A "targetable component" of a tumor cell, tumor vasculature or tumor stroma, is preferably a surface-expressed, surface-accessible or surface-localized component, although components released from necrotic or otherwise damaged tumor cells or vascular endothelial cells may also be targeted, including cytosolic and/or nuclear tumor cell antigens.

Biologics may also include anti-tumor cell immunotoxins or coaguligands such as antibodies exemplified by the group consisting of B3 (ATCC HB 10573), 260F9 (ATCC HB 8488), D612 (ATCC HB 9796) and KS1/4, said KS1/4 antibody obtained from a cell comprising the vector pGKC2310 (NRRL B-18356) or the vector pG2A52 (NRRL B-18357). Biologics may be anti-tumor stroma immunotoxins or coaguligands, for example, antibodies that bind to a connective tissue component, a basement membrane component or an activated platelet component; as exemplified by binding to fibrin, RIBS or LIBS.

Biologics such as anti-tumor vasculature immunotoxins or coaguligands may also comprise ligands, antibodies, or fragments thereof, that bind to a surface-expressed, surface-accessible or surface-localized component of the blood transporting vessels, preferably the intratumoral blood vessels, of a vascularized tumor. Such antibodies include those that bind to surface-expressed components of intratumoral blood vessels of a vascularized tumor, including aminophospholipids themselves, and intratumoral vasculature cell surface receptors, such as endoglin (TEC-4 and TEC-11 antibodies), a TGF.beta. receptor, E-selectin, P-selectin, VCAM-1, ICAM-1, PSMA, a VEGF/VPF receptor, an FGF receptor, a TIE, .alpha.sub.v.beta.sub.3 integrin, pleiotropin, endosialin and MHC Class II proteins. The antibodies may also bind to cytokine-inducible or coagulant-inducible components of intratumoral blood vessels.

Other anti-tumor vasculature immunotoxins or coaguligands may comprise antibodies, or fragments thereof, that bind to a ligand or growth factor that binds to an intratumoral vasculature cell surface receptor. Such antibodies include those that bind to VEGF/VPF (GV39 and GV97 antibodies), FGF, TGF.beta., a ligand that binds to a TIE, a tumor-associated fibronectin isoform, scatter factor/hepatocyte growth factor (HGF), platelet factor 4 (PF4), PDGF and TIMP. The antibodies, or fragments thereof, may also bind to a ligand:receptor complex or a growth factor:receptor complex, but not to the ligand or growth factor, or to the receptor, when the ligand or growth factor or the receptor is not in the ligand:receptor or growth factor:receptor complex.

Cytotoxic agents such as plant-, fungus- or bacteria-derived toxins (immunotoxins). Ricin A chain, deglycosylated ricin A chain, gelonin and angiopoietins may also be used in combination therapies.

Dosage may be based on the amount of the composition per kg body weight of the patient. Other amounts will be known to those of skill in the art and readily determined. Alternatively, the dosage of the subject invention may be determined by reference to the plasma concentrations of the composition. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

Dosage levels of between about 0.01 and about 5 mg/kg body weight per day, preferably between about 0.1 and about 2.5 mg/kg body weight per day of the modulators described herein are useful for the prevention and treatment of disease and conditions related to 4E activity. The amount of active ingredient that may be combined with the carrier materials to produce a single dosage form will vary depending upon the host treated and the particular mode of administration.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day. Toxicity and therapeutic efficacy of subject compounds may be determined by standard pharmaceutical procedures in cell cultures or experimental animals, e.g., for determining the LD50 and the ED50. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the ED50 with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

D. Compositions for Gene Therapy

Provided also are compositions comprising gene therapeutic vectors and viruses that, among other things, enhance regulation of mRNA nuclear to cytoplasmic transport and/or mRNA translation. The vectors and viruses may comprise nucleic acids, e.g., DNA constructs or mRNAs, encoding proteins contained within gene therapeutic vector/virus required for vector and/or viral replication and/or lysis, nucleic acids, e.g., mRNAs, encoding therapeutic proteins required for gene therapeutic activity including but not limited to toxins, lytic peptides and/or proteins and/or processes and therapeutic proteins including but not limited to prodrug converting enzymes (aka suicide genes), anti-angiogenic proteins, apoptosis cascade enzymes, tumor suppressors, cytokines and immunologically active proteins, RNAi anti-sense, and the like.

We explored the possibility that in the nucleus that 4E recognition of mRNA is fundamentally different than in the cytoplasm and identified a 100-nt sequence from the cyclin D1 3-UTR which sensitizes this mRNA to 4E in the nucleus, is required for nuclear to cytoplasmic transport of mRNAs containing this sequence and which participates in 4E mediated cellular transformation.

Provided accordingly is the 4E-SE sequence in FIG. 14c (SEQ ID NO:1). The sequence may serve as a 3'UTR, 5'UTR, or other control element of an mRNA or DNA construct, which may in some embodiments serve to make the nuclear to cytoplasmic transport and/or translation of said mRNA dependent upon the presence of elevated 4E activity. Allowing for the degeneracy of the genetic code, sequences that have at least about 70%, most usually about 80%, preferably at least about 90% and most preferably about 95% of nucleotides that are identical to SEQ ID NO: 1 are polynucleotides that may be used in the constructs and vectors described herein, provided that they include the minimal ~50 nucleotide region of FIG. 19a.

Such constructs and vectors comprising 4E-SE may have the following properties and uses. In certain embodiments, vector and viral replication may be placed under 4E-SE regulation. In other embodiments, vector/viral induced cellular lysis may be placed under 4E-SE control element regulation. In still other embodiments, nuclear to cytoplasmic transport and/or translation of one or more vector/virally encoded mRNAs may be placed under 4E-SE control element regulation. In other embodiments, the nuclear to cytoplasmic transport and/or translation of one or more of vector/virally encoded mRNAs required for cellular lysis may be placed under 4E-SE regulation.

Any of above described vectors may contain an intron encoding an RNA or mRNA as appropriate for one or more of the following: toxins; lytic peptides and/or proteins/processes; regulators of angiogenesis, apoptosis cascade enzymes, tumor suppressors, cytokines and immunologically active proteins (including but not limited to interferon, GMCSF, GCSF and others which have been demonstrated to enhance host immune response to tumors yet where systemic delivery is often associated with significant side/detrimental clinical effects), RNAi, RNA anti-sense, and the like.

The resultant vectors may provide for enhanced selectivity and restriction of gene therapeutic expression, enhanced selectivity and restriction of gene therapeutic expression to environments possessing elevated 4E activity, and/or enhanced selectivity and restriction of gene therapeutic expression to environments possessing elevated 4E activity thereby rendering the transport and/or translation subject to inhibition by any of the compounds of Formulas I and II disclosed above.

Inhibition of the gene therapeutic activity of any of the above vectors via the administration of any of the compounds of Formulas I and II provides a method of inhibiting gene therapeutic activity and thereby halting the therapeutic process should the administration of the gene therapeutic provide an unfavorable impact upon the subject mammal to which it has been administered. Targeted presentation within elevated 4E cellular and/or tissue environments provides enhanced selectivity and specificity to cells and/or tissues possessing an elevated 4E environment. Improved targeting of such gene therapeutics to increase the efficacy of such agents and/or to reduce systemic toxicity often reported subsequent to the systemic (non-targeted) administration of these classes of agents. Thus, the compounds of Formulas I and II may serve as inhibitors and/or dose-dependent regulators of any of the vectors disclosed herein. Various embodiments of combination therapies comprising vectors and the compounds of Formulas I and II are described in the next section.

Gene therapeutic vectors exhibiting enhanced efficacy profiles may also comprise any of the vectors described above containing an intron encoding an mRNA encoding an improved prodrug metabolizing/converting enzyme. The doubly improved prodrug metabolizing/converting enzyme may be selected from among (but not limited by) those disclosed by Black, Loeb and co-workers (thymidine kinases and/or cytosine deaminase) which provide but are not limited to possessing enhanced affinity and/or selectivity for prodrug substrate, and/or rate of prodrug conversion to active desired cytotoxic product and the like.

Any gene therapeutic intron or viral lytic replication element as disclosed herein may be replaced with any of the following therapeutic introns or RNAs including but without limitation to the following classes of agents: (1) anti-sense RNA, RNAi, ribozymes, single chain antibodies targeted and designed to inhibit either the RNAs and mRNAs expressed within elevated 4E environments and/or inhibit the activity of the translation products of mRNAs expressed within elevated 4E environments in cells, tissues and animals and (2) RNAi, antisense and/or ribozymes targeted to 4E-SE control element sequences. Such gene therapeutics are referred to as "inhibitory gene therapeutics" herein. They may be administered in vitro or in vivo using methods known in the art.

Constructs and vectors may contain (a) a transcriptional control element as described above, and (b) flanking DNA sequence from a target gene permitting the homologous recombination of the transcriptional control element into a host cell in association with the target gene. In other embodiments the construct or vector contains a desired gene and flanking DNA sequence from a target locus permitting the homologous recombination of the target gene into the desired locus. The construct or vector may also contain the responsive transcriptional control element, or the responsive element may be provided by the locus.

The constructs or vectors may also contain a selectable marker permitting transfection of the constructs into host cells and selection of transfectants containing the construct or vector. This invention further encompasses DNA vectors containing such constructs, whether for episomal transfection or for integration into the host cell chromosomes. The vector may be a viral vector, including for example an adeno-, adeno associated- or retroviral vector.

Vectors, such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Several recently issued patents are directed to methods and compositions for performing gene therapy. See U.S. Pat. Nos. 6,168,916; 6,135,976; 5,965,541 and 6,129,705. Each of the foregoing patents is incorporated by reference herein.

E. Additional Combination Therapies and Co-Therapies

In addition to the combination therapies described in Section D, the compounds of Formulas I and II may serve as inhibitors and/or dose-dependent regulators of any of the inhibitory gene therapeutics disclosed above. For example, the compounds of Formulas I and II may serve as inhibitors (whether present alone or in concert) of 4E-SE as described above, including when 4E-SE is a control element of an mRNA.

Further, in other embodiments, the compounds of Formulas I and II may serve as inhibitors (whether present alone or in concert) of mRNA transport and/or translation. For example, the compounds of Formulas I and II may serve as inhibitors (whether present alone or in concert) of the transport and/or translation of mRNAs containing 4E-SE as described above, including when 4E-SE is a control element of an mRNA.

In still other embodiments, the compounds of Formulas I and II may serve as inhibitors of vector or viral replication under 4E-SE regulation. Further, in other embodiments, the compounds of Formulas I and II may serve as inhibitors of vector or viral induced cellular lysis under 4E-SE regulation. In yet another embodiment, the compounds of Formulas I and II may serve as inhibitors of the nuclear to cytoplasmic transport and/or translation of one or more vector or virally encoded mRNAs, e.g., such as those required for cellular lysis, under 4E-SE regulation and/or of one or more therapeutic gene mRNAs or introns contained within any of the above vectors under 4E-SE regulation.

The gene therapeutics described herein and small molecule inhibitors of mRNA nuclear to cytoplasmic transport and/or protein translational processes (such as compounds of Formulas I and II) may be used together or in concert to inhibit elevated 4E activity within cells, tissues and mammals, to inhibit cellular proliferation within cells, tissues and mammals (e.g., those possessing elevated 4E activity), and/or to inhibit cellular proliferation within cancers and/or tumors (e.g., those possessing elevated 4E activity).

Such enhanced methods and compositions for the treatment of cell proliferative disorders in which there exists elevated 4E activity where administration of small molecules and/or gene therapeutics alone or in concert may fail to eradicate the cell proliferative disorder or cancer or tumor, yet inhibit its continued proliferation and expansion, thus providing either an entre for the host immune system to eradicate the cell proliferative disorder or tumor or cancer; or serving to make the cell proliferative disorder or tumor or cancer manageable through the routine administration of small molecules with or without the periodic co-administration of additional systemic agents/biologics, and/or the periodic co-administration of any one/more of the gene therapeutics methodologies disclosed herein. Where conditions are arrived at in the above embodiment so to render the cell proliferative disorder, cancer or tumor "phenotypically revertant" thereby transitioning the disease process from life threatening to a chronic disease state.

F. Protein Expression

Any of the gene therapeutics and/or gene diagnostics disclosed herein may be used to provide to the production of therapeutic proteins within eukaryotic protein expression systems such the following which are provided only as a non-exclusive list of the various expression systems (mammalian cells, insect cells and/or yeast and the like) where the selective nuclear to cytoplasmic transport and translation of proteins under 4E-SE control (as disclosed herein) within a cellular environment in which there exists elevated 4E activity.

The compounds of Formulas I and II may serve as inhibitors and/or dose-dependent regulators of any of the gene therapeutics disclosed herein. In vitro therapeutic protein production systems in which mRNAs which are translated into structural proteins which are detrimental to the isolation of therapeutic protein(s) of interest which can be improved via the introduction of 4E-SE control elements within these detrimental elements such that prior to the commencement of therapeutic protein isolation the addition of compounds of Formulas I and II acts to inhibit the transport and translation of the detrimental mRNAs. The inhibition (or the removal from compounds of Formulas I and II-mediated inhibition) of non-therapeutic protein synthesis via the addition (or removal) of compounds of Formulas I and II serves to enhance the subsequent isolation of the therapeutic protein of interest.

Protein expression systems in which the therapeutic protein of interest is under the control of an inducible promoter and where compounds of Formulas I and II can either serve to enhance the basal repression mediated by the inducible promoter (via inhibition of mRNA transport and translation) may serve to regulate in a dose-dependent fashion mRNA transport and translation post additional on the inducible promoter 'ligand' or inhibit transport and translation of the therapeutic protein also post-induction.

Within certain embodiments, expression vectors are employed. Expression requires that appropriate signals be provided in the vectors, which include various regulatory elements, such as enhancers/promoters from both viral and mammalian sources that drive expression of the genes of interest in host cells. Elements designed to optimize messenger RNA stability and translatability in host cells are also defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a polynucleotide coding for a gene product in which part or all of the polynucleotide encoding sequence is capable of being transcribed. The transcript may be translated into a protein, but it need not be. In certain embodiments, expression includes both transcription of a gene and translation of mRNA into a gene product. In other embodiments, expression only includes transcription of the polynucleotide encoding a gene of interest.

The polynucleotide encoding a gene product may be under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the polynucleotide to control RNA polymerase initiation and expression of the gene.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30 to 110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a polynucleotide sequence of interest is not believed to be important, so long as it is capable of directing the expression of the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter. The use of viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate.

In certain indications, it may be desirable to activate transcription at specific times after administration of the gene therapy vector. This may be done with such promoters as those that are hormone or cytokine regulatable. Cytokine and inflammatory protein responsive promoters that could be used include K and T Kininogen, c-fos, TNF-alpha, C-reactive protein, haptoglobin, serum amyloid A2, C/EBP alpha, IL-1, IL-6, Complement C3, IL-8, alpha-1 acid glycoprotein, alpha-1 antitypsin, lipoprotein lipase, angiotensinogen, fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

Tumor specific promoters such as osteocalcin; hypoxia-responsive element (HRE), MAGE-4, CEA, alpha-fetoprotein, GRP78/BiP and tyrosinase may also be used to regulate gene expression in tumor cells. Other promoters that could be used according to the present invention include Lac-regulatable, chemotherapy inducible (e.g. MDR), and heat (hyperthermia) inducible promoters, radiation-inducible (e.g., EGR), Alpha-inhibin, RNA pol III tRNA met and other amino acid promoters, U1 snRNA, MC-1, PGK, .beta.-actin and .alpha.-globin. Many other promoters that may be useful are listed in Walther and Stein (1996) *J. Mol. Med,* 74:379-392.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are frequently overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells contain polynucleotide constructs of the present invention, and a cell may be identified in vitro or in vivo by including a marker in the expression construct. Such markers will confer an identifiable change to the cell permitting easy identification of cells containing the expression construct. Usually the inclusion of a drug selection marker aids in cloning and in the selection of transformants, for example, genes that encode neomycin, puromycin, hygromycin, DHFR, GPT, HPRT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the polynucleotide encoding a gene product. Further examples of selectable markers are well known to one of skill in the art.

In certain embodiments of the invention, internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, (1988) *Nature* 334:320 325). IRES elements from two members of the picanovirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins, and selectable markers. In this way, expression of several proteins can be simultaneously engineered into a cell with a single construct and a single selectable marker.

There are a number of ways to introduce expression vectors into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells. The first viruses used as gene vectors were DNA viruses including the papovaviruses (simian virus 40, bovine papilloma virus, and polyoma) and adenoviruses. These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals.

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector, a polynucleotide encoding a gene of interest is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin. Using antibodies against major histocompatibility complex class I and class II antigens, they demonstrated the infection of a variety of human cells that bore those surface antigens with an ecotropic virus in vitro.

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes. Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination.

Lentiviruses can also be used as vectors in the present application. In addition to the long-term expression of the tran-transgene provided by all retroviral vectors, lentiviruses present the opportunity to transduce nondividing cells and potentially achieve regulated expression. The development of lentiviral vectors requires the design of transfer vectors to ferry the transgene with efficient encapsidation of the transgene RNA and with full expression capability, and of a packaging vector to provide packaging machinery in trans but without helper virus production. For both vectors, a knowledge of packaging signal is required—the signal to be included in the transfer vector but excluded from the packaging vector. Exemplary human lentiviruses are human immunodeficiency virus type 1 and type 2 (HIV-1 and HIV-2). HIV-2 is likely better suited for gene transfer than HIV-1 as it is less pathogenic and thus safer during design and production; its desirable nuclear import and undesirable cell-cycle arrest functions are segregated on two separate genes.

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100 200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Methods for culturing 293 cells and propagating adenovirus may include growing natural cell aggregates by inoculating individual cells into 1 liter siliconized spinner flasks (Techne, Cambridge, UK) containing 100 200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers, e.g., $10^9$ $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential as in vivo gene transfer vectors.

Adenovirus vectors have been used in eukaryotic gene expression and vaccine development. Recently, animal studies suggested that recombinant adenovirus could be used for gene therapy (Stratford-Perricaudet and Perricaudet, (1991) In: *Human Gene Transfer*, Eds, O. Cohen-Haguenauer and M. Boiron, Editions John Libbey Eurotext, France, pp. 51 61; Stratford-Perricaudet et al. (1990) *Hum. Gene Ther.*, 1:241 256; and Rich et al. (1993) *Hum. Gene Ther.*, 4:461 476). Studies in administering recombinant adenovirus to different tissues include trachea instillation, muscle injection, peripheral intravenous injections and stereotactic inoculation into the brain.

Adeno-associated virus (AAV) utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map-units, in the genome. These are, from left to right, p5, p19 and p40. Transcription gives rise to six transcripts, two initiated at each of three promoters, with one of each pair being spliced. The splice site, derived from map units 42 46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of an AAV vector can be obtained by restriction endonuclease digestion of AAV or a plasmid such as psub201, which contains a modified AAV genome, or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e. stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicle for gene delivery in vitro, and these vectors are now being developed and tested in pre-clinical and clinical stages for a wide range of applications in potential gene therapy, both ex vivo and in vivo.

Other viral vectors may be employed as expression constructs in the present invention. Vectors derived from viruses such as vaccinia virus (Baichwal and Sugden (1986) In: Gene Transfer, Kucherlapati R, ed., New York, Plenum Press, 117 148) adeno-associated virus (AAV) (Baichwal and Sugden, 1986) moloney murine leukemia virus (Mo-MuLV); VSV-G type retroviruses (U.S. Pat. No. 5,817,491, specifically incorporated herein by reference), papovaviruses such as JC, SV40, polyoma (U.S. Pat. No. 5,624,820, specifically incorporated herein by reference) Epstein-Barr Virus (EBV); papilloma viruses (U.S. Pat. No. 5,674,703, specifically incorporated herein by reference), and more particularly, bovine papilloma virus type I (BPV; U.S. Pat. No. 4,419,446, incorporated herein by reference); poliovirus herpesviruses and other human and animal viruses may be employed. These viruses offer several attractive features for various mammalian cells.

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsulated in an infectious viral particle.

Several non-viral methods for the transfer of expression constructs into cultured mammalian cells also are contemplated by the present invention. These include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection. Some of these techniques may be successfully adapted for in vivo or ex vivo use.

Once the expression construct has been delivered into the cell the polynucleotide encoding the gene of interest may be positioned and expressed at different sites. In certain embodiments, the polynucleotide encoding the gene may be stably integrated into the genome of the cell. This integration may be in the cognate location and orientation via homologous recombination (gene replacement) or it may be integrated in a random, non-specific location (gene augmentation). In yet further embodiments, the polynucleotide may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the polynucleotide remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. It is envisioned that DNA encoding a gene of interest may also be transferred in a similar manner in vivo and express the gene product.

In still another embodiment of the invention, transferring a naked DNA expression construct into cells may involve particle bombardment. This method depends on the ability to accelerate DNA-coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

Selected organs including the liver, skin, and muscle tissue of rats and mice have been bombarded in vivo. This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. Since these expression constructs have been successfully employed in transfer and expression of polynucleotides in vitro and in vivo, then they are applicable for the present invention. Where a bacterial promoter is employed in the DNA construct, it also will be desirable to include within the liposome an appropriate bacterial polymerase.

Other expression constructs which can be employed to deliver a polynucleotide encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin. Recently, a synthetic neoglycoprotein, which recognizes the same receptor as ASOR, has been used as a gene delivery vehicle and epidermal growth factor (EGF) has also been used to deliver genes to squamous carcinoma cells.

In other embodiments, the delivery vehicle may comprise a ligand and a liposome. For example, epidermal growth factor (EGF) may be used as the receptor for mediated delivery of a polynucleotide encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells in vitro, and then the return of the modified cells back into an animal. This may involve the surgical removal of tissue/organs from an animal or the primary culture of cells and tissues.

G. Methods of Diagnosing Elevated 4E Activity

The above-described methods and compositions may be incorporated into diagnostic methods to detect 4E activity, for example, detect elevated 4E levels, expression of 4E, activity or expression of 4E regulon components, etc. Such methods may provide enhanced detection of elevated 4E conditions in an animal, tissue or cell, new methods of diagnosing, detecting during surgery, following clinical course of therapeutic efficacy and disease progression/regression and methods for identifying compounds and/or biologics that inhibit the transport and or translation any/all/one of gene diagnostics as described herein. For example, a method for identifying a candidate therapeutic for treating cancer may comprise: (a) contacting a cell with said candidate therapeutic, (b) determining in the cell pre- and post-contact with said candidate therapeutic the level of 4E activity or 4E regulon component activity, wherein modulation of the level of 4E activity or 4E regulon component activity indicates that the candidate therapeutic may be a therapeutic agent for treating or preventing cancer. This approach may be used to further define and/or refine the appropriate human dosing levels in situations where pre- and post-contact samples consist of patient biopsies, samples, and the like. The candidate therapeutic may be part of a library of candidate therapeutics, for example, one generated using combinatorial synthetic methods.

Replacement of any gene therapeutic intron or viral lytic replication element as disclosed herein with a gene diagnostic permits the identification of situations were elevated 4E environments exist within cells and/or tissues. Such gene diagnostic introns can be administered in vitro or in vivo. The gene diagnostic introns can include without limitation those encoding mRNAs for any of the following: (1) in vivo diagnostic gene administration and methods of imaging as disclosed herein (see above), (2) prodrug metabolizing enzymes that convert appropriate imaging probes (PET probes and the like) thereby serving to concentrate and localize the imaging agent to the interior of cells and/or tissues where an elevated 4E environment exists, (3) prodrug metabolizing enzymes that convert prodrugs (GCV, ACV, 5FC and the like) to active cytotoxic metabolites which are concentrated and localized within environments possessing elevated 4E activity, thereby inhibiting cellular proliferation and/or inducing cell death, (4) fluorescent proteins (green fluorescent protein and the like for example) that serve to identify cells and/or tissues where an elevated 4E environment exists, (5) beta-galactosidase which when incubated together with appropriate substrates serves to identify cells and/or tissues where an elevated 4E environment exists and (6) viral replication elements thereby permitting detection of elevated 4E activity through cellular lysis.

Methods for determining the activity of 4E are well known in the art. 4E activity as defined herein also includes evaluating 4E regulon activation, expression and/or activity of components under control of the 4E regulon, elevated transport of selected messages (especially cyclin D1) from the nucleus to the cytoplasm and phosphorylation state of 4E and levels of eIF4eBP.

For example, the expression level of 4E regulon components can be determined by reverse transcription-polymerase chain reaction (RT-PCR); dotblot analysis; Northern blot analysis, total mRNA by real time PCR and in situ hybridization. Alternatively, the level of 4E regulon components can be analyzed using an appropriate antibody. In certain embodiments, the amount of a 4E regulon component is determined using antibodies against the 4E regulon component.

In certain embodiments, the level of a protein of interest is determined by determining its AQUA™ score, e.g., by using the AQUA™ automated pathology system. AQUA™ (for Automated Quantitative Analysis) is a method of analysis of absolute measurement of protein expression in situ. This method allows measurements of protein expression within sub-cellular compartments that results in a number directly proportional to the number of molecules expressed per unit area. For example, to measure nuclear estrogen receptor (ER), the tissue is "masked" using keratin in one channel to normalize the area of tumor and to remove the stromal and other non-tumor material from analysis. Then an image is taken using DAPI to define a nuclear compartment. The pixels within the mask and within the DAPI-defined compartment are defined as nuclear. The intensity of expression of ER is then measured using a third channel. The intensity of that subset of pixels divided by the number of pixels (to normalize the area from spot to spot) to give an AQUA™ score. This score is directly proportional to the number of molecules of ER per unit area of tumor, as assessed by a standard curve of cell lines with known levels of ER protein expression. This method, including details of out-of-focus light subtraction imaging methods, is described in detail in a Nature Medicine paper (Camp, R. L., Chung, G. G. & Rimm, D. L. Automated subcellular localization and quantification of protein expression in tissue microarrays. *Nat Med* 8, 1323-7 (2002)), as well as U.S. Ser. No. 10/062,308, filed Feb. 1, 2002, both of which reference are incorporated herein by their entireties.

In other embodiments, methods of detecting the level of expression of 4E regulon components or other molecule of interest may comprise the use of a microarray. Arrays are often divided into microarrays and macroarrays, where microarrays have a much higher density of individual probe species per area. Microarrays may have as many as 1000 or more different probes in a 1 cm$^2$ area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome. In certain embodiments, the binding site or site is a nucleic acid or nucleic acid analogue to which a particular cognate cDNA can specifically hybridize. The nucleic acid or analogue of the binding site may be, e.g., a synthetic oligomer, a full-length cDNA, a less-than full length cDNA, or a gene fragment.

Although in certain embodiments the microarray contains binding sites for products of all or almost all genes in the target organism's genome, such comprehensiveness is not necessarily required. Usually the microarray will have binding sites corresponding to at least 100, 500, 1000, 4000 genes or more. In certain embodiments, arrays will have anywhere from about 50, 60, 70, 80, 90, or even more than 95% of the genes of a particular organism represented. The microarray typically has binding sites for genes relevant to testing and confirming a biological network model of interest. Several exemplary human microarrays are publicly available.

The probes to be affixed to the arrays are typically polynucleotides. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, which result in amplification of unique fragments (e.g., fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In an alternative embodiment, the binding (hybridization) sites are made from plasmid or phage clones of genes, cDNAs (e.g., expressed sequence tags), or inserts therefrom (Nguyen et al., 1995, *Genomics* 29:207-209).

A number of methods are known in the art for affixing the nucleic acids or analogues to a solid support that makes up the array (Schena et al., 1995, *Science* 270:467-470; DeRisi et al., 1996, *Nature Genetics* 14:457-460; Shalon et al., 1996, *Genome Res.* 6:639-645; and Schena et al., 1995, *Proc. Natl. Acad. Sci. USA* 93:10539-11286).

Another method for making microarrays is by making high-density oligonucleotide arrays (Fodor et al., 1991, *Science* 251:767-773; Pease et al., 1994, *Proc. Natl. Acad. Sci. USA* 91:5022-5026; Lockhart et al., 1996, *Nature Biotech* 14:1675; U.S. Pat. Nos. 5,578,832; 5,556,752; and 5,510,270; Blanchard et al., 1996, 11: 687-90).

Other methods for making microarrays, e.g., by masking (Maskos and Southern, 1992, *Nuc. Acids Res.* 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989), could be used, although, as will be recognized by those of skill in the art.

The nucleic acids to be contacted with the microarray may be prepared in a variety of ways, and may include nucleotides of the subject invention. Such nucleic acids are often labeled fluorescently. Nucleic acid hybridization and wash conditions are chosen so that the population of labeled nucleic acids will specifically hybridize to appropriate, complementary nucleic acids affixed to the matrix. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array may be detected by scanning confocal laser microscopy. When two fluorophores are used, a separate scan, using the appropriate excitation line, is carried out for each of the two fluorophores used. Fluorescent microarray scanners are commercially available from Affymetrix, Packard BioChip Technologies, BioRobotics and many other suppliers. Signals are recorded, quantitated and analyzed using a variety of computer software.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

In addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In certain embodiments, the data obtained from such experiments reflects the relative expression of each gene represented in the microarray. Expression levels in different samples and conditions may now be compared using a variety of statistical methods.

In certain embodiments, the cell comprises a tissue sample, which may be present on a tissue microarray. For example, paraffin-embedded formalin-fixed specimens may be prepared, and punch "biopsy" cores taken from separate areas of the specimens. Each core may be arrayed into a separate recipient block, and sections cut and processed as previously described, for example, in Konenen, J. et al., Tissue microarrays for high-throughput molecular profiling of tumor specimens, (1987) *Nat. Med.* 4:844-7 and Chung, G. G. et al., *Clin. Cancer Res.* (In Press).

In other embodiments, the cell comprises a cell culture pellet, which may be present on a cell culture pellet microarray.

In certain embodiments, it is sufficient to determine the expression of one or only a few genes, as opposed to hundreds or thousands of genes. Although microarrays may be used in these embodiments, various other methods of detection of gene expression are available. This section describes a few exemplary methods for detecting and quantifying mRNA or polypeptide encoded thereby. Where the first step of the methods includes isolation of mRNA from cells, this step may be conducted as described above. Labeling of one or more nucleic acids may be performed as described above.

In one embodiment, mRNA obtained from a sample is reverse transcribed into a first cDNA strand and subjected to PCR, e.g., RT-PCR. House keeping genes, or other genes whose expression does not vary may be used as internal controls and controls across experiments. Following the PCR reaction, the amplified products may be separated by electrophoresis and detected. By using quantitative PCR, the level of amplified product will correlate with the level of RNA that was present in the sample. The amplified samples may also be separated on an agarose or polyacrylamide gel, transferred onto a filter, and the filter hybridized with a probe specific for the gene of interest. Numerous samples may be analyzed simultaneously by conducting parallel PCR amplification, e.g., by multiplex PCR.

"Dot blot" hybridization has gained wide-spread use, and many versions were developed (see, e.g., M. L. M. Anderson and B. D. Young, in *Nucleic Acid Hybridization—A Practical Approach*, B. D. Hames and S. J. Higgins, Eds., IRL Press, Washington D.C., Chapter 4, pp. 73-111, 1985).

In another embodiment, mRNA levels is determined by dot blot analysis and related methods (see, e.g., G. A. Beltz et al., in *Methods in Enzymology*, Vol. 100, Part B, R. Wu, L. Grossmam, K. Moldave, Eds., Academic Press, New York, Chapter 19, pp. 266-308, 1985). In one embodiment, a specified amount of RNA extracted from cells is blotted (i.e., non-covalently bound) onto a filter, and the filter is hybridized with a probe of the gene of interest. Numerous RNA samples may be analyzed simultaneously, since a blot may comprise multiple spots of RNA. Hybridization is detected using a method that depends on the type of label of the probe. In another dot blot method, one or more probes for 4E are attached to a membrane, and the membrane is incubated with labeled nucleic acids obtained from and optionally derived from RNA of a cell or tissue of a subject. Such a dot blot is essentially an array comprising fewer probes than a microarray.

Another format, the so-called "sandwich" hybridization, involves covalently attaching oligonucleotide probes to a solid support and using them to capture and detect multiple nucleic acid targets (see, e.g., M. Ranki et al. (1983) *Gene*, 21:77-85; A. M. Palva, et al, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. (1979) *Nucleic Acid Res.* 6, 11:3543; and B. J. Connor et al. (1983) *PNAS* 80:278-282). Multiplex versions of these formats are called "reverse dot blots."

mRNA levels may also be determined by Northern blots. Specific amounts of RNA are separated by gel electrophoresis and transferred onto a filter which is then hybridized with a probe corresponding to the gene of interest. This method, although more burdensome when numerous samples and genes are to be analyzed provides the advantage of being very accurate.

Another method for high throughput analysis of gene expression is the serial analysis of gene expression (SAGE) technique, first described in Velculescu et al. (1995) *Science* 270, 484-487. Among the advantages of SAGE is that it has the potential to provide detection of all genes expressed in a given cell type, provides quantitative information about the relative expression of such genes, permits ready comparison of gene expression of genes in two cells, and yields sequence information that may be used to identify the detected genes. Thus far, SAGE methodology has proved itself to reliably detect expression of regulated and nonregulated genes in a variety of cell types (Velculescu et al. (1997) *Cell* 88, 243-251; Zhang et al. (1997) *Science* 276, 1268-1272 and Velculescu et al. (1999) *Nat. Genet.* 23, 387-388.

Techniques for producing and probing nucleic acids are further described, for example, in Sambrook et al., *Molecular Cloning: A Laboratory Manual* (New York, Cold Spring Harbor Laboratory, 1989).

Alternatively, the level of expression of a 4E regulon component or other gene of interest is determined by in situ hybridization. In one embodiment, a tissue sample is obtained from a subject, the tissue sample is sliced, and in situ hybridization is performed according to methods known in the art, to determine the level of expression.

In other methods, the level of expression of a 4E regulon component or other gene of interest is detected by measuring the level of protein encoded by the gene. This may be done, e.g., by immunoprecipitation, ELISA, or immunohistochemistry using an agent, e.g., an antibody, that specifically detects the protein encoded by the gene. Other techniques include Western blot analysis Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which may be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, may be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, the level of expression of these polypeptides may be measured in biological fluids.

The above-described methods may be performed using cells grown in cell culture, or on cell or tissue specimens from a subject. Specimens may be obtained from an individual to be tested using either "invasive" or "non-invasive" sampling means. A sampling means is said to be "invasive"

if it involves the collection of nucleic acids from within the skin or organs of an animal (including, especially, a murine, a human, an ovine, an equine, a bovine, a porcine, a canine, or a feline animal). Examples of invasive methods include blood collection, semen collection, needle biopsy, pleural aspiration, umbilical cord biopsy, etc. Examples of such methods are discussed by Kim, C. H. et al. (1992) *J. Virol.* 66:3879-3882; Biswas, B. et al. (1990) *Annals NY Acad. Sci.* 590:582-583; Biswas, B. et al. (1991) *J. Clin. Microbiol.* 29:2228-2233. It is also possible to obtain a cell sample from a subject, and then to enrich it in the desired cell type. For example, cells may be isolated from other cells using a variety of techniques, such as isolation with an antibody binding to an epitope on the cell surface of the desired cell type.

In certain embodiments, a single cell is used in the analysis. It is also possible to obtain cells from a subject and culture the cells in vitro, such as to obtain a larger population of cells from which RNA may be extracted. Methods for establishing cultures of non-transformed cells, i.e., primary cell cultures, are known in the art.

When analyzing from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA and proteins in the tissue and cells may quickly become degraded. Accordingly, in a preferred embodiment, the cells obtained from a subject are snap frozen as soon as possible.

H. Diagnostic and Prognostic Applications of the 4E Regulon Components

1. Diagnostic Methods Comprising the Use of a Biological Sample

In certain embodiments are provided methods for diagnosing, monitoring, prognosing or staging, or predicting the outcome of a disease wherein 4E regulon activity is dysfunctional, or the likelihood of developing a disease wherein 4E regulon activity is dysfunctional, comprise detecting the level of, phosphorylation state of, or activity of at least one 4E regulon component in a biological sample of a subject. In an exemplary embodiment, the level of or activity of the 4E regulon component may be determined in a urine, saliva, blood or plasma sample from a subject.

The methods may comprise detecting the level of, phosphorylation state of, or activity of at least one 4E regulon component in a biological sample of a subject and comparing that level to a control. A nonspecific control, for example, may be GADPH or actin levels or activity. Any deviation from the control level, phosphorylation state of, or activity of the at least one 4E regulon component may be indicative of a subject suffering from a disease wherein 4E regulon activity is dysfunctional, having a particular stage of a disease wherein 4E regulon activity is dysfunctional, about to develop a disease wherein 4E regulon activity is dysfunctional, etc. The degree or severity of a disease wherein 4E regulon activity is dysfunctional may be determined based on the degree of deviation in the level of, phosphorylation state of, or activity of the at least one 4E regulon component in a subject as compared to a control. For example, a subject exhibiting a greater deviation in the level of, phosphorylation state of, or activity of the at least one 4E regulon component as compared to a control may indicate that the subject is more susceptible to, or suffering from a more severe case of, a disease wherein 4E regulon activity is dysfunctional.

In certain embodiments of the methods describing the use of 4E regulon components for diagnostic, screening and monitoring applications, the level of expression of, level/amount of, phosphorylation state of, or activity of at least one non-4E regulon component may be determined and compared as well. For example, the at least one non-4E regulon component may be selected from the group consisting of: ER (ER (alpha) gi: 62821793; ER (beta) gis: 94538327, 94538324, 94538323), PR (gi: 110611913), EGFR (gi: 41327737), HER2/neu (gi: 54792097, 54792095), and TMPRSS2:ETS gene fusions (Rubin, M A and Chinnaiyan, A M (2006) *Lab Invest* 86:1099).

The level of, phosphorylation state of, or activity of the at least one 4E regulon component may be determined using a method known in the art. In embodiments wherein the at least one 4E regulon component is a protein or a peptide corresponding to a region of a protein, the level of the protein or peptide may be evaluated directly. For example, the level of at least one 4E regulon component may be determined using immunoassays. The activity of at least one 4E regulon component may be evaluated using an assay specific for the activity of that at least one 4E regulon component.

Other methods for detecting the level or activity of 4E regulon components in a biological sample are described further in Section D below.

The level of, phosphorylation state of, or activity of the at least one 4E regulon component in a subject may be compared to a control either quantitatively or qualitatively. For example, a qualitative (or unitless) comparison may be carried out by determining whether the level of, phosphorylation state of, or activity of the at least one 4E regulon component in a subject is higher, lower, or about the same as a control. Optionally, a qualitative comparison may be used to estimate the magnitude of difference in the level of, phosphorylation state of, or activity of the at least one 4E regulon component in a subject as compared to a control, such as, for example, a 2-fold change, a 50% change, etc. For example, a quantitative comparison may be carried out by determining the quantity of at least one 4E regulon component in a subject as compared to the quantity in a control, wherein the quantity has some form of units attached (such as, for example, mg of protein, volume of a spot/band in a gel, intensity of a spot on a phosphoimager or autoradiogram exposure, volume of a spot on a chromatography plate, etc.).

In another embodiment, the level of, phosphorylation state of, or activity of at least one 4E regulon component in a biological sample of a subject may be used to calculate the physiological concentration of the at least one 4E regulon component found in a subject. The physiological concentration of the at least one 4E regulon component in a subject may then optionally be compared to a control.

In certain embodiments, subjects may be screened for levels of, phosphorylation state of, or activity of at least one 4E regulon component on a regular basis (or at regular intervals) for purposes of diagnosis of a disease wherein 4E regulon activity is dysfunctional, staging of a disease wherein 4E regulon activity is dysfunctional or to monitor the stage or development of a disease wherein 4E regulon activity is dysfunctional. In one embodiment, screening for levels of, phosphorylation states of, or activity of 4E regulon components may be carried out about once every month, once every 3 weeks, once every 2 weeks, once every 10 days, once every week, or about once every 144, 120, 96, 72, 48, 24, or 12 hours.

It may be desirable to monitor symptoms of a disease wherein 4E regulon activity is dysfunctional in addition to monitoring the level of, phosphorylation state of, or activity of at least one 4E regulon component in a subject.

2. Cell- and Tissue-Based Diagnostics

In certain embodiments, a method of evaluating the expression of at least one 4E regulon component in a cell or tissue from a subject may comprise determining in the cell the level of expression of at least one 4E regulon component. In other embodiments, it may comprise determining the level of, phosphorylation state of, or activity of at least one 4E regulon component protein or mRNA (i.e. a gene product).

Methods of evaluating gene expression and protein activity are well-known in the art. Exemplary methods by which the expression of the at least one 4E regulon component gene or gene product or the activity of, level of or phosphorylation state of the at least one 4E regulon components are further described in Section D below.

The above-described method may further comprise b) comparing the determined level of expression of at least one 4E regulon component gene or gene product with at least one reference set of levels of expression of the at least one 4E regulon component gene or gene product, wherein the reference set indicates the state of the cell associated with the particular level of expression of the at least one 4E regulon component gene or gene product.

Comparison to a reference set or profile is particularly useful in applications of the above-described methods, for example, when they are used in methods for diagnosing and prognosing and predicting the onset of a disease wherein 4E regulon activity is dysfunctional in a subject, or for screening candidate therapeutics for their efficacy in treating a disease wherein 4E regulon activity is dysfunctional.

For example, a method for diagnosing, prognosing or staging, or predicting the onset of a disease wherein 4E regulon activity is dysfunctional may comprise: (a) determining in a cell of a subject the level of expression of at least one 4E regulon component gene or gene product. The level of expression of at least one 4E regulon component obtained thereby may further be compared to a reference set of the levels of expression of the at least one 4E regulon component gene or gene product associated with various states of a disease wherein 4E regulon activity is dysfunctional.

Comparison of the expression level of at least one 4E regulon component gene or gene product with reference expression levels, e.g., expression levels in diseased cells of a subject having a disease wherein 4E regulon activity is dysfunctional or in normal counterpart cells, is preferably conducted using computer systems. In one embodiment, expression levels are obtained in two cells and these two sets of expression levels are introduced into a computer system for comparison. In a preferred embodiment, one set of expression levels is entered into a computer system for comparison with values that are already present in the computer system, or in computer-readable form that is then entered into the computer system.

In one embodiment, the invention provides computer readable forms of the gene expression profile data of the invention, or of values corresponding to the level of expression of at least one 4E regulon component gene or gene product. The values may be, for example, mRNA expression levels or AQUA™ scores. The values may also be mRNA levels, AQUA™ scores, or other measure of gene expression normalized relative to a reference gene whose expression is constant in numerous cells under numerous conditions. In other embodiments, the values in the computer are ratios of, or differences between, normalized or non-normalized levels in different samples.

The gene expression profile data may be in the form of a table, such as an Excel table. The data may be alone, or it may be part of a larger database, e.g., comprising other expression profiles. For example, the expression profile data of the invention may be part of a public database. The computer readable form may be in a computer. In another embodiment, the invention provides a computer displaying the gene expression profile data.

In one embodiment, the invention provides methods for determining the similarity between the level of expression of at least one 4E regulon component gene or gene product in a first cell, e.g., a cell of a subject, and that in a second cell, comprising obtaining the level of expression of at least one 4E regulon component gene or gene product in a first cell and entering these values into a computer comprising a database including records comprising values corresponding to levels of expression of the at least one 4E regulon component gene or gene product in a second cell, and processor instructions, e.g., a user interface, capable of receiving a selection of one or more values for comparison purposes with data that is stored in the computer. The computer may further comprise a means for converting the comparison data into a diagram or chart or other type of output.

In another embodiment, at least one value representing the expression level of at least one 4E regulon component gene or gene product is entered into a computer system, comprising one or more databases with reference expression levels obtained from more than one cell. For example, a computer may comprise expression data of diseased and normal cells. Instructions are provided to the computer, and the computer is capable of comparing the data entered with the data in the computer to determine whether the data entered is more similar to that of a normal cell or of a diseased cell.

In another embodiment, the computer comprises values of expression levels in cells of subjects at different stages of a disease wherein 4E regulon activity is dysfunctional and the computer is capable of comparing expression data entered into the computer with the data stored, and produce results indicating to which of the expression profiles in the computer, the one entered is most similar, such as to determine the stage of a disease wherein 4E regulon activity is dysfunctional in the subject.

In yet another embodiment, the reference expression profiles in the computer are expression profiles from cells of one or more subjects having a disease wherein 4E regulon activity is dysfunctional, which cells are treated in vivo or in vitro with a drug used for therapy of a disease wherein 4E regulon activity is dysfunctional. Upon entering of expression data of a cell of a subject treated in vitro or in vivo with the drug, the computer is instructed to compare the data entered to the data in the computer, and to provide results indicating whether the expression data input into the computer are more similar to those of a cell of a subject that is responsive to the drug or more similar to those of a cell of a subject that is not responsive to the drug. Thus, the results indicate whether the subject is likely to respond to the treatment with the drug or unlikely to respond to it.

In one embodiment, the invention provides systems comprising a means for receiving gene expression data for one or a plurality of genes; a means for comparing the gene expression data from each of said one or plurality of genes to a common reference frame; and a means for presenting the results of the comparison. A system may further comprise a means for clustering the data.

In another embodiment, the invention provides computer programs for analyzing gene expression data comprising (a) a computer code that receives as input gene expression data for at least one gene and (b) a computer code that compares said gene expression data from each gene to a common reference frame.

The invention also provides machine-readable or computer-readable media including program instructions for performing the following steps: (a) comparing at least one value corresponding to the expression level of at least one 4E regulon component gene or gene product in a query cell with a database including records comprising reference expression or expression profile data of one or more reference cells and an annotation of the type of cell; and (b) indicating to which cell the query cell is most similar based on similarities of expression profiles. The reference cells may be cells from subjects at different stages of a disease wherein 4E regulon activity is dysfunctional. The reference cells may also be cells from subjects responding or not responding to a particular drug treatment and optionally incubated in vitro or in vivo with the drug.

The reference cells may also be cells from subjects responding or not responding to several different treatments, and the computer system indicates a preferred treatment for the subject. Accordingly, the invention provides methods for selecting a therapy for a patient having a disease wherein 4E regulon activity is dysfunctional; the methods comprising: (a) providing the level of expression of at least one 4E regulon component gene or gene product in a diseased cell of the patient; (b) providing a plurality of reference profiles, each associated with a therapy; and (c) selecting the reference profile most similar to the subject expression profile, to thereby select a therapy for said patient. In a preferred embodiment step (c) is performed by a computer. The most similar reference profile may be selected by weighing a comparison value of the plurality using a weight value associated with the corresponding expression data.

A computer readable medium may further comprise a pointer to a descriptor of a stage of a disease wherein 4E regulon activity is dysfunctional or to a treatment for a disease wherein 4E regulon activity is dysfunctional.

In operation, the means for receiving gene expression data, the means for comparing the gene expression data, the means for presenting, the means for normalizing, and the means for clustering within the context of the systems of the present invention may involve a programmed computer with the respective functionalities described herein, implemented in hardware or hardware and software; a logic circuit or other component of a programmed computer that performs the operations specifically identified herein, dictated by a computer program; or a computer memory encoded with executable instructions representing a computer program that may cause a computer to function in the particular fashion described herein.

Those skilled in the art will understand that the systems and methods of the present invention may be applied to a variety of systems, including IBM®-compatible personal computers running MS-DOS® or Microsoft Windows®. In an exemplary implementation, expression profiles are compared using a method described in U.S. Pat. No. 6,203,987. A user first loads expression profile data into the computer system. Geneset profile definitions are loaded into the memory from the storage media or from a remote computer, preferably from a dynamic geneset database system, through the network. Next the user causes execution of projection software which performs the steps of converting expression profile to projected expression profiles. The projected expression profiles are then displayed.

In yet another exemplary implementation, a user first leads a projected profile into the memory. The user then causes the loading of a reference profile into the memory. Next, the user causes the execution of comparison software which performs the steps of objectively comparing the profiles.

Exemplary diagnostic tools and assays are set forth below, which comprise the above-described methodology.

In one embodiment, the invention provides methods for determining whether a subject has or is likely to develop a disease wherein 4E regulon activity is dysfunctional, e.g., predicting the onset of a disease wherein 4E regulon activity is dysfunctional, comprising determining the level of expression of at least one 4E regulon component gene or gene product in a cell of the subject and comparing these levels of expression with the levels of expression of the genes or gene products in a diseased cell of a subject known to have a disease wherein 4E regulon activity is dysfunctional, such that a similar level of expression of the genes or gene products is indicative that the subject has or is likely to develop a disease wherein 4E regulon activity is dysfunctional or at least a symptom thereof. In a preferred embodiment, the cell is essentially of the same type as that which is diseased in the subject.

In another embodiment the expression profiles of genes or gene products in the panels of the invention may be used to confirm that a subject has a specific type of a disease wherein 4E regulon activity is dysfunctional, and in particular, that the subject does not have a related disease or disease with similar symptoms. This may be important, in particular, in designing an optimal therapeutic regimen for the subject. It has been described in the art that expression profiles may be used to distinguish one type of disease from a similar disease. For example, two subtypes of non-Hodgkin's lymphomas, one of which responds to current therapeutic methods and the other one which does not, could be differentiated by investigating 17,856 genes in specimens of patients suffering from diffuse large B-cell lymphoma (Alizadeh et al. *Nature* (2000) 405:503). Similarly, subtypes of cutaneous melanoma were predicted based on profiling 8150 genes (Bittner et al. *Nature* (2000) 406:536). In this case, features of the highly aggressive metastatic melanomas could be recognized. Numerous other studies comparing expression profiles of cancer cells and normal cells have been described, including studies describing expression profiles distinguishing between highly and less metastatic cancers and studies describing new subtypes of diseases, e.g., new tumor types (see, e.g., Perou et al. (1999) *PNAS* 96: 9212; Perou et al. (2000) *Nature* 606:747; Clark et al. (2000) *Nature* 406:532; Alon et al. (1999) *PNAS* 96:6745; Golub et al. (1999) *Science* 286:531). Such distinction is known in the art as "differential diagnosis".

In yet another embodiment, the invention provides methods for determining the stage of a disease wherein 4E regulon activity is dysfunctional. It is thought that the level of expression of at least one 4E regulon component gene or gene product changes with the stage of the disease. This could be confirmed, e.g., by analyzing the level of expression of the gene or gene product in subjects having a disease wherein 4E regulon activity is dysfunctional at different stages, as determined by traditional methods. For example, the expression profile of a diseased cell in subjects at different stages of the disease may be determined as described herein. Then, to determine the stage of a disease wherein 4E regulon activity is dysfunctional in a subject, the level of expression of at least one 4E regulon component gene or gene product, which varies with the stage of the disease, is determined A similar level of expression of at least one 4E regulon component between that in a subject and that in a reference profile of a particular stage of the disease, indicates that the disease of the subject is at the particular stage.

Similarly, the methods may be used to determine the stage of the disease in a subject undergoing therapy, and thereby determine whether the therapy is effective. Accordingly, in one embodiment, the level of expression of at least one 4E regulon component gene or gene product is determined in a subject before the treatment and several times during the treatment. For example, a sample of RNA may be obtained from the subject before the beginning of the therapy and every 12, 24 or 72 hours during the therapy. Samples may also be analyzed one a week or once a month. Changes in expression levels of genes or gene products over time and relative to diseased cells and normal cells will indicate whether the therapy is effective.

In yet another embodiment, the invention provides methods for determining the likelihood of success of a particular therapy in a subject having a disease wherein 4E regulon activity is dysfunctional. In one embodiment, a subject is started on a particular therapy, and the effectiveness of the therapy is determined, e.g., by determining the level of expression of at least one 4E regulon component gene or gene product in a cell of the subject. A normalization of the level of expression of the gene, i.e., a change in the expression level of the gene or gene product such that their level of expression resembles more that of a non diseased cell, indicates that the treatment should be effective in the subject.

Prediction of the outcome of a treatment in a subject may also be undertaken in vitro. In one embodiment, cells are obtained from a subject to be evaluated for responsiveness to the treatment, and incubated in vitro with the therapeutic drug. The level of expression of at least one 4E regulon component gene or gene product is then measured in the cells and these values are compared to the level of expression of the at least one 4E regulon component in a cell which is the normal counterpart cell of a diseased cell. The level of expression may also be compared to that in a normal cell. The comparative analysis is preferably conducted using a computer comprising a database of expression profiles as described above. A level of expression of at least one 4E regulon component gene or gene product in the cells of the subject after incubation with the drug that is similar to their level of expression in a normal cell and different from that in a diseased cell is indicative that it is likely that the subject will respond positively to a treatment with the drug. On the contrary, a level of expression of at least one 4E regulon component gene or gene product in the cells of the subject after incubation with the drug that is similar to their level of expression in a diseased cell and different from that in a normal cell is indicative that it is likely that the subject will not respond positively to a treatment with the drug.

Since it is possible that a drug does not act directly on the diseased cells, but is, e.g., metabolized, or acts on another cell which then secretes a factor that will effect the diseased cells, the above assay may also be conducted in a tissue sample of a subject, which contains cells other than the diseased cells. For example, a tissue sample comprising diseased cells is obtained from a subject; the tissue sample is incubated with the potential drug; optionally one or more diseased cells are isolated from the tissue sample, e.g., by microdissection or Laser Capture Microdissection (LCM, see infra); and the expression level of at least one 4E regulon component is examined.

The invention may also provide methods for selecting a therapy for a disease wherein 4E regulon activity is dysfunctional for a patient from a selection of several different treatments. Certain subjects having a disease wherein 4E regulon activity is dysfunctional may respond better to one type of therapy than another type of therapy. In a preferred embodiment, the method comprises comparing the expression level of at least one 4E regulon component gene or gene product in the patient with that in cells of subjects treated in vitro or in vivo with one of several therapeutic drugs, which subjects are responders or non responders to one of the therapeutic drugs, and identifying the cell which has the most similar level of expression of at least one 4E regulon component to that of the patient, to thereby identify a therapy for the patient. The method may further comprise administering the therapy identified to the subject.

It will be appreciated by one of skill in the art that all of the afore-described methods may be modified to use the level or, activity of or phosphorylation state of a 4E regulon component protein in the same way as a gene expression level to achieve similar goals.

I. Methods of Identifying Therapeutics

1. Therapeutic Agent Screening

The present invention further relates to the use of at least one 4E regulon component in methods of screening candidate therapeutic agents for use in treating a disease wherein 4E regulon activity is dysfunctional. The candidate therapeutics may be selected from the following classes of compounds: nucleic acids, small molecules, polypeptides, proteins, peptidomimetics, or nucleic acid analogs. In some embodiments, the candidate therapeutics may be in a library of compounds. These libraries may be generated using combinatorial synthetic methods. In certain embodiments of the present invention, the ability of said candidate therapeutics to bind a target protein may be evaluated by an in vitro assay. In certain embodiments, combinations of compounds or biologics may be screened for their effect on 4E regulon component expression or activity to identify potential co-therapeutics or combination therapies. For example, Ribavirin or analogs or prodrugs thereof may be screened along with interferon, GMCSF, GCSF, IL-12, IL-2, compounds that inhibit or down-regulated tyrosine kinase activity, chemotherapeutic agents such as platinum compounds and others described in the definition above, biologics and cytotoxins etc. in addition to measurement of cell proliferation, cell division, and/or gene expression as noted.

Biologics may include antibodies or antigen binding fragments thereof, that bind to a targetable component of a tumor cell, tumor vasculature or tumor stroma. A "targetable component" of a tumor cell, tumor vasculature or tumor stroma, is preferably a surface-expressed, surface-accessible or surface-localized component, although components released from necrotic or otherwise damaged tumor cells or vascular endothelial cells may also be targeted, including cytosolic and/or nuclear tumor cell antigens.

Biologics may also include anti-tumor cell immunotoxins or coaguligands such as antibodies exemplified by the group consisting of B3 (ATCC HB 10573), 260F9 (ATCC HB 8488), D612 (ATCC HB 9796) and KS1/4, said KS1/4 antibody obtained from a cell comprising the vector pGKC2310 (NRRL B-18356) or the vector pG2A52 (NRRL B-18357). Biologics may be anti-tumor stroma immunotoxins or coaguligands, for example, antibodies that bind to a connective tissue component, a basement membrane component or an activated platelet component; as exemplified by binding to fibrin, RIBS or LIBS.

Biologics such as anti-tumor vasculature immunotoxins or coaguligands may also comprise ligands, antibodies, or fragments thereof, that bind to a surface-expressed, surface-accessible or surface-localized component of the blood transporting vessels, preferably the intratumoral blood vessels, of a vascularized tumor. Such antibodies include those that bind to surface-expressed components of intratumoral blood vessels of a vascularized tumor, including aminophospholipids themselves, and intratumoral vasculature cell surface receptors, such as endoglin (TEC-4 and TEC-11 antibodies), a TGF.beta. receptor, E-selectin, P-selectin, VCAM-1, ICAM-1, PSMA, a VEGF/VPF receptor, an FGF receptor, a TIE, .alpha.sub.v.beta.sub.3 integrin, pleiotropin, endosialin and MHC Class II proteins. The antibodies may also bind to cytokine-inducible or coagulant-inducible components of intratumoral blood vessels.

Other anti-tumor vasculature immunotoxins or coaguligands may comprise antibodies, or fragments thereof, that bind to a ligand or growth factor that binds to an intratumoral vasculature cell surface receptor. Such antibodies include those that bind to VEGF/VPF (GV39 and GV97 antibodies), FGF, TGF.beta., a ligand that binds to a TIE, a tumor-associated fibronectin isoform, scatter factor/hepatocyte growth factor (HGF), platelet factor 4 (PF4), PDGF and TIMP. The antibodies, or fragments thereof, may also bind to a ligand:receptor complex or a growth factor:receptor complex, but not to the ligand or growth factor, or to the receptor, when the ligand or growth factor or the receptor is not in the ligand:receptor or growth factor:receptor complex.

Cytotoxic agents such as plant-, fungus- or bacteria-derived toxins (immunotoxins). Ricin A chain, deglycosylated ricin A chain, gelonin and angiopoietins may also be used in combination therapies.

In some embodiments, candidate therapeutic agents, or "therapeutics", are evaluated for their ability to bind the at least one 4E regulon component. In other embodiments, candidate therapeutics are evaluated for their ability to bind the at least one 4E regulon component gene or gene product. The ability of the candidate therapeutic to bind the gene or protein may be evaluated by an in vitro assay. In either embodiment, the binding assay may also be in vivo.

In still other embodiments, therapeutic agents targeting the at least one 4E regulon component may be assessed by monitoring the symptoms of a disease wherein 4E regulon activity is dysfunctional in a subject, wherein the amelioration of or prevention of a disease wherein 4E regulon activity is dysfunctional indicates the therapeutic agent may be useful as a treatment.

The present invention further provides methods for evaluating candidate therapeutic agents for their ability to modulate the expression of the at least one 4E regulon component gene by contacting the cells of a subject with said candidate therapeutic agents. In certain embodiments, the candidate therapeutic will be evaluated for its ability to normalize the level of expression of the at least one 4E regulon component gene or gene product. In this embodiment, should the candidate therapeutic be able to normalize the gene expression so that a disease wherein 4E regulon activity is dysfunctional is ameliorated, inhibited or prevented, it may be considered a candidate therapeutic for a disease wherein 4E regulon activity is dysfunctional. The candidate therapeutic agents may be selected, for example, from the following classes of compounds: Ribavirin or ribavirin analogs, antisense nucleic acids, RNAi, small molecules, polypeptides, proteins, including antibodies, peptidomimetics, or nucleic acid analogs.

Alternatively, candidate therapeutic agents may be evaluated for their ability to inhibit the level of, phosphorylation state of, or activity of the at least one 4E regulon component protein by contacting the cells of a subject with said candidate therapeutic agents. In certain embodiments, a candidate therapeutic may be evaluated for its ability to inhibit the level of, phosphorylation state of, or activity of the at least one 4E regulon component. In this embodiment, a candidate therapeutic agent that exhibits the ability to modulate the protein's activity may be considered a candidate therapeutic for treating a disease wherein 4E regulon activity is dysfunctional.

Furthermore, a candidate therapeutic may be evaluated for its ability to normalize the level of turnover of a protein encoded by the at least one 4E regulon component gene. In another embodiment, a candidate therapeutic may be evaluated for its ability to normalize the translational level of a protein encoded by the at least one 4E regulon component. In yet another embodiment, a candidate therapeutic may be evaluated for its ability to normalize the level of turnover of an mRNA encoded by the at least one 4E regulon component gene from the panels of the present invention.

In another embodiment of the invention, a drug is developed by rational drug design, i.e., it is designed or identified based on information stored in computer readable form and analyzed by algorithms. More and more databases of expression profiles are currently being established, numerous ones being publicly available. By screening such databases for the description of drugs affecting the expression of the at least one 4E regulon component gene in a manner similar to the change in gene expression profile from a diseased cell to that of a normal cell corresponding to the diseased cell, compounds may be identified which normalize gene expression in a diseased cell. Derivatives and analogues of such compounds may then be synthesized to optimize the activity of the compound, and tested and optimized as described above.

2. Therapeutic Agent Screening Assays

Assays and methods of developing assays appropriate for use in the methods described above are well-known to those of skill in the art, and are contemplated for use as appropriate with the methods of the present invention. The ability of said candidate therapeutics to bind a target may be determined using a variety of appropriate assays known to those of skill in the art. In certain embodiments of the present invention, the ability of a candidate therapeutic to bind a target protein, other gene product or gene may be evaluated by an in vitro assay. In either embodiment, the binding assay may also be an in vivo assay. Assays may be conducted to identify molecules that modulate the expression and or activity of a gene or gene product. Alternatively, assays may be conducted to identify molecules that modulate the activity of a protein encoded by a gene or gene product.

Examples of assays contemplated for use in the present invention include, but are not limited to, competitive binding assay, direct binding assay, two-hybrid assay, cell proliferation assay, kinase assay, phosphatase assay, nuclear hormone translocator assay, fluorescence activated cell screening (FACS) assay, colony-forming/plaque assay, and polymerase chain reaction assay. Such assays are well-known to one of skill in the art and may be adapted to the methods of the present invention with no more than routine experimentation.

All of the above screening methods may be accomplished using a variety of assay formats. In light of the present disclosure, those not expressly described herein will nevertheless be known and comprehended by one of ordinary skill in the art. The assays may identify drugs which are, e.g., either agonists or antagonists, of expression of at least one 4E regulon component gene or gene product or of a protein: protein or protein-substrate interaction of at least one 4E regulon component, or of the role of at least one 4E regulon component gene product in the pathogenesis of normal or abnormal cellular physiology, proliferation, and/or differentiation and disorders related thereto. Assay formats which approximate such conditions as formation of protein complexes or protein-nucleic acid complexes, enzymatic activity, and even specific signaling pathways, may be generated in many different forms, and include but are not limited to assays based on cell-free systems, e.g. purified proteins or cell lysates, as well as cell-based assays which utilize intact cells.

3. Therapeutic Agent Efficacy Screening

The efficacy of candidate therapeutics identified using the methods of the invention may be evaluated, for example, by a) contacting cells of a subject with a candidate therapeutic and b) determining its ability to ameliorate, inhibit or prevent a disease wherein 4E regulon activity is dysfunctional or a symptom thereof in the subject. Alternatively, the efficacy of candidate therapeutics may be evaluated by comparing the expression levels of at least one 4E regulon component gene or gene product in a cell of a subject having a disease wherein 4E regulon activity is dysfunctional with that of a normal cell. In one embodiment, the expression level of the genes or gene products may be determined using microarrays or other methods of RNA quantitation, or by comparing the gene expression profile of a cell treated with a candidate therapeutic with the gene expression profile of a normal cell.

The efficacy of the compounds may then be tested in additional in vitro assays and in vivo, e.g. in animal studies. Expression of a 4E regulon component may also be measured before and after administration of the test compound to the animal A normalization of the expression of a 4E regulon component is indicative of the efficiency of the compound for treating a disease wherein 4E regulon activity is dysfunctional in the animal. Likewise the level of, phosphorylation state of, or activity of a 4E regulon component may be measured before and after administration of the test compound to the animal. A normalization of the level of, phosphorylation state of, or activity of a 4E regulon component is indicative of the efficiency of the compound for treating a disease wherein 4E regulon activity is dysfunctional in the animal.

In certain embodiments, wherein the efficacy is tested in vivo, changes 4E regulon component activity in response to a candidate therapeutic agent are monitored in PBMC. In other embodiments, fluid-based analysis of 4E regulon component levels, for example, VEGF, in response to a candidate therapeutic agent, are used.

J. Methods of Evaluating the Expression, Level or Activity of 4E Regulon Component Genes and Proteins The methods of diagnosing and prognosing a disease wherein 4E regulon activity is dysfunctional by evaluating the level of expression and/or the level of phosphorylation state of, or activity of at least one 4E regulon component and methods of screening candidate therapeutic agents which modulate the expression and/or the level of, phosphorylation state of, or activity of at least one 4E regulon component, described above, comprise determining the level of expression and/or the level of, phosphorylation state of, or activity of the at least one 4E regulon component.

Methods for determining the expression level of a gene and the level of, phosphorylation state of, or activity of a gene or protein are well known in the art. For example, the expression level of a 4E regulon component gene can be determined by reverse transcription-polymerase chain reaction (RT-PCR); dotblot analysis; Northern blot analysis and in situ hybridization. Alternatively, the level of a 4E regulon component can be analyzed using an appropriate antibody. In certain embodiments, the amounts of a 4E regulon component is determined using antibodies against the 4E regulon component.

In certain embodiments, the level of expression of a 4E regulon component is determined by determining its AQUA™ score, e.g., by using the AQUA™ automated pathology system. AQUA™ (for Automated Quantitative Analysis) is a method of analysis of absolute measurement of protein expression in situ. This method allows measurements of protein expression within sub-cellular compartments that results in a number directly proportional to the number of molecules expressed per unit area. For example, to measure nuclear estrogen receptor (ER), the tissue is "masked" using keratin in one channel to normalize the area of tumor and to remove the stromal and other non-tumor material from analysis. Then an image is taken using DAPI to define a nuclear compartment. The pixels within the mask and within the DAPI-defined compartment are defined as nuclear. The intensity of expression of ER is then measured using a third channel. The intensity of that subset of pixels divided by the number of pixels (to normalize the area from spot to spot) to give an AQUA™ score. This score is directly proportional to the number of molecules of ER per unit area of tumor, as assessed by a standard curve of cell lines with known levels of ER protein expression. This method, including details of out-of-focus light subtraction imaging methods, is described in detail in a Nature Medicine paper (Camp, R. L., Chung, G. G. & Rimm, D. L. Automated subcellular localization and quantification of protein expression in tissue microarrays. *Nat Med* 8, 1323-7 (2002)), as well as U.S. Ser. No. 10/062,308, filed Feb. 1, 2002, both of which references are incorporated herein by their entireties.

In certain embodiments, a reporter gene assay is used to detect the level of expression of a 4E regulon component or to determine whether 4E regulon component interactions are interrupted. Reporter systems that may be useful in this regard include but are not limited to colorimetric labeled substrate converted into product, a reporter gene that is responsive to changes in 4E activity, and binding assays known in the art, such as an two-hybrid or interaction trap assay (see also, U.S. Pat. No. 5,283,317; Zervos et al. (1993) *Cell* 72:223-232; Madura et al. (1993) *J Biol Chem* 268: 12046-12054; Bartel et al. (1993) *Biotechniques* 14:920-924; and Iwabuchi et al. (1993) *Oncogene* 8:1693-1696), for subsequently detecting agents which disrupt binding of the interaction components to one another.

In certain embodiments, mass spectroscopy is used to evaluate levels of protein or phosphoryation states of protein. Protein characterization by mass spectroscopy first requires protein isolation followed by either chemical or enzymatic digestion of the protein into smaller peptide fragments, whereupon the peptide fragments may be analyzed by mass spectrometry to obtain a peptide map. Liquid chromatography may be used in conjunction with mass spectrometry. Mass spectrometry may also be used to identify post-translational modifications (e.g., phosphorylation, etc.) of a polypeptide. Various mass spectrometers may be used within the present invention. Representative examples include: triple quadrupole mass spectrometers, magnetic sector instruments (magnetic tandem mass spectrometer, JEOL, Peabody, Mass.), ionspray mass spectrometers (Bruins et al., Anal Chem. 59:2642-2647, 1987), electrospray mass spectrometers (including tandem, nano- and nano-electrospray tandem) (Fenn et al., Science 246:64-71, 1989), laser desorption time-of-flight mass spectrometers (Karas and Hillenkamp, Anal. Chem. 60:2299-2301, 1988), and a Fourier Transform Ion Cyclotron Resonance Mass Spectrometer (Extrel Corp., Pittsburgh, Mass.).

Phosphorylation may be measured using any other method known in the art. Typically, methods of measuring phosphorylation are based on the radioactive detection method. In these methods, a sample containing the protein of interest is incubated with activators and a substrate in the presence of $\gamma$-$^{32}$P-ATP or $\gamma$-$^{32}$P-GTP. Often, a general and inexpensive substrate such as histone or casein is used. After a suitable incubation period, the reaction is stopped and the phosphorylated substrate (or protein) is separated from free phosphate using gel electrophoresis or by binding the substrate or protein to a filter and washing to remove excess radioactively-labeled free ATP. The amount of radio-labeled phosphate incorporated into the substrate or protein may measured by scintillation counting or by phosphorimager analysis. Alternatively, phosphorylation of a substrate or protein may be detected by immunofluorescence using antibodies specific for a phosphoserine, phosphothreonine or phosphotyrosine residue (e.g., anti-phosphoserine, Sigma #P3430; anti-phosphothreonine, Sigma #P3555; and anti-phosphotyrosine, Sigma #P3300).

In other embodiments, methods of detecting the level of expression of a 4E regulon component may comprise the use of a microarray. Arrays are often divided into microarrays and macroarrays, where microarrays have a much higher density of individual probe species per area. Microarrays may have as many as 1000 or more different probes in a 1 cm$^2$ area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome. In certain embodiments, the binding site or site is a nucleic acid or nucleic acid analogue to which a particular cognate cDNA can specifically hybridize. The nucleic acid or analogue of the binding site may be, e.g., a synthetic oligomer, a full-length cDNA, a less-than full length cDNA, or a gene fragment.

Although in certain embodiments the microarray contains binding sites for products of all or almost all genes in the target organism's genome, such comprehensiveness is not necessarily required. Usually the microarray will have binding sites corresponding to at least 100, 500, 1000, 4000 genes or more. In certain embodiments, arrays will have anywhere from about 50, 60, 70, 80, 90, or even more than 95% of the genes of a particular organism represented. The microarray typically has binding sites for genes relevant to testing and confirming a biological network model of interest. Several exemplary human microarrays are publicly available.

The probes to be affixed to the arrays are typically polynucleotides. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, which result in amplification of unique fragments (e.g., fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In an alternative embodiment, the binding (hybridization) sites are made from plasmid or phage clones of genes, cDNAs (e.g., expressed sequence tags), or inserts therefrom (Nguyen et al., 1995, *Genomics* 29:207-209).

A number of methods are known in the art for affixing the nucleic acids or analogues to a solid support that makes up the array (Schena et al., 1995, *Science* 270:467-470; DeRisi et al., 1996, *Nature Genetics* 14:457-460; Shalon et al., 1996, *Genome Res.* 6:639-645; and Schena et al., 1995, *Proc. Natl. Acad. Sci. USA* 93:10539-11286).

Another method for making microarrays is by making high-density oligonucleotide arrays (Fodor et al., 1991, *Science* 251:767-773; Pease et al., 1994, *Proc. Natl. Acad. Sci. USA* 91:5022-5026; Lockhart et al., 1996, *Nature Biotech* 14:1675; U.S. Pat. Nos. 5,578,832; 5,556,752; and 5,510,270; Blanchard et al., 1996, 11: 687-90).

Other methods for making microarrays, e.g., by masking (Maskos and Southern, 1992, *Nuc. Acids Res.* 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989), could be used, although, as will be recognized by those of skill in the art.

The nucleic acids to be contacted with the microarray may be prepared in a variety of ways, and may include nucleotides of the subject invention. Such nucleic acids are often labeled fluorescently. Nucleic acid hybridization and wash conditions are chosen so that the population of labeled nucleic acids will specifically hybridize to appropriate, complementary nucleic acids affixed to the matrix. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array may be detected by scanning confocal laser microscopy. When two fluorophores are used, a separate scan, using the appropriate excitation line, is carried out for each of the two fluorophores used. Fluorescent microarray scanners are commercially available from Affymetrix, Packard BioChip Technologies, BioRobotics and many other suppliers. Signals are recorded, quantitated and analyzed using a variety of computer software.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

In addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In certain embodiments, the data obtained from such experiments reflects the relative expression of each gene represented in the microarray. Expression levels in different samples and conditions may now be compared using a variety of statistical methods.

In certain embodiments, the cell comprises a tissue sample, which may be present on a tissue microarray. For example, paraffin-embedded formalin-fixed specimens may be prepared, and punch "biopsy" cores taken from separate areas of the specimens. Each core may be arrayed into a separate recipient block, and sections cut and processed as previously described, for example, in Konenen, J. et al., Tissue microarrays for high-throughput molecular profiling of tumor specimens, (1987) *Nat. Med.* 4:844-7 and Chung, G. G. et al., *Clin. Cancer Res.* (In Press).

In other embodiments, the cell comprises a cell culture pellet, which may be present on a cell culture pellet microarray.

In certain embodiments, it is sufficient to determine the expression of one or only a few genes, as opposed to hundreds or thousands of genes. Although microarrays may be used in these embodiments, various other methods of detection of gene expression are available. This section describes a few exemplary methods for detecting and quantifying mRNA or polypeptide encoded thereby. Where the first step of the methods includes isolation of mRNA from cells, this step may be conducted as described above. Labeling of one or more nucleic acids may be performed as described above.

In one embodiment, mRNA obtained from a sample is reverse transcribed into a first cDNA strand and subjected to PCR, e.g., RT-PCR. House keeping genes, or other genes whose expression does not vary may be used as internal controls and controls across experiments. Following the PCR reaction, the amplified products may be separated by electrophoresis and detected. By using quantitative PCR, the level of amplified product will correlate with the level of RNA that was present in the sample. The amplified samples may also be separated on an agarose or polyacrylamide gel, transferred onto a filter, and the filter hybridized with a probe specific for the gene of interest. Numerous samples may be analyzed simultaneously by conducting parallel PCR amplification, e.g., by multiplex PCR.

"Dot blot" hybridization has gained wide-spread use, and many versions were developed (see, e.g., M. L. M. Anderson and B. D. Young, in *Nucleic Acid Hybridization—A Practical Approach*, B. D. Hames and S. J. Higgins, Eds., IRL Press, Washington D.C., Chapter 4, pp. 73-111, 1985).

In another embodiment, mRNA levels is determined by dot blot analysis and related methods (see, e.g., G. A. Beltz et al., in *Methods in Enzymology*, Vol. 100, Part B, R. Wu, L. Grossmam, K. Moldave, Eds., Academic Press, New York, Chapter 19, pp. 266-308, 1985). In one embodiment, a specified amount of RNA extracted from cells is blotted (i.e., non-covalently bound) onto a filter, and the filter is hybridized with a probe of the gene of interest. Numerous RNA samples may be analyzed simultaneously, since a blot may comprise multiple spots of RNA. Hybridization is detected using a method that depends on the type of label of the probe. In another dot blot method, one or more probes for a 4E regulon component are attached to a membrane, and the membrane is incubated with labeled nucleic acids obtained from and optionally derived from RNA of a cell or tissue of a subject. Such a dot blot is essentially an array comprising fewer probes than a microarray.

Another format, the so-called "sandwich" hybridization, involves covalently attaching oligonucleotide probes to a solid support and using them to capture and detect multiple nucleic acid targets (see, e.g., M. Ranki et al. (1983) *Gene*, 21:77-85; A. M. Palva, et al, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. (1979) *Nucleic Acid Res.* 6, 11:3543; and B. J. Connor et al. (1983) *PNAS* 80:278-282). Multiplex versions of these formats are called "reverse dot blots."

mRNA levels may also be determined by Northern blots. Specific amounts of RNA are separated by gel electrophoresis and transferred onto a filter which is then hybridized with a probe corresponding to the gene of interest. This method, although more burdensome when numerous samples and genes are to be analyzed provides the advantage of being very accurate.

Another method for high throughput analysis of gene expression is the serial analysis of gene expression (SAGE) technique, first described in Velculescu et al. (1995) *Science* 270, 484-487. Among the advantages of SAGE is that it has the potential to provide detection of all genes expressed in a given cell type, provides quantitative information about the relative expression of such genes, permits ready comparison of gene expression of genes in two cells, and yields sequence information that may be used to identify the detected genes. Thus far, SAGE methodology has proved itself to reliably detect expression of regulated and nonregulated genes in a variety of cell types (Velculescu et al. (1997) *Cell* 88, 243-251; Zhang et al. (1997) *Science* 276, 1268-1272 and Velculescu et al. (1999) *Nat. Genet.* 23, 387-388).

Techniques for producing and probing nucleic acids are further described, for example, in Sambrook et al., *Molecular Cloning: A Laboratory Manual* (New York, Cold Spring Harbor Laboratory, 1989).

Alternatively, the level of expression of a 4E regulon component is determined by in situ hybridization. In one embodiment, a tissue sample is obtained from a subject, the tissue sample is sliced, and in situ hybridization is performed according to methods known in the art, to determine the level of expression of the 4E regulon component.

In other methods, the level of expression of a 4E regulon component is detected by measuring the level of protein encoded by the 4E regulon component. This may be done, e.g., by immunoprecipitation, ELISA, or immunohistochemistry using an agent, e.g., an antibody, that specifically detects the protein encoded by the gene. Other techniques include Western blot analysis Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which may be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, may be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, the level of expression of these polypeptides may be measured in biological fluids.

The above-described methods may be performed using cells grown in cell culture, or on cell or tissue specimens from a subject. Specimens may be obtained from an individual to be tested using either "invasive" or "non-invasive" sampling means. A sampling means is said to be "invasive" if it involves the collection of nucleic acids from within the skin or organs of an animal (including, especially, a murine, a human, an ovine, an equine, a bovine, a porcine, a canine, or a feline animal). Examples of invasive methods include blood collection, semen collection, needle biopsy, pleural aspiration, umbilical cord biopsy, etc. Examples of such methods are discussed by Kim, C. H. et al. (1992) *J. Virol.* 66:3879-3882; Biswas, B. et al. (1990) *Annals NY Acad. Sci.* 590:582-583; Biswas, B. et al. (1991) *J. Clin. Microbiol.* 29:2228-2233. It is also possible to obtain a cell sample from a subject, and then to enrich it in the desired cell type. For example, cells may be isolated from other cells using a variety of techniques, such as isolation with an antibody binding to an epitope on the cell surface of the desired cell type.

In certain embodiments, a single cell is used in the analysis. It is also possible to obtain cells from a subject and culture the cells in vitro, such as to obtain a larger population of cells from which RNA may be extracted. Methods for establishing cultures of non-transformed cells, i.e., primary cell cultures, are known in the art.

When analyzing from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA and proteins in the tissue and cells may quickly become degraded. Accordingly, in a preferred embodiment, the cells obtained from a subject are snap frozen as soon as possible.

K. Agents that Bind 4E Regulon Components

Provided also are agents that bind 4E regulon components. Preferably, such agents are 4E regulon component antibodies or antigen-binding fragments thereof, including polyclonal and monoclonal antibodies, prepared according to conventional methodology. Antibodies and antigen-binding fragments thereof that bind 4E regulon components are useful for determining 4E regulon component levels.

Antibodies and antigen-binding fragments thereof that bind a 4E regulon component and are useful for determining 4E regulon component levels, include but are not limited to: antibodies or antigen-binding fragments thereof that bind specifically to a 4E regulon component or fragments or analogs thereof.

Significantly, as is well-known in the art, only a small portion of an antibody molecule, the paratrope, is involved in the binding of the antibody to its epitope (see, in general, Clark, W. R. (1986) The Experimental Foundations of Modem Immunology, Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab') .sub.2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clark, W. R. (1986) The Experimental Foundations of Modem Immunology, Wiley & Sons, Inc., New York; Roitt, I. (1991) Essential Immunology, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859, 205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to 4E regulon component polypeptides and nucleic acids. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to 4E regulon component molecules. This process can be repeated through several cycles of reselection of phage that bind to the 4E regulon component molecules. Repeated rounds lead to enrichment of phage bearing particular sequences. DNA sequences analysis can be conducted to identify the sequences of the expressed polypeptides. The minimal linear portion of the sequence that binds to the 4E regulon component molecules can be determined One can repeat the procedure using a biased library containing inserts containing part of all of the minimal linear portion plus one or more additional degenerate residues upstream or downstream thereof. Yeast two-hybrid screening methods also may be used to identify polypeptides that bind to the 4E regulon component molecules. Thus, 4E regulon component molecules can be used to screen peptide libraries, including phage display libraries, to identify and select peptide binding partners of the 4E regulon component molecules.

As detailed herein, the foregoing antibodies and other binding molecules may be used for example to isolate and identify a 4E regulon component, e.g. to detect its expression in tissue samples. The antibodies may be coupled to specific diagnostic labeling agents for imaging of the protein or fragment thereof. Exemplary labels include, but are not limited to, labels which when fused to a 4E regulon component molecule produce a detectable fluorescent signal, including, for example, green fluorescent protein (GFP), enhanced green fluorescent protein (EGFP), *Renilla reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED). In another embodiment, a 4E regulon component polypeptide is conjugated to a fluorescent or chromogenic label. A wide variety of fluorescent labels are available from and/or extensively described in the *Handbook of Fluorescent Probes and Research Products* 8th Ed. (2001), available from Molecular Probes, Eugene, Oreg., as well as many other manufacturers.

In other embodiments, a 4E regulon component is fused to a molecule that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters.

L. Kits

The present invention provides kits for practice of any of the aforedescribed methods. The present invention provides kits, for example for treating various cancers. For example, a kit may comprise one or more pharmaceutical compositions (e.g. comprising compounds of Formulas I and II and/or gene therapy vectors) as described above and optionally instructions for their use. In still other embodiments, the invention provides kits comprising one or more pharmaceutical compositions and one or more devices for accomplishing administration of such compositions.

In certain embodiments, kits may comprise antibodies against a 4E regulon component. In other embodiments, a kit may comprise appropriate reagents for determining the level of protein activity in the cells of a subject.

In still other embodiments, a kit may comprise a microarray comprising probes of a 4E regulon component gene. A kit may comprise one or more probes or primers for detecting the expression level of a 4E regulon component and/or a solid support on which probes are attached and which may be used for detecting expression of a 4E regulon component. A kit may further comprise controls, buffers, and instructions for use.

Kits may also comprise a library of 4E regulon component gene expression levels associated with various cellular or disease states, e.g., reference sets. The kits may be useful for identifying subjects that are predisposed to developing a disease wherein 4E regulon activity is dysfunctional, as well as for identifying and validating therapeutics for a disease wherein 4E regulon activity is dysfunctional. In one embodiment, the kit comprises a computer readable medium on which is stored one or more gene expression patterns associated with various cellular or disease states, or at least values representing levels of expression of a 4E regulon component in various cellular or disease states. The kit may comprise expression profile analysis software capable of being loaded into the memory of a computer system.

Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, diagnosis, therapy, and other applications.

In addition to the embodiments, aspects and objects disclosed herein, including the claims appended hereto, the following paragraphs set forth additional, non-limiting embodiments and other aspects of the present invention.

One aspect relates to a method for diagnosing a disease wherein 4E regulon activity is dysfunctional, comprising: (a) determining in a biological sample from a subject the level of, phosphorylation state of, or activity of at least one 4E regulon component and (b) comparing the level of, phosphorylation state of, or activity of the at least one 4E regulon component with the level of, phosphorylation state of, or activity of the at least one 4E regulon component that is associated with a disease wherein 4E regulon activity is dysfunctional in a subject having a disease wherein 4E regulon activity is dysfunctional, wherein a similar level of, phosphorylation state of, or activity of the at least one 4E regulon component is indicative that the subject has or is likely to develop a disease wherein 4E regulon activity is dysfunctional or at least a symptom thereof.

In some embodiments, the method for prognosing or staging a disease wherein 4E regulon activity is dysfunctional, comprises: (a) determining in a biological sample from a subject the level of, phosphorylation state of, or activity of at least one 4E regulon component and (b) comparing the level of, phosphorylation state of, or activity of the at least one 4E regulon component with the level of or activity of the at least one 4E regulon component associated with a degree of, severity of or stage of the disease wherein 4E regulon activity is dysfunctional in a subject, wherein a similar level of, phosphorylation state of, or activity of the at least one 4E regulon component is indicative that the subject has that degree of, severity of or stage of the disease wherein 4E regulon activity is dysfunctional.

In some embodiments, the method for predicting the onset of a disease wherein 4E regulon activity is dysfunctional, comprises: (a) determining in a biological sample from a subject the level of, phosphorylation state of, or activity of at least one 4E regulon component and (b) comparing the level of, phosphorylation state of, or activity of the at least one 4E regulon component with the level of, phosphorylation state of, or activity of the at least one 4E regulon component associated with the likelihood of onset of the disease wherein 4E regulon activity is dysfunctional in a subject, wherein a similar level of, phosphorylation state of, or activity of at least one 4E regulon component is indicative that the subject has or is likely to develop the disease wherein 4E regulon activity is dysfunctional or at least a symptom thereof.

In some embodiments, the sample is selected from the group consisting of: plasma, blood, urine, saliva and tissue.

In some embodiments, the disease wherein 4E regulon activity is dysfunctional is selected from the group consisting of: cellular hypertrophy, cancer, and ischemia reperfusion.

In some embodiments, the at least one 4E regulon component is selected from the group consisting of: eIF4E; Cyclin D1; NBS/Nibrin; Pim-1; Cyclin B1; Cyclin A2; ODC; VEGF; Skp2; Cyclin E1; c-myc; FGF2; MMP-9; mdm2; caspase-9; bcl2; bcl/xL; Fbox1; CGGbp1; P54nrb/NONO.1; Selenoprotein S; eIF4E-BP1; Akt1; PI3K; GSK3B; HuR; and mTOR/FRAP1.

In some embodiments, the at least one 4E regulon component is selected from the group consisting of: 4E, NBS/Nibrin, Pim-1, VEGF, Cyclin D1, Cyclin A2, 4E-BP1, ODC and HuR.

In some embodiments, the level of, phosphorylation state of, or activity of at least two 4E regulon components is determined and compared.

In some embodiments, the level of, phosphorylation state of, or activity of at least one non-4E regulon component is determined and compared.

In some embodiments, the at least one non-4E regulon component is selected from the group consisting of: ER, PR, EGFR and Her2/neu.

In some embodiments, the level of the 4E regulon component is determined by either mass spectrometry in combination with gas chromatography, HPLC, liquid chromatography or thin layer chromatography.

In some embodiments, the activity of the 4E regulon component is determined by an immunoassay or an assay specific for the activity of that 4E regulon component.

In some embodiments, the method for diagnosing a disease wherein 4E regulon activity is dysfunctional, comprises: (a) determining in a cell of a subject the level of expression of at least one 4E regulon component gene or gene product and (b) comparing the level of expression of the at least one 4E regulon component gene or gene product with the level of expression of the at least one 4E regulon component gene or gene product associated with a disease wherein 4E regulon activity is dysfunctional in a subject having a disease wherein 4E regulon activity is dysfunctional, wherein a similar level of expression of the at least one 4E regulon component gene or gene product is indicative that the subject has or is likely to develop a disease wherein 4E regulon activity is dysfunctional or at least a symptom thereof.

In some embodiments, a method for prognosing or staging a disease wherein 4E regulon activity is dysfunctional, comprises: (a) determining in a cell of a subject the level of expression of at least one 4E regulon component gene or gene product and (b) comparing the level of expression of the at least one 4E regulon component gene or gene product with the level of expression of the at least one 4E regulon component gene or gene product associated with a degree of, severity of or stage of a disease wherein 4E regulon activity is dysfunctional in a subject, wherein a similar level of expression of the at least one 4E regulon component gene or gene product is indicative that the subject has that degree of, severity of or stage of a disease wherein 4E regulon activity is dysfunctional.

In some embodiments, a method for predicting the onset of a disease wherein 4E regulon activity is dysfunctional, comprises: (a) determining in a cell of a subject the level of expression of at least one 4E regulon component gene or gene product and (b) comparing the level of expression of the at least one 4E regulon component gene or gene product with the level of expression of the at least one 4E regulon component gene or gene product associated with the likelihood of onset of a disease wherein 4E regulon activity is dysfunctional in a subject, wherein a similar level of expression of the at least one 4E regulon component gene or gene product is indicative that the subject has or is likely to develop a disease wherein 4E regulon activity is dysfunctional or at least a symptom thereof.

In some embodiments, the disease wherein 4E regulon activity is dysfunctional is selected from the group consisting of: cellular hypertrophy, cancer, and ischemia reperfusion.

In some embodiments, the at least one 4E regulon component is selected from the group consisting of: eIF4E; Cyclin D1; NBS/Nibrin; Pim-1; Cyclin B1; Cyclin A2; ODC; VEGF; Skp2; Cyclin E1; c-myc; FGF2; MMP-9; mdm2; caspase-9; bcl2; bcl/xL; Fbox1; CGGbp1; P54nrb/NONO.1; Selenoprotein S; eIF4E-BP1; Akt1; PI3K; GSK3B; HuR; and mTOR/FRAP1.

In some embodiments, the at least one 4E regulon component is selected from the group consisting of: 4E, NBS/Nibrin, Pim-1, VEGF, Cyclin D1, Cyclin A2, eIF4E-BP1, ODC and HuR.

In some embodiments, the level of expression of at least two 4E regulon component genes or gene products is determined and compared.

In some embodiments, the level of expression of at least one non-4E regulon component gene or gene product is determined and compared.

In some embodiments, the at least one non-4E regulon component is selected from the group consisting of: ER, PR, EGFR, Her2/neu, and Ets oncogene.

In some embodiments, the level of expression of the at least one 4E regulon component gene or gene product is determined by determining the level of expression of the at least one 4E regulon component gene.

In some embodiments, the level of expression of the at least one 4E regulon component gene or gene product is determined by determining the amount of the at least one 4E regulon component gene or gene product in the cell.

In some embodiments, the level of expression of the at least one 4E regulon component gene or gene product is determined by determining the amount of the mRNA encoding the at least one 4E regulon component in the cell.

In some embodiments, the level of expression of the at least one 4E regulon component gene or gene product is determined by determining the AQUA™ score of the at least one 4E regulon component gene or gene product.

In some embodiments, the AQUA™ score of the at least one 4E regulon component gene or gene product is determined using the AQUA™ automated pathology system.

In some embodiments, the level of expression of the at least one 4E regulon component gene or gene product is determined using a microarray.

In some embodiments, the microarray comprises nucleic acids that are able to hybridize to the at least one 4E regulon component gene or gene product.

In some embodiments, the microarray comprises nucleic acids that are able to hybridize to a gene product of the at least one 4E regulon component gene.

In some embodiments, the microarray comprises polypeptides that are able to detect the at least one 4E regulon component gene or gene product.

In some embodiments, the cell comprises a tissue sample.

In some embodiments, the tissue sample is present on a microarray.

In some embodiments, the present invention relatest to an antibody specific for a 4E regulon component or a fragment thereof.

In some embodiments, a method for identifying at least one candidate therapeutic for treating a disease wherein 4E regulon activity is dysfunctional comprises: (a) contacting a cell with at least one candidate therapeutic, (b) determining in the cell pre- and post-contact with the at least one candidate therapeutic the level of, phosphorylation state of, or activity of at least one 4E regulon component, wherein modulation of the level of, phosphorylation state of, or activity of the at least one 4E regulon component indicates that at least one candidate therapeutic may be a therapeutic agent for treating or preventing the disease wherein 4E regulon activity is dysfunctional.

In some embodiments, a method for identifying at least one candidate therapeutic for treating a disease wherein 4E regulon activity is dysfunctional comprises: (a) contacting a cell with at least one candidate therapeutic, (b) determining in the cell pre- and post-contact with the at least one candidate therapeutic the level of expression of at least one 4E regulon component gene or gene product, wherein modulation of the level of expression of the at least one 4E regulon component gene or gene product indicates that at least one candidate therapeutic may be a therapeutic agent for treating or preventing the disease wherein 4E regulon activity is dysfunctional.

In some embodiments, a method for identifying at least one candidate therapeutic for treating a disease wherein 4E regulon activity is dysfunctional comprises: (a) contacting at least one cell with at least one candidate therapeutic, (b) determining in the at least one cell pre- and post-contact with the at least one candidate therapeutic whether cellular apoptosis has been restored, wherein restoration of cellular apoptosis indicates that the at least one candidate therapeutic may be a therapeutic agent for treating or preventing the disease wherein 4E regulon activity is dysfunctional.

In some embodiments, the disease is a proliferative disease or cancer.

In some embodiments, a method for identifying at least one candidate therapeutic for treating a disease wherein 4E regulon activity is dysfunctional comprises: (a) contacting at least one cell with at least one candidate therapeutic, (b) determining in the at least one cell pre- and post-contact with the at least one candidate therapeutic whether cellular apoptosis has been inhibited, wherein inhibition of cellular apoptosis indicates that the at least one candidate therapeutic may be a therapeutic agent for treating or preventing the disease wherein 4E regulon activity is dysfunctional.

In some embodiments, the disease is ischemia reperfusion injury

In some embodiments, the at least one candidate therapeutic is in a library of candidate therapeutics.

In some embodiments, the library is generated using combinatorial synthetic methods.

In some embodiments, the two candidate therapeutics are evaluated and wherein one candidate therapeutic is a known therapeutic for a disease wherein 4E regulon activity is dysfunctional.

In some embodiments, a method for selecting a therapy for a patient having a disease wherein 4E regulon activity is dysfunctional comprises:

providing at least one query value corresponding to the level of expression of at least one 4E regulon component gene or gene product whose expression is characteristic of a disease wherein 4E regulon activity is dysfunctional in a patient;

providing a plurality of sets of reference values corresponding to levels of expression of at least at least one 4E regulon component gene or gene product whose expression is characteristic of a disease wherein 4E regulon activity is dysfunctional in a patient, each reference value being associated with a therapy; and selecting the reference values most similar to the query values, to thereby select a therapy for said patient.

In some embodiments, selecting further includes weighing a comparison value for the reference values using a weight value associated with each reference values.

In some embodiments, the method comprises administering the therapy to the patient.

In some embodiments, the query values and the sets of reference values are expression profiles.

In some embodiments, a method for selecting a therapy for a patient having a disease wherein 4E regulon activity is dysfunctional comprises:

providing at least one query value corresponding to the level of, phosphorylation state of, or activity of at least one 4E regulon component whose expression is characteristic of a disease wherein 4E regulon activity is dysfunctional in a patient;

providing a plurality of sets of reference values corresponding to the levels of, phosphorylation states of, or activities of at least at least one 4E regulon component whose expression is characteristic of a disease wherein 4E regulon activity is dysfunctional in a patient, each reference value being associated with a therapy; and selecting the reference values most similar to the query values, to thereby select a therapy for said patient.

Also provided is a kit comprising reagents for the practice of any of the methods described herein and/or further comprising instructions for use.

EXAMPLES

The present invention is further illustrated by the following examples which should not be construed as limiting in any way. The contents of all cited references including literature references, issued patents, published or non published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, *Molecular Cloning A Laboratory Manual, 2nd Ed.*, ed. by Sambrook, Fritsch and Maniatis (Cold Spring Harbor Laboratory Press: 1989); *DNA Cloning*, Volumes I and II (D. N. Glover ed., 1985); Oligonucleotide Synthesis (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986) (Cold Spring Harbor Laboratory Press, Cold Spring Harbor, N.Y., 1986).

Example 1 Ribavirin Suppresses eIF4E-Mediated Oncogenic Transformation by Physical Mimicry of the 7-Methyl Guanosine mRNA Cap The eukaryotic translation initiation factor eIF4E is deregulated in many human cancers, and its overexpression in cells leads to malignant transformation. Oncogenic properties of eIF4E are directly linked to its ability to bind 7-methyl guanosine of the 5' end of the mRNA. Here, we observe that the antiviral guanosine analogue Ribavirin binds to eIF4E with micromolar affinity at the functional site used by 7-methyl guanosine mRNA cap, competes with eIF4E:mRNA binding, and, at low micromolar concentrations, selectively disrupts eIF4E subcellular organization and transport and translation of mRNAs posttranscriptionally regulated by eIF4E, thereby reducing levels of oncogenes such as cyclin D1. Ribavirin potently suppresses eIF4E-mediated oncogenic transformation of murine cells in vitro, of tumor growth of a mouse model of eIF4E-dependent human squamous cell carcinoma in vivo, and of colony formation of eIF4E-dependent acute myelogenous leukemia cells derived from human patients. These findings describe a specific, potent, and unforeseen mechanism of action of Ribavirin. Quantum mechanical and NMR structural studies offer directions for the development of derivatives with improved cytostatic and antiviral properties. In all, Ribavirin's association with eIF4E may provide a pharmacologic means for the interruption of post-transcriptional networks of oncogenes that maintain and enhance neoplasia and malignancy in human cancer.

General Methods

Reagents.

All reagents were of ACS grade from Sigma-Aldrich except for Tris-carboxyethyl phosphine (Pierce), Nonidet P-40 (ICN), isopropyl-β-D-thiogalactopyranoside (Lab Scientific), and Ribavirin (Calbiochem). Because of the presence of a highly toxic contaminant in commercially available Ribavirin (data not shown), Ribavirin and 7-methyl guanosine ($m^7G$) were purified by reverse-phase high-performance liquid chromatography (Waters) using a semi-preparative $C_8$ column (Vydac) and a linear acetonitrile gradient in 0.1% (vol/vol) aqueous trifluoroacetic acid, lyophilized, and stored in a dessicator at −20° C. until use. This yielded purity of >99.99% as measured by using thin-layer chromatography in 47:3 dichloromethane:methanol on aluminum oxide silica and electrospray ionization MS (data not shown). Rib4C (1-β-D-ribofuranosyl-1,2,3-triazole-4-carboxamide) was 99.98% pure and a kind gift of Zhi Hong (ICN). Ribavirin-5' triphosphate (RTP) was obtained from Jena Bioscience.

Protein Expression.

For fluorescence titrations, mouse eIF4E, which differs from human eIF4E by four nonconserved amino acids, was produced as described. For NMR spectroscopy, mouse eIF4E was expressed as a fusion with the B1 domain of protein G (G4E, kind gift of Gerhard Wagner, Harvard University, Cambridge, Mass.), in BL21 (DE-3) cells by induction with 0.8 mM isopropyl-β-D-thiogalactopyranoside at 18° C. for 20 h in M9 minimal media containing 1 g/l $^{15}NH_4Cl$ as the sole nitrogen source (Cambridge Isotopes). Cells were lysed at 4° C. by sonication in 0.1 M NaCl/50 mM Tris.HCl (pH 7.5/0.5 mM EDTA/0.5% (vol/vol) Nonidet P-40/10 mM 2-mercaptoethanol/1 mM PMSF. Lysates were cleared by centrifugation at 30,000×g, adsorbed onto $m^7G$ diphosphate-conjugated agarose (Amersham Pharmacia), and extensively washed with 0.1 M NaCl/20 mM Tris.HCl (pH 7.5)/0.5 mM EDTA (Buffer A) at 4° C. Subsequently, beads were washed with 0.1 mM GTP in Buffer A, and G4E was eluted with 5 mM $m^7G$ in Buffer A. Eluate was diluted with 20 mM $Na_2PO_4$ (pH 7.5) to reduce NaCl concentration to 50 mM, applied to Sepharose Q anion exchange column (Amersham Pharmacia), and eluted with a linear gradient of NaCl in 20 mM $Na_2PO_4$ (pH 7.5) at 4° C. Eluate was dialyzed extensively against 0.1 M NaCl/50 mM $Na_2PO_4$ (pH 6.5)/5 mM DTT at 4° C. to produce apo-G4E, as verified by using NMR spectroscopy and fluorescence titrations. Purity and identity of G4E were verified by using SDS/PAGE and electrospray ionization MS. Proteins were concentrated by using Amicon concentrators (Millipore).

Fluorescence Spectroscopy.

Fluorescence measurements were performed by using a home-built fluorimeter, as described. All titrations were performed in 0.3 M NaCl/10 mM $Na_2PO_4$ (pH 7.5)/1 μM zinc in 0.3×0.3 $cm^2$ fluorescence cuvette (Hellma), by using eIF4E concentration of 2 μM. Collected emission spectra were integrated between 300 and 450 nm, and spectral contribution of eIF4E was determined by subtraction of intrinsic fluorescence of added ligands by using extinction coefficients of 740 and 970 $M^{-1}cm^{-1}$ at 295 nm for Ribavirin and Rib4C, respectively (data not shown), and corrected for the inner filter effect and for the minor attenuation of signal that occurs as a result of fluorophore dilution in the course of the titrations. Corrected relative fluorescence intensities were normalized, and fluorescence quenching curves were fit to a heuristic single-site-binding expression:

$$I/I_0 = K_d^n / (x^n + K_d^n)$$

where x is ligand concentration, $K_d$ is the apparent dissociation constant, and n is the Hill coefficient.

m⁷G-Sepharose Affinity Chromatography.

m⁷G-Sepharose beads (Amersham Pharmacia, 20-μl slurry) were bound with 1.5 ml of 2 μM G4E, purified as described above, in 0.3 M NaCl/0.1 M sodium phosphate (pH 7.5)/10 μM protease-free BSA (USB)/0.1% Nonidet P-40 (Buffer B) for 30 min at room temperature. Beads were washed three times with Buffer B, and incubated with various concentrations of RTP or m⁷GTP in Buffer B for 30 min at room temperature. Upon washing released G4E three times with Buffer B, G4E remaining bound to m⁷G-Sepharose was boiled in Laemmli buffer (10% glycerol/2% SDS/100 mM DTT/80 mM Tris.HCl/0.06% bromophenol blue, pH 6.8), subjected to SDS/PAGE, and visualized by using Western blotting, as described below. Apparent inhibition constant was determined by using $K_i = IC_{50} \cdot K_d/(P+K_d)$, where $IC_{50}$ is the apparent 50% inhibitory nucleotide concentration, P is effective protein concentration, and $K_d$ is the apparent dissociation constant.

Cell Culture.

NIH 3T3 mouse fibroblasts were maintained under subconfluent conditions in DMEM (GIBCO/BRL)/10% (vol/vol) FBS/2 mM glutamate/0.1 mg/ml penicillin-streptomycin, at 37° C. in 5% $CO_2$. For cell treatments, drugs were dissolved in PBS (pH 7.4) and filter-sterilized. Untreated cells received filter-sterilized PBS.

Laser-Scanning Confocal Immunofluorescence Microscopy.

Cells were washed with PBS, fixed in methanol for 20 min at −20° C., and blocked in PBS, 10% (vol/vol) FBS, and 0.1% (vol/vol) Tween 20 for 30 min at room temperature. Blocked cells were stained with primary antibodies against Nopp140 [1:50 (2)], Sc35 (1:50, Becton Dickinson), and eIF4E (1:50, Transduction Laboratories) in blocking solution for 3 h at room temperature. Upon washing with PBS, cells were stained with secondary antibodies in blocking solution for 30 min. FITC-conjugated donkey anti-rabbit antibody (Jackson ImmunoResearch), Texas red-conjugated donkey anti-mouse antibody, and FITC-conjugated rabbit anti-mouse antibody, as appropriate. Subsequently, cells were washed with PBS and mounted in Vectashield supplemented with DAPI (Vector Laboratories). Fluorescence was observed by using 100× optical magnification and 2× digital zoom using Leica TCS-SP confocal microscope using excitation wavelengths of 488, 568, or 351/364 nm. All channels were detected separately, with no observable crosstalk. Micrographs represent single optical sections with a thickness of 300 nm, and are representative of 100 cells.

Cell Fractionation.

Cells were washed twice with PBS and lysed by slow pipetting in 0.14 M NaCl/10 mM Tris.HCl (pH 8.4)/1.5 mM $MgCl_2$/0.5% (vol/vol) Nonidet P-40/1 mM DTT/100 units/ml RNasin (Promega) at 4° C. Lysed suspensions were centrifuged at 1,000×g for 3 min at 4° C., and the supernatant was saved as the cytoplasmic fraction. Nuclear pellets were resuspended in lysis buffer, and 1/10th volume of 3.3% (wt/vol) sodium deoxycholate and 6.6% (vol/vol) Tween 40 was added under slow vortexing, and incubated at 4° C. for 5 min. Nuclei were sedimented by centrifugation at 1,000×g for 3 min at 4° C., and the supernatant (postnuclear fraction) was added to the cytoplasmic fraction. This yielded intact nuclei, as observed by using light microscopy, with no significant cytoplasmic contamination, as evaluated using $tRNA^{Lys}$ and β-actin contents. Fractionated cytoplasm was free of nuclear contamination, as indicated by absence of U6 snRNA and Sc35.

Northern Analysis.

RNA from whole cells or nuclear and cytoplasmic fractions was extracted by using Trizol according to manufacturer's instructions (GIBCO). Isolated RNAs were treated with RNase-free DNase I (Promega) and 5-1 μg aliquots were resolved on 1% formaldehydeagarose gel and transferred to a positively charged nylon membrane (Roche, Nutley, N.J.). Membranes were prehybridized in ULTRAhyb buffer (Ambion) and probed with 20 μM cyclin D1 cDNA probe, 5 μM β-actin cDNA probe, 30 μM biotinylated $tRNA^{Lys}$ antisense oligo probe, and 30 μM biotinylated U6 small nuclear RNA antisense oligo probe. cDNA probes were biotinylated by using BrightStar psoralen-biotin and observed by using CDP Star chemiluminescence according to the manufacturer's instructions (Ambion). Band intensity and film response were quantified by using NIH IMAGE.

Western Analysis.

Protein from whole cells or nuclear and cytoplasmic fractions was extracted by using 0.15 M NaCl/50 mM Tris.HCl (pH 7.4)/1% (vol/vol) Nonidet P-40/0.25% (wt/vol) sodium deoxycholate/1 mM EDTA/1 mM PMSF by incubating for 30 min at 4° C. Protein concentrations were determined by using bicinchoninic acid-copper reduction (Pierce) and 20-μg aliquots were resolved using SDS/PAGE, transferred to Immobilon-P membrane (Millipore), blocked, and probed by using primary antibodies against eIF4E (1:5000, Transduction Laboratories), cyclin D1 (1:500, Becton Dickinson), β-actin (1:5000, Sigma), c-myc (1:1000, Becton Dickinson), and Sc35 (1:5000, Santa Cruz Biotechnology). Bound antibodies were chemiluminescently detected by using horseradish peroxidase-conjugated secondary antibodies (Amersham Pharmacia) and SuperSignal West Pico reagent according to manufacturer's instructions (Pierce).

Immunopurification of eIF4E and Semiquantitative RT-PCR.

Nuclei isolated from 3×10⁷ cells were suspended 0.3 M NaCl/50 mM Tris.HCl (pH 7.4)/0.05% (vol/vol) Nonidet P-40 (NET-2 buffer), mechanically disrupted by using a manual homogenizer, incubated for 1 h at 4° C., and sedimented by centrifugation at 10,000×g. Soluble nuclear extracts were precleared by using Sepharose-conjugated protein G (Amersham Pharmacia) for 30 min at 4° C., incubated with 10 μg of mouse anti-eIF4E antibody (Transduction Laboratories) for 90 min at 4° C., and subsequently incubated overnight at 4° C. upon addition of 0.5 mg yeast tRNA (Sigma-Aldrich), 200 units/ml RNasin (Ambion), and Sepharose-conjugated protein G. Bound Sepharose was washed once with NET-2 buffer supplemented with 1 mg/ml heparin (Sigma-Aldrich) at 4° C., six times with NET-2 buffer alone, and suspended in 100 mM Tris.HCl (pH 6.8)/4% (wt/vol) SDS/20% (vol/vol) glycerol/12% (vol/vol) 2-mercaptoethanol, and incubated for 5 min at 98° C. RNA was extracted once with 25:24:1 phenol:chloroform:isopropanol, twice with chloroform:isopropanol, precipitated overnight at −20° C. with 2.5 volumes of absolute ethanol, 0.1 volume of 5 M sodium acetate (pH 5.2), and 20 μg glycogen (Sigma-Aldrich), washed with 75% (vol/vol) ethanol, and resuspended in water. Messenger RNA of cyclin D1 was amplified by using the ProStar first-strand RT-PCR system according to the manufacturer's instructions (Stratagene), using forward 5'-TCTACACTGACAACTCTATCCG-3' (SEQ ID NO:2) and reverse 5'-TAGCAGGAGAGGAAGT-TGTTGG-3' (SEQ ID NO: 3) primers. Although Ribavirin depletes the levels of eIF4E in the nucleus, eIF4E was still readily detected in the IPs (data not shown), and importantly, the same amounts of mRNA were used for RT-PCR independent of the Ribavirin concentration used. Thus, eIF4E-RNA binding from the nuclear fraction could be evaluated.

Purification of Ribosomes and Quantitative RT-PCR.

Cell pellets (500 mg) were homogenized in 1 ml of ice cold lysis buffer (20 mM Hepes/10 mM magnesium acetate/100 mM potassium acetate, pH 7.5) supplemented with protease inhibitors (EDTA-free Complete, Roche) and 400 units/ml of SUPERasine (Ambion), and incubated for 30 min on ice with occasional vortexing. Lysates were sedimented at 3,000×g for 10 min at 4° C. to pellet nuclei and cell debris. Supernatants were sedimented at 12,000×g for 20 min at 4° C. to pellet mitochondria. Cleared supernatants were then sedimented at 50,000 rpm (SW 50.1 rotor, Beckman) for 50 min at 4° C. to pellet ribosomes. Ribosomal pellets were resuspended in 200 µl of ice-cold lysis buffer and layered on top of 10-40% sucrose gradient buffered with the lysis buffer, and centrifuged at 50,000 rpm for 80 min at 4° C. RNA content of fractions was ascertained by using the ratio of absorbance at 260:280 nm. RNA was isolated by using Trizol according to manufacturer's instructions (GIBCO). RNA from each fraction was quantified by spectrophotometry and 40 ng was converted into cDNA by using the Sensiscript reverse transcription kit (Qiagen, Valencia, Calif.). Quantitative real-time PCR was carried out in triplicate by using the QuantiTect SYBR green real-time PCR Kit (Qiagen) in an Opticon thermal cycler (MJ Research, Waltham, Mass.). The following gene specific primers were used: forward 5'-ACCACAGTCCATGCCATCAC-3' (SEQ ID NO: 4) and reverse 5'-TCCACCACCCTGTTGCTGTA-3' (GAPDH, SEQ ID NO: 5), forward 5'-CCTGACAC-CAATCTCCTCAACG-3' (SEQ ID NO: 6) and reverse 5'-TCTTCGCACTTCTGCTCCTCAC-3' (cyclin D1, SEQ ID NO:7), forward 5'-TGCCAAGTGGTCCCAGGCTG-3' (SEQ ID NO: 8) and reverse 5'-CGGCTTGAAGATG-TACTCTAT-3' (VEGF, SEQ ID NO: 9), and forward 5'-GCATCAGCTTTCACGCTTG-3' (SEQ ID NO: 10) and reverse 5'-TCACCCACATGCATTTCAGG-3' (ODC, SEQ ID NO: 11). Obtained real-time PCR profiles were analyzed by using Opticon software (MJ Research).

Transformation Assay.

Cells were transfected with 5 µg of pMV, pMV-eIF4E, or pMV-eIF4E mutants by using GeneJammer reagent according to manufacturer's instructions (Stratagene), and selected using 1 mg/ml G418 sulfate for 48 h. Selected transfectants were plated at a density of 20,000 cells per 100-mm$^2$ dish, and maintained in the presence of 1 mg/ml G418 sulfate for 10 days. Dishes were washed with PBS, fixed with methanol, and stained with Giemsa. Foci were counted manually and experiments were repeated independently three times. Probability of focus formation is expressed as the number of foci, defined as having reduced light refraction and being >50 cells, divided by 20,000 (per 100-mm$^2$ dish).

Fluorescence-Activated Cell Scanning.

For assessment of necrosis and apoptosis, cells were washed twice with PBS, suspended in 0.14 M NaCl/10 mM Na-Hepes (pH 7.4/2.5 mM CaCl$_2$ at 4° C. at a density of $10^6$ cell per ml, and stained with 5 µg/ml propidium iodide and FITC-conjugated annexin V (Becton Dickinson) for 15 min at room temperature Immediately thereafter, cells were washed and analyzed by using a FACSCalibur fluorescence-activated cell scanner (Becton Dickinson). For assessment of cell-cycle profiles, cells were washed twice with PBS, fixed, and permeabilized in 70% (vol/vol) ethanol for 30 min at 4° C., and incubated in PBS containing 10 µg/ml propidium iodide and 30 units/ml RNase A at 37° C. for 30 min. For both measurements, detector gain and compensation settings were adjusted to minimize autofluorescence of unstained cells and channel crosstalk. For cell-cycle analysis, the propidium iodide channel was gated based on light scattering to exclude clumped cells, which may artifactually skew the observed fluorescence intensity.

Tetrazolium Dye Reduction.

Cells were seeded at a density of 5,000 cells per well and maintained in 100 µl per well in 96-well plates. Upon warming the reagents to 37° C., 5 ml of sodium 3'-[1-(phenylamino-carbonyl)-3,4-tetrazolium]-bis(4-methoxy-6-nitro)benzene sulfonic acid hydrate (XTT, Roche) dissolved at 1 mg/ml in RPMI medium 1640 without phenol red (GIBCO) was mixed with 0.1 ml of N-methyl dibenzopyrazine methyl sulfate (PMS, Roche) dissolved at 0.38 mg/ml in PBS Immediately after mixing, 50 µl of XTT-PBS solution was added to each well, and cells were incubated for 2-4 h at 37° C. Production of formazan was quantified by using a µ Quant plate reader (Bio-Tek Instruments) by monitoring the difference in absorbance at 492 and 690 nm, as referenced to the difference in absorbance of samples containing 50 µl of RPMI medium 1640 without phenol red. All experiments were repeated three times.

Clonogenic Assay by Using Primary Human Leukemia Patient Cells.

Acute myelogenous leukemia (AML) M1, M5, and normal bone marrow specimens were isolated from patients and processed as described. Primary AML cells were obtained from peripheral blood of patients at the Markey Cancer Center, University of Kentucky Medical Center (Lexington, Ky.). Normal bone marrow was obtained as waste material after pathological analysis, surgical marrow harvest, or from the National Disease Research Interchange (Philadelphia). All tissues were obtained with the approval of the Institutional Review Board and appropriate informed consent. Frozen CD34$^+$ progenitor cells were thawed in Iscove's modified Dulbecco's (IMD) medium supplemented with 10% (vol/vol) FBS. Viable cells were counted by using Trypan blue exclusion, and resuspended in 1% (vol/vol) H4100 methylcellulose IMD medium (Stem Cell Research), supplemented with 10% (vol/vol) BIT 9500 (Stem Cell Research), 2 mM glutamine (Sigma), 50 µg/ml low density lipoprotein (Sigma), and 50 µM 2-mercaptoethanol. Cells were plated at a density of 2,000 viable cells/1.1 ml of medium per 35 mm dish, and cultured in the presence of varying concentrations of Ribavirin for 14 days. Colonies with >20 cells were counted manually and experiments were repeated four times.

Mouse Model of Human Squamous Cell Carcinoma.

Female 5- to 7-week-old athymic NCr-nu/nu mice were obtained from Taconic Farms. Human FaDu cells, derived from a hypopharyngeal squamous cell carcinoma, were obtained from the American Type Culture Collection. Mice were inoculated s.c. into the right flank with 0.5×10$^6$ cells in 50 µl PBS, and were randomly segregated into two groups of 10 mice each. After 1 week of engraftment, treatment was administered orally each day at a dose of 40 µg/kg Ribavirin. Tumor size was ascertained by measuring tumor diameter, and statistical significance was ascertained by using a paired t test.

Calculation of Electrostatic Properties.

Molecular geometries of guanosine, m$^7$G, Ribavirin (1-β-D-ribofuranosyl-1,2,4-triazole-3-carboxamide), Rib4C (1-β-D-ribofuranosyl-1,2,3-triazole-4-carboxamide), ICN3297 (1-β-D-ribofuranosyl-1,2,4-triazole-3-carboxylate), and tiazofurin (2-β-D-ribofuranosyl-4-thiazolecarboxamide) were generated by using AMBER94, as implemented in INSIGHT 2000 (Accelrys, San Diego), optimized by using Møller-Plesset (MP2) perturbation theory with the 6-31G+

(d) orbital basis set, and parameterized by point charge fitting in vacuum, as implemented in Gaussian 03 (Gaussian). Electrostatic potentials in aqueous solution were calculated by using the Poisson-Boltzmann approximation with a dielectric constant of 80, as implemented in GRASP.

NMR Spectroscopy.

$^1$H, $^{15}$N heteronuclear single-quantum correlation (HSQC) spectra were recorded by using 500 MHz Bruker DRX spectrometer, in 0.1 M NaCl/50 mM Na$_2$PO$_4$ (pH 6.5)/5 mM DTT/5% (vol/vol) D$_2$O, at 288 and 298 K, by using protein concentration of 0.8 mM. Backbone $^1$H, $^{15}$N resonances of G4E were obtained from $^1$H, $^{13}$C, $^{15}$N resonance assignments of human eIF4E by direct spectral matching with a tolerance of 0.02 and 0.2 ppm in the $^1$H and $^{15}$N dimensions, respectively, leading to assignment of 64 unambiguous resonances in G4E, widely distributed in the eIF4E structure. HSQC titrations were carried out by using m$^7$G and Ribavirin in 0.1 M NaCl/50 mM Na$_2$PO$_4$ (pH 6.5)/5 mM DTT/5% (vol/vol) D$_2$O, and ligand:protein ratios ranging from 0.3:1 to 5:1. Structural parameters of Ribavirin binding were determined by using $^{15}$N-edited, $^{15}$N-filtered, and double $^{15}$N-edited, filtered $^1$H, $^1$H NOESY spectroscopy. The contribution of spin diffusion to the observed nuclear Overhauser effect intensities was assessed by using mixing times ranging from 50 to 250 msec, with no significant contribution of spin diffusion using mixing time of 180 ms, as assessed from the linear dependence of nuclear Overhauser effect transfer on mixing time. Spectra were processed by using NMRPIPE/NMRDRAW and analyzed by using NMRVIEW.

Results and Discussion

High-affinity binding of the m7G mRNA cap to mammalian eIF4E occurs by way of specific recognition of the methylated and consequently positively charged quaternary amine m7Gbase by two conserved tryptophans, W56 and W102, which form an aromatic stack as a result of cation-pi and pi-pi interactions.

Figure 1:
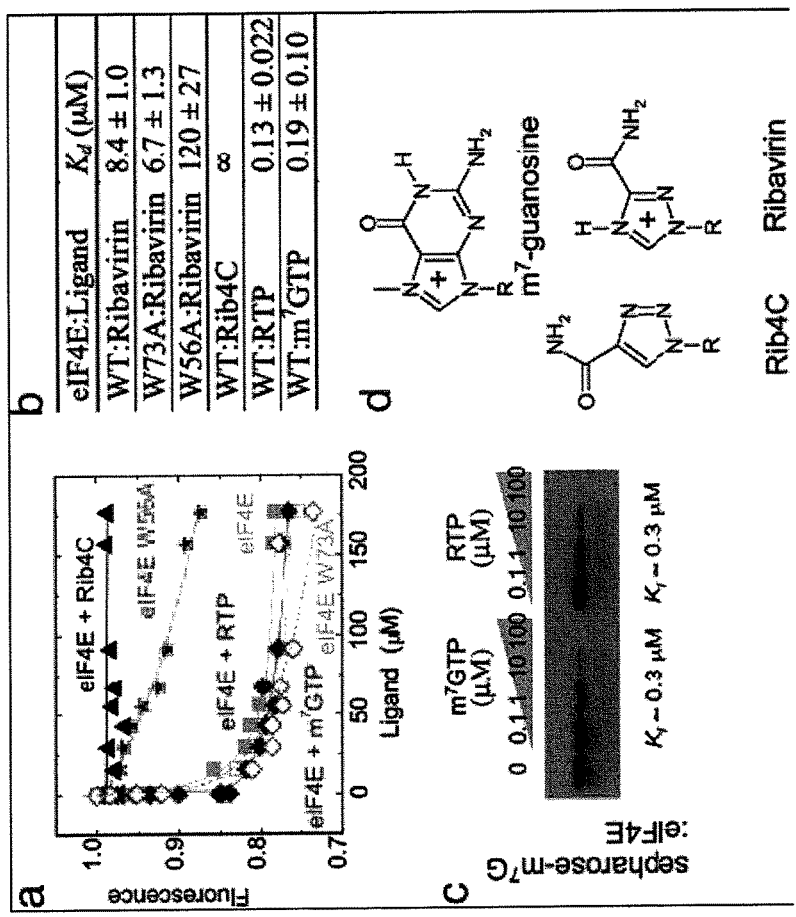
FIG. 1. Ribavirin, but not Rib4C, binds to the functional m7Gcap-binding site of eIF4E with the same affinity as m7G mRNA cap. (a) Normalized corrected tryptophan fluorescence intensity quenching and their fits for binding to Ribavirin to eIF4E wild-type (Filled squares), W73A (Open squares), W56A (stars), Rib4C to wild-type eIF4E (Filled triangles), RTP to wild-type eIF4E (Filled diamonds), and m7GTP to wild-type eIF4E (Open diamonds). (b) Apparent dissociation constants in micromolar for nucleoside/nucleotide:eIF4E binding. (c) Western blot of eIF4E remaining bound to m7G-Sepharose upon competition with various concentrations of m7GTP or RTP. Both m7GTP and RTP lead to 50% reduction of binding at a concentration of approximately 1 uM. (d) Chemical structures of the keto forms of m7G, Ribavirin, and Rib4C nucleosides. Note: +, positive charge; R, ribose.

Binding of the uncharged tertiary amine guanosine to eIF4E is >5000-fold weaker. Because the pKa values of 1,2,4-triazoles are >12, making them protonated and thus positively charged at physiological pH, we investigated whether eIF4E binds to the putatively cationic 1,2,4-triazole-3-carboxamide of Ribavirin (FIG. 1). The affinity of eIF4E for its nucleoside ligands in vitro can be measured by using tryptophan fluorescence emission spectroscopy, whereby binding of ligand quenches fluorescence of tryptophans that stack with it. Ribavirin binds to eIF4E with an apparent Kd of 8.4 uM, similar to that of m7G nucleoside (FIGS. 1a and 1b). Mutation of one of the tryptophans, W56A, in the cap-binding site reduces affinity by 14-fold, whereas mutation of W73A on the dorsal surface of eIF4E away from the cap-binding site has no significant effect on Ribavirin affinity (FIGS. 1a and 1b). Similar results are obtained by using m7G. Furthermore, the Ribavirin analogue 1-B-D-ribofuranosyl-1,2,3-triazole-4-carboxamide (Rib4C), which exhibits reduced antiviral and cellular effects and contains an uncharged 1,2,3-triazole with a reduced pKa, fails to bind eIF4E. Because Ribavirin is nearly completely converted to RTP in cells, we measured the affinity of eIF4E for RTP. eIF4E binds RTP and m7GTP with equal apparent dissociation constants of ca. 0.1 uM (FIGS. 1a and 1b). By using m7G-Sepharose affinity chromatography, we observe that RTP competes with eIF4E: m7G binding with an apparent inhibition constant (Ki) of ca. 0.3 uM, nearly indistinguishable from m7GTP itself (FIG. 1c). In all, these results indicate that Ribavirin binds eIF4E with high affinity, at the functional site used by 5' m7G mRNA cap, as a result of cationic interaction with the cap-binding tryptophans, and suggest that Ribavirin competes with m7G 5' mRNA cap binding to eIF4E in cells.

In mammalian cells, functions of eIF4E depend on its subcellular organization. In the cytoplasm, eIF4E associates with ribosomes and functions in m7G cap-dependent mRNA translation. Up-regulation of eIF4E increases translation of only a specific set of sensitive mRNAs, those that are posttranscriptionally regulated by eIF4E at the level of mRNA translation. In the nucleus, eIF4E forms multiprotein structures, termed eIF4E nuclear bodies, and plays a role in nucleocytoplasmic mRNA transport of a specific set of mRNA transcripts. The formation and function of these structures are linked with eIF4E's mRNA cap binding because treatment of permeabilized cells with excess m7G cap analogue disrupts eIF4E nuclear bodies but not other subnuclear structures. Consistently, disruption of eIF4E bodies impedes nucleocytoplasmic eIF4E-dependent mRNA transport.

Because Ribavirin binds eIF4E with high affinity and competes with eIF4E:m7G binding in vitro, we examined whether it affects subcellular organization of eIF4E in cells. Thus, we treated NIH 3T3 fibroblasts with varying concentrations of Ribavirin for 48 h and monitored their subcellular organization by using immunofluorescence in conjunction with confocal microscopy.

Figure 2:
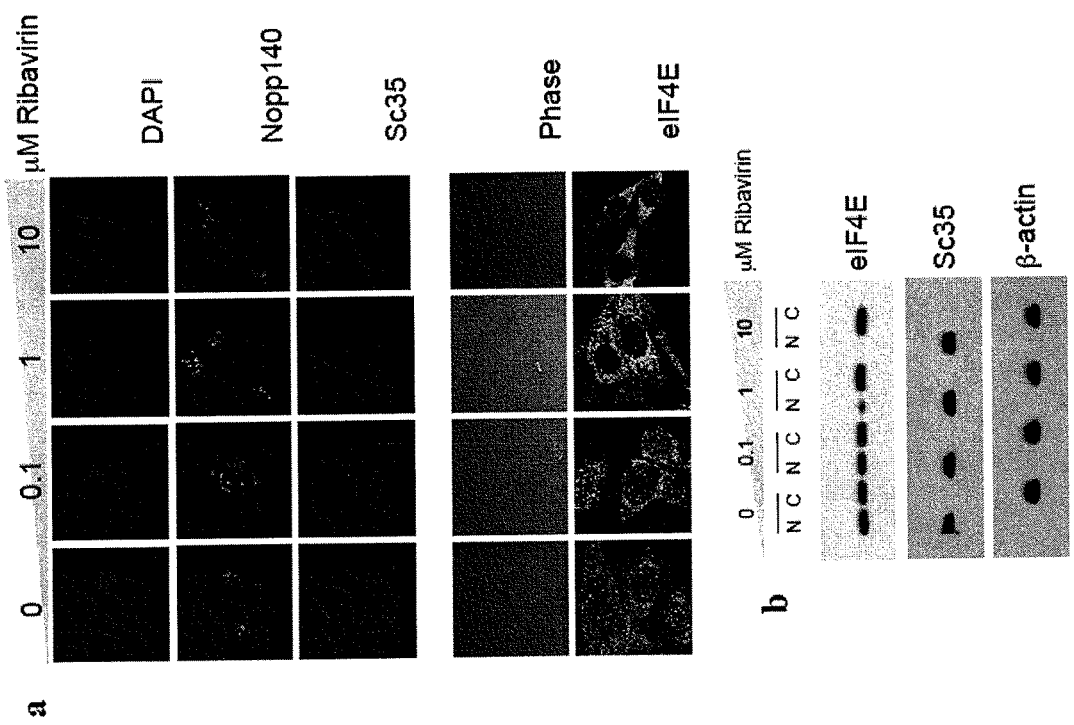
FIG. 2. Ribavirin specifically disrupts subcellular eIF4E organization. (a) Confocal immuno-fluorescence micrographs of Ribavirin-treated NIH 3T3 cells stained with DAPI (chromatin), Nopp140 (Cajal bodies and nucleoli), Sc35 (splicing speckles), and eIF4E (eIF4E nuclear bodies and cytoplasmic eIF4E). (b) Western blots of protein extracts of nuclear (N) and cytoplasmic (C) fractions of Ribavirin-treated NIH 3T3 cells, probed for nuclear and cytoplasmic eIF4E, and for predominantly nuclear Sc35, and predominantly cytoplasmic β-actin, as controls of fractionation and loading. Ribavirin treatment leads to specific disruption of nuclear eIF4E bodies and cytoplasmic retention of eIF4E with an $EC_{50}$ of 0.1-1 µM.

Ribavirin treatment has no apparent effects on chromatin structure (DAPI), organization of nucleoli and Cajal bodies (nucleolar protein Nopp140), structure of splicing speckles (Sc35 domains), and cellular morphology (FIG. 2a). In contrast, Ribavirin treatment disrupts eIF4E nuclear bodies, with this effect evident at 1 uM and nearly complete at 10 uM (FIG. 2a). To confirm this effect, we fractionated cells and examined relative protein abundance in nuclear and cytoplasmic fractions by using Western blotting methods. In agreement with the above microscopy studies, Ribavirin treatment leads to redistribution of eIF4E without affecting the distributions of predominantly nuclear Sc35 and cytoplasmic B-actin (FIG. 2b). Importantly, Ribavirin treatment does not alter total protein levels of eIF4E but, rather, relocalizes the majority of the protein to the cytoplasm. Thus, Ribavirin may interfere with mRNA transport and translation of genes posttranscriptionally regulated by eIF4E.

To test this possibility directly, we fractionated cells treated with Ribavirin and assessed effects on nucleocytoplasmic mRNA transport by monitoring cyclin D1 mRNA levels of nuclear and cytoplasmic fractions by using subcellular fractionation and Northern methods or independently, using quantitative PCR. Ribavirin treatment impedes nucleocytoplasmic transport of cyclin D1 mRNA with an apparent EC50 of approx 1 uM, with nearly complete nuclear retention at 100 uM.

On the other hand, nucleocytoplasmic transport of B-actin and VEGF mRNAs is not affected even at 100 uM (FIGS. 3a and 4b), which is consistent with insensitivity of their transport to eIF4E activity. Ribavirin treatment does not appear to affect splicing and 5' capping of pre-mRNAs because co-transcriptional capping is required for pre-mRNA splicing, and both cyclin D1 and B-actin mRNAs are correctly spliced (FIG. 3a). Moreover, Ribavirin does not appear to affect expression or localization of nuclear RNAs with methylphosphate cap structures such as U small nuclear RNAs, because the levels and distribution of U6 small nuclear RNA are not affected (FIG. 3a). Similarly, Ribavirin treatment has no effect on mRNA transcription and stability, because the total steady-state levels of cyclin D1, VEGF, and B-actin mRNAs are not affected (FIGS. 3b and 4).

We extended our studies to examine the effects of Ribavirin on mRNA translation in the cytoplasm by monitoring polysomal loading of mRNAs translationally regulated by eIF4E. Polysomal fractions were prepared, and mRNA content was assessed by using real-time PCR. Ribavirin treatment has no significant effect on the polysomal loading profile of cyclin D1 mRNA (FIG. 4a), which is consistent with lack of regulation by eIF4E of cyclin D1 levels at the level of translation. In contrast, Ribavirin treatment leads to a shift of VEGF and ODC mRNAs from heavier polysomal to lighter monosomal fractions, which have decreased translational efficiency. The decrease of polysomal loading is >1,000-fold (FIG. 4a), in agreement with translational regulation of VEGF and ODC levels by eIF4E. Thus, the apparent sensitivity of genes to Ribavirin parallels their sensitivity to regulation by eIF4E, in terms of which genes are affected and the level(s) of regulation. Because many genes are post-transcriptionally regulated by eIF4E, we focused on cyclin D1 as a model transcript because eIF4E's ability to modulate its mRNA transport is well characterized.

Figure 3:
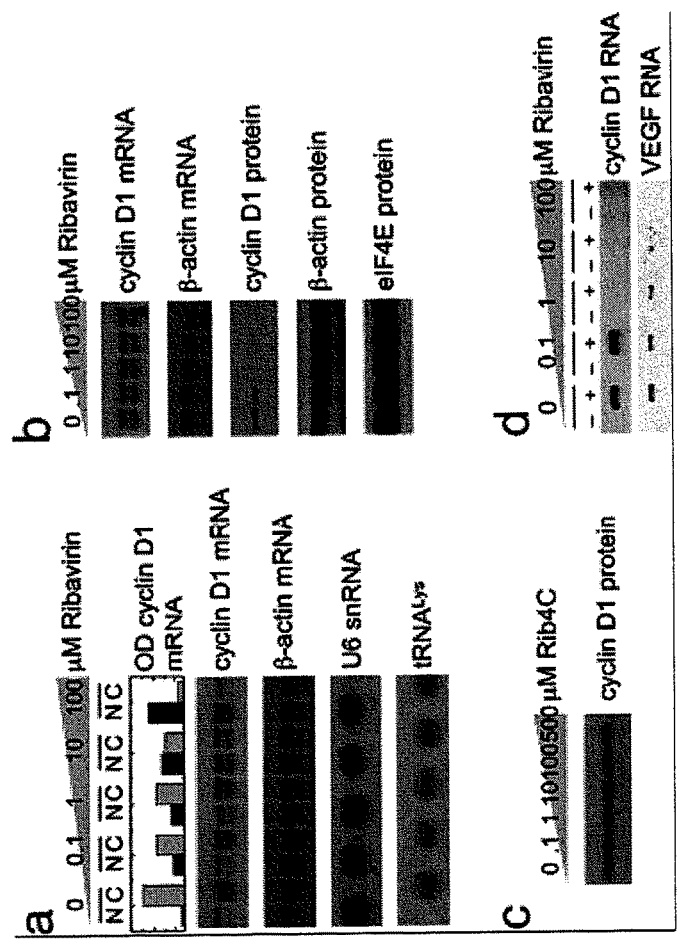
FIG. 3. Ribavirin specifically inhibits eIF4E:mRNA binding, inhibits nucleocytoplasmic mRNA transport, and depletes levels of transport-regulated proteins. (a) Northern blots of RNA extracts of nuclear and cytoplasmic fractions of Ribavirin treated NIH 3T3 cells, which were probed as indicated. U6 small nuclear RNA and tRNALys serve as controls for quality of the fractionation. Ribavirin inhibits nucleocytoplasmic mRNA transport of cyclin D1, but not B-actin, with an apparent EC50 of ca. 1 uM, as judged from the bar graph quantification (top row). N, nuclear; C, cytoplasmic. This effect was confirmed by using quantitative real-time PCR (FIG. 4b). (b) Northern and Western blots of total extracts of Ribavirin-treated cells, exhibiting depletion of cyclin D1, without affecting transcription, mRNA stability, and protein synthesis. (c) Western blot of total protein extract of Rib4C-treated cells that were probed for cyclin D1. (d) Semiquantitative RT-PCR of cyclin D1 mRNA contained in eIF4E purified from the nuclei of Ribavirin-treated cells. Control samples were purified by using IgG antibody (−) instead of antibody specific for eIF4E (+). Semiquantitative PCR of VEGF from cytoplasmic extracts was immunopurified as above.
Figure 4:
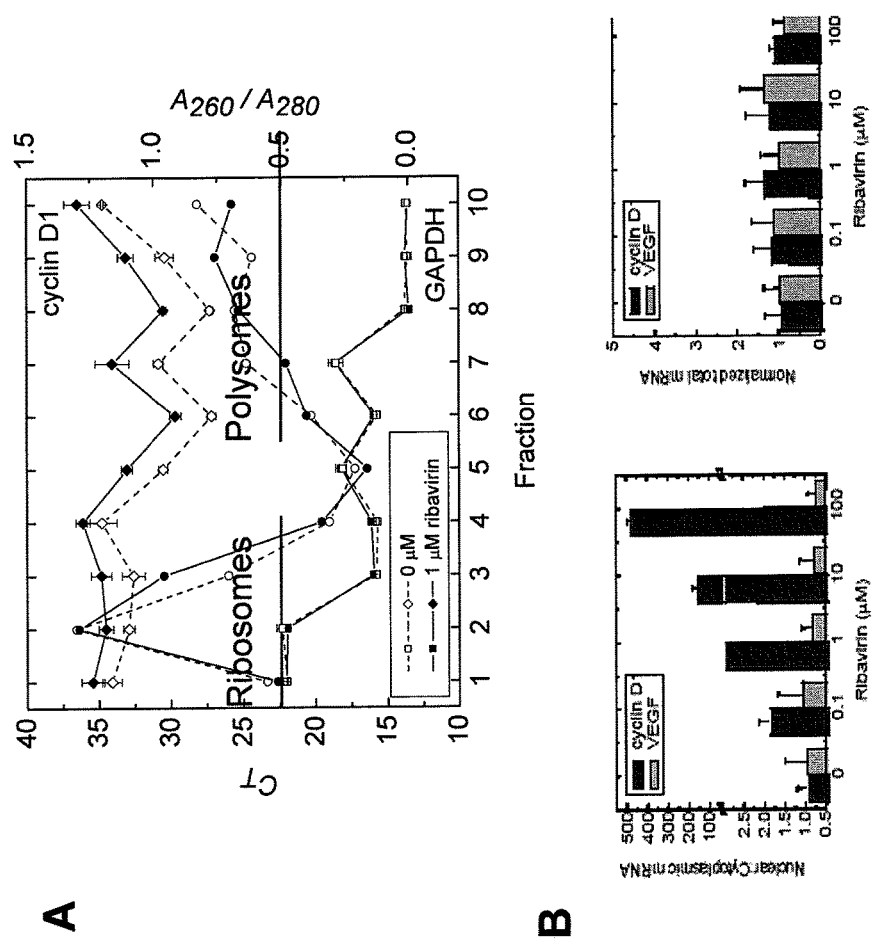
FIG. 4. (a) RNA profiles ($A_{260}/A_{280}$) of ribosomal purification fractions and their cyclin D1, GAPDH, ODC, and VEGF mRNA content as measured using quantitative RT-PCR and represented using threshold cycle ($C_T$). Error bars represent ±1σ of three independent experiments. Treatment of cells with 1 µM Ribavirin has no significant effect on ribosomal loading and initiation of mRNA translation of cyclin D1 and GAPDH mRNAs. Lower $C_T$ values indicate higher mRNA abundance. A $C_T$ difference of n is equivalent to $n^2$-fold difference in concentration. Note that whereas the cytoplasmic levels of cyclin D1 mRNA are reduced by Ribavirin treatment, the efficiency of its loading onto polysomes relative to monosomes is unaffected, in contrast to ODC and VEGF mRNAs, whose loading on polysomes is significantly reduced as compared with monosomal loading. (b) Normalized ratios of nuclear to cytoplasmic (Left) and total (Right) mRNA levels of cyclin D1 (red) and VEGF (green) of NIH 3T3 cells treated with various concentrations of Ribavirin, as measured by using quantitative real-time PCR. Note that 2-fold nuclear retention of cyclin D1 mRNA is evident at 0.1 µM Ribavirin FIG. 5. (a) Western blot of protein extracts of transfected NIH 3T3 cells, probed for eIF4E. (b) Percentage of nonpermeabilized NIH 3T3 cells binding annexin V (apoptosis) and those taking up propidium iodide (necrosis), as measured using FACS (left axis), and efficiency of tetrazolium dye reduction (metabolism), as measured using optical density (OD) of formazan (right axis), upon Ribavirin treatment for the same length of time as foci formation assays (see Examples). Error bars represent ±1σ of three independent experiments. Significant effects on viability and metabolism are observed only at Ribavirin concentrations of 100 µM and greater, consistent with its poisoning of guanosine pathways, such as mRNA misincorporation, only at these high millimolar concentrations. (c) DNA content histograms as measured using propidium iodide binding of permeabilized NIH 3T3 cells (left axis) and their cumulative probability distributions (right axis) of untreated cells (blue) and cells treated with 0.1 µM Ribavirin (red). Ribavirin treatment increases the proportion of cells restricted to the $G_1$ phase from 58% to 91%. Oncogenic transformation of NIH 3T3 cells mediated by eIF4E is specifically suppressed by Ribavirin with an apparent $EC_{50}$ of 0.1-1 µM and correlates with $G_1$ cell-cycle arrest.

Ribavirin treatment reduces levels of cyclin D1 protein with an apparent EC50 of 0.1-1 uM (FIG. 3b), which is consistent with its inhibition of nucleocytoplasmic cyclin D1 mRNA transport with an EC50 of approx. 1 uM (FIGS. 3a and 4). In contrast, treatment with Rib4C, which does not bind to eIF4E in vitro (FIG. 1), cannot repress cyclin D1 protein production in cells (FIG. 3c). Furthermore, levels of B-actin and eIF4E proteins, which are not post-transcriptionally regulated by eIF4E (FIG. 3a), are not reduced by Ribavirin treatment (FIG. 3b). Thus, Ribavirin's specific interaction with eIF4E is required for Ribavirin's ability to suppress eIF4E dependent mRNA transport of cyclin D1.

We tested the ability of Ribavirin to directly alter the ability of eIF4E to form ribonucleoproteins with transcripts sensitive to eIF4E-dependent mRNA transport (e.g., cyclin D1) and at the translation level (e.g., VEGF). Thus, we immunopurified eIF4E from nuclei of Ribavirin-treated cells and assessed its mRNA content by using semiquantitative RT-PCR (FIG. 3d). Ribavirin treatment leads to inhibition of eIF4E binding to cyclin D1 mRNA in cells with an apparent EC50 of ca. 1 uM (FIG. 3d), similar to the Kd for binding of its triphosphate to eIF4E in vitro (FIG. 1) and to the EC50 for inhibition of nucleocytoplasmic cyclin D1 mRNA transport and depletion of cyclin D1 protein in cells (FIG. 3). Similarly, cytoplasmic eIF4E:VEGF mRNA complexes are partly abrogated, even by 1 uM Ribavirin (FIG. 3d), which is consistent with the observed alterations in polysomal loading by Ribavirin (FIG. 4).

Figure 5:
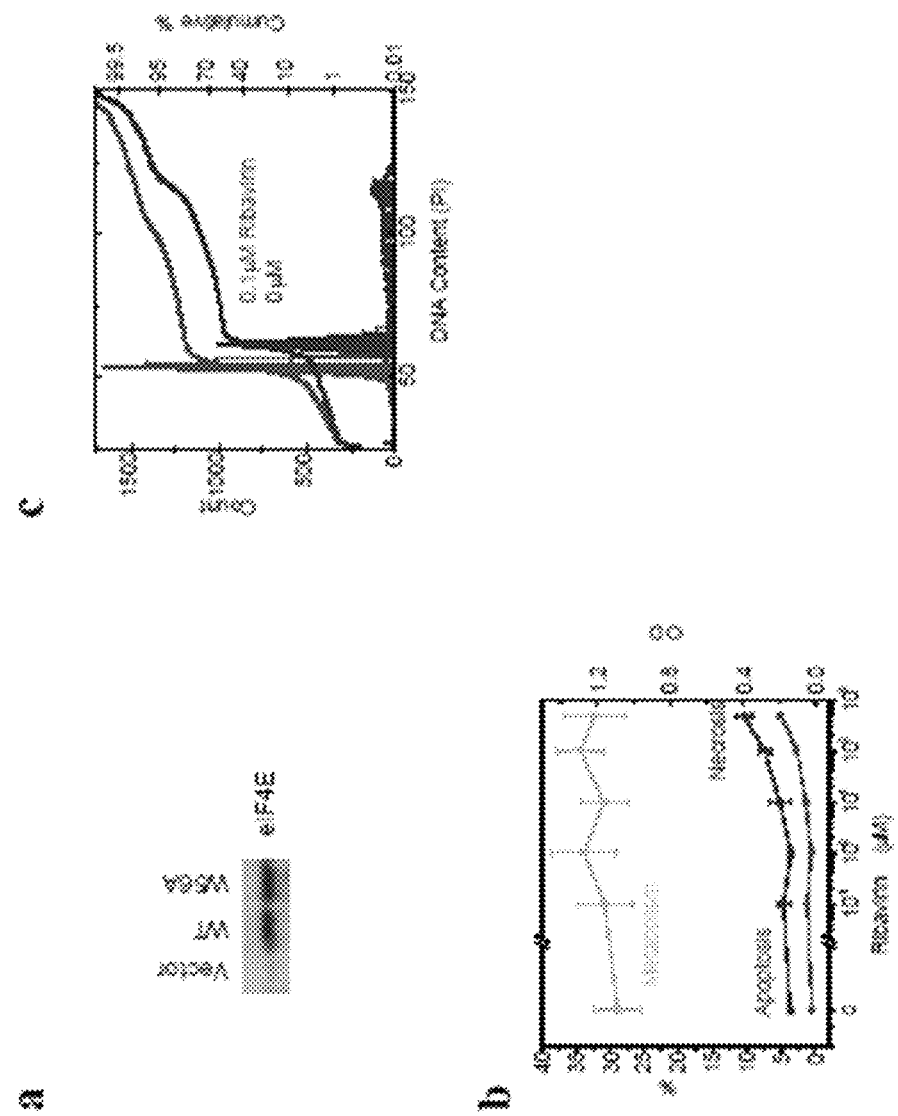
Figure 6:
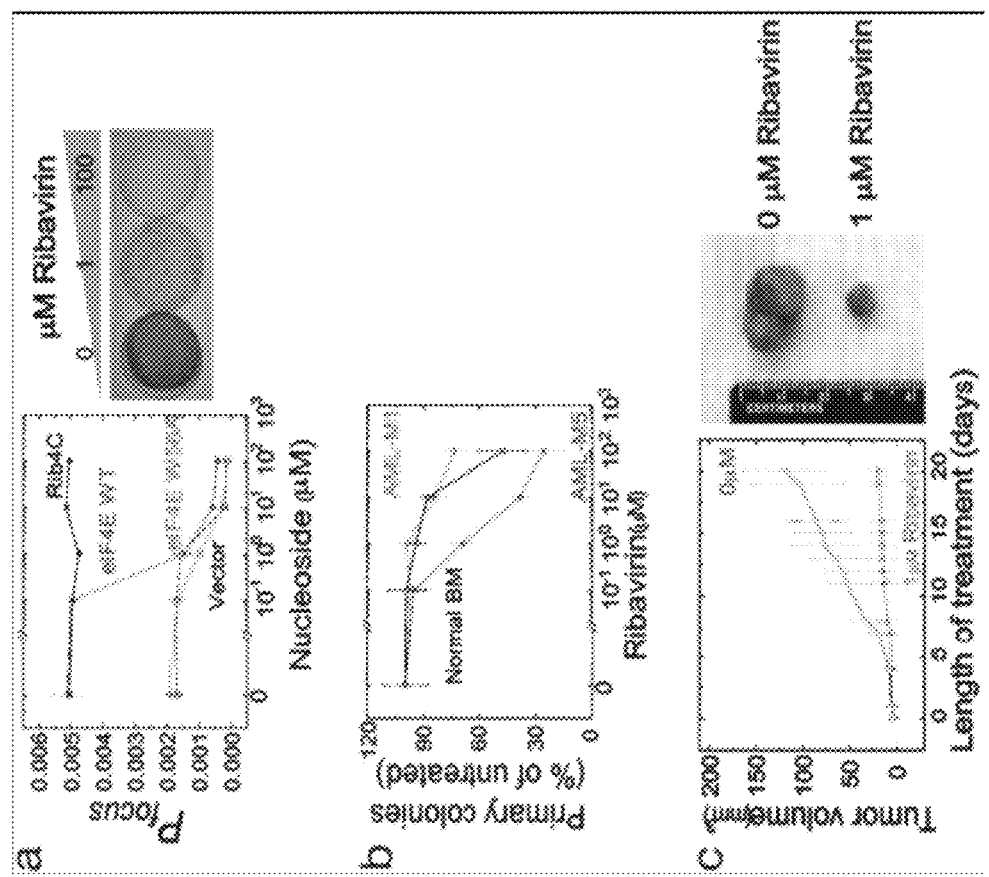
FIG. 6. Ribavirin suppresses eIF4E-mediated oncogenic transformation. (a) (Left) Anchorage-dependent foci formation of NIH3T3 cells treated with Ribavirin and transfected with empty vector (black dashed line), eIF4EWT (blue line), eIF4E W56A (red line), and cells treated with Rib4C and transfected with eIF4E WT (black solid line). Error bars represent +/−1 sigma of three independent experiments. Probability of focus formation (Pfocus) is defined as the number of foci formed divided by the number of cells plated. (Right) Photograph of Giemsa-stained dishes of Ribavirin-treated cells transformed by eIF4E. (b) Colony formation of primary human CD34+ myeloid progenitors isolated from patients with AML (M1, solid circles; M5, solid squares) and normal bone marrow (BM, open squares), as a function of Ribavirin concentration. Ribavirin reduces colony formation of eIF4E-dependent AML-M5 with an apparent IC50 of ca. 1 uM, and with no effect on M1 and normal bone marrow myeloid progenitor cells at this concentration. Note that data are internally normalized and that absolute colony formation efficiencies of AML myeloid progenitors are greater than that of BM (data not shown). Error bars represent +/−1sigma of four independent experiments. (c) (Left) Mean tumor volume in nude mice engrafted with cells derived from a hypopharyngeal eIF4E dependent tumor, as a function of treatment with daily 1 uM Ribavirin orally at a dose of 40 ug per kg per day (solid squares). Error bars represent +/−1 sigma of 10 mice. (Right) Photograph of tumors resected after 20 days of treatment.

Importantly, cytoplasmic eIF4E:actin mRNA complexes are not disrupted, even at 100 uM Ribavirin, which is consistent with the insensitivity of actin protein levels to Ribavirin. Ribavirin's effects are likely not limited to eIF4E-mediated regulation of cyclin D1 mRNA transport and VEGF mRNA translation and include other genes regulated posttranscriptionally by eIF4E.

eIF4E causes malignant transformation of cells when overexpressed. Mutagenesis studies indicate that its oncogenic properties are due, at least in part, to deregulated transport of mRNAs of oncogenes and growth regulatory genes such as cyclin D1. Thus, we examined whether Ribavirin treatment and its inhibition of eIF4E-dependent mRNA transport and translation suppress eIF4E-mediated oncogenic transformation. We overexpressed eIF4E in NIH 3T3 cells and assayed transformation by monitoring foci formation as a result of loss of contact growth inhibition. eIF4E levels in transfected cells are 10-fold greater than endogenous levels in control cells (FIG. 5a), leading to transformation and a significant increase in foci formation (FIG. 6a). Overexpression of eIF4E W56A cap-binding mutant fails to transform cells (FIG. 6a), in agreement with earlier studies, even though it is expressed to similar levels as wild-type eIF4E. Ribavirin suppresses eIF4E-mediated transformation with an apparent EC50 of 0.1-1 uM (FIGS. 3a and 3b). In contrast, addition of Rib4C fails to reduce the number of foci formed, even at 100 uM (FIG. 3a), which is consistent with its inability to bind eIF4E in vitro and inhibit eIF4E-mediated regulation of mRNA transport and translation in cells (FIGS. 1 and 3c). Observed suppression of transformation is not due to nonspecific effects such as metabolic toxicity or cell death (FIG. 5b). Furthermore, low micromolar concentrations of Ribavirin induce G1 cell-cycle arrest (FIG. 5c), which is consistent with Ribavirin's down-regulation of cyclin D1 (FIG. 3b).

To examine the effect of Ribavirin on tumor growth in vivo, we obtained specimens of primary myeloid progenitor cells from patients with acute myelogenous leukemias (AMLs) and comparable cells from normal bone marrow. Previous studies indicated that a subset of AMLs have very high levels of nuclear eIF4E and that cyclin D1 mRNA transport is substantially upregulated in these cells. Reduction of nuclear eIF4E levels led to a decrease in cyclin D1 mRNA transport to normal levels. Thus, we examined whether Ribavirin specifically alters growth of this subset of AMLs. Isolated CD34+ progenitor cells were resuspended in methylcellulose medium and cultured in the presence of various concentrations of Ribavirin for 14 days to assess their ability to form colonies. Ribavirin potently repressed colony formation of primary AML-M5 (French-American-British classification) progenitor cells with an apparent IC50 of ca. 1 uM (FIG. 6b), which is consistent with their overexpression and dysregulation of eIF4E.

In contrast, similar concentrations of Ribavirin failed to repress colony formation of AML-M1 progenitor cells (FIG. 6b), which is consistent with non-up-regulated eIF4E levels and nondysregulated cyclin D1 mRNA transport in these cells. This tumor suppressive effect of Ribavirin at micromolar concentrations is distinct from its cellular toxicity at millimolar concentrations (FIG. 5b), as is evident from the lack of an effect on colony formation of normal bone marrow myeloid progenitors at micromolar concentrations (FIG. 6b). Treatment with Ribavirin caused a marked suppression of tumor growth in a mouse model of human squamous cell carcinoma (FIG. 5c). We used FaDu cells derived from a hypopharyngeal squamous cell carcinoma because they overexpress eIF4E, and form tumors in nude mice, as compared with nonmalignant epithelial cells.

Importantly, when levels of eIF4E are reduced to nonmalignant levels by using antisense RNA, these cells are markedly less tumorigenic. Thus, nude mice were engrafted by using subcutaneous injection of eIF4E-dependent FaDu cells and treated with 40 ug/kg Ribavirin orally each day, yielding a mean body concentration of ca. 1 uM. After 20 days of Ribavirin treatment, mean tumor volume of animals in the treatment group was 6-fold less than those in the untreated control group (P=0.023, n=10; FIG. 6c). At this low concentration, Ribavirin was apparently well tolerated and minimally toxic, as suggested by the absence of treatment associated mortality and of effect on body weight (data not shown). Thus, Ribavirin's inhibition of eIF4E at low micromolar concentrations is correlated with inhibition of eIF4E-mediated oncogenic transformation and tumor suppression in vitro and in vivo.

Binding of m7G mRNA cap by eIF4E is required for its nucleocytoplasmic mRNA transport, cytoplasmic translation, and oncogenic transformation. High-affinity binding of m7G cap by eIF4E is accomplished as a result of specific recognition of the cationic methylated base. Because Ribavirin, but not its neutral analogue, Rib4C, binds to eIF4E in vitro with the same apparent affinity as the m7G cap and inhibits eIF4E's ability to bind mRNA and function in mRNA transport and translation in cells, we assessed the extent of similarity and molecular recognition by eIF4E of Ribavirin and m7G mRNA cap. Thus, we performed $^1$H, $^{15}$N heteronuclear single-quantum correlation NMR spectroscopy (HSQC NMR) titrations of eIF4E with m7G and Ribavirin. $^1$H, $^{15}$N HSQC NMR spectroscopy reports on the chemical environment of the individual $^{15}$NH amides of the polypeptide backbone, thereby providing a sensitive probe of ligand binding and accompanying conformational rearrangements.

In solution, eIF4E exists in low- and high affinity conformations, the interconversion of which is regulated by binding of partner proteins such as PML and ligands such as m7G mRNA cap, as observed by using CD spectroscopy titrations. Here, we observe a similar phenomenon upon the conversion from apo- to m7G-bound eIF4E by using HSQC NMR titrations, with the structuring or reorganization of 19 of 64 assigned residues of 217 residues in eIF4E (FIG. 7a), distributed throughout the structure (FIG. 7c), in agreement with CD measurements. These residues include the S7/S8 loop with W102, which stacks with the m7Gbase, and K106, which coordinates the ribose (FIG. 7c). On the other hand, the S1/S2 loop is preorganized in apo-eIF4E in the high-affinity conformation, with W56 showing no significant changes in resonance intensity or chemical shift upon cap binding (FIG. 7a). Strikingly, conversion of apo-eIF4E to Ribavirin-bound eIF4E involves an almost identical conformational rearrangement, with little perturbation of the S1/S2 loop and W56 and significant structuring of the S7/S8 loop and W102 (FIG. 7b), as indicated by nearly exact overlay of cap- and Ribavirin-bound spectra of eIF4E (FIG. 7b). These data are consistent with the reduced Ribavirin affinity of W56A mutant and Ribavirin's ability to efficiently compete with m7G for binding to eIF4E (FIG. 1).

Double $^{15}$N-edited, filtered 1H, 1H NOESY spectra of nucleoside-saturated eIF4E, which specifically identify $^{15}$NH groups of eIF4E in close proximity (<5 Å) to nucleoside as a result of intermolecular NOE transfer, are consistent with the binding sites of Ribavirin and m7G overlapping (data not shown). Thus, eIF4E binds and recognizes Ribavirin in a manner similar to m7G cap, which is consistent with their similar binding activities (FIG. 1). To assess the physical origin of Ribavirin's mimicry of m7G, we calculated electrostatic properties of guanosine and Ribavirin analogues by using ab initio quantum mechanical and continuum electrostatic methods. Only m7G and Ribavirin exhibit significant electropositive character in their aromatic rings (FIG. 8). Other nucleoside bases exhibit various degrees and patterns of electronegativity, including the inactive Ribavirin analogue Rib4C, which is not protonated and uncharged at neutral pH due to its 1,2,3-triazole, inactive Ribavirin metabolite ICN3297, which is neutral because of its oxidized carboxamide (data not shown), guanosine analogue and inosine monophosphate dehydrogenase inhibitor tiazofurin, which is neutral due to its thiazole, and uncharged guanosine itself (FIG. 7). Thus, Ribavirin is a physical mimic of m7G.

There are two major cap-binding proteins in the cell, eIF4E and the cap-binding complex (CBC). Although both proteins intercalate m7G between two aromatic residues, the affinity of the CBC for m7GpppG cap is substantially higher (Kd ca. 10 nM), as compared with eIF4E (Kd ca. 200 nM), because of more extensive interactions of the CBC with the methylated base, as well as with the adjacent pyrophosphate nucleotide as compared with eIF4E. Because Ribavirin's triazole ring would be missing many of these additional contacts with the CBC and is missing the adjacent base, Ribavirin interferes only with the functions of eIF4E, and not those of the CBC, as observed here (FIG. 3).

Conclusions

Although widely studied, mechanisms of cellular action of Ribavirin and origins of its antiviral effects remain enigmatic. Because of its similarity to guanosine, Ribavirin is suggested to inhibit 5' mRNA capping by competing with guanosine for guanylyl transferase, to inhibit guanosine biogenesis by mimicking guanosine for interaction with inosine monophosphate dehydrogenase, and to be a mutagen by competing with guanosine for mRNA incorporation by RNA polymerases. Indeed, at millimolar concentrations, such effects occur, leading to lethal mutagenesis of poliovirus (EC50 ca. 0.2 mM) and depletion of cellular guanosine pools (EC50 ca. 0.1 mM), for example. Importantly, at low micromolar concentrations, Ribavirin does not appear to participate in guanosine metabolism, likely because of structural and energetic differences in m7G and/or guanosine-binding sites of involved proteins. Ribavirin does not appear to cause physiologic depletion of guanosine pools, as suggested by lack of metabolic toxicity (FIG. 5), and is not apparently mutagenic, as suggested by lack of cell death and unaffected synthesis and stability of produced proteins (FIGS. 3 and 5). Here, we observe that Ribavirin inhibits the ability of eIF4E to promote mRNA transport and translation of eIF4E-sensitive transcripts by antagonizing eIF4E:m7G mRNA cap binding and disrupting subcellular eIF4E organization. eIF4E overexpression does not increase protein synthesis globally but, rather, affects the expression of a subset of transcripts defined as eIF4E-sensitive, including those studied here, such as cyclin D1, ODC, and VEGF.

Although the major point of this work was to elucidate a mechanism of action of Ribavirin and to characterize its potential anti-cancer activities, our findings have implications for mRNA translation as well. We show that selectivity of Ribavirin's inhibition of eIF4E stems from the selectivity of eIF4E's activity itself in terms of eIF4E's posttranscriptional regulation of a specific set of eIF4E-sensitive transcripts. Thus, just as eIF4E overexpression does not globally increase protein translation, Ribavirin is not a global inhibitor. Sensitivity to eIF4E appears to be inversely related to the complexity of UTRs of corresponding transcripts. Hence, Ribavirin-induced inhibition of eIF4E specifically reduces translation of the transcripts that contain long and highly structured 5' UTRs, including a number of protooncogenic mRNAs, e.g., VEGF, c-myc, and ODC. Conversely, Ribavirin does not affect translational rates of housekeeping mRNAs, such as GAPDH, that bear short, unstructured 5' UTRs. Electrostatic properties of guanosine-related nucleosides correlate directly with their point of action in cellular guanosine metabolism. For example, tiazofurin, despite having the same molecular geometry as Ribavirin, is electronically similar to guanosine (FIG. 8) and, consequently, is a potent inosine monophosphate dehydrogenase inhibitor, binding to the guanosine allosteric effector site on inosine monophosphate dehydrogenase. Similarly, Rib4C is neutral (FIG. 8) and neither binds nor inhibits eIF4E. On the other hand, Ribavirin is positively charged at physiological pH because of its electronic structure (FIG. 8) and, as a result, antagonizes m7G mRNA cap binding by eIF4E. Ribavirin and its derivatives offer a pharmacologic means to interrupt networks of tumor suppressors and oncogenes that maintain and enhance neoplasia and malignancy. For instance, deregulation of eIF4E leads to deregulation of oncogenes such as cyclin D1 and myc, which, in turn, leads to further deregulation of eIF4E. eIF4E is a target of mitogenic stimulation and a direct transcriptional target of myc. Consistent with such self reinforcing behavior, inactivation of myc leads to differentiation and sustained regression of tumors in a transgenic mouse model of osteogenic sarcoma. Similarly, antisense cyclin D1 reverts the phenotype of human carcinoma cells toward normal and prevents tumor formation in mice. Complementarily, rapamycin suppresses chemoresistance in a mouse lymphoma model, and this effect is reversed by dysregulation of eIF4E. Here, we demonstrate that a similar effect can be accomplished pharmacologically by inhibiting eIF4E-dependent nucleocytoplasmic mRNA transport and translation. It is becoming increasingly evident that posttranscriptional regulation of gene expression plays a paramount role in regulation of growth and development in eukaryotes, and disruption of this level of regulation contributes to a variety of human cancers.

Our findings indicate that Ribavirin acts in a previously unsuspected manner, at the level of post-transcriptional, eIF4E-mediated regulation of growth regulatory genes. It is likely that the apparent potency of Ribavirin's suppression of eIF4E-mediated oncogenic transformation in vitro and in vivo involves down-regulation of a combination of oncogenes, with cyclin D1 being a model transcript examined here. Further characterization of this unforeseen mechanism of Ribavirin action and development of derivatives with improved antiviral and cytostatic properties are important directions for future work.

Example 2 eIF4E Specifically Binds to Ribavirin Using the Cap-Binding Site

The mechanism of action of Ribavirin (Virazole), a triazole carboxamide ribonucleoside, has remained enigmatic since its discovery in the early 1970s. Much of the confusion stemmed from its apparent activity against a wide variety of seemingly unrelated viruses, as well as pleiotropic cellular effects dependent on concentration. Based on the similarities in the arrangement of hydrogen-bonding groups of Ribavirin and guanosine, Ribavirin was postulated to be a guanosine analog. This notion is consistent with Ribavirin's effects at millimolar concentrations on guanylyl transferases, inosine monophosphate dehydrogenase, and RNA-dependent RNA polymerases.

The prior Example sought to identify the nature of these specific effects, and thereby help to define the specific mechanism of action of Ribavirin. Using ab initio quantum mechanics, we characterized the physical properties of a variety of guanosine analogs, noting a striking similarity in the electronic structure of Ribavirin and 7-methyl guanosine. Using tryptophan emission fluorescence spectroscopy and nucleotide affinity chromatography, we measured the dissociation and inhibition constants of Ribavirin and the 7-methyl guanosine (m7G) binding protein eIF4E to be in the low micromolar range. Using fluorescence microscopy, cell fractionation, Northern and Western analyses, and quantitative PCR, we observed Ribavirin's disruption of subcellular eIF4E localization, disruption of nuclear and cytoplasmic eIF4E:mRNA binding, inhibition of nucleocytoplasmic eIF4E-sensitive mRNA transport, and inhibition of eIF4E-sensitive mRNA translation in living cells, all at similar low micromolar concentrations. Using flow cytometry, colony formation, and tumor growth assays, we observed cytostatic and tumor-suppressive effects of Ribavirin in models of eIF4E-dependent cancers in vitro and in vivo, as well as using eIF4E-overexpressing leukemic blasts isolated from human patients, also at low micromolar concentrations. While Ribavirin exhibited physical properties similar to those of 7-methyl guanosine, its circularly permuted chemical analog Rib4C did not, failing to bind eIF4E, to inhibit its functions in mRNA transport, translation, and tumorigenesis. This led us to conclude that Ribavirin is a physical mimic of the 7-methyl guanosine mRNA cap.

In recent issues of RNA, Yan et al. (2005) and Westman et al. (2005) present findings that dispute this conclusion. Their results are twofold: that Ribavirin does not bind to recombinant eIF4E in vitro, and that Ribavirin does not inhibit cap-dependent translation of exogenous mRNAs in extracts prepared from cells. We are concerned that these experiments failed to elicit Ribavirin's effects and, similarly to the authors, would like to discuss possible reasons for this. First, it is well established that the binding of the m7G cap to eIF4E is highly dependent on solution conditions. Variations of several orders of magnitude (nanomolar to micromolar) can occur as a result of changes in ionic strength, pH, and temperature. This likely depends on the physical properties and exact geometries of the cap binding site in the apo form of eIF4E under these conditions (data not shown), which themselves are dependent on the relative populations of various structural substrates that apo-eIF4E is known to adopt in solution. Given that Ribavirin binds the cap-binding site of eIF4E, its apparent affinity for eIF4E would also be condition dependent. Furthermore, given that Ribavirin's triazole carboxamide likely makes fewer atomic contacts with eIF4E as compared to 7-methyl guanosine, Ribavirin's high-affinity binding to eIF4E would be expected to occur in a narrower range of solution conditions.

With this in mind, we reproduced our original affinity chromatography experiment using an independent operator and new reagents side by side with the experiment of Yan et al. (2005). We reproduced experimental conditions as published by us (0.3 M NaCl, 0.1 M sodium phosphate, 0.1% Nonidet P-40, 10 mM BSA at pH 7.5, room temperature), and those described by Yan et al. (2005) (0.1 M KCl, 10 mM HEPES-KOH, 0.2 mM EDTA at pH 8.0, presumed 4° C.). In agreement with our reported findings (Kentsis et al. 2004), micromolar concentrations of Ribavirin triphosphate (RTP) compete with the binding of eIF4E:m7G, similarly to that of m7GTP itself (FIG. 9a). In contrast, using the protocol of Yan et al. (2005) leads to an apparent failure of RTP to compete with m7G binding (FIG. 9b). Thermodynamic meta-stability of eIF4E under various solution conditions is well described in the literature (Matsuo et al. 1997; McGuire et al. 1998; Kentsis et al. 2001, 2004), leading to aggregation and linkage effects that can confound the apparent binding of ligands (Fletcher and Wagner 1998; Cohen et al. 2001), particularly when using matrix-immobilized proteins, as in the experiments of Yan et al. (2005). In addition, the structure of apo-eIF4E is sensitive to differences in pH between 7.5 and 8, as assessed by NMR chemical shift perturbation (data not shown). Thus, the reported failure of Ribavirin to bind eIF4E in vitro by Yan et al. (2005) appears to be due, at least in part, to the use of different solution conditions.

In contrast to Yan et al. (2005), who fail to observe Ribavirin's binding to eIF4E altogether, Westman et al. (2005) observe that Ribavirin binds to recombinant eIF4E in vitro, but does so with an affinity two to four orders of magnitude lower than that measured by us (Kentsis et al. 2004; Westman et al. 2005). Measurements of ligand binding using quenching of fluorescence emission often require corrections for the intrinsic fluorescence of added ligand and its inner filter effect (Lakowicz 1999), neither of which appears to be considered in our reading of Westman et al. (Niedzwiecka et al. 2002; Westman et al. 2005). While fluorescence quantum yields of nucleotides are lower than those of amino acids, they can be significant at concentrations used in the above studies, potentially compensating for quenching of protein fluorescence upon binding, especially when Ribavirin's quenching efficiency is twofold lower than that of 7-methyl guanosine because of differences of the two compounds (Kentsis et al. 2001, 2004). In addition to this, titration of nucleotides leads to absorption of incident and/or emitted light, potentially reducing the apparent emission of fluorescence. The lower extinction coefficient of Ribavirin as compared to 7-methyl guanosine (740 vs. 1600 M-1 cm-1 at 295 nm, respectively) may also contribute to the differences in apparent quenching (Kentsis et al. 2001, 2004).

Unfortunately, a direct methodological comparison is precluded by our monitoring of fluorescence emission of tryptophans including those that directly bind 7-methyl guanosine (Kentsis et al. 2001, 2004), while Westman et al. measured emission by both tryptophans and tyrosines (Niedzwiecka et al. 2002; Westman et al. 2005), which may be preferentially quenched (excitation wavelengths of 295 nm and 280 nm, respectively). In addition, differences in solution conditions may also contribute to the observed differences in binding affinities. As suggested by Westman et al. (2005), these methodological differences may explain the apparent differences in the measured affinities.

Nevertheless, in order to provide a decisive demonstration of binding of Ribavirin to eIF4E, one that does not involve indirect or ambiguous probes of binding such as competition affinity chromatography and fluorescence quenching, we examined the binding of Ribavirin and eIF4E by using electrospray mass spectrometry. A mixture of 20 mM purified recombinant eIF4E and fourfold excess of both Ribavirin and GTP was electrosprayed directly, and its mass/ionization spectrum was measured. The recorded spectrum is shown in FIG. 10a and contains two sets of multiply charged ions, one with a population-weighted mean molecular mass of 31,402 Da, corresponding to apo-G4E (Zhou et al. 2001; Kentsis et al. 2004), and another of 31,649 Da (FIG. 10b). This mass shift of 247 Da is due to specific binding of Ribavirin (243 Da), and not of GTP (523 Da). In our published study, the specificity of Ribavirin's binding to eIF4E was established using mutation of the cap-binding site W56A, which disrupts binding of Ribavirin, but not folding of the protein, similar to its disruption of binding of the 7-methyl guanosine cap (Kentsis et al. 2004).

Ribavirin's circularly permuted version Rib4C, which is chemically identical but is not positively charged, failed to bind eIF4E. And finally, Ribavirin's binding leads to a similar conformational rearrangement of eIF4E, as observed using NMR spectroscopy, as the one induced by the binding of 7-methyl guanosine cap, consistent with Ribavirin's binding of the cap-binding site (Kentsis et al. 2004). A ligand-induced conformational change is also suggested by the cap-free crystallographic structure reported by Volpon, et al. (2006) *EMBO J.* 25(21):5138-49. Epub 2006 Oct. 12. Additional specificity controls are described in Kentsis et al. (2004). Thus, eIF4E specifically binds to Ribavirin using the cap-binding site, and experimental failure to observe this interaction may be due to challenges of the particular techniques used.

Another question examined by Yan et al. (2005) and Westman et al. (2005) concerns the effect of Ribavirin on eIF4E function. Both groups examined functional effects in vitro, whereas we were concerned with Ribavirin's effects in vivo (Kentsis et al. 2004). Cell extracts for translation of exogenous mRNAs in vitro are well known for their unique properties, having altered compositions, stoichiometries, and activities, as compared to those in living cells, where compartmentalization and molecular organization are maintained and are of paramount importance for a process as complex and regulated as mRNA translation. Although such extracts have been used with considerable success for the discovery of translation factors, their significance for the characterization of mechanisms of translation remains controversial. In this light, assessment of eIF4E activity by way of discrimination between efficiencies of translation of 7-methyl guanosine cap- and internal ribosome binding site (IRES)-driven transcripts is problematic for a number of reasons. The activity of each extract is optimized empirically in order to maximize the translational contribution of a particular feature of an exogenous mRNA, a process that in no way guarantees the overall mechanistic and functional fidelity that is absolutely required for the characterization of novel activities such as that of Ribavirin.

For example, both Yan et al. (2005) and Westman et al. (2005) use cell extracts, albeit prepared from different cells and with different modifications, carefully optimized in order to maximize the translational synergy between the 50-cap and 30-poly(A) mRNA elements (Bergamini et al. 2000; Svitkin and Sonenberg 2004), a feature that depends neither solely nor specifically on the activity of eIF4E. This apparent synergy is due to the scaffolding activity of eIF4G, which concomitantly binds eIF4E, poly(A) binding proteins (PABPs), and the ribosome (Michel et al. 2000), thereby coupling the affinities of eIF4E and PABPs for the 50-cap and 30-poly(A) tail, respectively. Yet, the presence of the poly(A) tail alone can also stimulate translation from IRES in vitro (Svitkin et al. 2001), and eIF4E can recruit ribosomes in the absence of cap binding (De Gregorio et al. 2001). Thus, in the experiments of Westman et al. (2005), although competition with m7GpppG and m7GTP inhibits cap-driven translation at analog concentrations of ca. 0.1 mM while RpppG does not, specificity of this difference and its mechanistic interpretation are indeterminate considering that the concentration of m7GpppG-capped transcript is ca. 1 nM (an excess of >100,000-fold) (Westman et al. 2005).

The interpretation of the findings of Yan et al. (2005) is even more complicated by their use of a bicistronic construct containing both the 50-cap and an IRES that minimizes relative differences in efficiency as a result of competition for rate-limiting translation factors (Yan et al. 2005). Thus, treatment with 1 mM m7GDP leads to a reduction of activity of cap-driven firefly luciferase from ca. 8× to 2×10^5 light units: a fourfold effect, rather insignificant as compared to the molar excess of cap analog to mRNA of >1,000,000-fold (mRNA concentration of 5 mg/mL) (Yan et al. 2005). Considering that the concentration of eIF4E in similarly used cell extracts is estimated to be ca. 400 nM (Rau et al. 1996), the requirement of such high cap analog concentrations suggests that the examined process is not dependent strictly on eIF4E activity during mRNA translation.

While we do not dispute that Ribavirin can be misincorporated into 50-mRNA caps at millimolar concentrations, based on measurements of viral production by Yan et al. (2005) and careful analysis of cap structures by Westman et al. (2005), we question the specificity of the observed differences in translational efficiency between cap- and IRES-driven constructs in vitro, and their mechanistic interpretation with respect to the mechanism of action of Ribavirin and our findings of its inhibition of eIF4E sensitive translation in vivo. In this context, although Ribavirin failed to inhibit cap-dependent translation in vitro in the work of Yan et al. (2005) and Westman et al. (2005), this lack of an effect may have to do with the lack of sensitivity of current cell extracts to eIF4E activity. In this regard, the distinction between cap- and eIF4E sensitive translation may be of paramount significance. Although the interaction of the 5' 7-methyl guanosine cap with eIF4E is required for the translation of cap-dependent mRNAs, up-regulation of eIF4E in cells does not increase levels of all proteins produced from cap-dependent transcripts, but only of a specific subset including cyclin D1 and VEGF, but not b-actin and GAPDH, for example (De Benedetti and Graff 2004). This effect occurs at the level of nucleocytoplasmic transport for some mRNAs, at the level of translation for others, and for some at both (Rousseau et al. 1996). Thus, just as eIF4E up-regulation does not globally increase cellular protein translation, Ribavirin is not a global inhibitor. Such specificity of Ribavirin's effects on translation in cells was precisely observed in our measurements of polysomal loading of mRNAs of cyclin D1, GAPDH, VEGF, and ODC (Kentsis et al. 2004).

In summary, just like that of the 7-methyl guanosine cap, Ribavirin's binding to eIF4E is dependent on solution conditions, but nevertheless occurs robustly and specifically (FIGS. 9 and 10). To determine the physiological relevance of interactions assessed in vitro, it is important to assess their functionality in vivo. Thus, we assessed the physiological relevance of Ribavirin's binding to eIF4E in cells, in animal models, as well as in tissues isolated from human patients (Kentsis et al. 2004). In all of these systems, Ribavirin antagonized eIF4E functions in transport and translation of eIF4E-sensitive mRNAs at low micromolar concentrations, similar to those at which it dissociates from purified eIF4E in vitro. We hope that future collaborative work will continue to define the specific mechanism and cellular effects of this rather simple chemically, but biologically complex, drug.

Example 3 Identification of a 100-Nt Sequence from the Cyclin D1 3'UTR which Sensitizes this mRNA to eIF4E in the Nucleus and is Involved in eIF4E Mediated Cell Transformation Abstract The eukaryotic translation initiation factor eIF4E is a critical modulator of cellular growth with functions in the nucleus and cytoplasm. In the cytoplasm, recognition of the 5' m7 G cap moiety on all mRNAs is sufficient for their functional interaction with eIF4E. In contrast, we have shown that in the nucleus eIF4E associates and promotes the nuclear export of cyclin D1, but not GAPDH or actin mRNAs. We determined that the basis of this discriminatory interaction is a 100-nt sequence in the 3' untranslated region (UTR) of cyclin D1 mRNA, we refer to as an eIF4E sensitivity element (4E-SE). We found that cyclin D1 mRNA is enriched at eIF4E nuclear bodies, suggesting these are functional sites for organization of specific ribonucleoproteins. The 4E-SE is required for eIF4E to efficiently transform cells, thereby linking recognition of this element to eIF4E mediated oncogenic transformation. Our studies demonstrate previously uncharacterized fundamental differences in eIF4E-mRNA recognition between the nuclear and cytoplasmic compartments and further a novel level of regulation of cellular proliferation.

Introduction

The eukaryotic translation initiation factor eIF4E is involved in modulation of cellular growth. Moderate overexpression of eIF4E leads to dysregulated growth and malignant transformation. The levels of eIF4E are elevated in several human malignancies including a subset of myeloid leukemias and breast cancer. Importantly, both the nuclear and cytoplasmic functions of eIF4E contribute to its ability to transform cells. In the cytoplasm, eIF4E is required for cap-dependent translation, a process highly conserved from yeast to humans. Here, eIF4E binds the methyl 7-guanosine (m7G) cap moiety present on the 5' end of mRNAs and subsequently recruits the given mRNA to the ribosome.

In the nucleus, eIF4E functions to promote export from the nucleus to the cytoplasm of at least two reported mRNAs, cyclin D1 and ornithine decarboxylase (ODC), but does not alter GAPDH or actin mRNA export. Since the first report of the nuclear localization of eIF4E 12 years ago, studies showed that up to 68% of cellular eIF4E is in the nucleus, where it associates with nuclear bodies in a wide variety of organisms including yeast, Drosophila, Xenopus, and humans. These bodies are found in all cell types reported including nearly 30 cell lines and primary cells from diverse lineages such as NIH3T3, HEK293T, U205, K562, and U937. In mammalian cells, a large subset of eIF4E nuclear bodies coincides with those associated with the promyelocytic leukemia protein PML. PML was the first identified regulator of eIF4E-dependent mRNA export. The RING domain of PML directly binds the dorsal surface of eIF4E, reducing its affinity for the m7G cap by >100-fold. This loss of cap binding activity correlates with a loss of the mRNA export function and loss of transformation activity.

There is evidence that the mRNA export function of eIF4E is linked to its oncogenic transformation activity. In a subset of primary human myeloid leukemia specimens, eIF4E dependent cyclin D1 mRNA export is substantially up-regulated. Additionally, a mutant form of eIF4E, W73A, enters the nucleus colocalizing with endogenous eIF4E nuclear bodies, enhances the transport of cyclin D1 mRNAs to the cytoplasm and subsequently transforms immortalized cells. This occurs despite the fact that W73A eIF4E cannot bind eIF4G and thus cannot act in translation.

Observations made by our group and the Sonenberg laboratory that eIF4E functionally discriminates between cyclin D1 and GAPDH mRNAs are surprising because the traditional view is that eIF4E binds the m7G cap found on all mRNAs regardless of other sequence specific features. Thus, this functional discrimination presents a conundrum in terms of our understanding of eIF4E mRNA recognition in the nucleus.

We explore the possibility that in the nucleus, eIF4E recognition of mRNA is fundamentally different than in the cytoplasm. Here, we identify a 100-nt sequence from the cyclin D1 3'UTR which sensitizes this mRNA to eIF4E in the nucleus and is involved in eIF4E mediated cell transformation.

Materials and Methods

Constructs.

All UTR-LacZ fusion constructs were made in pcDNA3.1LacZ vector (Invitrogen) and positioned 5' or 3' of the coding region of LacZ as appropriate. For cloning of cyclin D1 3'UTR, the NotI restriction site was created in pD1-1 construct (human cyclin D1 gene in pGEM7Zf), 150 bp upstream of stop codon by in vitro mutagenesis (Quickchange kit; Stratagene) and full-length 3'UTR was cloned using NotI and XbaI downstream of LacZ (referred here as LacZ-3'UTRFull). Fragments containing the first part of cyclin D1 3'UTR were generated using NotI and EcoRI, and second part of cyclin D1 3'UTR using EcoRI and XbaI (note that there is EcoRI site at the position 2,824 bp in human cyclin D1 cDNA) and cloned under NotI-XbaI and EcoI-XbaI, downstream of LacZ (LacZ 3'UTRA and LacZ 3'UTRB). Individual sequences were amplified using specific primers containing NotI or XbaI restriction sites at their 5' ends. LacZ 3'UTR2/3 contains segment 2,091-2,459 bp from cyclin D1 mRNA, LacZ 3'UTR 3 contains sequence 2,361-2,459 bp, LacZ3/4 contains segment 2,361-2,565 and LacZ 3'UTR4 contains sequence 2,481-2,565 bp from human cDNA. The 5'UTR was amplified from cyclin D1 cDNA (ATCC MGC-2316) and cloned using the HindIII site, upstream of AUG codon for Xpress tag. pcDNA2Flag-eIF4E construct was made by inserting of eIF4E cDNA into the EcoRI NotI sites (pcDNA2F vector was gift from Z. Ronai, Burnham Institute, La Jolla, Calif.). eIF4E mutants in pcDNA2Flag were made by in vitro mutagenesis (Quickchange kit; Stratagene). pMV vector, pMV-eIF4E wild type (a gift from N. Sonenberg, McGill University, Montreal, Quebec, Canada) or mutants, pLINKSV40-PML and bacterial expression constructs were described previously. Human cyclin D1 cDNA without the full-length 3'UTR (ATCC MGC-2316) was cloned in pMV vector using EcoRI and HindIII (cyclin D1 truncated). Cyclin D1 full construct was made by using HindIII-XbaI fragment from pcDNALacZ-3'TR that was blunt ended and cloned under HindIII in pMV-cyclin D1Trunc (note that there is HindIII site in human cyclin D1 cDNA at position 1,206 bp). 4E-SE-4 from cyclin D1 3'TR was PCR amplified, blunt ended and cloned under HindIII in pMV-cyclin D1Trunc (cycD14E-SE).

Antibodies and Western Analysis.

Antibodies used against PML were described previously (a gift from P. Freemont, Imperial College, London, UK and L. de Jong, University of Amsterdam, Amsterdam, Netherlands). Additional antibodies used include mouse monoclonal anti-eIF4E Ab (BD Transduction Laboratories), polyclonal anti-IF4E Ab (a gift from S. Morley, University of Sussex, Brighton, UK), mouse monoclonal anti-cyclin D1 Ab (BD Biosciences), mouse monoclonal anti-Xpress Ab (Invitrogen), mouse monoclonal anti-GAPDH antibody (MAB374; CHEMICON International, Inc.), anti-CBP80 pAb (a gift from L. Maquat, University of Rochester, Rochester, N.Y.; Ishigaki et al., 2001) anti-CBP-20 (a gift from E. Izaurralde, EMBL, Heidelberg, Heidelberg, Germany). Western analysis was performed as described previously (Topisirovic et al., 2002, 2003).

Cell Culture and Transfection.

NIH3T3, U205, HEK293T, and N log (a gift from H. Land, University of Rochester; cyclin D1-/- Perez-Roger et al., 1999) cells were maintained in 5% CO2 at 37 C in DME (GIBCO BRL; Life Technologies), supplemented with 10% FBS, 100 U/ml penicillin, and 100 U/ml streptomycin. eIF4E and PML stably transfected NIH3T3 were made as described previously (Topisirovic et al., 2002, 2003a). Transient transfection of NIH3T3 was performed using either GeneJammer Transfection Reagent (Stratagene) or Lipofectamine Plus reagent (Invitrogen) according to the manufacturer's instructions. Transient transfections of HEK293T cells were performed using Calcium Phosphate Transfection kit (Invitrogen). Stable transfections of cyclin D1-/- cells were performed using Fugene 6 Transfection Reagent (Roche) according to the manufacturer's instructions. Anchorage-dependent foci formation assays were conducted as described previously (Cohen et al., 2001; Topisirovic et al., 2003a).

Immunopurification of eIF4E, Isolation of RNA Bound to eIF4E and RT-PCR.

Nuclei were isolated from $3 \times 10^9$ HEK293T cells aliquoted appropriately, as previously described (Topisirovic et al., 2002), resuspended in ice-cold NET-2 buffer (50 mM Tris-HCL, pH 7.4, 300 mM NaCl, 0.5% [vol/vol] NP-40, 1× complete protease inhibitors [Roche], 200 U/ml SUPERasein [Ambion]) and mechanically disrupted in dounce homogenizer (type B) on ice. Obtained nuclear extracts were cleared by centrifugation at 16,000 g for 20 min at 4 C. 1/20 of the supernatant was split in two and used to obtain nuclear RNA and protein, respectively. 19/20 were split in three aliquots, two of which, when indicated in the text, were incubated with 50 uM m7GpppG and 50 uM GpppG (NEB) in NET-2 buffer for 30 min at 4° C. Each of the aforementioned aliquots was split in two and immunoprecipitated as described previously (Ishigaki et al., 2001) with the following modifications: 10 u of anti-eIF4E mouse mAb (Transduction Laboratories) or 10 u of mouse IgG (Calbiochem) was used per reaction and after immunoprecipitation, the beads were washed once with NET-2 buffer supplemented with 1 mg/ml of heparin (Sigma-Aldrich). Obtained RNA was treated with RNase free DNase (Promega) according to the manufacturer's instruction. RNA was converted into cDNA using the Sensiscript Reverse Transcription kit (QIAGEN). RT-PCR was performed in triplicate with the QuantiTect SYBR green RT-PCR Kit (QIAGEN) in Opticon thermal cycler (MJR). Obtained RT-PCR data was analyzed with Opticon software (MJR). Primers used for cyclin D1 RT-PCR were cycF, 5'CAGCGAGCAGCAGAGTCCGC-3' (SEQ ID NO: 12) and cycR, 5'-ACAGGAGCTGGTGTTC-CATGGC-3' (SEQ ID NO: 13); and for GAPDH amplification GAPDHF, 5'-ACCACAGTCCATGCCATCAC-3' (SEQ ID NO: 14) and GAPDHR 5'-TCCACCACCCGTTGCT-GTA-3' (SEQ ID NO: 15). For RT-PCR methods, calculations were done as described by Applied Biosystems. For semi-quantitative PCR, 30 cycles were used, and for RT-PCR, standard methods were used. Primers used for semi-quantitative amplification of GAPDH were the same as for RT-PCR, and for cyclin D1 and actin amplification the following primers were used: cycHMF, 5'-CACTTC-CTCTCCAAAATGCCA-3' (SEQ ID NO: 16); cycHMR, 5'-CCTGGCGCAGGCTTGACTC-3' (SEQ ID NO: 17); ActF, 5'-ATCTGGCACCACACCTTCTACAATGAGCT-GCG-3' (SEQ ID NO: 18); and ActR, 5'-CGTCATACTC-CTGCTTGCTGATCCACATCTGC-3' (SEQ ID NO: 19).

Controls for Quality of Immunoprecipitation and Fractionations.

Several steps were taken to ensure that variability between experiments did not lead to false positive or false negative results. The immunoprecipitated sample was tested to ensure that eIF4E immunoprecipitated itself and that IgG did not bind eIF4E as determined by Western blotting. The specificity of the immuno-precipitation was determined using known positive and negative controls for eIF4E in the nuclear fraction. Thus, the ability of eIF4E antibodies to immunoprecipitate eIF4E but not CBP80 (FIG. 11g) or RNA Polymerase II was determined (Lai and Borden, 2000). These results are consistent with the findings from the Maquat and our laboratories where it was shown that the nuclear fraction of eIF4E does not associate with these proteins. Furthermore, positive controls for interactions of eIF4E include the ability to associate with the PML protein (Cohen et al., 2001; Topisirovic et al., 2003a,b), as have been reported numerous times. In addition, we demonstrate that the transduction laboratory antibody against eIF4E used here colocalizes with eIF4E antibodies produced in other laboratories (Topisirovic et al., 2004) indicating that the antibody is robust and reliable. Importantly, these experiments ensure that differences in association of various mRNAs with eIF4E are NOT a result of differences in immunoprecipitation efficiency or fractionation quality between experiments.

For fractionation controls, the quality of each nuclear and cytoplasmic fraction was assessed by monitoring the subcellular distribution of U6snRNA (nuclear) and tRNALys (cytoplasmic) as we reported previously and show throughout the text. Additional controls performed for each fractionation include Western analysis of the splicing speckles protein which served as a nuclear marker (Sc35) and B-actin, which served as a cytoplasmic marker (Topisirovic et al., 2003 a,b). Additional fraction controls were done when sufficient material was available (Topisirovic et al., 2003 a,b). SNAAP protocol was performed as described previously (Trifillis et al., 1999) with the following modifications. Precleared 250 ug of nuclear extracts were added to 50 ug of GST-protein beads in 500 ul RBB buffer containing 0.5% NP-40, and after incubation of 30 min at 4 C, 500 ug of yeast tRNA was added per reaction and incubated overnight at 4° C. All washing of beads was performed in RBB buffer containing 0.25% Triton X-100 and 0.5% NP-40.

Cellular Fractionation and Northern Analysis.

Fractionation and RNA isolation were described previously (Lai and Borden, 2000; Topisirovic et al., 2002). For LacZ, PolyA RNA was purified from fractionated RNA using Oligotex mRNA Mini Kit (QIAGEN). Probes for cyclin D1, GAPDH, U6, and tRNALys for Northern blot analysis were also previously described (Topisirovic et al., 2002). LacZ probe was made by PCR amplification using primers LacZF, 5'-CGGTCGCTACCATTACCAGTT-3' (SEQ ID NO: 20) and LacZR, 5'-GACGTTGTAAAAC-GACGGGAT-3' (SEQ ID NO: 21), and labeled using Bright-Star Psoralen-Biotin kit (Ambion).

Immunofluorescence, In Situ Hybridization, and Laser Scanning Confocal Microscopy.

Immunofluorescence experiments were as described previously (Cohen et al., 2001; Topisirovic et al., 2002). Fluorescence was observed using 100× optical magnification and 2× digital zoom, unless indicated otherwise, on an inverted laser scanning confocal microscope (model TCS-SP (UV); Leica) exciting at 488, 568, or 351/364 nm (at RT). All channels were detected separately, and no cross talk between the channels was observed. Micrographs represent single sections through the plane of cells with a thickness of ca. 300 nm. Experiments were repeated three times with more than 500 cells in each sample. In situ hybridization was performed according to Spector et al. (1998), using nick-translated DIG-11-dUTP-labeled (Nick Translation Kit; Roche) cyclin D1 and GAPDH PCR-amplified fragments (cyclin D1 specific SSA, 5'-CATGGAACACCAGCTC-CTGT-3' (SEQ ID NO: 22) and 3SA, 5'-CGCAGCCAC-CACGCTCCC-3' (SEQ ID NO: 23); and GAPDH specific GAPDHHF, 5'-ACCACAGTCCATGCCATCAC-3' (SEQ ID NO: 24) and GAPDHMR, 5'-TCCACCACCCTGTT-GCTGGGG-3' (SEQ ID NO: 25)) and detected using anti-DIG Fab fragments (Roche) followed by donkey anti-sheep Texas red (Jackson ImmunoResearch Laboratories). PML was detected using 5E10 mAb (for U205 cells) followed by Alexa Fluor 350-conjugated goat anti-mouse Ab (Molecular Probes) or rabbit polyclonal anti-PML Ab (for NIH 3T3 cells) followed Alexa Flour 350-conjugated anti-rabbit Ab (Molecular Probes). eIF4E was detected using FITC-conjugated mouse monoclonal anti-eIF4E Ab (BD Transduction Laboratories). Cells were mounted in Vectashield supplemented with DAPI (Vector Laboratories). Images were obtained using TCS-SP software and displayed using Adobe Photoshop CS 8.0.

Results eIF4E Physically Associates with Cyclin D1 mRNAs in the Nucleus

To understand the underlying basis for the specificity of eIF4E's effects on promotion of mRNA export, we examined the novel possibility that eIF4E physically associated only with specific mRNAs in the nucleus. In this way, eIF4E-dependent promotion of export of cyclin D1 mRNAs could arise through a specific physical interaction of this mRNA with eIF4E in the nucleus. First, we examined whether eIF4E immunoprecipitates with cyclin D1 or housekeeping genes like GAPDH and actin mRNAs in total cell lysates and subsequently in nuclear and cytoplasmic fractions in a variety of cell lines including U205, NIH3T3, K562, U937, and HEK293T cells. Results were the same across cell lines so only representative results are shown here (FIG. 11). Note that both the mRNAs, and the eIF4E examined here, are endogenous. RNAs were detected for each experiment independently using multiple PCR strategies including quantitative RT-PCR and semi-quantitative PCR. Consistent results were always obtained using these different methodologies.

Immunoprecipitation studies indicated that in total cell lysates, eIF4E bound both cyclin D1 and GAPDH mRNAs, as expected because these mRNAs are capped (FIG. 11a). In the nuclear fraction, eIF4E physically associates with a readily detectable fraction of cyclin D1 mRNA (FIG. 11b). Yet, no detectable association between eIF4E and GAPDH mRNA or actin mRNA is observed in the nuclear fraction in contrast to total cell lysates or the cytoplasmic fractions (FIG. 11a and not depicted). These results are confirmed by our semi-quantitative and independently RT-PCR analysis (FIGS. 11b, d, and e). Also, eIF4E associates only with processed cyclin D1 mRNAs in the nucleus, as observed using specific primers and RT-PCR (not depicted). Importantly, the ability of eIF4E to associate with GAPDH or cyclin D1 mRNAs was monitored using material from the same eIF4E immunoprecipitations. Thus, differences in binding affinity between GAPDH and cyclin D1 are not a result of differences in immunoprecipitation efficiency or in the quality of the fractionation between experiments. Controls for the quality of these immunoprecipitations and fractionations are given below and discussed in the Materials and methods.

The above findings suggested that eIF4E-mRNA recognition in the nucleus could be substantially different to that in the cytoplasm. In particular, it was critical to establish the importance of cap binding for eIF4E-mRNA recognition in the nucleus. Thus, we examined which features of eIF4E were required for interaction with cyclin D1 mRNA in the nuclear fraction using the GST pull-down approach referred to as specific nucleic acids associated with protein (SNAAP; Trifillis et al., 1999). Here nuclear lysates were incubated with glutathione sepharose-bound wild-type or mutant forms of eIF4EGST or GST (FIG. 11c). Consistent with the immunoprecipitation findings, wild-type eIF4E associates with cyclin D1 but not GAPDH mRNAs. No association is observed with GST (FIG. 11c) or an unrelated mRNA-binding protein alpha-CP1-GST (not depicted) for either mRNA. The W56A eIF4E mutant, which does not bind the cap, does not bind cyclin D1 indicating that eIF4E still requires its cap-binding activity to associate with mRNAs in the nuclear fraction (FIG. 11c). We extended these studies to test whether the dorsal surface mutant, W73A, can still associate with cyclin D1 mRNA in the nucleus, because this mutant readily enhances transport of cyclin D1 when expressed (Topisirovic et al., 2002, 2003a). Importantly, W73A mutant is deficient in translation but not transport. This mutation does not detectably reduce binding to cyclin D1 mRNA as compared with wild type (FIG. 11c). Note that previous biophysical studies indicate that W56A and W73A mutants have structures indistinguishable from wild-type eIF4E (Kentsis et al., 2001). Thus, there appears to be a correlation between the ability of eIF4E to physically associate with cyclin D1 mRNA in the nucleus and the ability of eIF4E to enhance transport of these mRNAs.

We extended these findings to further demonstrate the requirement for the m7G cap for association of mRNA with eIF4E in the nucleus (FIGS. 11d and e). We monitored the ability of m7G cap analogue (m7GpppG) to compete for mRNA binding using semi-quantitative PCR and independently, quantitative RT-PCR methods. Consistent with the above results using the W56A mutant, the cap analogue successfully disrupts the association of cyclin D1 mRNAs with eIF4E. In contrast, GpppG, which does not bind eIF4E, does not disrupt its association with cyclin D1. In either case eIF4E does not associate with GAPDH mRNA. Together, these findings indicate that eIF4E requires the m7G cap in order to associate with specific mRNAs in the nucleus. Note that treatment with m7GpppG or GpppG did not alter the amount of eIF4E immunoprecipitated by eIF4E antibody in these reactions (unpublished data).

Interestingly, when the cytoplasmic fractions of cells were incubated with eIF4E-GST, all mRNAs bound, similar to the results we observed for immunoprecipitation experiments using the total lysates or cytoplasmic fraction (unpublished data). It is of interest that even when nuclear lysates are incubated with recombinant eIF4E in the SNAAP assay, we do not observe an association with GAPDH mRNA (FIG. 11c). This raises the possibility that eIF4E-mRNA recognition is restricted in nuclear lysates by other regulatory elements that are not present in the cytoplasm, where cap binding is sufficient to mediate these interactions. As a positive control, we extended our experiments to determine whether both GAPDH and cyclin D1 mRNA bound to the other nuclear cap-binding proteins, CBP 80 and CBP 20 which together form the cap-binding complex (CBC). In general, CBC associates with all transcripts cotranscriptionally (Visa et al., 1996). Immunoprecipitations were performed using an antibody to CBP 80. Results were monitored by semiquantitative and independently by RT-PCR methods. Parallel experiments were performed with eIF4E antibodies using the same nuclear fractions. As expected, CBC associates with both cyclin D1 and GAPDH transcripts, whereas eIF4E associates only with cyclin D1 mRNA (FIG. 11f). We further determined whether the CBC associates with eIF4E. Using immunoprecipitation (FIG. 11g) and separately immunofluorescence (not depicted), we observed no association between the CBC and eIF4E. These findings are consistent with previous reports showing no coimmunoprecipitation between CBC and eIF4E (Ishigaki et al., 2001; Lejeune et al., 2002). However, we cannot rule out the possibility of a transient interaction between the CBC and eIF4E that we cannot detect by these methods. Together, these data suggest that eIF4E-cyclin D1 mRNA and CBC-cyclin D1 mRNA complexes are distinct complexes in the nucleus.

We cannot rule out the possibility that, in the nucleus, eIF4E binds a low level of GAPDH mRNA, which is beyond the detection limits of our RT-PCR methods. Even if this is the case, we readily detect an enrichment of up to 1,000-fold for cyclin D1 relative to GAPDH mRNAs despite the relative differences in abundance, with GAPDH being the much more abundant mRNA in both fractions (FIG. 11c and see FIG. 13b). Thus, using two independent methods, immunoprecipitation and SNAAP, we demonstrate that eIF4E physically associates with specific mRNAs in the nuclear fraction. Furthermore, eIF4E requires its cap-binding activity for this association but not W73 on the dorsal surface. Recent findings by another laboratory suggest that eIF4E associates with all mRNAs in the nuclear fraction (Lejeune et al., 2002), whereas the data we present here clearly indicate that eIF4E binds cyclin D1 but not GAPDH or actin mRNAs in the nuclear fraction. The most likely reason for this discrepancy is differences in experimental approach. One major difference is that we monitor association of eIF4E with endogenous, not overexpressed, mRNAs (FIG. 11). Overexpression could lead to the formation of RNPs that are different from endogenous RNPs. Thus, we initiated our studies with endogenous eIF4E as well as endogenous mRNAs. Detection of bound mRNAs in immunoprecipitated fractions is also critical for optimal interpretation of these experiments. We confirmed our results with quantitative RT-PCR methods in order to ensure that background binding of mRNAs was not mistaken for real binding. Furthermore, we obtain the same results using different eIF4E antibodies or reconstituting the complexes with eIF4E-GST. Clearly, our specificity correlates well with previous observations by our group and the Sonenberg group that eIF4E overexpression up-regulates cyclin D1 but not GAPDH or actin mRNA transport and correspondingly up-regulates cyclin D1 but not GAPDH and actin protein levels.

Cyclin D1 mRNAs are Localized to a Subset of eIF4E Nuclear Bodies

Because eIF4E specifically associates with cyclin D1 mRNA in the nucleus, we examined whether cyclin D1 mRNA specifically associates with eIF4E nuclear bodies. In this way, eIF4E nuclear bodies could be sites of assembly of specific RNPs or functional storage sites. Studies were performed in U2OS and NIH3T3 cells. The localization of cyclin D1 or GAPDH mRNAs was determined using in situ hybridization and the localization of eIF4E and another component of the nuclear body, PML, through immunofluorescence. The results were monitored using confocal microscopy. Similar results are observed in both U2OS and NIH3T3 cells (FIGS. 12a and b). These studies reveal that cyclin D1 mRNAs (red) are found throughout the cytoplasm and nucleoplasm but are additionally enriched in bodies in the nucleus. These local sites of enrichment colocalize with a subset of eIF4E nuclear bodies (green). Sites of colocalization of eIF4E nuclear bodies and cyclin D1 mRNAs are shown in yellow with two of several such sites marked with arrows (FIG. 12). Note that the objective for all experiments in FIG. 12 was 100× with further magnifications as follows: twofold for A-C; and 1.5-fold for D. The current resolution of these studies does not enable us to distinguish whether cyclin D1 mRNAs are found on the surface or within the eIF4E bodies. Consistent with previous studies (Lai and Borden, 2000; Cohen et al., 2001), there are two populations of eIF4E nuclear bodies, those, which contain PML, and those, which do not. The majority of eIF4E (green) and PML (blue) colocalize to the same nuclear bodies (light blue) and, as observed previously for many cells, there are additional eIF4E bodies (FIG. 12a, green; Lai and Borden, 2000; Cohen et al., 2001).

Importantly, mRNAs were never observed to colocalize with PML nuclear bodies consistent with previous studies showing RNA did not localize with PML nuclear bodies (Boisvert et al., 2000). Thus, cyclin D1 mRNAs localize to the subset of eIF4E nuclear bodies that do not contain PML. As expected, GADPH mRNAs do not localize with either PML or eIF4E nuclear bodies (FIG. 12b). These results are consistent with the observation that nuclear GAPDH mRNAs do not physically associate with eIF4E and do not have their export modulated by eIF4E overexpression (Topisirovic et al., 2002, 2003a). As a negative control, probes for cyclin D1 in situ hybridization in cyclin D1−/− cells revealed no signal indicating that these probes are specific for cyclin D1 (FIG. 12c). Furthermore, RNase treatment completely abolishes signals (not depicted). As expected given the above results, immunoprecipitation studies with a PML antibody reveal no association with either cyclin D1 or GAPDH mRNAs. These data are consistent with our previous findings that PML reduces the affinity of eIF4E for the m7G cap by >100-fold (Kentsis et al., 2001), thus disabling RNA binding. Because eIF4E requires its cap-binding activity for interaction with cyclin D1 (FIGS. 11d and e), it is consistent that cyclin D1 mRNAs are not found at PML containing eIF4E nuclear bodies.

In summary, cyclin D1 mRNAs localize to a subset of eIF4E nuclear bodies. Localization of mRNAs to the bodies is specific and is likely to be functionally important for their subsequent transport to the cytoplasm. In this way, eIF4E nuclear bodies may be assembly sites for specific eIF4E-RNPs, which enable promotion of export to the cytoplasm. Furthermore, it appears that, in the nucleus, there must be features particular to the bound mRNAs that impart the observed specificity of eIF4E.

Physical Association of eIF4E with mRNAs is Correlated with Enhanced mRNA Transport Above, we demonstrate that both wild-type eIF4E and the W73A mutant physically associate with cyclin D1 mRNA in the nuclear fraction but that the W56A mutant, which is deficient in cap binding, does not (FIG. 11c). To determine whether there is a correlation between binding and mRNA transport, we assessed the ability of these mutants to promote transport of cyclin D1 mRNA. Stably transfected NIH3T3 cells expressing mutant or wild-type proteins were fractionated and mRNAs monitored by Northern analysis (FIG. 13a and Table I) as described previously (Topisirovic et al., 2002). U6snRNA and tRNALys serve as fractionation controls. Note that GAPDH is not altered in any case, as expected. Furthermore, the mutant proteins are expressed to similar levels (FIG. 13c) and total levels of cyclin D1 mRNA are not altered by any of the constructs (FIG. 13b). Furthermore, the stability of the cyclin D1 transcript is not affected by eIF4E (FIG. 13d and Table II).

Importantly, eIF4E and the W73A mutant promote cyclin D1 mRNA transport where more cyclin D1 transcripts are clearly visible in the cytoplasmic fractions versus vector controls. Importantly, the W56A mutant does not alter the subcellular distribution of cyclin D1 mRNA transcripts (FIG. 13a and Table I). One of the consequences of eIF4E-dependent mRNA transport is increased protein levels due to higher concentrations of these mRNAs in the cytoplasm and thus increased availability of these mRNAs to the translational machinery. Consistent with the above fractionation studies, cyclin D1 protein levels are elevated in wild-type and W73A mutant experiments but there is no increase when the W56A mutant is overexpressed. Thus, the physical association of cyclin D1 mRNA with the nuclear fraction of eIF4E is strongly correlated with the enhanced transport of cyclin D1 mRNA from the nucleus to the cytoplasm.

PML overexpression leads to the nuclear retention of cyclin D1 but not GAPDH mRNAs (FIG. 13a), as well as reduced cyclin D1 but not GAPDH or actin protein levels (FIG. 13c). This is consistent with the results from immunoprecipitation and in situ studies, where PML inhibits formation of eIF4E-cyclin D1 mRNA complexes (FIG. 11 b and FIG. 12a). Once again it links the ability of eIF4E to physically interact with RNAs to the ability to promote mRNA transport. Previous studies demonstrated that eIF4E could enter the nucleus by interaction with the 4E transporter protein (4ET; Dostie et al., 2000). Here, mutation of the dorsal surface (W73A) impaired association with the 4ET and thus impaired nuclear entry (Dostie et al., 2000). Thus, we performed experiments to ensure that the W73A mutant still entered the nucleus and formed nuclear bodies (FIG. 13e). Using confocal microscopy, we examined the subcellular distribution of overexpressed eIF4E or the W73A mutant using the Xpress epitope tag and additionally an antibody to eIF4E, which recognizes both endogenous and overexpressed protein.

It is clear from the confocal micrographs that the W73A mutant is readily detectable in the nucleus and associates with endogenous eIF4E nuclear bodies (FIG. 13e). Thus, it appears that when the W73A mutant is overexpressed it uses an alternate route or can overcome the weaker binding to 4ET, gets transported into the nucleus and associate with nuclear bodies (FIG. 13e). Similar studies with the W56A mutant indicated no alteration in subcellular distribution as compared with wild type (not depicted). In addition, wild-type and mutant forms of eIF4E are expressed to similar levels (FIG. 13c). eIF4E levels are expressed to similar levels (FIG. 13c). Note that the objective was 100× for these micrographs with a further 1.5-fold magnification.

TABLE I

Relative Nc/Cyt ratio of cyclin D1 mRNA in cells transfected as indicated (densitometry analysis of Northern blot experiments)a

| Vector | 1.110 +/− 0.490 |
|---|---|
| WT4E | 0.171 +/− 0.0828 |
| W56A4E | 1.194 +/− 0.365 |
| W73A4E | 0.216 +/− 0.102 |
| PML | 4.552 +/− 0.632 | a- Cyclin D1 mRNA levels were normalized to GAPDH mRNA;
+/− value represents SD from three independent experiments.

TABLE II

Relative cyclin D1 mRNA level after actinomycin D treatment of cells transfected with eIF4EWT or vector control (measured by RT-PCR) - a

| Time | 4EWT | Vector |
|---|---|---|
| 0 | 1 +/− 0.3422 | 1 +/− 0.5820 |
| 2 h | 0.1654 +/− 0.04 | 0.1314 +/− 0.04600 |
| 4 h | 0.0718 +/− 0.0120 | 0.0567 +/− 0.0108 |
| 6 h | 0.0199 +/− 0.0028 | 0.0218 +/− 0.0084 | a - Cyclin D1 mRNA levels were normalized to GAPDH mRNA;
+/− value represents SD from three independent experiments.

Identification of an RNA Structural Element that Mediates eIF4E Sensitivity in the Nuclear Compartment To determine if the association of mRNAs with eIF4E in the nucleus and eIF4E-dependent mRNA transport are mediated through some specific mRNA sequence, we analyzed 3' and 5' UTRs from our model mRNA cyclin D1. A series of chimeric constructs were made fusing the coding region of LacZ to the 5' or 3' UTRs of cyclin D1 (FIG. 14a). We assessed whether these sequences were necessary and sufficient to enable chimeric mRNAs to associate with endogenous eIF4E in the nucleus and subsequently have their export modulated. Experiments were performed in NIH3T3 and HEK293T cells, which gave identical results. Note that HEK293T cells form nuclear bodies similar in size and morphology to those observed for NIH3T3 cells (FIG. 12d). Initial semi-quantitative PCR results were confirmed by quantitative RT-PCR methods using the standard curves method (FIG. 14b). We monitored the ability of the nuclear fraction of eIF4E to associate with these mRNAs using immunoprecipitation in conjunction with PCR (FIG. 14b). Importantly, eIF4E does not immunoprecipitate with LacZ mRNA, does not immunoprecipitate with Lac Z-cyclin D1 5' UTR chimeric mRNA, but does associate with chimeric LacZ mRNA that contains the entire 3'UTR of cyclin D1. We made additional chimeric LacZ constructs with two different parts of the 3' UTR using an EcoRI site positioned approximately in the center of 3' UTR of cyclin D1 cDNA, and showed that chimeric RNA that contains first part of cyclin D1 3' UTR (3' UTRA) immunoprecipitates with nuclear eIF4E whereas the second part (3' UTRB) does not.

Analysis of additional chimeric constructs containing different elements from the first part of cyclin D1 3' UTR revealed that the 100-bp sequence from the 3' UTR of cyclin D1 (located 2,471-2,565 bp in human cyclin D1 cDNA) is necessary and sufficient for association with eIF4E, so we refer to it as an eIF4E-sensitive element (4E-SE). Importantly, this element is the highly conserved between human, mouse, rat, and chicken sequences (FIG. 14c). In fact, the 4E-SEs between humans and chicken are nearly identical with 94% conservation versus 59% similarity over the rest of the 3'UTR.

The presence of the 4E-SE in mammals and birds suggests that it is evolutionarily conserved. To assess if the interaction of chimeric mRNAs with eIF4E was functional, we examined the effects of eIF4E expression on their export (FIG. 15). mRNA export was monitored using subcellular fractionation in conjunction with semiquantitative RT PCR (FIG. 15a), northern methods (FIG. 15b through 15d) or quantitative RT-PCR (Table III). eIF4E does not modulate the transport of LacZ or LacZ chimeras that do not contain the 4E-SE (FIG. 15 and Table III), which is consistent with the observation that eIF4E does not bind these mRNAs (FIG. 14b). Note that total mRNA levels determined from the same transfected cells indicated that LacZ mRNAs levels were not modulated (FIG. 16b) nor were their stability (FIG. 16c). Thus, there is a strong correlation with the ability of eIF4E to associate (directly or indirectly) with the 3' UTRs of these mRNAs and promote their transport. Increased export of LacZ mRNA, and thus the higher levels of cytoplasmic mRNAs when the 4E-SE is present, is correlated with higher levels of LacZ protein (FIG. 16a). Consistent with our earlier observations, overexpression of the W56A mutant does not alter transport of either LacZ or LacZ-4E-SE as compared with wild-type eIF4E nor did the W56A mutant alter protein production of either LacZ construct (FIG. 15d and FIG. 16a; Table III). Thus, the mRNAs retain their cap dependence. Furthermore, all of the chimeric constructs had similar levels of total mRNA indicating that differences observed at the protein level were posttranscriptional and that differences in association with eIF4E and transport were not due to differences in expression of the constructs (FIG. 16b). Importantly, LacZ-4E-SE transport is negatively regulated by PML (FIG. 16a), as we observed for endogenous cyclin D1 mRNA (FIG. 13a through c). Together, these results indicate that both the 4E-SE and the m7G cap are required for eIF4E to enhance transport of these mRNAs.

TABLE III

Relative ratio of cytoplasmic versus nuclear LacZ mRNA of cells transfected as indicated (measured by RT-PCR)a Construct Relative C:N LacZ mRNA ratio

| | |
|---|---|
| 4EWT +/− LacZ | 1 +/− 0.082 |
| 4EWT +/− 3' UTR4 | 462.496 +/− 38.114 |
| 4EWT +/− 3' UTR Full | 373.934 +/− 30.195 |
| 4EWT +/− 3' UTR 2/3 | 0.823 +/− 0.069 |
| 4EWT +/− 3' UTR B | 1.187 +/− 0.119 |
| W56A +/− lacZ | 1.159 +/− 0.124 |
| W56A +/− 3' UTR 4 | 1.918 +/− 0.286 | a- LacZ mRNA levels were normalized to GAPDH mRNA
+/− value represents SD from three independent experiments.

The 4E-SE Contributes to eIF4E Mediated Oncogenic Transformation

We extended these studies to establish whether the 4E-SE contributed to the physiological activities of eIF4E and thereby to assess the functional significance of this RNA element (FIG. 17). Our previous studies correlated eIF4E-dependent promotion of cyclin D1 mRNA export with the transformation activities of eIF4E so we examined the contribution of the 4E-SE to this activity. Transformation activity was assessed by monitoring the number of foci formed upon eIF4E overexpression in a cyclin D1−/− fibroblast cell line. Note that the distribution of eIF4E nuclear bodies is not altered in cyclin D1−/− as compared with other cell types (FIG. 12c). First, we determined that eIF4E transformed cyclin D1−/− cells relative to vector controls. Reintroduction of cyclin D1 constructs containing the full-length 3'UTR (cycFull) led to substantially more foci than cells transfected with eIF4E alone (FIG. 17a). However, eIF4E's transformation activity was not augmented by introduction of cyclin D1 with no 3'UTR (cycTrunc) being the same as eIF4E overexpressing cells alone. Importantly, introduction of eIF4E and cyclin D1, with only the 100 nt 4E-SE (cyc4E-SE), transformed cells as well as constructs containing the full-length 3'UTR. Thus, in the context of cyclin D1−/− cells, the transformation activity of eIF4E is only increased by reintroduction of cyclin D1 when the 4E-SE is present. Consistently, only those cells transfected with cyclin D1-3'UTR (cycFull) or cyclin D1-4E-SE (cyc4E-SE) showed increased cyclin D1 protein levels in contrast to vector controls or cells transfected with cyclin D1 with truncated 3'UTR (cycTrunc; FIG. 17b).

Thus, the presence of the 4E-SE is tightly tied to eIF4E's ability to export cyclin D1 and subsequently to efficiently transform cells. These effects can be extended to endogenous eIF4E. Cells expressing cycFull or cyc4E-SE, even in the absence of overexpressed eIF4E, produce more cyclin D1 protein than those cells expressing the truncated version of cyclin D1 (FIG. 17b). We confirm this is occurring at the mRNA transport level by fractionation and RT-PCR methods (FIG. 17c). We demonstrate that the ratio of nuclear to cytoplasmic cyclin D1 mRNA is ~250 times greater in those cyclin D1−/− cells expressing the cycTrunc construct than those expressing the cycFull or cyc4E-SE constructs. Thus, the cycTrunc is not as efficiently transported to the cytoplasm as cycFull and cyc4E-SE constructs are. Importantly, the distribution of GAPDH was not altered by any of these constructs (unpublished data). Northern analysis confirmed these findings and indicated that fractionations were clean (unpublished data). Thus, the presence of the 4E-SE allows more efficient export of cyclin D1 mRNA using either endogenous or exogenous eIF4E.

Discussion

These studies reveal that eIF4E associates with and regulates nuclear mRNAs in a fundamentally different manner than cytoplasmic mRNAs. Unlike the cytoplasmic fraction of eIF4E where cap binding is sufficient for its functional interaction with mRNAs, in the nucleus eIF4E appears to associate with regulatory factors that restrict its association with mRNA lacking 4E-SEs. Because eIF4E binds the m7G cap, we hypothesize that other factors directly bind the 4E-SE in the 3'UTR and through physical association with eIF4E increase its affinity for this subset of mRNAs (FIG. 18). An mRNA looping model is another possibility, where eIF4E cap binding is stabilized by direct contact with the 4E-SE, through an unknown mechanism (FIG. 18). It seems likely that not only cyclin D1 but also many other mRNAs could be regulated in this way (unpublished data), especially given that ODC also has its transport regulated in this manner (Rousseau et al., 1996). Our studies and recent reports indicate that eIF4E does not associate with the CBC nor does it associate with unspliced mRNA (Ishigaki et al., 2001; Lejeune et al., 2002). These studies suggest that the transfer of capped cyclin D1 mRNA transcripts from the CBC to eIF4E happens after splicing and before cyclin D1 mRNA gets exported from the nucleus. Because eIF4E and CBC do not coimmunoprecipitate or colocalize, this interaction is likely transient one. We cannot rule out the possibility of a completely novel mechanism by which the cap of cyclin D1 mRNA is protected by some unknown means between leaving the CBC RNP and associating with eIF4E. This is an area of future investigation.

mRNAs that get exported in an eIF4E-dependent fashion may undergo some alternative, eIF4E-dependent type of mRNA quality surveillance. Previous studies suggested that the nuclear fraction of eIF4E might be involved in low level nuclear translation as part of mRNA quality surveillance (Iborra et al., 2001). However, our studies with the W73A mutant indicate that nuclear translation is not required for the observed transport function because this mutant is active in transport but not translation, because it cannot bind eIF4G (Sonenberg and Gingras, 1998; Gingras et al., 1999). Specialized pathways for transport of growth-promoting mRNAs such is cyclin D1, and control of this process by factors such as PML, may have evolved in order to coordinate gene expression with cellular proliferation. eIF4E nuclear bodies must be intact in order to act in mRNA export because their disruption is correlated with a loss of export activity (Topisirovic et al., 2003a; Kentsis et al., 2004). Our data suggest that assembly of eIF4E transport RNPs happens in or around eIF4E bodies. The colocalization of cyclin D1 mRNAs with PML-negative eIF4E nuclear bodies suggests that these sites are areas for assembly of specific subtypes of RNPs which permit more efficient export of this restricted subset of mRNAs to the cytoplasm. In this way, expression of these targeted mRNAs could be modulated quite quickly. It seems likely that nuclear eIF4E RNPs involved in promotion of mRNA export are different from those functioning in translation, because the W73A mutant is still active in transport (Cohen et al., 2001; Topisirovic et al., 2003a). Consistently, eIF4E does not appear to bind eIF4G in the nucleus (McKendrick et al., 2001) but eIF4G is an integral part of the eIF4E RNP in the cytoplasm (Sonenberg and Gingras, 1998). Clearly these results suggest major differences in functionalities of the corresponding nuclear and cytoplasmic eIF4E RNPs. eIF4E-dependent promotion of mRNA export could provide an immediate response system by which the cell responds to stress and/or growth conditions before transcriptional reprogramming.

We speculate that this process is not limited just to cyclin D1 mRNA but that other mRNAs involved in growth regulation could be regulated this way, including ODC (Rousseau et al., 1996) and many others (unpublished data). The ability of eIF4E to promote the export of growth promoting mRNAs such as cyclin D1 allows it to turn on a cellular growth promoting program thereby positioning eIF4E as a critical node in the growth regulatory network. eIF4E regulating proteins, such as PML (this paper) and nuclear homeodomain proteins such as PRH, which directly bind eIF4E (Topisirovic et al., 2003a) are well positioned to act upstream of eIF4E. Although, this network also includes important regulation of translation by the eIF4E-binding proteins (4EBPs; Sonenberg and Gingras, 1998), our findings suggest that these transport and translation networks may not completely overlap. For instance, cyclin D1 mRNA is sensitive to eIF4E at the transport level, but not at the translation level (Rousseau et al., 1996). In contrast, ODC mRNA is sensitive to eIF4E at both levels (Rousseau et al., 1996). ODC mRNA, like cyclin D1 mRNA, contains a 4E-SE element (unpublished data). PML appears to be a critical negative regulator of this nuclear network, thereby shutting down production of a wide variety of growth promoting proteins simultaneously and thus, inhibiting eIF4E-mediated growth and transformation. These activities rely on eIF4E RNA recognition through both the m7G cap and the 4E-SE. eIF4E promotion of export of specific mRNAs represents an exciting new point of growth regulation in the cell and a novel regulatory pathway which when dysregulated could contribute to human cancers.

Example 4 eIF4E is a Central Node of a RNA Regulon that Governs Cellular Proliferation Abstract Eukaryotic translation initiation factor eIF4E is a critical node in an RNA regulon that impacts nearly every stage of cell cycle progression. Specifically, eIF4E coordinately promotes the mRNA export, and in some cases also translation, of several genes involved in cell cycle progression. A common feature in these mRNAs is a structurally conserved ~50 nucleotide element in the 3'UTR denoted an eIF4E sensitivity element (4E-SE). This element is sufficient for localization of capped mRNAs to eIF4E nuclear bodies, formation of eIF4E specific RNPs in the nucleus, and eIF4E dependent mRNA export. These studies indicate that roles of eIF4E in translation and mRNA export are distinct, relying on different sequence elements in mRNA and formation of distinct RNPs. Furthermore, eIF4E dependent mRNA export is independent of on-going RNA or protein synthesis. Unlike export of bulk mRNAs, which is NXF1 dependent, eIF4E dependent mRNA export is CRM1 mediated. These data provide a novel perspective into the molecular mechanism of the proliferative and oncogenic properties of eIF4E.

Introduction

RNA regulons have been proposed as a means by which eukaryotic cells coordinate gene expression. In contrast to prokaryotes where coordinated regulation of genes is achieved by genomic organization, eukaryotes coordinate the regulation of subsets of mRNAs involved in the same biological processes at the post-transcriptional level by manipulating compositions and activities of discrete subsets of RNPs. It has been postulated that related RNA sequences termed "untranslated sequence elements for regulation" (USER codes), similar to zipcodes for RNA localization, are used for specific association with variety of regulatory proteins involved in different levels of post-transcriptional regulation. mRNA nuclear export is one level of control that could be coordinated in this way. Initially, mRNA export was thought to be a general process by which all mRNAs were transported from the nucleus to the cytoplasm irregardless of sequence specific features. More recent findings indicate that mRNA export can be coordinated with other events in RNA metabolism, particularly transcription and splicing, and thus, that nuclear history of transcripts can modulate the cytoplasmic fate of targeted mRNAs. This way, nuclear export can be coordinated through compartmentalization via mRNP organization, coupling coordinated export of functional classes of mRNAs with their functions in biological processes such as proliferation, differentiation and development.

Studies with eukaryotic translation initiation factor eIF4E provide an example of a factor that differentially effects expression of a subset of mRNAs. Even though it associates with all transcripts through the common 5' methyl-7-guanosine ($m^7G$) cap structure, many groups showed that eIF4E overexpression does not lead to global increases in protein expression. In the cytoplasm, mRNAs deemed eIF4E sensitive have their protein levels modulated by eIF4E more so than other mRNAs. This sensitivity is attributed to the complexity of the 5'UTRs in these transcripts. Up to 68% of eIF4E is found in the nucleus in a broad variety of species ranging from yeast to humans. Here, eIF4E overexpression leads to increased export of cyclin D1 but not GAPDH mRNA. Specific association of eIF4E with cyclin D1 mRNA in the nucleus requires the $m^7G$ cap, and a small element in its 3' UTR referred as an eIF4E sensitivity element (4E-SE).

Overexpression of eIF4E is correlated with oncogenic transformation in tissue culture, cancers in animal models, and poor prognosis in a number of human cancers. Several lines of evidence suggest that the mRNA export function of eIF4E contributes to its oncogenic potential. For instance, cyclin D1 mRNA export is upregulated in specific subtypes of human leukemia. These specimens contain unusually high levels of eIF4E, the vast majority of which is located in the nucleus. Also, inhibitors of eIF4E dependent mRNA export, the promyelocytic leukemia protein (PML) and homeoprotein PRH, bind eIF4E in the nucleus, inhibit eIF4E dependent mRNA export and eIF4E mediated oncogenic transformation. Further, mutagenesis studies strongly link the activity of eIF4E in mRNA export to its ability to oncogenically transform cells.

Although cyclin D1 plays a key role in the cell cycle that links eIF4E's proliferative properties and its mRNA export function, it is possible that eIF4E coordinately alters the expression of some other growth promoting mRNAs as well, in order to drive its proliferative potential. This study shows that several mRNAs involved in cell cycle progression are also targets of eIF4E dependent mRNA export, and that the subsets of mRNAs regulated at the level of eIF4E dependent mRNA export are distinct from those that are preferentially translated in the cytoplasm. We identified an underlying USER code for export of eIF4E sensitive transcripts. This code is required for the subnuclear distribution of these RNAs, as well as for the formation of relevant eIF4E RNPs. Interestingly, the 4E-SE USER code is a structurally conserved element rather than a sequence based one. eIF4E dependent mRNA export can be decoupled from translation. Finally, eIF4E dependent mRNA export occurs via an alternative mRNA export pathway than bulk mRNA. These results provide the basis for a novel paradigm for eIF4E-mediated tumorigenesis.

Materials and Methods

Reagents and Constructs.

Chimeric constructs in pcDNA3.1LacZ vector (Invitrogen) were positioned 3' of the coding region of LacZ. Cyclin D1 minimal 4E-SE (c4E-SE) was amplified using primers containing EcoRI or XbaI restriction sites at the 5' ends, and the LacZ3'UTR construct as a template (Culjkovic et al, 2005). The same approach was used for the cloning of Pim-1 constructs, where pRBK-Pim-1 (kind gift from Nancy Magnuson (Hoover et al., 1997) was used as a template. Primer sequences are available in Supplemental Table 1. For the TetON system, chimeric LacZ constructs were cloned into pTREMyc vector (Clontech) using EcoRI and XbaI. pcDNA2Flag-eIF4E, pMV, pMV-eIF4E wild type or mutants, pLINKSV40-PML, MSCV, MSCV-eIF4E WT or mutants and bacterial expression constructs were previously described (Cohen et al., 2001; Culjkovic et al., 2005; Topisirovic and Borden, 2005; Topisirovic et al., 2003b). Reagents used were all analytical grade from Sigma, unless mentioned otherwise.

Antibodies.

Antibodies for immunoblotting: mAb anti-PML (5E10 (Stuurman et al., 1992)), mAb anti-eIF4E (BD PharMingen), mAb anti-cyclinD1 (BD PharMingen), mAb anti-Xpress (Invitrogen), rabbit pAb anti-cyclin E1 (M20, Santa Cruz Biotechnology), mAb anti-GAPDH (MAB374, Chemicon), mAb anti-c-Myc (9E10 Santa Cruz Biotechnology), rabbit pAb anti-cyclin A (C-19, Santa Cruz), rabbit pAb anti-nibrin (Cell Signaling), mAb anti-Pim-1 (19F7 Santa Cruz) and mAb cyclin-B1 (GNS1 Santa Cruz).

Cell Culture and Transfection.

eIF4E and PML stably transfected NIH3T3 and U937 cells were as described (Topisirovic et al., 2002; Topisirovic et al., 2003a). U937 cells were used to analyze endogenous Pim1, which is not expressed in NIH3T3 cells. LacZ/LacZ-4E-SE with or without 2Flag-eIF4E as well as TetON LacZ system were stably transfected in U2OS cells. For NXF1 depletion, U2OS cells were transfected with Lipofectamine 2000 and 10 nM siRNA duplex HSC.RNAI.N006362.1.3 (IDT) according to the manufacturer's instruction. Cells were analyzed 72 h after transfection. Actinomycin D, cycloheximide and leptomycin B were all cell culture grade (Sigma).

Immunopurification of eIF4E and RT-PCR.

Immunopurification was as previously published (Culjkovic et al., 2005). Real Time PCR analyses were performed using Sybr Green PCR Master mix (ABI) in Mx3000P™ thermal cycler (Stratagene), and data analyzed with MxPro software (Stratagene). All conditions were described previously (Culjkovic et al., 2005). All calculations were done using the relative standard curve method described in Applied Biosystems User Bulletin #2.

Differential display of immunopurified RNA was performed using RNAimage™ kit (GeneHunter Corporation) according to the manufacturer's instructions.

SNAAP protocol used for differential display was performed as described (Trifillis et al., 1999).

Western blots were performed as described (Topisirovic et al., 2002; Topisirovic et al., 2003a).

Cellular Fractionation and Northern Analysis.

Fractionation and RNA isolation were as described (Lai and Borden, 2000; Topisirovic et al., 2002). Probes for U6 and tRNAlys for Northern blot analysis were previously described (Topisirovic et al., 2002).

Immunofluorescence and Laser Scanning Confocal Microscopy.

Experiments were as described (Cohen et al., 2001; Topisirovic et al., 2002). Fluorescence was observed using 100× optical magnification and 3 or 4× digital zoom, as indicated, on LSM 510 Meta (Carl Zeiss Jena) inverted laser scanning confocal microscope exciting at 488, 543 or 405 nm (at RT). All channels were detected separately, and no cross talk between the channels was observed. The confocal micrographs represent a single optical section through the plane of the cell.

In situ hybridization was as previously described (Culjkovic et al., 2005) using nick translated Biotin-11-dUTP-labeled probes (Nick Translation kit, Roche). Probes were detected using Cy3 IgG Fraction mouse mAb Anti-Biotin (1:100; Jackson ImmunoResearch Laboratories).

EMSA analyses were performed as published (Wein et al., 2003) with the following modifications: 20-50 µg nuclear lysate were incubated with $^{32}$P-3' end labeled LacZ, LacZ-c4E-SE or LacZ-p4E-SE transcript (~50000 cpm) in 2Sµl NET-2 buffer supplemented with 5 mg yeast tRNA (Sigma) and 3 mM MgCl$_2$ for 30 min at room temperature with an additional 15 minutes after addition of 2 mg/ml heparin. For competition studies the nonlabeled competitor RNAs were pre-incubated for 10 minutes with nuclear lysates before labeled RNAs were added. For supershift experiments nuclear lysates were pre-incubated with mAb anti-eIF4E (BD PharMingen) for 15 minutes prior to addition of labeled RNAs Immunodepleated lysates were from IPs with rabbit pAb anti-eIF4E (Abcam). All mRNAs were in vitro transcribed using mMessage mMachine™ T7 kit (Ambion) and 3' end labeled using [$^{32}$P]pCp and T4 RNA Ligase (Amersham). Samples were separated by electrophoresis on 5% native (19:1) polyacrylamide gels for 2 h at 250V using 1× Tris-Borate-EDTA buffer.

UV Crosslinking.

50 µg of nuclear lysates were incubated with radiolabeled probes (1-2×10$^5$ cpm) using the same conditions as for the EMSA. After incubation with heparin, samples were placed on ice and UV irradiated for 15 minutes in a Stratalinker UV 1800 (Stratagene). Crosslinked RNA:protein complexes were treated with 10 U RNase A and 10 U RNase T1 for 15 minutes at 37° C. The reactions were stopped by the addition of 30 µl 2×SDS sample buffer and heating 10 min 95° C. Samples were loaded on 10 or 12% SDS polyacrylamide gels and separated at 50V for 16 h at RT.

RNase mapping analyses were performed as described (Clever et al., 1995) and according to the manufacturer's instructions (Ambion). Briefly, approximately 0.5-1×10$^5$ cpm $^{32}$P-5'-end labeled c4ESE or p4ESE RNA oligo probes (IDT) were mixed with 3 µg yeast tRNA and incubated with 1, 0.1 or 0.01 U RNase V1 (Ambion) for 15 minutes at RT; 1, 0.1 or 0.01 U RNase A (Ambion) for 5 min at RT; 1, 0.1 or 0.01 U RNase T1 (Sigma) for 15 min RT; 1, 0.1 or 0.01 U RNase T2 (Invitrogen) for 5 min RT, or alkaline buffer for 1, 2 or 5 min at 95° C. (alkaline hydrolysis). Reactions were stopped by EtOH/NaAc precipitation. Samples were resolved on 6% polyacrylamide-8M urea gels in 1× Tris/Borate/EDTA buffer.

Results and Discussion eIF4E Alters the mRNA Transport of a Wide Variety of Transcripts eIF4E dependent mRNA export is potentially a broadly based mechanism by which eIF4E controls gene expression and thereby modulates growth and proliferation. We sought to determine if mRNAs other than cyclin D1 might be regulated in an eIF4E dependent manner. Using nuclear lysates, we isolated mRNAs associated with endogenous eIF4E via immunoprecipitation or with recombinant eIF4E using a GST pulldown based method (the SNAAP method of (Trifillis et al., 1999)) and identified them by differential display. Given that many of the identified genes are involved in cell cycle progression, eIF4E immunoprecipitated fractions were also tested for other genes known to be involved in this processes, as well as for known growth inhibitory mRNAs (Table IV). All target identification was confirmed by eIF4E immunoprecipitation and quantitative or semi-quantitative RT-PCR analysis (FIG. 18a). Importantly, the list provided in Table IV is not intended to be totally inclusive but rather to represent a sampling of the target mRNA population, since results from differential display data suggest that hundreds of mRNAs are likely regulated in this manner; here we identified only a subset of these (data not shown).

Many of the mRNAs that physically associate with the nuclear fraction of eIF4E code for gene products that act in cell cycle progression and survival, consistent with the physiological functions associated with eIF4E (see Table IV). Importantly, eIF4E does not bind all mRNAs tested (Table IV). For instance, eIF4E does not associate with the mRNAs corresponding to negative regulators of growth such as PML or p53, or housekeeping genes such as GAPDH, β-actin or α-tubulin. Also, this specificity is not a simple reflection of the sensitivity of mRNAs for regulation at the translational level, as mRNAs sensitive only at the translation level (such as VEGF (Clemens and Bommer, 1999)) are not associated with the nuclear fraction of eIF4E (Table IV). It is important to note that mRNAs that were not found in the eIF4E immunoprecipitated fractions were readily detected in our nuclear lysates (Table IV). Note that that the estimated efficiency of IP with anti-eIF4E mAb is up to 80%.

Since eIF4E associates with the m$^7$G cap of mRNAs, we examined whether this was required for the association of eIF4E with mRNAs in the nuclear fraction (FIG. 18a). eIF4E was immunoprecipitated from the nuclear fraction and mRNAs treated with excess m$^7$GpppG or an analogue that does not bind eIF4E, GpppG. All mRNAs tested associate with eIF4E in a cap dependent manner i.e., m$^7$GpppG competes for binding whereas GpppG does not. These data indicate that the association of eIF4E with mRNAs in the nucleus is m$^7$G cap dependent.

Physical Association of eIF4E with mRNAs is Correlated with Enhanced mRNA Export To test whether there is a correlation between the ability of eIF4E to associate with mRNAs in the nuclear fraction and the ability of eIF4E overexpression to enhance eIF4E dependent mRNA export, the subcellular distribution of identified mRNAs as a function of eIF4E overexpression was analyzed (Table V). U937 and NIH3T3 cells overexpressing eIF4E or appropriate mutants were fractionated and mRNAs levels monitored by real time PCR or Northern analysis. eIF4E overexpression increases the amount of eIF4E sensitive mRNAs in the cytoplasmic fraction versus vector controls (Table V). Conversely, transcripts that did not associate with eIF4E in the nuclear fraction did not have their export altered by eIF4E overexpression (Table V). As expected, the subcellular distribution of β-actin, GAPDH, U6snRNA and tRNA$_{Lys}$ were unaffected (Table V). There is no alteration in total mRNA levels (data not shown). Consistently, when eIF4E could not bind these mRNAs because of a mutation in its cap-binding site (W56A), the subcellular distribution of these mRNAs is not altered (Table V). Further, the dorsal surface mutant W73A which does not act in translation but promotes cyclin D1 mRNA export (Sonenberg and Gingras, 1998; Topisirovic et al., 2002), also promotes export of other eIF4E sensitive mRNAs (Table V). Thus, it is likely that all sensitive mRNAs will require the $m^7G$ cap binding activity of eIF4E but not w73 on the dorsal surface for their interaction with eIF4E in the nucleus. Importantly, circular dichroism studies indicate that both W73A and W56A mutants have structures indistinguishable from wild type eIF4E (Kentsis et al., 2001).

One of the consequences of eIF4E dependent promotion of mRNA export is increased availability of these mRNAs to the translation machinery, leading to increased protein levels. Thus we examined if protein levels for a subset of identified genes are elevated by eIF4E. Consistent with enhanced mRNA export, overexpression of wild type eIF4E or the W73A mutant leads to increased protein levels of a subset of genes examined (FIG. 18b), while there is no increase in protein levels when the cap binding mutant (W56A) is overexpressed. Importantly, wild type eIF4E and the W73A and W56A mutants were expressed to similar levels for all experiments (FIG. 18b).

In order to determine if these mRNAs are regulated through the same mechanism, it was important to examine the effect of PML, an inhibitor of eIF4E dependent cyclin D1 mRNA export (Cohen et al., 2001; Topisirovic et al., 2002), on the export of target mRNAs. We observed decreased export (data not shown), and reduced protein levels of ODC, c-Myc, cyclin D1 and cyclin E1 mRNAs (data not shown) in cells overexpressing PML. Also, PML did not reduce levels of eIF4E, β-actin or GAPDH proteins (FIG. 18c) and there was no alteration in total mRNA levels for any of these transcripts when PML was overexpressed (data not shown). Thus, PML acts as an inhibitor of eIF4E dependent mRNA export, not just as an inhibitor of cyclin D1 mRNA export.

In summary, the physical association of mRNAs with the nuclear fraction of eIF4E is strongly correlated with their enhanced nuclear export. In the cytoplasm, these mRNAs may (i.e. ODC) or may not (i.e. cyclin D1) be a subject of modulation by eIF4E at the level of translation. Thus, eIF4E mediated modulation at the nuclear level neither precludes nor necessitates such modulation at the cytoplasmic level.

The RNA USER Code for eIF4E Dependent mRNA Export

Since we previously identified a 100 nucleotide eIF4E sensitivity element (4E-SE) in the 3' UTR of cyclin D1 which sensitizes cyclin D1 and corresponding chimeric LacZ constructs to regulation by eIF4E at the mRNA export level (Culjkovic et al., 2005), we carried out an extensive bioinformatics analysis to identify 4E-SE like elements in the other target RNAs identified in Table IV. Sequence analysis indicated that the 4E-SE was well conserved in cyclin D1 transcript (from birds to humans) (Culjkovic et al., 2005), but comparison of cyclin D1 and the other eIF4E sensitive transcripts identified here failed to reveal any shared sequence homology. We therefore examined the possibility that the 4E-SE element is a structurally conserved element.

To best identify the common elements in the target mRNAs, we decided to compare the cyclin D1 4E-SE with the 4E-SE from one of the newly identified target mRNAs, Pim-1 (we mapped the region of Pim-1 3'UTR to functional 4E-SE, FIG. 19c). We mapped the 4E-SE from cyclin D1 and the 4E-SE from Pim-1 to a minimal ~50 nucleotide region (FIG. 19a). These minimal domains, when fused to heterologous LacZ mRNA, immunoprecipitate with eIF4E and have their mRNA export promoted by eIF4E (FIG. 19c). Thus, we show that both of these minimal ~50 nucleotide elements are functional 4E-SE. Although there was no sequence homology observed, both elements contain two predicted adjacent stem loop pairs.

We used nuclease digestion methods to determine if this two functional 4E-SEs had conserved secondary structural features, such as the predicted stem loop structures. Importantly, these studies revealed that both elements fold into similar secondary structures. We refer to this element as adjacent stem loop pair (FIGS. 19a and 19b). Consistently, biophysical analysis indicates that Pim-1 and cyclin D1 4E-SEs have similar biophysical properties. For instance, circular dichroism analysis of thermal melting curves using purified RNA oligomers for cyclin D1 and Pim-1 4E-SEs revealed multiphase behavior consistent with the presence of multiple structural elements with different Tm's (Topisirovic et al., in preparation). Thus, both Pim-1 and cyclin D1 4E-SEs have similar secondary structures, consisting a two adjacent stem loop elements.

An initial problem we encountered in these studies is that the presence of stem loop elements is common in the 3' UTRs of cyclin D1 and Pim-1. In cyclin D1 alone, the PatSearch programme (Grillo et al., 2003) predicts ten potential stem loop structure pairs, and yet our previous studies indicate that the only part of the cyclin D1 3'UTR that can impart eIF4E sensitivity is the above defined 4E-SE (Culjkovic et al., 2005). Similarly, the Pim-1 3' UTR contains two predicted adjacent stem loop pairs, while only one is a functional 4E-SE. Thus, we compared the secondary structures of Pim-1 and cyclin D1 4E-SEs, to determine features that would enable us to distinguish functional 4E-SEs from other stem loop pairs. Visual inspection of the secondary structures reveal the conservation of a set of A and U nucleotides ($UX_2UX_2A$, highlight in FIG. 19a). Importantly, these patterns of nucleotides were not found in any of the other stem loop pairs found in cyclin D1 or Pim-1 3'UTR. Thus, these are features that can be used to distinguish functional 4E-SEs from other elements that have potential to fold into similar secondary structures.

Further analyses showed that the stem loop pair structure with the conserved pattern of nucleotides is also present in all of the other eIF4E sensitive targets identified here. Importantly, none of the mRNAs that are not eIF4E sensitive contain stem loop pairs with the conserved pattern of nucleotides found in the functional 4E-SEs. In summary, we have identified a structural motif, consisting of two adjacent stem loop pairs, which impart eIF4E sensitivity. Importantly, there exist in this motif sequence features of 4E-SEs that can be used to distinguish functional 4E-SEs from other paired stem loop structures.

The 4E-SE is Sufficient for Localization with eIF4E Nuclear Bodies

To assess whether the 4E-SE acted as an RNA zipcode for eIF4E nuclear bodies, LacZ chimeric constructs with either Pim-1 or cyclin D1 4E-SE were expressed in U2OS cells. Both chimeric mRNAs co-localize with eIF4E nuclear bodies (FIG. 19d). In the absence of the 4E-SE, no localization of LacZ transcripts to eIF4E nuclear bodies is observed (FIG. 19d). Importantly, LacZ-4E-SE does not associate with eIF4E bodies that contain the negative regulator, PML. This is consistent with our previous studies showing that there are two classes of eIF4E nuclear bodies: those that co-localize with PML and those that co-localize with endogenous cyclin D1 mRNA. Thus, endogenous cyclin D1 mRNAs co-localize with eIF4E nuclear bodies that do not contain PML (Culjkovic et al., 2005). In this way, LacZ-4E-SE transcripts and endogenous mRNAs behave similarly.

These experiments demonstrate that the 4E-SE is sufficient to localize capped mRNAs into eIF4E nuclear bodies irrespective of the rest of the mRNA sequence. Moreover, the 4E-SE from Pim-1 and cyclin D1 are functionally equivalent in terms of localization activity. Thus, the 4E-SE provides an RNA zipcode for localization to eIF4E nuclear bodies.

The 4E-SE Makes eIF4E Dependent Complexes

To establish whether the 4E-SE functions simply as a localization signal, or whether it acts in the formation of eIF4E dependent mRNPs, we carried out EMSA assays. Studies were carried out with both the LacZ-cyclin D1-4E-SE (c4E-SE) and the LacZ-Pim-1-4E-SE (p4E-SE) to ensure that assembly of these complexes is dependent on the 4E-SE itself and not features specific to either 4E-SE. RNA probes were $^{32}$P 3' end labeled and m$^7$G capped. Addition of either mouse eIF4E with a 6 kD solubility tag (m4E), or untagged human eIF4E (h4E) led to the formation of slower migrating species for both LacZ-4E-SE constructs (FIGS. 20a and 20b). Importantly, addition of nuclear lysates led to the formation of significantly higher molecular weight complexes, indicating that proteins other than eIF4E are likely to be present. Complex sizes were approximately the same for both 4E-SE constructs. Addition of cold competitor 4E-SE RNAs led to a reduction in signal, consistent with the 4E-SE element competing for the labeled 4E-SE containing transcripts (FIG. 20e). Addition of nuclear lysates to LacZ transcripts lacking the 4E-SE did not lead to formation of these complexes (FIG. 20b).

To determine whether the 4E-SE complexes formed from nuclear lysates were dependent on eIF4E, EMSA assays were performed with nuclear lysates depleted of eIF4E via immunoprecipitation. We estimated that lysates were at least 80% depleted of eIF4E (data not shown). Lysates immunodepleted of eIF4E did not produce high molecular weight complexes (FIG. 20b). Addition of purified tagged eIF4E to immunodepleted lysates led to a partial restoration of the complex, which could be expected, since only eIF4E, but not other factors that were depleted during the anti-eIF4E immunoprecipitation, were re-introduced. Thus, eIF4E and associated factors are required for formation of these RNPs. In addition, an antibody to eIF4E leads to a super shift of complexes formed from nuclear lysates (FIG. 20b). Identical results are observed for LacZ-p4E-SE. Finally, a mutant that disrupts the first stem loop ($G_{10}C_{11}G_{12}$ mutated to CAC) in the p4E-SE is defective in complex formation (FIG. 20c). Thus, the 4E-SE element forms complexes dependent on eIF4E and on the structure of the 4E-SE.

To further characterize these complexes, LacZ-4E-SE constructs were UV-cross-linked followed by RNase digestion and SDS-gel electrophoresis (FIG. 20d). As for the EMSA studies, transcripts were m$^7$G capped and 3' end labeled and the effects of addition of purified eIF4E or nuclear lysates to the size of cross-linked complexes was monitored. Since mRNAs were 3' end labeled, binding of the cap only by purified eIF4E was not sufficient to protect the rest of the RNA from RNase digestion. Addition of the nuclear lysate leads to substantial shifts in molecular weight. Importantly, the LacZ-c4E-SE and the LacZ-p4E-SE form complexes similar in size. Three discrete species of between 75-90 kD are observed (indicated by arrows). The same complexes are absent in eIF4E depleted nuclear lysate, indicating that these require eIF4E to form. Consistently, treatment of the nuclear lysate with the m$^7$GpppG cap analogue (nc cap) also disrupts 75-90 kD range complexes. These species are absent from the LacZ controls, which lack the 4E-SE. A lower band, at ~64 kD, is present in all the experiments, likely indicating the formation of some general RNP, not directly involved with eIF4E and the 4E-SE. In summary, we observe two types of complexes: those ones that can form in the absence of eIF4E and are cap and 4E-SE independent (see asterisk), and the second type that depends on eIF4E, the m$^7$G cap and a structurally intact 4E-SE. The UV-cross-linking studies together with the EMSA results indicate that the 4E-SE acts both as a zipcode localizing mRNAs to bodies (FIG. 19d) as well as USER code for the eIF4E nuclear mRNP (FIG. 20).

eIF4E Dependent mRNA Export is Independent of On-Going Protein or RNA Synthesis

We examined the importance of new protein synthesis and transcription for eIF4E dependent mRNA export. To inhibit protein synthesis, cells were treated with 100 µg/ml cycloheximide for 1 hour. (FIG. 21a). Also, export of endogenous cyclin D1 mRNA was not modulated by cycloheximide treatment (data not shown). Similarly, actinomycin D treatment (10 µg/ml) did not affect export of these mRNAs (FIG. 21a). Although cycloheximide treatment did not modify export, it is still possible that the 4E-SE could modulate polysomal loading in an eIF4E dependent manner. Thus, we monitored polysomal profiles of LacZ as a function of the 4E-SE and of eIF4E overexpression. The profiles of LacZ and LacZ-c4E-SE are indistinguishable and are not altered by eIF4E overexpression (data not shown). This is consistent with the finding that eIF4E overexpression does not change cyclin D1 mRNA polysomal loading (Rousseau et al., 1996). Given that eIF4E dependent mRNA export is independent of on-going protein synthesis and that the 4E-SE does not alter polysomal loading, the functions of eIF4E in mRNA export and translation appear to be decoupled.

We previously demonstrated that LacZ-c4E-SE transcripts did not have altered stability relative to LacZ transcripts using actinomycin D over the course of several hours (Culjkovic et al., 2005). However, it is still possible that mRNA turnover could be substantially more rapid than hours. Thus, we constructed LacZ and LacZ-4E-SE TetON-inducible cell lines and examined the stability of these mRNAs immediately upon doxicycline addition. The presence of the 4E-SE does not substantially alter stability of the LacZ transcripts in either short (minutes) or long term (hours) (data not shown).

eIF4E Dependent mRNA Export Pathway is Saturated by Excess 4E-SE

We reasoned that if the 4E-SE is required for export, overexpression of LacZ-c4E-SE or LacZ-p4E-SE should specifically inhibit export of other (endogenous) 4E-SE containing mRNAs by competing for the 4E-SE specific export machinery (FIGS. 21b and 21c). Using our TetON-inducible LacZ, LacZ-p4E-SE or LacZ-c4E-SE constructs, we monitored export of chimeric mRNAs as a function of total mRNA levels. At early time points, when levels of LacZ mRNAs are low, 4E-SE export is more efficient with higher ratios of cytoplasmic to nuclear chimeric mRNAs. As the levels of these mRNAs increase, 4E-SE export becomes saturated and the ratio of cytoplasmic to nuclear chimeric mRNAs decreases (FIG. 21b). At the same time, export of endogenous cyclin D1 mRNA was competed (impaired) by expression of 4E-SE chimeric mRNAs (FIG. 21b). Further, export of VEGF mRNA was not affected, consistent with its insensitivity to eIF4E at the mRNA export level (FIG. 21b). Thus, overexpression of the 4E-SE element leads to competition for the 4E-SE specific export machinery.

4E-SE Mediated Export is NXF1 Independent but CRM1 Dependent

Since the best-described cellular mRNA export pathway involves the NXF1/p15 heterodimer which appears to mediates bulk mRNA export (Cullen, 2000; Cullen, 2003a), the dependence of the 4E-SE mRNA export on NXF1 was examined (data not shown). Consistent with previous studies, as well as our own, eIF4E does not immunoprecipitate with NXF1 in the nuclear fraction of cells ((Lejeune et al., 2002) and data not shown). However, this does not preclude a NXF1 dependent mechanism where eIF4E does not need to physically associate with NXF1. To further investigate NXF1 involvement in 4E-SE export, Flag tagged NXF1 or NXF1/p15 overexpressing cells were immunoprecipitated with anti-Flag antibodies and the presence of LacZ or LacZ-c4E-SE mRNAs was monitored by real time PCR (FIG. 22a). In contrast to LacZ mRNA that is enriched in the NXF1 fractions, LacZ-c4E-SE mRNA appears to be rather excluded. These results are independent of the presence or absence of p15 (data not shown).

We extended these studies to examine the effects of knocking down NXF1 expression on LacZ-c4E-SE export (FIG. 21b). Overexpression of eIF4E enhanced export of LacZ-c4E-SE transcripts, even when NXF1 levels were substantially reduced, indicating that export of LacZ-c4E-SE in the presence of overexpressed eIF4E is independent of NXF1. In the absence of the 4E-SE, LacZ mRNA cytoplasmic/nuclear ratio was substantially reduced by NXF1 depletion. Analysis of LacZ protein levels confirmed the above findings (FIG. 22c). As expected, siRNA treatment led to reduction in NXF1 levels whereas treatment with scrambled controls did not (FIG. 22c). Further, levels of eIF4G were not altered consistent with studies which show longer siRNA treatments (>72 hours) are needed to reduce eIF4G levels (Herold et al., 2001). Thus, export of 4E-SE containing transcripts is independent of the NXF1 pathway. This does not rule out the possibility that a subset of 4E-SE transcripts do transit through this pathway, simply that they do not require this pathway to be exported.

Since many RNAs can be exported through the CRM1 pathway, we examined this possibility by using leptomycin B (LMB), a specific inhibitor of CRM1 (Cullen, 2003a; Cullen, 2003b). The export of LacZ or LacZ-c4E-SE mRNAs as a function of overexpressed eIF4E and LMB treatment was monitored using real time PCR (data not shown). Strikingly, LMB suppressed export of the LacZ-4E-SE constructs but not of LacZ or β-actin transcripts. LMB leads to retention of 18S rRNA (FIG. 22c), consistent with previous studies showing that ribosomal RNA export requires CRM1 (Moy and Silver, 2002).

Novel Export Pathway Involving eIF4E and 4E-SE Containing mRNAs

Since it was described, no underlying mechanism for eIF4E dependent export has been determined (Rousseau et al., 1996). There are several characteristic features that differentiate eIF4E mediated export from the pathway used for bulk mRNA (summarized in FIG. 23): 1) 4E-SE saturates export of the eIF4E pathway but does not effect export of bulk mRNA (FIG. 21b); 2) LMB inhibits eIF4E dependent export (FIG. 21d); 3) the $m^7G$ cap is required for the eIF4E pathway (FIG. 18b, Table V). Interestingly, there are many parallels between the eIF4E pathway and UsnRNA export: both are CRM1 dependent and both require the $m^7G$ cap. However, in contrast to the eIF4E pathway, UsnRNA export depends on RNAs being CBC bound in complex to PHAX, which acts as an adaptor for CRM1 (Cullen, 2000; Cullen, 2003a; Cullen, 2003b; Ishigaki et al., 2001; Izaurralde et al., 1995).

In general, CRM1 mediated mRNA export requires co-factors which depend on the type of RNA being exported i.e. large rRNA, small rRNA, 5S rRNA or UsnRNA (Cullen, 2003a; Cullen, 2003b). Our previous studies indicate that eIF4E overexpression does not modulate the export of 18S or 28S rRNA, which is CRM1 dependent, or tRNA, which is exported using the exportin-t receptor (Sarkar and Hopper, 1998). Thus, we hypothesize that eIF4E, or some subset of factors associated with the 4E-SE RNP, require CRM1-adaptor proteins specific to the eIF4E dependent pathway. Further, these adaptors are found in limiting amounts and titratable by high 4E-SE levels or by immunodepletion of eIF4E. Identifying such adaptor proteins will be an area of intense future work.

A conundrum in understanding eIF4E dependent mRNA export results from the observation that eIF4E stimulates the export of mRNAs that can be still exported under physiological eIF4E levels. Thus, eIF4E dependent mRNA export is a means by which the cell rapidly upregulates gene expression by stimulating the export of mRNAs that can be exported through other pathways, albeit less efficiently. When eIF4E levels are low, or in the absence of the $m^7G$ cap or 4E-SE, transcripts are exported (presumably) through the NXF1 pathway. This idea is consistent with previous suggestions that the NXF1 pathway is a default mRNA export pathway for those mRNAs that do not have any special features associated with them (Cullen, 2003b). In this way, eIF4E levels can act as a "cellular rheostat". As levels increase, eIF4E sensitive mRNAs are exported much more efficiently, and in a coordinated fashion, through the eIF4E dependent CRM1 sensitive pathway described here. A recent report indicates that CRM1 dependent mRNA export can occur during T cell activation indicating that external cellular signals can lead to alterations in mRNA export pathways (Schutz et al., 2006).

The Role of eIF4E in 4E-SE Containing mRNA Export and Implications for Cancer

The studies reported here suggest the possibility that the proliferative and transforming properties associated with eIF4E are, at least partially, a result of dysregulation of eIF4E dependent mRNA export. These studies indicate a role for eIF4E in coordinating export and expression of transcripts involved in cell cycle progression, proliferation and survival. Importantly, eIF4E does not promote the expression of negative regulators of itself, i.e., PML. eIF4E also promotes the expression of c-Myc, a factor which upregulates transcription of eIF4E in some cellular growth conditions (Schmidt, 2004). Thus, eIF4E modulates the expression of many genes involved in multiple points of cell cycle progression.

The 4E-SE provides a USER code for targeting these transcripts for export in an eIF4E sensitive manner. Other transcripts may be regulated by eIF4E at translation level using USER codes different from the 4E-SE. Further, the 4E-SE may associate with other, as yet to be identified RNPs. In this way, the effects of eIF4E and regulation of 4E-SE containing transcripts are likely to be complex and combinatorial. For instance, translation of export sensitive mRNAs does not depend on the 4E-SE, but rather the complexity of the 5'UTR. Transcripts such as Pim-1 and ODC(Hoover et al., 1997; Rousseau et al., 1996) serve as examples of the combinatorial use of USER codes for modulating gene expression and support the idea of the use of such a network. Consistently, our studies indicate that the translation and export functions of eIF4E can be decoupled based on the composition of the 3' and 5' UTRs (i.e. eIF4E enhances the export of cyclin D1, but enhances the translation of VEGF).

Several key regulators of eIF4E dependent mRNA export have been identified including PML (Cohen et al., 2001) and several homeodomain proteins which contain conserved eIF4E binding sites (Topisirovic et al., 2003a; Topisirovic et al., 2005). These regulators are positioned to modulate the entire RNA regulon, potently modulating cell cycle progression and cell survival. Our studies demonstrate that PML and PRH impede eIF4E dependent export of cyclin D1 and other 4E-SE containing transcripts ((Culjkovic et al., 2005; Topisirovic et al., 2003a) and this report). Stimulators of this growth regulon include HOXA9, which promotes both the mRNA export and translation of genes in the regulon (Topisirovic et al., 2005). The far-reaching activities of these regulators, particularly those that regulate multiple eIF4E functions simultaneously, likely lies in their ability to modulate eIF4E, a key nexus in this regulon.

The physiological importance of this regulation is clear. In primary specimens from acute myeloid leukemia patients, PRH is both downregulated and de-localized from eIF4E nuclear bodies (Topisirovic et al., 2003b). At the same time, HOXA9 is upregulated and becomes associated with eIF4E in both the nuclear and cytoplasmic compartments, leading to upregulation of both eIF4E dependent mRNA export and translation (Topisirovic et al., 2005).

In conclusion, eIF4E dependent modulation of mRNA export could provide an immediate response system by which the cell responds to extra cellular stimuli prior to transcriptional reprogramming Our results indicate that modulation of mRNA export allows coordinated modulation of cellular proliferation, and provide one of the first examples of an RNA regulon that is positioned to directly impact on human disease. Ability of eIF4E to modulate coordinated gene expression impacting on proliferation and cell survival pathways ensures maximum efficiency for its growth promoting potential. Certainly, these findings do not preclude, but rather complement, critical modulation of gene expression by eIF4E at other levels of mRNA metabolism, in particular translation and mRNA stability/sequestration. In summary, we define a novel mRNA export pathway, which is used for coordinate expression of genes that govern cell cycle progression and survival.

RNA Regulons as Therapeutic Targets

Identification of nodes in networks clearly defines such nodes as positions in the cellular gene expression circuitry which could be potent drug targets (FIG. 24).

Recent studies have focused on the mTOR inhibitor, rapamycin, as a means to downregulate protein synthesis in part by inhibiting phosphorylation of the eIF4E binding proteins (eIF4Ebp or 4E-BP) and thereby allowing these to interact and inhibit eIF4E activity in the cytoplasm (Sarbassov, D. D., Ali, S. M. & Sabatini, D. M. (2005) *Curr Opin Cell Biol* 17:596-603). However, treatment with rapamycin in these patients has led to increased levels of activated Akt in their tumours which support clinical data indicating that rapamycin may be of limited use as a single agent cancer therapy (O'Reilly, K. E. et al. (2006) *Cancer Res* 66:1500-8. Furthermore, cells overexpressing eIF4E show increased resistance to rapamycin and the combination of this drug with doxorubicin (Wendel, H. G. et al. (2006) Cancer Res 66, 7639-46). Ribavirin provides an alternative strategy to target eIF4E activity as it directly targets eIF4E via its mimicry of the $m^7G$ cap (Kentsis, A., et al. (2004) *Proc Natl Acad Sci USA*; Kentsis, A. et al. RNA 11:1762-6). Thus, it is positioned to efficiently shut down the eIF4E regulon.

TABLE IV

List of mRNAs that associate (or not) with nuclear eIF4E.

| Target RNA | Function/Growth Promoting properties | Translationally Sensitive to eIF4E |
|---|---|---|
| Cyclin D1 (gi: 77628152) | G1/S cell cycle progression (Liang and Slingerland, 2003) | no (Rousseau et al., 1996) |
| Cyclin E1 (gi: 17318558) | G1/S cell cycle progression (Liang and Slingerland, 2003) | n.d. |
| Cyclin A2 (gi: 16950653) | S/G2/M cell cycle progression (Liang and Slingerland, 2003) | n.d. |
| Cyclin B1 (gi: 34304372) | G2/M cell cycle progression (Liang and Slingerland, 2003) | yes (Cao and Richter, 2002) |
| ODC (gi: 4505488) | Polyamine synthesis/tumor promoting (Pegg, 2006) | yes (Clemens and Bommer, 1999) |
| Pim-1 (gi: 31543400) | S/T kinase (Bachmann and Moroy, 2005) | yes (Clemens and Bommer, 1999) |
| Mdm2 (gi: 46488903) | Survival/apoptotic rescue (Liang and Slingerland, 2003) | n.d. |
| c-Myc (gi: 71774082) | Facilitates G1/S progression Transcriptionally upregulates eIF4E (Liang and Slingerland, 2003; Schmidt, 2004) | yes (Clemens and Bommer, 1999) |
| Nibrin/NBS1 (gi: 67189763) | DNA repair/Akt activation/ promotes growth (Chen et al., 2005) | n.d. |
| Fbox1 (gi: 16306583) | Promotes cell cycle progression (Liang and Slingerland, 2003) | n.d. |
| CGGbp1 (gi: 56550052) | Influences FMR1 expression (Naumann et al., 2004) | n.d. |
| P54nrb/NONO.1 (gi: 34932413) | RNA binding protein/Promotes survival (Stier et al., 2005) | n.d. |
| Selenoprotein S (gi: 45439347) | Glucose regulated ER protein (Gao et al., 2004) | n.d. |
| GAPDH (gi: 83641890) | Housekeeping/apoptotic | no (Clemens and Bommer, 1999; Rousseau et al., 1996) |
| VEGF (gi:71051577) | Mitogen/Angiogenesis/tumor invasion (Roy et al., 2006) | yes (Clemens and Bommer, 1999) |
| P53 (gi: 8400737) | Pro-apoptotic/reduces eIF4E transcription (Zhu et al., 2005) | no (Clemens and Bommer, 1999) |
| β-actin (gi: 5016088) | Cytoskeletal | no (Rousseau et al., 1996) |
| α-tubulin (gi: 57013275) | Cytoskeletal | no |
| eIF4E (gi: 54873625) | Translation and mRNA export/ Promotes growth and survival (Strudwick and Borden, 2002) | no (Clemens and Bommer, 1999; Strudwick and Borden, 2002) |
| PML (gi: 67089161) | Pro-apoptotic/G1 arrest (Borden, 2002) | no (Strudwick and Borden, 2002) |
| α-globin (gi: 14456711) | Housekeeping | No |
| c-ebpa (gi: 28872793) | Arrests proliferation (Wang et al., 2001) | n.d. | n.d. not determined.

TABLE V

Cytoplasmic/nuclear ratio of different mRNAs in U937 cells overexpressing eIF4E wt or mutants.

| MRNA | MSCV vector ctrl | 4Ewt | W73A | W56A |
|---|---|---|---|---|
| Cyclin D1 | 1 ± 0.035 | 11.995 ± 0.860 | 11.450 ± 860 | 1.110 ± 0.036 |
| Cyclin E1 | 1 ± 0.022 | 3.442 ± 0.05 | 3.172 ± 0.208 | 1.200 ± 0.015 |
| Cyclin A2 | 1 ± 0.044 | 5.472 ± 0.580 | 7.736 ± 0.540 | 1.002 ± 0.058 |
| Cyclin B1 | 1 ± 0.108 | 4.720 ± 0.750 | 4.073 ± 0.434 | 1.475 ± 0.122 |
| ODC | 1 ± 0.010 | 6.847 ± 0.373 | 7.138 ± 0.852 | 1.272 ± 0.018 |
| Pim-1 | 1 ± 0.051 | 3.435 ± 0.194 | 3.391 ± 0.251 | 1.029 ± 0.029 |
| Mdm2 | 1 ± 0.325 | 15.698 ± 0.160 | 15.097 ± 0.793 | 1.379 ± 0.014 |
| c-Myc | 1 ± 0.033 | 2.980 ± 0.233 | 2.857 ± 0.226 | 0.925 ± 0.042 |
| Nibrin | 1 ± 0.030 | 4.728 ± 0.145 | 4.958 ± 0.230 | 1.226 ± 0.024 |
| F-box 1 | 1 ± 0.069 | 11.202 ± 0.866 | 10.713 ± 0.633 | 1.363 ± 0.062 |
| Selenoprotein S | 1 ± 0.072 | 14.520 ± 1.164 | 11.839 ± 0.257 | 1.193 ± 0.234 |
| VEGF | 1 ± 0.111 | 0.835 ± 0.063 | 0.980 ± 0.261 | 1.387 ± 0.022 |
| β-Actin | 1 ± 0.173 | 1.020 ± 0.238 | 1.220 ± 0.203 | 1.313 ± 0.180 |
| P53 | 1 ± 0.016 | 0.892 ± 0.006 | 1.392 ± 0.230 | 0.994 ± 0.008 |
| α-globin | 1 ± 0.379 | 0.861 ± 0.237 | 1.265 ± 0.232 | 1.275 ± 0.346 |

Cytoplasmic/nuclear (n/c) values represent relative fold ± sd, normalized to vector control (MSCV), which was set to 1. Average values ± sd were calculated for each set of triplicates. Average values of all analyzed mRNAs obtained for each fraction of each sample were divided by GAPDH mRNA values obtained for the same fraction/sample. After dividing cytoplasmic with nuclear values of each sample, obtained c/n values ± sd were normalized by setting MSCV vector control c/n value to 1.

Example 5 Pre-Clinical and Clinical Evaluation of Ribavirin as a Novel Therapy for Breast Cancer Breast cancer is an important and biologically complex human disease which is newly diagnosed in 200,000 individuals per year and accounts for over 40,000 deaths annually within the United States. Over the past several decades clinicians have come to realize that breast cancer is not a single uniform disease but one that can be segmented into different clinical subtypes. Until recently subtype designations were largely clinically based, but with the introduction of multiplexed gene expression and tissue microarray technologies our capacity to identify novel clinical subtypes within the overall breast cancer milieu has been significantly enhanced. For the purposes of this Example, breast cancers will be considered to belong to discrete clinical subtypes based upon a set of widely employed biomarkers [estrogen receptor (ER), progesterone receptor (PR), erbB2/neu/HER2 receptor (HER2)] and/or their pathologic grade (I to III). These attributes, together with age, tumor size and axillary lymph node status, provide important prognostic and predictive inputs into the clinical management of breast cancer. For example, ER/PR positive status correlates with enhanced short-term prognosis and is predictive for response to tamoxifen therapy, while HER2 amplification or overexpression correlates with increased recurrence rates, tumor aggressiveness, increased mortality in node-positive patients and is a positive predictor of response to trastuzumab. By contrast, breast cancers belonging to the basal-like subtype (aka 'triple negative' since they lack all three ER/PR/HER2 receptor biomarkers) are considered to be distinct from all others classes and generally have a poor prognosis. Despite these defined differences between subtypes, high-grade tumors (poor prognosis) exist in all three major classes including: ER/PR positive (ca. 15% all breast cancers), HER2 positive (ca. 20% all breast cancers) and basal-like (ca. 20% all breast cancers).

Development of effective therapeutic strategies for breast cancers with a poor prognosis (basal-like, HER2-positive and hi-grade tumors) represents an important unmet medical need. Anthracyclines, taxanes, trastuzubab (monoclonal antibody against the extracellular domain of HER2) and bevacizumab (anti-vascular endothelial growth factor monoclonal antibody) and combinations thereof represent many of the established and/or investigational therapies available for the treatment of breast cancer. Even when clinically effective their use is often associated with significant cardiac and neuronal toxicities, neutropenia and even gastrointestinal perforation and hemorrhaging in the case of bevacizumab. Development of effective breast cancer therapies with limited/no associated toxicity is another important unmet medical need.

In human malignancies, including breast cancer, eIF4E overexpression correlates with enhanced metastatic potential and an overall poor clinical prognosis. Relevant to breast cancer is the finding that eIF4E levels are significantly increased in the vascularized malignant ducts of invasive carcinomas and that within the surgical margins of breast cancer patients elevated levels of eIF4E correlate with an increased rate of disease recurrence that is independent of nodal status. Recently, Li and co-workers determined that elevated eIF4E levels in breast cancers correlate with higher VEGF levels and increased microvessel density. Further, eIF4E-dependent activation of the translation initiation complex eIF4F has been determined to be essential for the genesis and maintenance of the malignant phenotype in human mammary epithelial cells. Increased eIF4E activity plays an important prognostic role in human breast cancer.

Critical to our overall hypothesis that eIF4E activity is elevated in breast cancers will be our identification of which clinical subtype(s) possess elevated levels of eIF4E. Multiplexed gene expression and tissue microarray analyses will permit us to identify breast cancer eIF4E subytpes. To date, direct correlation to other clinical subtypes on a patient by patient based is not available.

A breast cancer cohort analyzed consists of 688 samples of invasive ductal carcinoma selected from the Yale University Department of Pathology archives as available from 1961 to 1983 with approximately half node-positive specimens and half node-negative specimens. Analysis performed using a HistoRx's robust method of objective in situ quantification of protein expression that employs immunofluorescence staining and fluorescence microscopy technology (AQUA™ analysis) that was originally developed by Dr. Robert Camp and Dr. David Rimm at Yale University. The AQUA™ system allows for high-throughput, quantitative high resolution analysis of tissue microarrays, whole tissue sections and core biopsy samples of human tissues, animal tissues, xenografts and cell lines. In contrast to many automated imaging methods, AQUA™ analysis is not morphology based, but rather is based on molecular co-localization of different fluorophores tagged to different antibody- or stain-defined compartments. By use of two different analysis algorithms, the resulting AQUA™ scores are objective and are proportional to the concentration per unit area on a continuous scale equivalent to an ELISA, while maintaining critical spatial information of tissue samples.

Expression of eIF4E was assessed by AQUA using the Epitomics anti-eIF4E antibody at a dilution of 1:500. eIF4E expression was compartmentalized using cytokeratin as a tumor marker and DAPI as a nuclear marker. Appropriate images were captured using the PM1000. AQUA was validated for compartmentalization of expression. AQUA scores were linked to clinical data and analyzed. Unsupervised hierarchical clustering analysis (FIG. 19, average linkage of mean-based Z-scores) was performed using AQUA scores for estrogen receptor (ER), progesterone receptor (PR), epidermal growth factor receptor (EGFR), Her2, and eIF4E. High eIF4E clustered predominantly with the basal (triple-expression and AQUA analyses we conclude that the clinical inhibition of eIF4E activity (by Ribavirin) may demonstrate the largest benefit in patients presenting with basal-like/eIF4E+ breast cancers and selected HER2/eIF4E (+/+) and ER/eIF4E (+/+) cancers. Therefore, we will focus our initial pre-clinical and clinical development efforts on Basal/eIF4E (+), HER2(+)/eIF4E(+) breast cancer clinical subtypes and to a lesser extent due to its more limited association to ER(+)/eIF4E(+) breast cancers. The identification of eIF4E clinical subtypes will serve to focus our pre-clinical and clinical studies and the detection methodologies will insure that we can detect changes within human clinical samples.

Breast cancer cell lines corresponding to established clinical subtypes will be obtained and evaluated for eIF4E activity using the same set of study attributes used to characterize human clinical samples in our expression and tissue microarray cohorts, namely: eIF4E protein level, eIF4E phosphorylation status, eIF4E-BP1 level and its phosphorylation status. The following cell lines are available for study and have been characterized with regards to their biomarker status by expression profiling (D. Iglehart, Dana-Faber Cancer Institute):

| HER2+/ER+ | HER2+/ER− | HER2−/ER+ | Basal-like HER2−/ER− | EGFR |
|---|---|---|---|---|
| BT474 (x) | SKBR3 (x) | MCF-7(x)(4E) | BT20, HCC38 | MDA231(x)(4E) |
| MDA361 | MDA 453 | T47d (x) | HCC1187, HCC1143 | MDA468(x) |
| | | | HCC1599, HCC1183 | |
| | | | HCC1954 | |

Code:
(x) = Grows as xenograft;
(4E) = Elevated eIF4E;
Absence of label = To be determined negative tumors—ER/PR/Her2 negative) phenotype—Defined herein as BASAL/eIF4E+. Not all basal-like tumors showed elevated eIF4E expression, suggesting that eIF4E may be a novel biomarker defining a specific sub-population of basal-like tumors. While eIF4E expression is clearly most closely linked a particular Basal-like sub-phenotype, it also associates to a lesser extent with the Her2+ molecular subtype and the ER+/PR− molecular subtype.

FIG. 25 depicts unsupervised hierarchical clustering analysis of protein expression level in breast cancers performed using AQUA scores for estrogen receptor (ER), progesterone receptor (PR), epidermal growth factor receptor (EGFR), Her2, and 4E. FIG. 26 depicts expression analysis performed from bulk tumor RNA extracted from 141 primary breast cancers and run on Affymetrix U133 plus 2.0 arrays (Andrea Richardson Dana-Farber Cancer Institute). The analysis was performed using hierarchical clustering function of dChip software. Comparison of high 4E expressors to low expressor tumors one finds that 4E is co-overexpressed with a set of genes from chromosome 4q 21-31 (indicated by black bar on right), and co-overexpressed with other cell-cycle proliferation genes.

High 4E clustered predominantly with the basal (triple-negative tumors—ER/PR/Her2 negative) phenotype ("BASAL/4E+"). Not all basal-like tumors showed elevated 4E expression, suggesting that 4E may be a novel biomarker defining a specific sub-population of basal-like tumors. While 4E expression is clearly most closely linked a particular basal-like sub-phenotype, it also associates to a lesser extent with the Her2+ molecular subtype and the ER+/PR− molecular subtype. Based upon our preliminary gene Breast cancer cell lines determined to possess elevated eIF4E activity will be selected for further study with preference being given to cell lines corresponding to human clinical subtypes determined to possess elevated eIF4E activity. Based upon our preliminary results we will focus our efforts on Basal, HER2+/ER− and ER+/HER− cell lines.

Depending upon the cell line under consideration our analysis of eIF4E activity will be performed cells cultured under a variety of conditions including: +/− serum, +/− hormone-stripped serum medium, and heregulin or EGF for cell lines expressing EGFR and HER2.

We will examine the ability of Ribavirin to inhibit in a dose-dependent fashion eIF4E functions at several levels. Specifically, we will examine the impact of Ribavirin on (i) eIF4E-dependent mRNA transport and translation of select mRNAs and (ii) nuclear/cytoplasmic distribution of eIF4E and select mRNAs. Select mRNAs will include at least cyclin D1, VEGF, FGF2 and as warranted HER2 and EGFR. Controls will use eIF4E-insensitive mRNA (housekeeping gene such as actin and GAPDH).

Lastly, we will examine the impact of Ribavirin on colony formation, cellular proliferation and induction of apoptosis using normal and breast cancer cells lines using established methodologies.

Cell lines corresponding to human clinical subtypes possessing elevated levels of eIF4E protein (basal-like, HER2+, ER+ subtypes per our preliminary results) will be vetted for use in xenograft studies. We anticipate examining cell lines determined to utilize any/all of the more subtle mechanisms of providing for elevated eIF4E activity, namely eIF4E phosphorylation; eIF4E-BP1 levels and phosphorylation; or for example subtypes with distinctive changes in nuclear:cytoplasmic localization especially if they are found to correlate with additional novel eIF4E breast cancer clinical subtypes.

We will also examine whether Ribavirin decreases the resistance of breast cancer cell lines to classical chemotherapeutic agents and/or taxanes as might be predicted given the fact that we would anticipate Ribavirin inhibiting eIF4E's anti-apoptotic activity, especially in the presence and absence of FGF2.

In addition to studying the synergistic effects of Ribavirin on classical breast cancer chemotherapeutic agents, we will investigate whether Ribavirin acts synergistically with targeted agents [i.e. inhibitors of HER2, ER and EGFR and/or intracellular kinase activities including NFkB (using the specific IKK peptide inhibitor NBD) and PI3K/Akt (using the specific PI3K inhibitor Ly294002)]. Breast cancer cell lines will be obtained from ATCC or from the laboratory of D. Iglehart (Dana-Farber). Cells will be grown using established culture conditions. Western (protein) analyses will employ commercially available antibodies against eIF4E, phospho-eIF4E, eIF4E-BP1 and phospho-eIF4E-BP1 and appropriate positive and negative controls. Similarly (mRNA) analyses will employ commercially available RNA extraction and mRNA probes. Required growth factors, chemotherapeutic agents and kinase inhibitors are commercially available and cell cycle analysis and apoptosis analyses will be performed using established methods and analyzed by fluorescent activated cell sorting.

Ribavirin's activity against breast cancers clinical subtypes will be determined in vivo using a mouse xenograft tumor model system and cell lines vetted corresponding to the human breast eIF4E clinical subtypes identified above. Specifically, we will examine Ribavirin's effect on tumor growth and protein expression of eIF4E sensitive molecules (at minimum FGF2, VEGF, cyclin D1 and Her2/neu or EGFR as warranted). Use of artificial gene reporter constructs containing 3'UTR and/or 5'UTR mRNA control structures coupled to an 'internal' reporter gene (LacZ, GFP) will enhance our ability to visualize Ribavirin eIF4E-sensitive mRNAs in vivo. When feasible tumors will evaluated for apoptosis status. And control proteins and mRNAs to be analyzed will include housekeeping genes (actin and GADPH).

Initially we will confirm that xenografts can be established uniformly using the human breast cancer cell line(s) of interest. If xenografts do not take uniformly we will then 'passage' tumors from animals where tumors take as this as been proven as one way to facilitate the establishment of tumor xenografts. Alternatively we will implant human breast cancer cells in the presence of matrigel which has also proven useful in xenograft model systems (Iglehart, personal communication).

Once appropriate xenograft models corresponding to eIF4E-relevant human clinical subtypes are established it will be important to establish the dose relationship between the concentration of Ribavirin administered to animals and the impact on tumor growth. Control animals will be given vehicle control. Our initial focus will be on vetting breast cancer xenograft models corresponding to human clinical subtypes possessing elevated levels of eIF4E protein (basal-like, HER2+, ER+ per our preliminary results) for use in xenograft studies. It is further our intention to examine breast cancer xenograft models corresponding to employ any/all of the more subtle mechanisms of providing for elevated eIF4E activity, namely eIF4E phosphorylation; eIF4E-BP1 levels and phosphorylation; or for example subtypes with distinctive changes in nuclear:cytoplasmic localization), in particular should these lines be found to correspond to novel eIF4E breast cancer clinical subtypes that we identify above. We will also examine whether Ribavirin decreases the resistance of breast cancer xenograft tumors to classical chemotherapeutic agents and/or taxanes, if our in vitro data supports this line of investigation. Lastly, in addition to studying the synergistic effects of Ribavirin on classical breast cancer chemotherapeutic agents, we will investigate whether Ribavirin acts synergistically with targeted agents [i.e. inhibitors of HER2, ER and EGFR and/or intracellular kinase activities including NFkB (using the specific IKK peptide inhibitor) and PI3K/Akt (using for example the specific PI3K inhibitor Ly294002)] using appropriate eIF4E-based breast cancer xenograft model systems. These investigations will be driven by our analysis of eIF4E-activity based classification of human breast cancers using tissue microarray and gene expression analysis.

Nude mice ('athymic') will be obtained from The Jackson Laboratory. Other reagents and supplies required have been described above.

We hypothesize that strategies targeting eIF4E in patients with cancers characterized by elevated eIF4E levels is indicated. Ribavirin is a well-characterized, orally available, anti-viral drug. Ribavirin has been determined to physically mimic the m7G mRNA cap structure and to inhibit thereby eIF4E activity and function. We propose to study Ribavirin as a novel and targeted treatment of patients with breast cancers characterized as having elevated levels of eIF4E activity.

Example 6 4E Modulates the Akt Pathway for its Survival Function

In this example we demonstrate that a small molecule can be used to inhibit a RNA regulon. Specifically, we demonstrate that ribavirin, through its inhibitory actions on eIF4E, can inhibit Akt survival signalling. In this way, ribavirin impedes both activation of Akt and production of downstream effectors of Akt.

Abstract

The coordinated regulation of post-transcriptional events is a means by which to modulate physiological processes. We postulate that the eukaryotic translation initiation factor, 4E, modulates gene expression, and thus biological activities, via coordinate mRNA export and translation of a subset of mRNAs. 4E not only promotes proliferation, but also rescues cells from apoptotic stimuli. Here we examine the molecular basis for 4E mediated apoptotic rescue of serum deprived fibroblasts. First, we demonstrate that 4E overexpression leads to enhanced survival signaling by leading to activation of Akt. Next, we demonstrate that 4E requires the presence of Akt1 in order to rescue fibroblasts. Further, we show that a mutant form of 4E, W73A 4E, rescues cells as readily as wildtype 4E. This mutant is active in promoting the mRNA export function of 4E but not its translation activity. We show that 4E mediates Akt activation through the upregulation of NBS1, a factor known to activate the PI3K/Akt pathway. 4E modulates the expression of NBS1 at the level of mRNA export, and requires NBS1 to activate Akt and to rescue cells from apoptosis. Further, 4E coordinately upregulates the expression of downstream effectors of the Akt pathway thereby amplifying the effects of Akt. The promyelocytic leukemia protein PML, a known regulator of 4E, inhibits 4E mediated increases in NBS1 export, in Akt activation and in apoptotic rescue. These studies provide a molecular basis for 4E mediated apoptotic rescue.

Introduction

Elevated levels of the eukaryotic translation initiation factor 4E (4E) are associated with oncogenic transformation in cell culture, tumorigenesis in mouse models and with poor prognosis in a significant subset of human cancers (Graff and Zimmer 2003). 4E promotes proliferation and rescues cells from a variety of apoptotic stimuli including serum deprivation (Polunovsky et al. 1996; Sonenberg and Gingras 1998; Tan et al. 2000; Graff and Zimmer 2003). At the molecular level, 4E modulates gene expression at two distinct levels: mRNA translation and mRNA nuclear export (Sonenberg and Gingras 1998; Culjkovic et al. 2005, Culjkovic et al., 2006; Culjkovic et al. 2007). To act in either of these processes, 4E must bind the m7G cap moiety found on the 5' end of mRNAs (Sonenberg and Gingras 1998; Culjkovic et al. 2005, Culjkovic et al., 2006; Culjkovic et al. 2007). In the cytoplasm, 4E recruits mRNA to the ribosome as a critical step in translation initiation (Sonenberg and Gingras 1998). Not all transcripts are affected equally by 4E (Sonenberg and Gingras 1998; Culjkovic et al. 2005, Culjkovic et al., 2006; Culjkovic et al. 2007; Mamane et al. 2007). For instance, the translation of a subset of genes with complex 5'UTRs is more sensitive to 4E levels (and are deemed 4E sensitive) than transcripts with short, unstructured UTRs. In this case, translation enhancement is defined as the association of these transcripts with heavier polysomes. In the nucleus, 4E upregulates the mRNA export of a substantial subset of growth promoting mRNAs which contain a 50 nucleotide element known as the 4E sensitivity element (4E-SE) in their 3'UTR (Rousseau et al. 1996; Culjkovic et al. 2005, Culjkovic et al., 2006; Culjkovic et al. 2007). Increased protein production of the corresponding export sensitive mRNAs arises through two mechanisms: 1. a concentration effect whereby the increased levels of cytoplasmic transcripts means that more protein is made, and/or 2. a subset of these transcripts are subsequently loaded more efficiently onto the heavier polysomes because they are translationally sensitive to 4E (Culjkovic et al. 2005, Culjkovic et al., 2006; Culjkovic et al. 2007). Thus, 4E effects gene expression at multiple levels.

Recent studies indicate that there is a poor correlation between the proteomes and transcriptomes of cells (Lu et al. 2006). This implies that post-transcriptional regulation plays a critical role in gene expression and thereby impacts on the resulting physiology of the cell. Keene and colleagues proposed the RNA regulon model to describe a means by which post-transcriptional gene regulation can be coordinated (Tenenbaum et al. 2000; Keene and Tenenbaum 2002; Keene and Lager 2005). In this model, the expression of transcripts that act in the same biological pathway, such as cell cycle progression, is coordinately controlled by the presence of elements in the 3' or 5' UTR of these mRNAs. These RNA elements are referred to as USER codes. For example, a set of mRNAs which encode proteins involved in the same biochemical pathway would have their mRNA export coordinated by having a common USER code in their 3'UTR, such as the 4E-SE. The USER codes work by recruiting proteins involved in a given process to the RNAs in question, in order to facilitate said process. Thus mRNAs containing the 4E-SE USER code would recruit the appropriate export factors to the RNAs, facilitating the export process. Any level of RNA metabolism could be modulated this way, as long as the appropriate USER codes were present.

Our studies strongly suggest that 4E is a node in an RNA regulon governing cell cycle progression by (at least in part) the combinatorial modulation of the export of a wide variety of transcripts involved in nearly every step of the cell cycle. Similarly, translationally sensitive mRNAs likely contain USER codes in their 5' UTR (Mamane et al. 2007). In this way, control at the mRNA export and translation levels can be decoupled i.e. mRNAs would require both the 3' 4E-SE and the 5' USER code in order to be modulated by 4E at both levels. This model of gene expression provides network level control of the fate of mRNAs that encode proteins involved in the same biochemical and thus biological processes. Control of nodes (such as 4E) in these regulons is critical for determining the fate of the cell.

Here, we examine the possibility that 4E rescues cells by coordinately regulating the expression of factors in such networks in order to achieve cell survival. We demonstrate that 4E potentiates Akt activation and that this activity is required for its ability to rescue cells from serum deprivation induced apoptosis. The RNA regulon model serves as a theoretical context to understand how 4E coordinately, and potently, activates the Akt signaling pathway. First, 4E overexpression leads to the upregulation of the expression of NBS1, a factor which mediates phosphorylation of Akt. Second, 4E overexpression leads to the coordinated mRNA export and thereby upregulation of several downstream effectors of Akt. Further, a cellular inhibitor of 4E, the promyelocytic leukemia protein PML, inhibits 4E dependent Akt activation and also reduces the expression of a subset of downstream effectors of Akt. In this way, 4E and PML coordinately modulate an RNA regulon which controls the Akt pathway and thus potently modulates cell survival.

Results

4E Overexpression Promotes Akt Activation

We examined the possibility that 4E overexpression could lead to activation of Akt. Akt activation was assessed by monitoring its phosphorylation at T308 and S473 using phospho-specific antibodies and western analysis of immortalized murine embryonic fibroblasts (MEFs). Phosphorylation of these two sites is a well-characterized indicator of Akt activation (Alessi et al. 1996; Alessi et al. 1997; Stokoe et al. 1997; Nicholson and Anderson 2002; Vivanco and Sawyers 2002; Song et al. 2005). Clearly, 4E overexpression leads to increased phosphorylation of Akt at both sites (FIG. 27A). Importantly, the m7G cap binding mutant of 4E (W56A), which is unable to act in translation or mRNA export (Culjkovic et al. 2005, Culjkovic et al., 2006), does not have this effect. In contrast, an 4E mutant (W73A) that acts in mRNA export but does not promote translation of sensitive mRNAs (Culjkovic et al. 2005, Culjkovic et al., 2006), also activates Akt. Consistent with Akt activation, 4E and W73A mutant overexpression lead to enhanced phosphorylation of S6 and BP1, whereas the inactive W56A mutant does not (FIG. 27A). In terms of these activities, similar experiments in other cell types (NIH 3T3, U20s and U937s) showed the same pattern of results (data not shown). Importantly, overexpression of wildtype or mutant forms of 4E did not lead to modulation of total Akt levels.

For comparison, we examined the effects of 4E overexpression in Akt1−/− cells (FIG. 27A and data not shown). For these studies, we used a cell line derived from MEFs (Akt1−/− cells) in which Akt1, the prevalent Akt form, was knocked out. The wildtype fibroblasts used above are the littermate controls for these Akt1−/− cells. The Akt antibody used recognizes all three isoforms of Akt, and thus, one observes these isoforms in the Akt1−/− cells (FIG. 27A).

Clearly, 4E does not induce phosphorylation of Akt1 due to the knockout of this protein. Interestingly, there is more phosphoBP1 in general, in Akt wildtype versus Akt1−/− cells. This was observed previously and is likely due to the fact that the loss of Akt leads to reduced BP1 phosphorylation as expected. Similar results were observed for phospho-S6. Further, there is no alteration in total levels of BP1 or S6 in knockout cells relative to vector controls. Interestingly, 4E still elevates BP1 and S6 phosphorylation in the knockout cells (without changing total levels of either protein), suggesting that 4E can use Akt2 or Akt3 to activate mTOR and thereby lead to phosphorylation of these proteins (Easton et al. 2005; Skeen et al. 2006).

We tested whether 4E mediated Akt activation occurred in a PI3K dependent manner. In cells overexpressing 4E, there is clearly more phosphorylation of Akt at both T308 and 5473 relative to vector controls. However, treatment of 4E overexpressing cells with the PI3K inhibitor, LY294002 (Yao and Cooper 1995), led to a drastic reduction in phosphorylation of Akt at both sites (FIG. 27B), while Akt protein levels were not altered (FIGS. 27A and 27B). Further, treatment did not impede the 4E dependent increases in NBS1, an 4E dependent mRNA export target (Culjkovic et al. 2006). Thus, LY294002 did not alter this 4E activity. As expected, LY294002 inhibited phosphorylation of S6 and BP1 (Sanchez-Margalet et al. 1994; Gingras et al. 1998). The potential implications of 4E modulation of BP1 phosphorylation are addressed in the Discussion.

4E Requires Akt1 for its Survival Functions

We examined the relevance of Akt activation to 4E's established physiological effects in cell survival. The ability of 4E to rescue wildtype or Akt1−/− cells from serum deprivation induced apoptosis was monitored using annexin V/propidium iodide staining in conjunction with flow cytometry and separately, TUNEL analysis (FIG. 28, data not shown). For comparison, cells that were not serum deprived are also shown. Importantly, 4E overexpression rescued wildtype cells (~80% viable cells) versus vector controls (~40% viable cells). The extent of rescue is similar to those shown in the original report describing the survival function of 4E (Polunovsky et al. 1996).

Interestingly, the mRNA export competent mutant (W73A) rescued cells to a similar extent as cells overexpressing wildtype 4E. This suggests that 4E's rescue function is, at least in part, mediated via its mRNA export function. In contrast, the inactive W56A 4E mutant did not rescue cells, with a similar number of viable cells as the vector controls.

A comparison of vector controls for Akt1−/− cells versus wildtype cells showed that serum deprivation of Akt1−/− cells had slightly reduced viability relative to wildtype cells (~20% versus ~40%). This reduction in viability was observed in other studies involving serum deprivation of these cells (Chen et al. 2001). Strikingly, neither wildtype 4E nor the W73A mutant rescued Akt1−/− cells from apoptosis. In both cases, the number of viable cells was around 20%, the same as seen in the vector controls. As a control to demonstrate it is possible to rescue Akt1−/− cells, we examined whether the antiapoptotic factor, Bcl2 (data not shown), could rescue these cells. Substantially more viable Akt1−/− cells (~80%) were present upon overexpression of Bcl2, indicating that these cells can be rescued. Thus, 4E's survival function, in the context of serum deprivation, requires the presence of Akt1.

Loss of Akt1 does not Impair 4E's mRNA Export or Translation Functions

The results in Akt1−/− cells suggest that one or more biochemical activities of 4E could be impaired by the loss of Akt, or that 4E modulates the expression of target genes involved in activation of the Akt pathway. First, we examined whether 4E dependent mRNA export was impaired in Akt1−/− cells compared to wildtype controls (FIG. 29A). We examined the nuclear mRNA export of cyclin D1 mRNA by monitoring the mRNA content in cytoplasmic versus nuclear fractions using quantitative real time PCR (qPCR) as we have described previously (Culjkovic et al. 2005, Culjkovic et al., 2006). tRNAlys and U6snRNA are shown as fractionation controls for monitoring the quality of cytoplasmic and nuclear fractions respectively as we have reported previously (Culjkovic et al. 2005, Culjkovic et al., 2006) (FIG. 29A). The ratio of cytoplasmic to nuclear mRNA levels are shown in FIG. 29A. Cyclin D1 mRNA was chosen as it is the best-described 4E dependent mRNA export target (Rousseau et al. 1996; Culjkovic et al. 2005, Culjkovic et al., 2006). Our results show that overexpression of 4E or the W73A export-competent mutant, promoted cyclin D1 mRNA export in either wildtype or Akt1−/− cells as compared to vector controls. Another 4E dependent mRNA export target, NBS1 (Culjkovic et al. 2005, Culjkovic et al., 2006), gave similar results. Second, we examined the possibility that the loss of Akt1 impaired 4E sensitive translation. We examined the levels of VEGF protein, a well-established translational target of 4E (Clemens and Bommer 1999). Clearly, loss of Akt1 did not impair the ability of 4E to promote VEGF translation relative to vector controls (FIG. 29B, bottom). VEGF mRNA export is not altered by 4E overexpression in either wildtype or Akt1−/− cells (FIG. 29A). Further, mRNA export of GAPDH and actin are unchanged (FIG. 29B, data not shown). This is consistent with previous studies showing that VEGF, GAPDH and actin are not export targets of 4E, and that VEGF is a translation target (Clemens and Bommer 1999; Culjkovic et al. 2006).

We examined whether alterations in 4E mRNA export activity led to increased protein production of cyclin D1, NBS1 and VEGF using western analysis in Akt1−/− cells as compared to wildtype controls (FIG. 29B, bottom). Further, overexpression of the W73A mutant (which is competent in export but does not enhance translation) leads to increased cyclin D1 and NBS1 protein levels, consistent with their enhanced nuclear mRNA export, but does not enhance production of VEGF protein levels. There was no change in the total levels of cyclin D1, NBS1 or VEGF mRNA as monitored by qPCR as a function of 4E or mutant overexpression (FIG. 29B, top). In summary, the loss of Akt1 does not impair 4E dependent mRNA export or translation of the 4E sensitive transcripts examined. This led us to hypothesize that one (or more) of the mRNA targets of 4E could potentiate Akt activation.

The 4E Dependent mRNA Export Target, NBS1, is Required for 4E Dependent Akt Activation Our previous studies demonstrated that the ability of 4E to coordinately modulate mRNA export of a wide variety of transcripts contributes to its proliferative potential (Culjkovic et al. 2005, Culjkovic et al., 2006; Culjkovic et al. 2007). Examination of these mRNA targets revealed a potential mechanism for 4E mediated activation of Akt. 4E overexpression led to enhanced mRNA export of Nijmegen breakage protein 1 (NBS1) (Culjkovic et al. 2006). Traditionally, NBS1 has been associated with DNA double strand break repair (Karran 2000; Petrini 2000; Costanzo et al. 2001). However, recent studies revealed that elevation of NBS1 results in activation of PI3K, and subsequently activation of Akt and its downstream effectors, including S6 (Chen et al. 2005). Consistently, NBS1 overexpression is associated with oncogenic transformation and proliferation in cell culture, and tumorigenesis in xenograft mouse models (Chen et al. 2005; Yang et al. 2006; Yang et al. 2007).

Thus, we examined the possibility that the ability of 4E to activate Akt relied, at least in part, on its ability to modulate expression of NBS1. 4E overexpression led to the upregulation of NBS1 mRNA export, similar to that observed for cyclin D1 mRNA (FIG. 29B) (Rousseau et al. 1996). Consistent with the ability of 4E to promote the mRNA export of NBS1, 4E overexpression correlated with increased levels of NBS1 protein and this was independent of the presence or absence of Akt1 (FIG. 29B).

These studies led us to hypothesize that NBS1 is an important effector of 4E dependent activation of Akt. To determine whether 4E required NBS1 for Akt activation, NBS1 was knocked down using siRNA methods. Knockdown was confirmed by western blot analysis (FIG. 30A). Importantly, siRNA treatment for NBS1 did not alter expression of 4E or Akt (FIG. 30A), nor 4E mRNA targets cyclin D1 or VEGF (data not shown). We observe that upon siRNA treatment for NBS1, 4E overexpression no longer increases phosphorylation of Akt at either T308 or 5473 as observed by western analysis as compared to scrambled siRNA controls (FIG. 30A).

It is possible that knockdown of NBS1 modulates 4E's ability to enhance mRNA export, and thus we postulate could regulate the ability of 4E to activate Akt in some manner independent of the NBS1-PI3K-Akt axis. Further, we examined mRNA export in 4E overexpressing cells treated with siRNA for NBS1 (siNBS1) or scrambled controls (scram). Our results clearly demonstrate that export of cyclin D1 mRNA is not reduced by knockdown of siNBS1 (data not shown). Thus, cyclin D1 mRNA export is enhanced in 4E overexpressing cells versus vector controls whether or not these cells were treated with siNBS1 or scrambled controls (data not shown). Consistently, cyclin D1 protein levels are upregulated in 4E overexpressing cells relative to controls regardless of siRNA treatments. Interestingly, export of the remaining NBS1 mRNA was also elevated in the presence of 4E wildtype or W73A 4E overexpression, again indicating that the mRNA export pathway is intact in cells treated for siNBS1 (data not shown). Thus knockdown of NBS1 does not impair either 4E dependent mRNA export. Taken together with the previously reported data on the effects of NBS1 on PI3K activation (Chen et al. 2005) and the ability of the PI3K inhibitor LY294002 to inhibit this 4E activity (FIG. 27B), it appears that the requirement for NBS1 in 4E mediated activation of Akt is linked to the ability of NBS1 to activate PI3K (probably indirectly) and thus, for PI3K to activate Akt.

4E Requires NBS1 for Apoptotic Rescue of Serum Deprived Fibroblasts

We extended our studies to examine whether the ability of 4E to upregulate NBS1 was required, at least in part, for its apoptotic rescue function. Akt wildtype cells were treated with siRNA for NBS1 (siNBS1) or scrambled controls (scram), serum deprived and monitored for apoptosis as a function of 4E overexpression (FIGS. 30B and C). Treatment of stable cell lines with scrambled controls, which requires the introduction of lipofectamine, slightly reduced viability of cells relative to untreated controls for both serum deprivation (FIG. 28, ~40% to ~35% observed here, FIG. 30B) and normal conditions (~80% relative to ~90% in FIG. 28). Knockdown of NBS1 led to a further reduction in viability of cells that were not serum deprived as well as serum deprived. This is consistent with previous studies indicating that NBS1 is required for viability in mouse models (Zhu et al. 2001; Dumon-Jones et al. 2003).

The most striking result from these studies is that knockdown of NBS1 severely impaired the survival activity of 4E (FIGS. 30B and C). Specifically, 4E overexpressing cells treated with scrambled controls were approximately ~70% viable relative to vector controls which were ~35% viable. This is a very striking extent of rescue and is approximately the same extent of rescue (2 fold) as observed in FIG. 28. However, the 4E overexpressing cells treated with siRNA for NBS1, have only ~20% of viable cells, 3 fold less than the scrambled control treated 4E overexpressing cells which were ~70% viable. Taken together with the observations that 4E requires Akt for its rescue function and requires NBS1 to activate Akt, our data strongly suggest that the survival function, in this context, of 4E requires its ability to activate Akt through NBS1.

PML is a Negative Regulator of this 4E Activity

Clearly, the cell has developed mechanisms to control the proliferative and survival functions of 4E. Our previous studies indicated that the promyelocytic leukemia protein PML is a potent inhibitor of 4E dependent mRNA export (Cohen et al. 2001; Topisirovic et al. 2003a; Culjkovic et al. 2005, Culjkovic et al., 2006; Culjkovic et al. 2007). The RING domain of PML directly interacts with the dorsal surface of 4E (including W73), and through a conformational change, reduces the affinity of 4E for the m7G cap by over 100 fold (Kentsis et al. 2001). Previous studies indicated that mutations of PML in the RING domain (RING) or of the dorsal surface of 4E (W73A) impaired the PML-4E interaction and thereby relieved the PML mediated inhibition of 4E dependent mRNA export (Cohen et al. 2001; Kentsis et al. 2001; Culjkovic et al. 2005, Culjkovic et al., 2006; Culjkovic et al. 2007). Thus we examined the possibility that the PML protein impairs export of NBS1 mRNA and thereby, impairs 4E dependent activation of Akt. Further, we utilized out mutants to determine if these effects were dependent on the PML-4E interaction.

PML overexpression suppressed mRNA export of NBS1 relative to vector controls or 4E overexpressing cells (FIG. 31). Consistently, PML impaired export of cyclin D1 mRNA relative to vector controls (by acting on endogenous 4E) and relative to cells overexpressing 4E (FIG. 31B). In cells expressing both PML and 4E, PML clearly reduces the export of both NBS1 and cyclin D1 mRNAs relative to cells overexpressing 4E alone. Consistently, NBS1 and cyclin D1 protein levels are reduced relative to cells overexpressing 4E alone (FIG. 31A). Next, we examined whether PML reduces 4E dependent Akt activation. Co-expression of PML and 4E led to reduction in phosphorylation of Akt at both T308 and 5473 relative to cells overexpressing 4E alone (FIG. 31A). Consistently, PML overexpression leads to reduced phosphorylation of S6 as well as BP-1 relative to vector or 4E overexpressing cells. Thus, PML impairs 4E dependent Akt activation and subsequent downstream events.

In order to demonstrate that these effects of PML are indeed dependent on its interactions with 4E, we monitored the effects of the PML mutant deficient in 4E binding (RING). In parallel, we monitored the ability of PML to suppress the W73A 4E mutant, which cannot bind PML. PML overexpression impairs 4E mediated Akt activation whereas PML RING cannot. Further, PML cannot impair Akt activation mediated by the W73A 4E mutant. As expected, the PML RING mutant could not inhibit 4E dependent mRNA export of either NBS1 or cyclin D1 mRNA (PML RING+4E versus PML+4E; FIG. 31B). Furthermore, wildtype PML could not inhibit the W73A 4E mutant (PML+W73A 4E versus W73A). Consistently, NBS1 protein levels were elevated to a similar extent in the PML+W73A or W73A 4E expressing cells (FIG. 31A). Thus, PML requires its ability to directly bind to 4E in order to impair 4E dependent NBS1 mRNA export and subsequent NBS1 protein levels and Akt activation. Co-expression of PML RING and 4E or of PML and W73A 4E did not lead to impairment in 4E dependent Akt activation, as observed by western blot for both T308 and S473 Akt sites, relative to cells expressing 4E alone (FIG. 31A). Importantly, expression of PML or PMLRING did not alter the expression of 4E or Akt. Further, expression of 4E or W73A 4E did not modulate PML levels.

We hypothesized that PML should impair 4E dependent rescue of serum deprived fibroblasts. We monitored apoptosis as described above. Prior to serum starvation, PML and 4E do not appear to impact on viability (FIG. 32). However, in serum deprived cells, PML overexpression results in reduced viability relative to vector controls (2 fold, FIG. 32A) consistent with our earlier studies (Borden et al. 1997)). 4E overexpressing cells result in enhanced viability versus vector controls (2 fold) and PML (4 fold) expressing cells. In contrast in cells co-expressing PML and 4E, viability was substantially reduced relative to 4E overexpressing cells (~40% versus ~80%). TUNEL assays yielded consistent results (FIG. 32B) Thus, PML impairs 4E mediated apoptotic rescue under serum deprivation conditions.

4E is Positioned to have a Two Tier Effect on Akt Expression

Given that 4E modulates gene expression combinatorially (Culjkovic et al. 2007), we investigated whether other known targets of 4E dependent mRNA export and 4E sensitive translation also acted in Akt signaling. Inspection of previously reported 4E mRNA export targets demonstrated that this is indeed the case i.e. 4E coordinately upregulated effectors of the Akt pathway including cyclins A2 (Heron-Milhavet et al. 2006), B1 (Lee et al. 2005), and E (Hlobilkova et al. 2006; Kim et al. 2006), c-myc (Ahmed et al. 1997; Chen and Sytkowski 2001), and Mdm2 (Mayo and Donner 2001; Gottlieb et al. 2002), as well as cyclin D1 (Muise-Helmericks et al. 1998; Gille and Downward 1999; Takuwa et al. 1999) and NBS1 (Chen et al. 2005) (FIG. 5, (Culjkovic et al. 2006)). This list is not inclusive, and as more 4E mRNA targets are identified, it is likely many of these will also be downstream effectors of the Akt pathway. Thus, 4E is positioned to effect Akt pathway at two levels: Akt activation and upregulation of downstream effectors of Akt.

Discussion

We provide evidence that 4E, via the RNA regulon model, modulates the PI3K/Akt signaling axis, and coordinates its regulation (FIG. 33). This is consistent with previous studies which indicated that 4E is a node in a regulon that governs cell cycle progression via coordinately modulating expression of genes involved in this process (Culjkovic et al. 2005, Culjkovic et al., 2006). The studies reported here indicate that 4E, using the same strategies, can enhance survival signaling, enabling 4E to drive proliferation whilst inhibiting apoptosis in immortalized cell lines. Our studies also suggest that these two biological effects of 4E overexpression, proliferation and apoptotic rescue, are intrinsically linked through modulation of this RNA regulon.

In this model, 4E coordinately exports mRNAs of protein affected by the Akt pathway, allowing their enhanced production (FIG. 33). Coordinated mRNA export is achieved by a common element in the 3'UTR of these mRNAs, the 4E-SE. To date, our results indicate that 4E impacts on the Akt pathway at least at two levels. First, 4E acts at the level of phosphorylation of Akt via enhancing production of the NBS1 protein. NBS1 was shown to be an upstream activator of PI3K by other groups (Chen et al. 2005). NBS1 also activates Atm kinases where it is believed to play an active role and directly associates with Atm (Karran 2000; Petrini 2000; Viniegra et al. 2005). NBS1 contains a PI3K like binding domain, and may use this domain to directly interact with PI3K (Cerosaletti et al. 2006). However, the precise mechanism by which NBS1 activates PI3K, and thereby Akt, is not yet known. Our report is consistent with previous studies showing that NBS1 activation is PI3K dependent since LY294002 impairs this activation (Chen et al. 2005). Interestingly, 4E enhances production of ODC, at both the mRNA export and translation levels (Rousseau et al. 1996). ODC overexpression can lead to Akt activation independent of PI3K (Hayes et al. 2006), indicating that in some contexts, 4E may be able to activate Akt independently of the NBS1-PI3K-Akt axis we describe here. Second, 4E overexpression leads to increased protein levels for several downstream effectors of Akt (FIGS. 1 & 5, (Culjkovic et al. 2006)). Thus 4E is positioned to amplify the effects of Akt survival signaling.

4E overexpression in transgenic mouse models of lymphoma correlates with aggressive disease and the development of tumours which are rapamycin resistant (Wendel et al. 2006). In previous models of Akt signaling, it was difficult to understand how rapamycin resistance would develop given that 4E was thought to be only downstream of Akt. Rapamycin inhibits mTOR and thus mTOR mediated phosphorylation of BP1. In fact, mTOR inhibition leads to Akt activation in some cells and patient specimens due to the fact that mTOR is part of a negative feedback loop on Akt activity (O'Reilly et al. 2006). Our data provide a possible molecular basis for 4E mediated rapamycin resistance. 4E is known to enhance levels of Pim1 (at both the mRNA export and translation level) (Hoover et al. 1997; Clemens and Bommer 1999; Culjkovic et al. 2006) and Pim1 can directly phosphorylate BP1 independently of Akt (Hammerman et al. 2005). Thus, 4E can bypass mTOR-rapamycin and directly relieve inhibition via Pim1 mediated phosphorylation of BP1. There are likely several other similar means by which 4E can achieve this result.

The effects of 4E overexpression on BP1 phosphorylation are interesting and suggest that that 4E could be involved in a positive feedback loop where it activates its translational activity by indirectly using its mRNA export activity to increase levels of hyperphosphorylated BP1 without changing levels of total BP1 protein. However, translation of 4E sensitive mRNAs is not significantly elevated in BP1-/-, BP2-/- or BP1-/-/BP2-/- cells (Blackshear et al. 1997; Tsukiyama-Kohara et al. 2001; Banko et al. 2006; Le Bacquer et al. 2007). Enhancement of the formation of translationally active 4E complexes is estimated to be within error of the measurements (~1.5 fold) (Banko et al. 2006) and enhanced polysomal loading of 4E sensitive mRNAs has not been reported for any of these knockout cells. These animals are normal in terms of their size with BP1-/- and BP1-/-/BP2-/- having only significant defects in adipogenesis and the insulin response (Le Bacquer et al. 2007). Interestingly, BP1-/- cells respond to rapamycin (in terms of growth arrest) to the same extent as wildtype controls (Blackshear et al. 1997). The phenotype for these mice was predicted to be much more marked, where it was assumed that mice would be subject to a wide range of cancers. This is not the case. These studies suggest that there is significant redundancy in the factors that regulate 4E. Thus, although BP1 phosphorylation is clearly a marker of Akt activation, it is not clear the extent to which BP1 phosphorylation alone can be predictive of the translational activity of 4E. Thus, in the case of our studies, although 4E does stimulate BP1 phosphorylation through Akt activation, the extent of this effect alone on 4E activity will require further studies to unravel. However, these studies do show that 4E mediated Akt activation leads to the expected signaling events with respect to S6 and BP1.

The cell has clearly developed master control switches to control RNA regulon, in this case in the form of PML, to attenuate the effects of 4E (Culjkovic et al. 2006; Culjkovic et al. 2007). Thus the cell can use PML to shut down this complicated survival network by directly targeting just one part of the network, 4E. PML is a potent inhibitor of 4E where it not only inhibits 4E dependent mRNA export, but when in the cytoplasm can inhibit cap dependent translation as well (Kentsis et al. 2001). Further, the ability of PML to promote apoptosis via inhibiting 4E dependent rescue (FIG. 32) provides the first molecular explanation for previous observations that the ability of PML to promote apoptosis is independent of on-going transcription (Quignon et al. 1998), since at the time of this study the link between PML and 4E was not known. Given the model we propose, it is now clear how PML can stimulate apoptosis in a transcriptionally independent manner. Finally, our results are consistent with recent observations that Akt is more activated in PML−/− cells than in littermate controls (Trotman et al. 2006). Although another mechanism for PML inactivation of Akt was proposed by Trotman and colleagues, our results do not exclude the possibility that PML acts as a negative regulator of Akt directly and/or indirectly through inhibition of the 4E regulon. Also, overexpression of PRH, another negative regulator of 4E (Topisirovic et al. 2003a), decreases phosphorylation of Akt (data not shown).

Clearly, other cellular modulators of 4E function, such as En2, HoxA9 and 4E-BPs are also positioned to potently modulate this regulon (Sonenberg and Gingras 1998; Topisirovic et al. 2003a; Brunet et al. 2005; Topisirovic and Borden 2005). Regulators such as HoxA9 are particularly potent as HoxA9 stimulates both 4E dependent mRNA export and 4E dependent translation (Topisirovic et al. 2005).

Further, there are likely feedback loops on this regulon. For instance, c-Myc is an mRNA export and translational target of 4E (Clemens and Bommer 1999; Culjkovic et al. 2006). Interestingly, both 4E and NBS1 are direct transcriptional targets of c-myc (Chiang et al. 2003; Schmidt 2004). This provides a model for an interesting positive feedback loop between these proteins and Akt activation.

In all, these findings open up to the concept of "oncogene addiction" (Jonkers and Berns 2004; Weinstein and Joe 2006), whereby transformation is dependent upon one or a few genes for the maintenance of a malignant phenotype. 4E could therefore be a suitable candidate for such a role, since we postulate it is a central node in the survival signaling regulon. This points to 4E as a potent therapeutic target. A small molecule inhibitor of 4E, ribavirin, a physical mimic of the m7G cap, is positioned to inhibit this survival signaling network.

Materials and Methods

Constructs.

pLINKSV40-PML, pcDNA 4E, MSCV-pgk-GFP-4E WT or mutant expression constructs were previously described (Cohen et al. 2001; Topisirovic et al. 2003b; Culjkovic et al. 2005; Topisirovic and Borden 2005). The PML RING mutant (double point mutation in the RING domain of PML, required for PML function) was previously described (Borden et al. 1998).

Cell Culture and Treatments.

Cells used were maintained in DMEM with 100 units/ml penicillin G sodium and 100n/ml streptomycin sulfate (all from GibcoBRL), with the addition of: 10% newborn calf serum for MEF Akt1 wt and −/− derived cells; 10% fetal calf serum for Bosc-23 cells; and 10% calf serum with 1 mg/ml G418 (GibcoBRL) and 1 µg/ml puromycin (Sigma) for NIH3T3 derived cells. 4E WT and W56 and W73 mutant retroviral vectors were transiently transfected into Bosc-23 Eco packaging line (kind gift from Guy Sauvageau), and retroviral supernatants were used to infect MEF Akt1 wt and Akt1−/− cells (kind gift from Morris Birnbaum). GFP+ cells were isolated using the BD FACSAria cell sorter. 4E and PML stably transfected NIH3T3 cells were generated as described (Topisirovic et al. 2002; Topisirovic et al. 2003a). For siRNA studies, 4E over-expressing MEF Akt1 wt cells were transfected with Lipofectamine 2000 (GibcoBRL) and 20 nM siRNA duplex MMS.RNAI.NO13752.2.2 (IDT) according to the manufacturer's instruction. Cells were analyzed 72 h after transfection. LY294002 (LY), used in treatment studies was cell culture grade (Sigma) and used at 50 µM for 1 hr.

Western Analysis and Antibodies.

Western analysis was performed as described (Topisirovic et al. 2002; Topisirovic et al. 2003a), with a modified lysis buffer (40 mM HEPES (pH 7.5), 120 mM NaCl, 1 mM EDTA, 10 mM ß-glycerophosphate, 50 mM NaF, 0.5 µM NaVO3, 1% (v/v) Triton X100, supplemented with complete protease inhibitors (all from Sigma)). In addition, blots for immuno-phosphoprotein detection were blocked in BSA blocking solution (2% (w/v) BSA (Sigma) in TBST), and primary antibodies diluted in BSA blocking solution. Antibodies used for immunoblotting were from Cell Signaling unless otherwise mentioned: mAb anti-4E (BD PharMingen); mAb anti-PML (5E10 (Stuurman et al. 1992)); pAb anti-NBS1; mAb anti-cyclinD1 (BD PharMingen); pAb anti-VEGF (Santa Cruz); pAbs anti-Akt, anti-Phospho Thr 308 Akt, and mAb anti-Phospho Ser 473 Akt; pAbs anti-S6 and anti-Phospho S6 ribosomal protein; pAbs anti-4E-BP1 and anti-Phospho 4E-BP1; mAb anti-GAPDH (MAB374, Chemicon); mAb anti-ß-actin (AC-15, Sigma).

Apoptosis Assays.

Exponentially growing cell cultures derived from MEF Akt1 wt and −/−, and NIH3T3 cells were shifted to 0.1% serum conditions for 18 hrs. For Annexin VAPC (Ann. V, BD Biosciences) and propidium iodide (PI, Sigma) staining, cells and initial PBS washes were collected, and treated according to the manufacturer's instructions (BD Biosciences). Stained cells were analysed on a BD LSR11 flow cytometer, with early apoptotic cells scored as annexin V positive, PI negative to exclude necrotic cells. Assays were performed in triplicate on at least three separate occasions. For TUNEL staining, pre-seeded cells on coverslips were serum withdrawn, fixed and stained with the In situ Cell Death Detection kit, TMR red (Roche) according to manufacturer's instruction, then mounted in Vectorshield with 4',6-diamidino-2-phenylindole (DAPI; Vector Laboratories, Inc). Fluorescence from several fields was observed using a 20× objective lens on a Zeiss LSM 510 laser scanning confocal microscope.

Cellular Fractionation and qPCR.

Fractionation and RNA isolation were as described (Lai and Borden 2000; Topisirovic et al. 2002). qPCR analyses were performed using Sybr Green PCR Master mix (ABI) in Mx3000P™ thermal cycler (Stratagene), and data analyzed with MxPro software (Stratagene). All conditions and primers were described previously (Culjkovic et al. 2005). All calculations were done using the relative standard curve

Example 7 Ribavirin Inhibits the Anti-Apoptotic Activity of the 4E Regulon and Rapamycin Activates the 4E Regulon Growth factor/cytokine signaling pathway via normal physiological processes and/or oncogenic activation of 4E regulon pathway members results in a positive feedback loop which in the case of cancer provides for increased cancer cell survival and proliferation. 4E overexpression rescues cell from apoptosis-4E rescue of cells from apoptosis is dependent upon Akt since Akt(−/−) cells cannot be rescued by 4E. Increased 4E is one way of accomplishing such an event but also is Akt-activation, Pim-1 activation and/or over-expression, Cyclin D1 overexpression, VEGF/FGF2 overexpression and/or various mixtures of overexpression and/or activation of the components of the 4E regulon. Inhibition of 4E activity produces an opposing effect with anticipated therapeutic benefit such as through treatment of cells, tumors and/or individuals with 4E inhibitors as epitomized by Ribavirin and related compounds denoted herein and in the literature including compounds upon which the structure of Ribavirin was initially based.

By contrast, application of rapamycin and rapamycin analogs known/unknown in the art can be expected since they activate Akt via phosphorylation to (i) increase the rate of growth of human cancers and (ii) to provide a mechanism by which cell survival can be provided and thereby provide a clinical benefit in situations where in direct contrast to the over-activation of the 4E regulon (i.e. cancer) where activation of the regulon would be therapeutically beneficial, such as in ischemia reperfusion injury and the like as suggested by Amaravadi and Thompson (J Clin Invest 115 2618, 2005) and demonstrated by Rosen and co-workers (Cancer Research 66: 1500, 2006).

As shown in FIGS. 35 and 36, Akt phosphorylation is required for activation of Akt. Ribavirin inhibits Akt phosphorylation while Rapamycin increases Akt phosphorylation providing for methods to both inhibit (Ribavirin and compounds with similar regulon activity modifying activity) and stimulate (Rapamycin and additional compounds with similar regulon activity modifying activity) the 4E growth/survival regulon. FIG. 27 shows that Ribavirin blocks 4E mediated apoptotic rescue and Rapamycin partially inhibits Ribavirin effect on 4E mediated apoptotic rescue.

Discussion

Inhibition of 4E activity can be anticipated to provide therapeutic benefit by rescuing cells which have become resistant to apoptosis (for example cancer cells), thereby providing enhanced therapeutic benefit by therapeutic regimens (including but not limited to chemotherapy, cytotoxic drugs, radiation and targeted therapeutics) by restoring the cell's sensitivity to apoptosis. Further, co-administration either sequentially and/or simultaneously of 4E inhibitors such as Ribavirin, Ribavirin analogues or molecules upon which the structure of Ribavirin was based—together—with radiation chemotherapies and/or targeted chemo/bio-therapeutics will provide for superior clinical benefit.

By contrast administration of Rapamycin alone or together with additional agents known to promote cell survival will provide for superior clinical benefit where promotion of cell survival is desirous such as subsequent to ischemia-reperfusion injury and the like.

Further, elevation of components of the 4E regulon can be used to provide diagnostic insight and determination that the 4E regulon is activated or inactivated (thereby promoting cell survival and apoptosis respectively). And in those situations treatment with Ribavirin and compounds previously designated herein or Ribavirin analogues known in the art or molecules upon which the structure of Ribavirin was initially based/conceived can be used to inhibit the 4E survival regulon thereby promoting apoptosis. By contrast, treatment with Rapamycin, rapamycin analogues or activators of mTOR can be used to stimulate the 4E survival regulon thereby promoting cell survival which in opposing clinical situations from those described above can also be of clinical benefit Determination of 4E and 4E targets protein and/or activation levels (i.e. molecules regulated at the mRNA transport and/or translational level and/or phosphorylation (directly/indirectly) can each provide alone or in combination diagnostic insight into the activation-state of the 4E regulon. Determining cases where the administration of Ribavirin (et al) or Rapamycin (et al) will provide for the restoration of cellular apoptosis or the inhibition of cellular apoptosis, respectively. Conditions where restoration of cellular apoptosis provides clinical benefit include cancer and proliferative diseases and disease states in which the 4E regulon is activated abnormally and the like. Conditions where decreasing cellular apoptosis would provide clinical benefit include ischemia-reperfusion injury and the like Current cancer chemotherapeutic strategies often do not provide for the coordinated regulation of biological systems, rather they seek to activate/inhibit a single target and thereby derive therapeutic benefit. By contrast the coordinated therapeutic modulation of a biological system is likely to provide superior therapeutic since all components of a pathway are regulated in concert. Few biological systems provide an avenue for just such a coordinated modulation of a biological system and fewer still have been described in sufficient detail to permit the development of coordinated therapeutic regulators of such systems.

The current art provides for the coordinate regulation of the 4E regulon via its therapeutic manipulation. 4E, 4E targets (mRNA transport and/or translational regulated molecules) and the kinase activities represent important participants in the oncogenic process and in human cancers. Ribavirin, a high-affinity inhibitor of 4E, inhibits the 4E regulon in a coordinated fashion. By contrast it appears that Rapamycin coordinately up-regulates (at least in part) this pathway.

As noted above both the inhibition of the 4E regulon and its activation provide therapeutic benefits, inhibition of cell growth and survival/resistance to chemotherapeutic agents in the case of cancers and hyperproliferative conditions/disease; and activation of cell growth/survival in the case of ischemia reperfusion injury and the like. The ability to coordinately regulate (i.e. inhibit) this pathway via the administration of micromolar concentrations of Ribavirin can provide a wide range of therapeutic benefits in cancer and hyperproliferative conditions, cancers and tuberous sclerosis to name but two categories.

An alternate to targeting single point/members of biological networks is the more recent development of multi-kinase inhibitors. These agents have been developed in an attempt to provide greater therapeutic coverage of target biological systems. The ability of Ribavirin to coordinately and selectively regulate the activity of numerous kinase activities directly/indirectly far exceeds that capabilities provided by even the broadest multi-kinase inhibitors that have been developed and to provide superior specificity and selectivity of action. Further Ribavirin in and of itself is not a kinase inhibitor, rather through its inhibition of 4E activity it inhibits the transport and/or translation of mRNAs encoding either these important regulatory kinase activities or modulators/activators thereof. Further still, Ribavirin inhibits the transport and/or translation of mRNAs encoding molecules that provide for tumor metastasis, angiogenesis and resistance to apoptosis as noted in the FIG. 34.

Clearly Ribavirin's ability to coordinately inhibit the 4E regulon provides superior regulation and thereby therapeutic benefit in conditions (cancer and hyperproliferative disease) where this regulon's activity is in all or partially elevated. It follows directly that in addition to cancer with elevated 4E that cancers with elevated levels of one or more of the 4E target molecules, 4E activated molecules and 4E activating molecules represent (and many have been so characterized previously) oncogenes. As such it is expected that conditions wherein one or more of the members of the 4E regulon is elevated at the level of gene expression, protein synthesis or activity) will represent conditions where the administration of Ribavirin is anticipated to provide therapeutic benefit. These are likely to include cancers in which while 4E activity is normal 4E targets/activators/effectors are elevated. For example, in prostate cancer Pim-1 kinase is elevated in a vast majority of advanced prostate cancers. Owing to the fact that Pim-1 is a 4E regulated molecule (both at the mRNA transport and mRNA translational levels) is appears likely that administration of Ribavirin to Pim-1 positive prostate cancers will likely provide therapeutic benefit. Similarly, determination in various cancers which of the 4E regulon components are elevated or present in an constitutively active form will serve to define which indications are most likely to respond and derived therapeutic benefit from low-dose Ribavirin administration. Ribavirin provides for coordinated and therapeutic modulation of the regulon including modulation of important survival kinases (Akt and Pim-1) but also the therapeutic modulation of Akt/Pim-1 target effector molecules (most commonly via the reduction of the amount of the target protein/effector molecule present in cells) This provides superior control of this central regulatory mechanism which is involved in regulating cell growth, cell survival and in many many cases these processes in cancerous cells and/or tumors.

Example 8 Studies of Additional Components of the 4E Regulon

HuR could Modulate the 4E Regulon by Modulating the Levels of 4E mRNA and the Activity of the 4E Protein Directly In this section, we describe a novel mechanism for upregulation of 4E levels, whereby 4E mRNA stability is increased through interactions with HuR. HuR is overexpressed in several cancers and can transform cells, thus this link might be particularly relevant to elevation of 4E levels in some cancers. In our studies, we found that HuR protein immunoprecipitates with 4E mRNA (data not shown). HuR protein is known to modulate cyclin D1 mRNA stability through an interaction with the ARE element in the cyclin D1 mRNA. Thus, cyclin D1 is a positive control for these assays. Note that the 4E protein does not immunoprecipitate with HuR mRNA (data not shown). Further, 4E overexpression does not change HuR expression (data not shown). Thus it appears that HuR modulates 4E mRNA stability but that 4E does not modulate gene expression of HuR.

HuR is well established to stabilize transcripts with ARE elements in their 3' UTR. Thus we examined whether overexpression of HuR would modulate 4E mRNA levels. As observed by western blot analysis, HuR overexpression led to increased levels of endogenous cyclin D1 protein. As expected, HuR also increased levels of endogenous cyclin D1 protein levels. This is consistent with previous studies showing that HuR stabilizes cyclin D1 mRNA. Consistently, parallel studies demonstrate that siRNA knockdown of HuR leads to reduction in 4E levels (data not shown).

We extended these studies to examine the effects of HuR overexpression on endogenous 4E mRNA stability using actinomycin D. HuR overexpression substantially stabilizes 4E mRNA but not GAPDH (a negative control) relative to vector controls. Given that HuR binds many mRNAs which are also downstream targets of 4E mRNA export, we examined whether HuR bound to chimeric IacZ constructs which contain the 4E-SE. LacZ without the 4E-SE was used as a control. As expected, HuR did not associate with either the LacZ4E-SE or LacZ mRNAs (data not shown). This is consistent with previous observations that HuR associated with ARE elements. These studies suggest that the ARE elements in the HuR sensitive mRNAs are distinct from the 4E-SE. In this way, HuR and 4E could potentially associate with the same transcripts at the same time (using different USER codes), coordinately modulating export and stability.

We show by immunoprecipitation of endogenous proteins that HuR protein binds to 4E protein in an RNA dependent manner (data not shown). The interaction is observed in both the nuclear and cytoplasmic fractions indicating that HuR could modulate 4E in both mRNA export and translation of sensitive mRNAs. Note that HuR and 4E proteins still immunoprecipitate in the presence of heparin, but not in the presence of RNAse. This indicates that a specific RNA interaction mediates the HuR 4E protein HuR interaction. Note that 4E does not immunoprecipitate its own mRNA, thus HuR 4E protein complexes are distinct from HuR-4E mRNA complexes.

Taken together, our preliminary data for HuR suggests that HuR could modulate the 4E regulon by modulating the levels of 4E mRNA and the activity of the 4E protein directly. Further, HuR stimulates the expression of a downstream target of 4E, cyclin D1 (and others, see below). Thus, HuR is positioned to amplify 4E activity. It is thus possible, that the previously reported transforming and oncogenic properties of HuR could be mediated, in part, through its interaction with 4E mRNA and 4E protein. Thus far, our data suggest that HuR can modulate 4E levels and activity, but that 4E does not modulate expression of HuR (data not shown). Indeed, our previous data indicate that 4E overexpression does not lead to alterations in mRNA stability of target mRNAs such as cyclin D1, ODC, or model mRNAs such as IacZ-4E-SE (or IacZ controls). Taken together, these data indicate that a subset of mRNAs associate with both HuR and 4E proteins. These mRNAs likely contain at least two distinct non-overlapping USER codes, the ARE (for HuR) and the 4E-SE (for 4E). In this way, 4E and HuR can modulate the expression of a common set of transcripts and thus, mediate their biological effects on cell growth.

Hence, we propose that HuR potentially has a three tier effect on the 4E regulon: 1. it amplifies the regulon by elevating levels of 4E, 2. it increases the levels of 4E mRNA export targets through stabilizing these transcripts thereby increasing the effectiveness of 4E and 3. it directly modulates the function of the 4E via the HuR-4E protein-protein interaction. Overexpression of HuR itself is known to lead to oncogenic transformation in cell culture, to tumours in xenograft mouse models and is elevated in some human cancers. It seems likely that the oncogenic potential of HuR may arise, at least in part, through its ability to modulate the 4E regulon.

Outcome.

The mechanism by which 4E expression itself is controlled is a subject that has received very little attention. Our studies indicate that HuR enhances 4E expression by stabilizing 4E mRNA. This is the first time such a mechanism has been proposed for 4E, with previous studies focusing on enhanced transcription or gene amplification being the basis for elevated 4E levels in cancer cells.

Example 9 Human Head and Neck SCC Cell Line Experiment

FaDu cells were grown in culture as described previously and treated with Ribavirin for 48 hours prior to preparation of protein extracts and western blot analysis. Actin and eIF4E protein levels remain unchanged after Ribavirin treatment (FIG. 38). By contrast the protein level of NBS1, Cyclin D1 and ODC (proteins whose mRNAs are eIF4E regulated at the nuclear to cytoplasmic transport level) are decreased by Ribavirin treatment (FIG. 38).

REFERENCES

All publications and patents mentioned herein, including those references listed below, are hereby incorporated by reference in their entirety as if each individual publication or patent was specifically and individually incorporated by reference. In case of conflict, the present application, including any definitions herein, will control.

Weinstein, I. B. (2000) *Carcinogenesis* 21, 857-864; Pomeroy, S. L., et al. (2002) *Nature* 415, 436-442; Colomer, R., et al. (1994) *Br. J. Cancer* 70, 819-825; Jain, M., et al. (2002) *Science* 297, 102-104; Kerekatte, V., et al. (1995) *Int. J. Cancer* 64, 27-31; Rosenwald, I. B., et al. (1999) *Oncogene* 18, 2507-2517; Nathan, C. A., et al. (1997) *Oncogene* 15, 1087-1094; Wang, S., et al. (1999) *Am. J. Pathol.* 155, 247-255; Topisirovic, I., et al. (2003) *Mol. Cell. Biol.* 23, 8992-9002; Lazaris-Karatzas, A., et al. (1990) *Nature* 345, 544-547; Gingras, A. C., et al. (1999) *Annu. Rev. Biochem.* 68, 913-963; Iborra, F. J., et al. (2001) *Science* 293, 1139-1142 Rousseau, D., et al. (1996) *Proc. Natl. Acad. Sci. USA* 93, 1065-1070; Cohen, N., et al. (2001) *EMBO J.* 20, 4547-4559; Topisirovic, I., et al. (2003) *EMBO J.* 22, 689-703; Topisirovic, I., et al. (2002) *Mol. Cell. Biol.* 22, 6183-6198; De Benedetti, A. & Harris, A. L. (1999) *Int. J. Biochem. Cell Biol.* 31, 59-72; Strudwick, S. & Borden, K. L. (2002) *Differentiation* 70, 10-22; Sidwell, R. W., et al. (1972) *Science* 177, 705-706; Tam, R. C., Lau, J. Y. & Hong, Z. (2001) *Antiviral Chem. Chemother.* 12, 261-272; Crotty, S., et al. (2000) *Nat. Med.* 6, 1375-1379; Crotty, S., et al. (2001) *Proc. Natl. Acad. Sci. USA* 98, 6895-6900; Maag, D., et al. (2001) *J. Biol. Chem.* 276, 46094-46098; Zoulim, F., et al. (1998) *J. Viral Hepat.* 5, 193-198; Kentsis, A., et al. (2001) *J. Mol. Biol.* 312, 609-623; DeFatta, R. J., Nathan, C. A. & De Benedetti, A. (2000) *Laryngoscope* 110, 928-933; Capili, A. D., et al. (2004) *J. Mol. Biol.* 340, 1117-1129; McGuire, A. M., Matsuo, H. & Wagner, G. (1998) *J. Biomol. NMR* 12, 73-88; Marcotrigiano, J., et al. (1997) *Cell* 89, 951-961; Niedzwiecka, A., et al. (2002) *J. Mol. Biol.* 319, 615-635; O'Neil, M. J., Smith, A., Heckelman, P. E. & Obenchain, J. R., Jr. (2001) *The Merck Index* (Merck, Whitehouse Station, N.J.), 13th Ed.; Smith, R. A., Knight, V. & Smith, J. A. D. (1984) *Clinical Applications of Ribavirin* (Academic, Orlando, Fla.); Page, T. & Conner, J. D. (1990) *Int. J. Biochem.* 22, 379-383; Dostie, J., Lejbkowicz, F. & Sonenberg, N. (2000) *J. Cell Biol.* 148, 239-247; von der Haar, T., et al. (2004) *Nat. Struct. Mol. Biol.* 11, 503-511; Graff, J. R. & Zimmer, S. G. (2003) *Clin. Exp. Metastasis* 20, 265-273; Sorrells, D. L., et al. (1999) *Head Neck* 21, 60-65; Wang, Y., et al. (1996) *Biochim. Biophys. Acta* 1297, 207-213; Kentsis, A., Gordon, R. E. & Borden, K. L. (2002) *Proc. Natl. Acad. Sci. USA* 99, 15404-15409; et al. (2002) *Nat. Struct. Biol.* 9, 912-917; Hong, Z. & Cameron, C. E. (2002) *Prog. Drug Res.* 59, 41-69; Fouchier, F., et al. (1996) *J. Recept. Signal Transduct. Res.* 16, 39-58; Graff, J. R., et al. (1997) *Biochem. Biophys. Res. Commun.* 240, 15-20; Colby, T. D., et al. (1999) *Proc. Natl. Acad. Sci. USA* 96, 3531-3536; Rijnbrand, R. C. & Lemon, S. M. (2000) *Curr. Top Microbiol. Immunol.* 242, 85-116; Sonenberg, N. & Pelletier, J. (1989) *BioEssays* 11, 128-132; Crotty, S., Cameron, C. & Andino, R. (2002) *J. Mol. Med.* 80, 86-95; Campbell Dwyer, E. J., et al. (2000) *J. Virol.* 74, 3293-3300; von Grotthuss, M., Wyrwicz, L. S. & Rychlewski, L. (2003) *Cell* 113, 701-702; Zimmer, S. G., DeBenedetti, A. & Graff, J. R. (2000) *Anticancer Res.* 20, 1343-1351; Wendel, H. G., et al. (2004) *Nature* 428, 332-337.

Bergamini, G., et al. (2000) *RNA* 6: 1781-1790; Carberry, S. E., et al. (1989) *Biochemistry* 28: 8078-8083; Cohen, N., et al. (2001) *EMBO J.* 20: 4547-4559; De Benedetti, A. and Graff, J. R. (2004) *Oncogene* 23: 3189-3199; De Gregorio, E., et al. (2001) *RNA* 7: 106-113; De Hoffmann, E. and Stroobant, V. (2001) *Mass spectrometry: Principles and applications.* John Wiley and Sons, New York; Fletcher, C. M. and Wagner, G. (1998) *Protein Sci.* 7: 1639-1642; Hong, Z. and Cameron, C. E. (2002) *Prog. Drug Res.* 59: 41-69; Kentsis, A., et al. (2001) *J. Mol. Biol.* 312: 609-623; Kentsis, A., Gordon, R. E., and Borden, K. L. (2002) *Proc. Natl. Acad. Sci.* 99: 15404-15409; Kentsis, A., et al. (2004) *Proc. Natl. Acad. Sci.* 101: 18105-18110; Lakowicz, J. R. (1999) *Principles of fluorescence spectroscopy.* Kluwer Academic/Plenum Publishers, New York; Matsuo, H., et al. (1997) *Nat. Struct. Biol.* 4: 717-724; McGuire, A. M., Matsuo, H., and Wagner, G. (1998) *J. Biomol. NMR* 12: 73-88; Michel, Y. M., et al. (2000) *J. Biol. Chem.* 275: 32268-32276; Niedzwiecka, A., et al. (2002) *J. Mol. Biol.* 319: 615-635; Rau, M., et al. (1996) *J. Biol. Chem.* 271: 8983-8990; Rousseau, D., et al. (1996) *Proc. Natl. Acad. Sci.* 93: 1065-1070; Smith, R. A., Knight, V., and Smith, J. A. D. (1984) *Clinical applications of Ribavirin.* Academic Press, Orlando, Fla.; Svitkin, Y. V. and Sonenberg, N. (2004) *Methods Mol. Biol.* 257: 155-170; Svitkin, Y. V., et al. (2001) *RNA* 7: 1743-1752; Westman, B., et al. (2005) *RNA* (in press); Yan, Y., et al. (2005) *RNA* 11: 1238-1244; Zhou, P., Lugovskoy, A. A., and Wagner, G. (2001) *J. Biomol. NMR* 20: 11-14.

Boisvert, F. M., M. J. Hendzel, and D. P. Bazett-Jones. (2000) *J. Cell Biol.* 148:283-292; Borden, K. L. B., et al. (1995) *EMBO J.* 14:1532-1541; Cohen, N., et al. (2001) *EMBO J.* 20:4547-4559; Dostie, J., et al. (2000) *EMBO J.* 19:3142-3156; Gingras, A. C., B. Raught, and N. Sonenberg. (1999) *Annu. Rev. Biochem.* 68:913-963; Iborra, F. J., D. A. Jackson, and P. R. Cook. (2001) *Science.* 293:1139-1142; Ishigaki, Y., et al. (2001) *Cell.* 106:607-617; Izaurralde, E., et al. (1995) *Nature.* 376:709-712; Kentsis, A., et al. (2001) *J. Mol. Biol.* 312:609-623; Kentsis, A., et al. (2004) *Proc. Natl. Acad. Sci. USA*

101:18105-18110; Lai, H. K., and K. L. Borden. (2000) *Oncogene.* 19:1623-1634; Lang, V., et al. (1994) *J. Biol. Chem.* 269:6117-6123; Lazaris-Karatzas, A., K. S. Montine, and N. Sonenberg. (1990) *Nature.* 345:544-547; Lazaris-Karatzas, A., and N. Sonenberg. (1992) *Mol. Cell. Biol.* 12:1234-1238; Lejbkowicz, F., et al. (1992) *Proc. Natl. Acad. Sci. USA.* 89:9612-9616; Lejeune, F., Y. Ishigaki, X. Li, and L. E. Maquat. (2002) *EMBO J.* 21:3536-3545; Marcotrigiano, J., et al. (1997) *Cell.* 89:951-961; McKendrick, L., et al. (2001) *Mol. Cell. Biol.* 21:3632-3641; Morley, S. J., and V. M. Pain. (1995) *J. Cell Sci.* 108:1751-1760; Motokura, T., and A. Arnold. (1993) *Genes Chromosomes Cancer.* 7:89-95; Nathan, C. A., et al. (1997) *Oncogene.* 15:1087-1094; Perez-Roger, I., et al. (1999) *EMBO J.* 18:5310-5320; Rousseau, D., et al. (1996) *Proc. Natl. Acad. Sci. USA.* 93:1065-1070; Sonenberg, N., and A. C. Gingras. (1998) *Curr. Opin. Cell Biol.* 10:268-275; Spector, D. L., R. D. Goldman, and L. A. Leinwand. (1998) *Cells: A Laboratory Manual*. Cold Spring Harbor, Cold Spring Harbor, N.Y. 116.8-116.16; Strudwick, S., and K. L. Borden. (2002) *Differentiation.* 70:10-22; Stuurman, N., et al. (1992) *J. Cell Sci.* 101: 773-784; Thompson, J. D., D. G. Higgins, and T. J. Gibson. (1994) *Nucleic Acids Res.* 22:4673-4680; Topisirovic, I., A. D. Capili, and K. L. Borden. (2002) *Mol. Cell. Biol.* 22:6183-6198; Topisirovic, I., et al. (2003a). *EMBO J.* 22:689-703; Topisirovic, I., et al. (2003b). *Mol. Cell. Biol.* 23:8992-9002; Topisirovic, I., M. Ruiz-Gutierrez, and K. L. B. Borden. (2004) *Cancer Res.* 64:8639-8642; Trifillis, P., N. Day, and M. Kiledjian. (1999) *RNA.* 5:1071-1082; Visa, N., et al. (1996) *J. Cell Biol.* 133:5-14.

Bachmann, M., and T. Moroy. (2005) *Int J Biochem Cell Biol.* 37:726-30; Borden, K. L. (2002) *Mol Cell Biol.* 22:5259-69; Cao, Q., and J. D. Richter. (2002) *Embo J.* 21:3852-62; Chen, Y. C., et al. (2005) *J Biol. Chem.* 280:32505-11; Clemens, M. J., and U. A. Bommer (1999) *Int J Biochem Cell Biol.* 31:1-23; Clever, J., C. Sassetti, and T. G. Parslow. (1995) *J. Virol.* 69:2101-9; Cohen, N., et al. (2001) *Embo J.* 20:4547-59; Culjkovic, B., et al. (2005) *J Cell Biol.* 169:245-56; Cullen, B. R. (2000) *Mol Cell Biol.* 20:4181-7; Cullen, B. R. (2003a) *Trends Biochem Sci.* 28:419-24; Cullen, B. R. (2003b) *J Cell Sci.* 116:587-97; Gao, Y., et al. (2004) *FEBS Lett.* 563:185-90; Grillo, G., et al. (2003) *Nucleic Acids Res.* 31:3608-12; Herold, A., T. Klymenko, and E. Izaurralde. (2001) *Rna.* 7:1768-80; Hieronymus, H., and P. A. Silver. (2003) *Nat. Genet.* 33:155-61; Hieronymus, H., and P. A. Silver. (2004) *Genes Dev.* 18:2845-60; Hieronymus, H., M. C. Yu, and P. A. Silver. (2004) *Genes Dev.* 18:2652-62; Hoover, D. S., et al. (1997) *Cell Growth Differ.* 8:1371-80; Iborra, F. J., D. A. Jackson, and P. R. Cook. (2001) *Science.* 293:1139-42; Ishigaki, Y., X. Li, G. Serin, and L. E. Maquat. (2001) *Cell.* 106:607-17; Izaurralde, E., et al. (1995) *Nature.* 376:709-12; Keene, J. D., and P. J. Lager. (2005) *Chromosome Res.* 13:327-37; Keene, J. D., and S. A. Tenenbaum. (2002) *Mol. Cell.* 9:1161-7; Kentsis, A., et al. (2001) *J Mol. Biol.* 312:609-23; Lai, H. K., and K. L. Borden. (2000) *Oncogene* 19:1623-34; Lejeune, F., Y. Ishigaki, X. Li, and L. E. Maquat. (2002) *Embo J.* 21:3536-45; Liang, J., and J. M. Slingerland. (2003) *Cell Cycle.* 2:339-45; Moy, T. I., and P. A. Silver. (2002) *J Cell Sci.* 115:2985-95; Naumann, F., et al. (2004) *Genomics.* 83:106-18; Pegg, A. E. (2006) *J Biol. Chem.* 281:14529-32; Rousseau, D., et al. (1996) *Proc Natl Acad Sci USA.* 93:1065-70; Roy, H., S. Bhardwaj, and S. Yla-Herttuala. (2006) *FEBS Lett.* 580:2879-87; Sarkar, S., and A. K. Hopper. (1998) *Mol Biol Cell.* 9:3041-55; Schmidt, E. V. (2004) *Oncogene.* 23:3217-21; Schutz, S., et al. (2006) *J Mol. Biol.* 358:997-1009; Sonenberg, N., and A. C. Gingras. (1998) *Curr Opin Cell Biol.* 10:268-75; Stier, S., et al. (2005) *J Biochem Mol. Biol.* 38:447-56; Strudwick, S., and K. L. Borden. (2002) *Differentiation.* 70:10-22; Stuurman, N., et al. (1992) *J Cell Sci.* 101:773-84; Topisirovic, I., and K. L. Borden. (2005) *Histol Histopathol.* 20:1275-84; Topisirovic, I., A. D. Capili, and K. L. Borden. (2002) *Mol Cell Biol.* 22:6183-98; Topisirovic, I., et al. (2003a) *Embo J.* 22:689-703; Topisirovic, I., M. L. et al. (2003b) Aberrant eukaryotic translation initiation factor 4E-dependent mRNA transport impedes hematopoietic differentiation and contributes to leukemogenesis. *Mol Cell Biol.* 23:8992-9002; Topisirovic, I., et al. (2005) *Mol Cell Biol.* 25:1100-12; Trifillis, P., N. Day, and M. Kiledjian. (1999) *Rna.* 5:1071-82; Wang, H., et al. (2001) *Mol Cell.* 8:817-28; Zhu, N., et al. (2005) *Biochem Biophys Res Commun.* 335:1272-9.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A method for diagnosing and treating a disease wherein eIF4E regulon activity is dysfunctional in a subject, wherein the disease is selected from the group consisting of cellular hypertrophy, cancer, and ischemia reperfusion, the method comprising the steps of:
   (a) obtaining a biological sample from the subject;
   (b) performing a mass spectroscopy assay on the biological sample to determine the levels of, phosphorylation states of, or activities of eIF4E, HuR and at least one eIF4E regulon component gene product selected from the group consisting of Cyclin Dl; NBS/Nibrin; Pim-1; Cyclin Bl; Cyclin A2; ODC; VEGF; Skp2; Cyclin El; c-myc; FGF2; MMP-9; mdm2; caspase-9; bcl2; Bcl/xL; Fbox1; CGGbp1; P54nrb/NONO.1; Selenoprotein S; eIF4E-BP1; Akt1; PI3K; GSK3B; and mTOR/FRAP1;
   (c) determining whether the subject has or is likely to develop the disease when the levels of, phosphorylation states of, or activities of eIF4E, Hur and the at least one eIF4E regulon component gene products in the sample are similar to the levels of, phosphorylation states of, or activities of the eIF4E, HuR and at least one eIF4E regulon component gene products that are associated with the disease; and
   (d) administering a prodrug form of a compound of Formula I to the subject having or who has developed the disease, wherein the compound of Formula I is represented by:

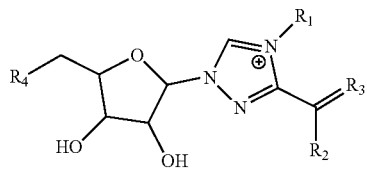

wherein:
R1 is selected from the group consisting of null, a linear or branched alkyl, alkenyl, hydrogen, and alkynyl group;

R2 is selected from the group consisting of a primary amine, a secondary amine, a tertiary amine, an aromatic amine, an amino group and an amido group;

R3 is selected from the group consisting of nitrogen, oxygen and sulfur; and

R4 is hydroxyl, and wherein the prodrug form of a compound of Formula I excludes Ribavirin.

2. The method of claim 1, wherein the sample is selected from the group consisting of: plasma, blood urine, saliva and tissue.

3. The method of claim 1, wherein the at least one eIF4E regulon component gene product is selected from the group consisting of NBS/Nibrin, Pim-1, VEGF, Cyclin Dl, Cyclin A2, eIF4E-BP1, and ODC.

4. The method of claim 1, further comprising determining the levels of, phosphorylation states of, or activities of at least one non-eIF4E regulon component gene product.

5. The method of claim 4, wherein the non-eIF4E regulon component gene product is selected from the group consisting of: estrogen receptor (ER), progesterone receptor (PR), epidermal growth factor receptor (EGFR), and Her2/neu.

6. The method of claim 1, wherein the levels of the eIF4E and Hur and the at least one eIF4E regulon component gene products are determined by determining the amounts of the eIF4E and Hur and the at least one eIF4E regulon component gene products in the sample.

7. The method of claim 1, wherein the levels of the eIF4E and Hur and the at least one eIF4E regulon component gene products are determined by determining the amount of the mRNAs encoding the eIF4E and Hur and the at least one eIF4E regulon component gene products in the sample.

8. The method of claim 1, wherein R1 is —$CH_3$ or $CH_2CH_3$.

9. The method of claim 1, wherein R2 is selected from the group consisting of —$NH_2$, —$NHCH_3$, —$NHCH_2CH_3$, —$NHCH_2CH_2CH_3$, —$NHCH(CH_3)_2$, —$NHCH_2CH_2OH$, —$NHCH_2CH(OH)CH_3$, and —$NHCH(CH_2OH)CH_3$.

10. The method of claim 1, wherein the compound is administered to the subject and the compound is administered at levels of between about 0.1 and about 1 mg/kg body weight of said subject.

11. The method of claim 10, wherein the compound is administered to the subject and the compound is administered at levels of between about 0.01 and about 5 mg/kg body weight per day.

12. The method of claim 1, further comprising administering an inhibitor of HER2, ER, PR, or EGFR, or combination thereof.

13. A method for prognosing or staging and treating a disease wherein eIF4E regulon activity is dysfunctional, wherein the disease is selected from the group consisting of cellular hypertrophy, cancer, and ischemia reperfusion, the method comprising the steps of:
(a) obtaining a biological sample from a subject;
(b) performing a mass spectroscopy assay on the biological sample to determine the levels of, phosphorylation states of, or activities of eIF4E, HuR and at least one eIF4E regulon component gene product selected from the group consisting of Cyclin D1; NBS/Nibrin; Pim-1; Cyclin B1; Cyclin A2; ODC; VEGF; Skp2; Cyclin E1; c-myc; FGF2; MMP-9; mdm2; caspase-9; bcl2; Bcl/xL; Fboxl; CGGbpl; P54nrb/NONO.1; Selenoprotein S; eIF4E-BP1; Aktl; PI3K; GSK3B; and mTOR/FRAPl;
(c) prognosing or staging the subject as having the disease when the levels of, phosphorylation states of, or activities of eIF4E, Hur and the at least one eIF4E regulon component gene products are similar to the levels of, phosphorylation states of, or activities of the eIF4E, HuR and at least one eIF4E regulon component gene products that are associated with the degree of, severity of, or stage of the disease; and
(d) administering a prodrug form of a compound of Formula I to the subject having or who has developed the disease, wherein the compound of Formula I is represented by:

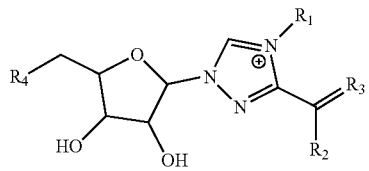

wherein:
R1 is selected from the group consisting of null, a linear or branched alkyl, alkenyl, hydrogen, and alkynyl group;
R2 is selected from the group consisting of a primary amine, a secondary amine, a tertiary amine, an aromatic amine, an amino group and an amido group;
R3 is selected from the group consisting of nitrogen, oxygen and sulfur; and
R4 is hydroxyl, and
wherein the prodrug form of a compound of Formula I excludes Ribavirin.

14. The method of claim 13, wherein R1 is —$CH_3$ or $CH_2CH_3$.

15. The method of claim 13, wherein R2 is selected from the group consisting of —$NH_2$, —$NHCH_3$, —$NHCH_2CH_3$, —$NHCH_2CH_2CH_3$, —$NHCH(CH_3)_2$, —$NHCH_2CH_2CH_2OH$, —$NHCH_2CH_2CH(OH)CH_3$, and —$NHCH(CH_2OH)CH_3$.

16. The method of claim 13, wherein the compound is administered to the subject and the compound is administered at levels of between about 0.1 and about 1 mg/kg body weight of said subject.

17. The method of claim 16, wherein the compound is administered to the subject and the compound is administered at levels of between about 0.01 and about 5 mg/kg body weight per day.

18. The method of claim 13, further comprising administering one or more non-eIF4E component modulator.

19. A diagnostic method for selecting a therapeutic regimen for a subject having a disease, wherein the disease is selected from the group consisting of cellular hypertrophy, cancer, and ischemia reperfusion, the method comprising:
(a) obtaining a biological sample from the subject;
(b) performing a mass spectroscopy assay on the biological sample to determine the levels of, phosphorylation states of, or activities of eIF4E, HuR and at least one eIF4E regulon component gene product selected from the group consisting of Cyclin D1; NBS/Nibrin; Pim-1; Cyclin B1; Cyclin A2; ODC; VEGF; Skp2; Cyclin E1; c-myc; FGF2; MMP-9; mdm2; caspase-9; bcl2; Bcl/xL; Fboxl; CGGbpl; P54nrb/NONO.1; Selenoprotein S; eIF4E-BP1; Aktl; PI3K; GSK3B; and mTOR/FRAPl;
(c) performing a mass spectroscopy assay on the biological sample previously obtained from the subject, to determine the levels of, phosphorylation states of, or activities of eIF4E, HuR and at least one non-eIF4E regulon component gene products selected from the group consisting of estrogen receptor (ER), progesterone receptor (PR), epidermal growth factor receptor (EGFR), and Her2/neu;
(d) determining the relative changes in the levels of, phosphorylation states of, or activities of the eIF4E or non-eIF4E component gene products, to thereby select a therapy for said subject; and
(e) administering a prodrug form of a compound of Formula I to the subject having the disease, wherein the compound of Formula I is represented by:

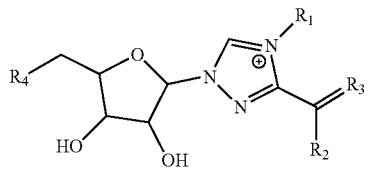

wherein:
R1 is selected from the group consisting of null, a linear or branched alkyl, alkenyl, hydrogen, and alkynyl group;
R2 is selected from the group consisting of a primary amine, a secondary amine, a tertiary amine, an aromatic amine, an amino group and an amido group;
R3 is selected from the group consisting of nitrogen, oxygen and sulfur; and
R4 is hydroxyl, and
wherein a prodrug form of a compound of Formula I excludes Ribavirin, when the relative changes of the levels of, phosphorylation states of, or activities of eIF4E component gene products are increased; or
(f) administering an inhibitor of HER2, ER, PR, or EGFR, or combination thereof to the subject having the disease, when the relative changes of the levels of, phosphorylation states of, or activities of non-eIF4E component gene products are increased, or
(g) administering both (e) and (f), when the relative changes of levels of, phosphorylation states of, or activities of the eIF4E and non-eIF4E component gene products are increased.

20. The method of claim 19, wherein R1 is —CH$_3$ or CH$_2$CH$_3$.

21. The method of claim 19, wherein R2 is selected from the group consisting of —NH$_2$, —NHCH$_3$, —NHCH$_2$CH$_3$, —NHCH$_2$CH$_2$CH$_3$, —NHCH(CH$_3$)$_2$, —NHCH$_2$CH$_2$CH$_2$OH, —NHCH$_2$CH$_2$CH(OH)CH$_3$, and —NHCH(CH$_2$OH)CH$_3$.

22. The method of claim 19, wherein the compound is administered to the subject and the compound is administered at levels of between about 0.1 and about 1 mg/kg body weight of said subject.

23. The method of claim 22, wherein the compound is administered to the subject and the compound is administered at levels of between about 0.01 and about 5 mg/kg body weight per day.

* * * * *